US011236335B2

(12) United States Patent
Oestergaard et al.

(10) Patent No.: US 11,236,335 B2
(45) Date of Patent: Feb. 1, 2022

(54) SELECTIVE ANTISENSE COMPOUNDS AND USES THEREOF

(71) Applicant: Ionis Pharmaceuticals, Inc., Carlsbad, CA (US)

(72) Inventors: Michael Oestergaard, Carlsbad, CA (US); Punit P. Seth, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/793,119

(22) Filed: Feb. 18, 2020

(65) Prior Publication Data

US 2021/0002636 A1    Jan. 7, 2021

Related U.S. Application Data

(63) Continuation of application No. 16/141,781, filed on Sep. 25, 2018, now abandoned, which is a continuation of application No. 15/468,489, filed on Mar. 24, 2017, now abandoned, which is a continuation of application No. 14/434,885, filed as application No. PCT/US2013/064666 on Oct. 11, 2013, now abandoned.

(60) Provisional application No. 61/840,722, filed on Jun. 28, 2013, provisional application No. 61/760,596, filed on Feb. 4, 2013, provisional application No. 61/713,459, filed on Oct. 12, 2012.

(51) Int. Cl.
C07H 21/04        (2006.01)
C07H 21/02        (2006.01)
C12N 15/113       (2010.01)

(52) U.S. Cl.
CPC ........... *C12N 15/113* (2013.01); *C07H 21/02* (2013.01); *C12N 2310/11* (2013.01); *C12N 2310/313* (2013.01); *C12N 2310/315* (2013.01); *C12N 2310/3125* (2013.01); *C12N 2310/3231* (2013.01); *C12N 2310/335* (2013.01); *C12N 2310/3341* (2013.01); *C12N 2310/341* (2013.01); *C12N 2310/345* (2013.01); *C12N 2310/346* (2013.01); *C12N 2320/34* (2013.01)

(58) Field of Classification Search
CPC ........................... C12N 15/113; C12N 2310/11
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |

(Continued)

FOREIGN PATENT DOCUMENTS

JP    2008-513507    5/2008
WO   WO 99/14226    3/1999

(Continued)

OTHER PUBLICATIONS

Abifadel et al., "Mutations and polymorphisms in the proprotein convertase subtilisin kexin 9 (PCSK9) gene in cholesterol metabolism and disease" Hum Mutat. (2009) 30(4): 520-529.
Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.
Altmann et al., "Second-generation antisense oligonucleotides: structure-activity relationships and the design of improved signal-transduction inhibitors" Biochem. Soc. Trans. (1996) 24:630-637.

(Continued)

Primary Examiner — Amy H Bowman
(74) Attorney, Agent, or Firm — McNeill Baur PLLC

(57) ABSTRACT

The present invention provides oligomeric compounds. Certain such oligomeric compounds are useful for hybridizing to a complementary nucleic acid, including but not limited, to nucleic acids in a cell. In certain embodiments, hybridization results in modulation of the amount, activity, or expression of the target nucleic acid in a cell. In certain embodiments, hybridization results in selective modulation of the amount, activity, or expression of a target Huntingtin gene or Huntingtin transcript in a cell.

24 Claims, No Drawings
Specification includes a Sequence Listing.

(56) References Cited

U.S. PATENT DOCUMENTS

| | | |
|---|---|---|
| 7,741,457 B2 | 6/2010 | Swayze et al. |
| 7,951,934 B2 | 5/2011 | Freier et al. |
| 8,084,437 B2 | 12/2011 | Freier et al. |
| 8,093,222 B2 | 1/2012 | Freier et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,679,750 B2 | 3/2014 | Hayden et al. |
| 9,157,120 B2 | 10/2015 | Hayden et al. |
| 9,695,418 B2 | 7/2017 | Seth et al. |
| 10,202,599 B2 | 2/2019 | Seth et al. |
| 10,260,069 B2 | 4/2019 | Oestergaard et al. |
| 2002/0187931 A1 | 12/2002 | Hayden et al. |
| 2004/0171570 A1 | 9/2004 | Allerson et al. |
| 2005/0130923 A1 | 6/2005 | Bhat et al. |
| 2005/0176045 A1 | 8/2005 | Fedorov et al. |
| 2007/0123484 A1 | 5/2007 | Bhat et al. |
| 2007/0161590 A1 | 7/2007 | Van Bilsen et al. |
| 2007/0287831 A1 | 12/2007 | Seth et al. |
| 2008/0039618 A1 | 2/2008 | Allerson et al. |
| 2011/0213010 A1 | 9/2011 | Hayden et al. |
| 2011/0245327 A1 | 10/2011 | Wengel et al. |
| 2014/0303235 A1 | 10/2014 | Oestergaard et al. |
| 2015/0051389 A1 | 2/2015 | Seth et al. |
| 2015/0184153 A1 | 7/2015 | Freier et al. |
| 2017/0096668 A1 | 4/2017 | Bhat |
| 2020/0056187 A1 | 2/2020 | Oestergaard et al. |
| 2020/0377946 A1 | 12/2020 | Bennett et al. |
| 2021/0238591 A1 | 8/2021 | Seth et al. |

FOREIGN PATENT DOCUMENTS

| | | |
|---|---|---|
| WO | WO 2001/079283 | 10/2001 |
| WO | WO 2004/106356 | 12/2004 |
| WO | WO 2005/021570 | 3/2005 |
| WO | WO 2006/034348 | 3/2006 |
| WO | WO 2007/002904 | 1/2007 |
| WO | WO 2007/134181 | 11/2007 |
| WO | WO 2008/101157 | 8/2008 |
| WO | WO 2008/147887 | 12/2008 |
| WO | WO 2008/147930 | 12/2008 |
| WO | WO 2008/150729 | 12/2008 |
| WO | WO 2008/154401 | 12/2008 |
| WO | WO 2009/006478 | 1/2009 |
| WO | WO 2009/061851 | 5/2009 |
| WO | WO 2009/067647 | 5/2009 |
| WO | WO 2009/100320 | 8/2009 |
| WO | WO 2009/124295 | 10/2009 |
| WO | WO 2009/135322 | 11/2009 |
| WO | WO 2010/036698 | 4/2010 |
| WO | WO 2010/048585 | 4/2010 |
| WO | WO 2011/017521 | 2/2011 |
| WO | WO 2011/097388 | 8/2011 |
| WO | WO 2011/097643 | 8/2011 |
| WO | WO 2011/097644 | 8/2011 |
| WO | 2011139702 A2 | 11/2011 |
| WO | WO 2012/109395 | 8/2012 |
| WO | WO 2013/022967 | 2/2013 |

OTHER PUBLICATIONS

Alves et al., "Allele-Specific RNA Silencing of Mutan Ataxin-3 Mediates Neuroprotection in a Rat Model of Machado-Joseph Disease" PLoS One (2008) 3(10): e3341.

Anderson et al., "An Overview of Psychiatric Symptoms in Huntington's Disease" Current Psychiatry Reports (2001) 3:379-388.

Boado et al., "Antisense-mediated down-regulation of the human huntington gene" *Journal of Pharmacology and Experimental Therapeutics* (2000) 295:239-243.

Braasch et al., "Locked nucleic acid (LNA): fine-tuning the recognition of DNA and RNA" Chem. Biol. (2001) 8:1-7.

Braasch et al., "Novel antisense and peptide nucleic acid strategies for controlling gene expression" Biochemistry (2002) 41(14):4503-4510.

Brookes, "The essence of SNPs" Gene (1999) 234(2):177-186.

Bruge et al., "A novel Real Time PCR strategy to detect SOD3 SNP using LNA probes" Mutation Res (2009) 669(1): 80-84.

Bruijn et al., "Aggregation and Motor Neuron Toxicity of an ALS-Linked SOD1 Mutant Independent from Wild-Type SOD1" Science (1998) 281: 1851-1854.

Caplen et al., "Rescue of polyglutamine-mediated cytotoxicity by double-stranded RNA-mediated RNA interference" Human Molecular Genetics (2002) 11(2):175-184.

Carrell et al., "Alpha1-Antitrypsin Deficiency—A Model for Conformational Diseases" New Engl J Med (2002) 346: 45-53.

Carroll et al., "Potent and Selective Antisense Oligonucleotides Targeting Single-Nucleotide Polymorphisms in the Huntington Disease Gene / Allele-Specific Silencing of Mutant Huntingtin" Molecular Therapy (2011) 19(12):2178-2185.

Chen et al., "Allelic origin of the abnormal prion protein isoform in familial prion diseases." Nat. Med. (1997) 3(9): 1009-1015.

Crooke et al., "Basic Principles of Antisense Therapeutics" Antisense Research and Application (1998) Chapter 1: 1-50.

Crooke et al., "Pharmacokinetic Properties of Several Novel Oligonucleotide Analogs in mice" J. Pharmacol. Exp. Ther. (1996) 277(2):923-937.

Daiger et al., "Mutations in known genes account for 58% of autosomal dominant retinitis pigmentosa (adRP)." Adv Exp Med Biol (2008) 613: 203-219.

Dawson et al., "Rare genetic mutations shed light on the pathogenesis of Parkinson disease." J. Clin. Invest. (2003) 111(2): 145-151.

De Gobbi et al., "A regulatory SNP causes a human genetic disease by creating a new transcriptional promoter." Science (2006) 312(5777): 1215-1217.

Elayadi et al., "Application of PNA and LNA oligomers to chemotherapy" Curr. Opinions Invens. Drugs (2001) 2:558-561.

Englisch et al., "Chemically Modified Oligonucleotides as Probes and Inhibitors" Angewandte Chemie, International Edition (1991) 30(6): 613-629.

Ewart-Toland et al., "A gain of function TGFB1 polymorphism may be associated with late stage prostate cancer." Cancer Epidemiol Biomarkers Prey (2004) 13(5): 759-764.

Feng et al., "Allele-specific silencing of Alzheimer's disease genes: The amyloid precursor protein genes with Swedish or London mutations" Gene (2006) 371: 68-74.

Fluiier et al., "Killing cancer by targeting genes that cancer cells have lost: allele-specific inhibition, a novel approach to the treatment of genetic disorders." Cell Mol Life Sci (2003) 60: 834-43.

Fontana et al., "P2Y12 H2 Haplotype Is Associated With Peripheral Arterial Disease: a case-control study" Circulation (2003) 108: 2971-2973.

Freer et al., "The ups and downs of nucleic acid duplex stability: structure-stability studies on chemically-modified DNA:RNA duplexes" Nucleic Acids Res. (1997) 25:4429-4443.

Frieden et al., "Expanding the design horizon of antisense oligonucleotides with alpha-L-LNA" Nucleic Acids Research (2003) 21:6365-6372.

Gagnon et al. "Allele-selective inhibition of mutatn huntington expression with antisense oligonucleotides targeting the expanded CAG repeat" Biochemistiy (2010) 49:10166-78.

Gallo et al., "2'-C-Methyluridine phosphoramidite: a new building block for the preparation of RNA analogues carrying the 2'-hydroxyl group" Tetrahedron (2001) 57:5707-5717.

Gow et al., "The unfolded protein response in protein aggregating diseases" NeuroMol. Med. (2003) 4(1-2):73-94.

Gray et al., "Full-Length Human Mutant Huntingtin with a Stable Polyglutamine Repeat Can Elicit Progressive and Selective Neuropathogenesis in BACHD Mice" J. Neurosc. (2008) 28(24):6182-6195.

Gryk et al., "Local knowledge helps determine protein structures" PNAS (2008) 105: 4533-4534.

Guillerm et al., "Synthesis of 4'-fluoroadenosine as an inhibitor of S-adenosyl-L-homocysteine hydrolase" Bioorganic and Medicinal Chemistry Letters (1995) 5(14): 1455-1460.

(56) References Cited

OTHER PUBLICATIONS

Hagemann et al., "Alexander Disease-Associated Glial Fibrillary Acidic Protein Mutations in Mice Induce Rosenthal Fiber Formation and a White Matter Stress Response" J. Neurosci. (2006) 26(43): 11162-11173.

Hizawa et al., "Functional single nucleotide polymorphisms of the CCL5 gene and nonemphysematous phenotype in COPD patients" Eur. Respir. J. (2008) 32(2):372-378.

Hu et al., "Serotonin transporter promoter gain-of-function genotypes are linked to obsessive-compulsive disorder." Am J Hum Genet (2006) 78(5): 815-826.

Jacobson et al., "Methanocarba Analogues of Purine Nucleosides as Potent and Selective Adenosine Receptor Agonists" J. Med. Chem. Lett. (2000) 43(11): 2196-2203.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.

Kabashi et al., "Gain and loss of function of ALS-related mutations of TARDBP (TDP-43) cause motor deficits in vivo." Hum Mol Genet (2010) 19(4): 671-683.

Kai et al. "A genetic linkage map for the tiger pufferfish, *Takifugu rubripes*" Genetics (2005) 171(1): 227-238.

Kawasaki et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. (1993) 36: 831-841.

Kordasiewicz et al., "Sustained Therapeutic Reversal of Huntington's Disease by Transient Repression of Huntingtin Synthesis" Neuron (2012) 74:1031-1044.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kroshwitz, The Concise Encyclopedia Of Polymer Science And Engineering, Kroschwitz, J.I., Ed., John Wiley & Sons, 1990, 858-859.

Kurreck et al., "Design of antisense oligonucleotides stabilized by locked nucleic acids" Nucleic Acids Research (2002) 30: 1911-1918.

Kurreck et al., "Antisense Technologies Improvement Through Novel Chemical Modifications" European Journal of Biochemistry (2003) 270: 1628-1644.

Lai et al., "Molecular genetic studies in atrial fibrillation" Cardiology (2003) 100(3):109-113.

Landgraf, "The involvement of the vasopressin system in stress-related disorders." CNS Neurol. Disord. Drug Targets (2006) 5(2): 167-179.

Lee et al., "Ring-Constrained (N)-Methanocarba nucleosides as adenosine receptor agonists: independent 5'-Uronamide and 2'-deoxy modifications" Bioorganic and Medicinal Chemistry Letters (2001) 11: 1333-1337.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann, "DNA Analogues: From Supramolecular Principles to Biological Properties" Bioorganic & Medicinal Chemistry (2002) 10:841-854.

Li et al., "Gain-of-function polymorphism in mouse and human Ltk: implications for the pathogenesis of systemic lupus erythematosus" Hum Mol Gen (2004) 13(2): 171-179.

Liu et al., "Linking SNP identity to CAG repeat length in Huntington's Disease patients," Nature Methods (2008) 5(11): 951-953.

Lombardi et al., "A majority of Huntington's disease patients may be treatable by individualized allele-specific RNA interference" Experimental Neurology (2009) 217(2): 312-319.

Manoharan et al., "Chemical Modifications to Improve Uptake and Bioavailability of Antisense Oligonucleotides" Ann. N.Y. Acad. Sci. (1992) 660:306.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Mantaring et al., "Genotypic variation in ATP-binding cassette transporter-1 (ABCA1) as contributors to the high and low high-density lipoprotein-cholesterol (HDL-C) phenotype" Transl Res (2007) 149(4): 205-210.

Margolis et al., "Expansion explosion: new clues to the pathogenesis of repeat expansion neurodegenerative diseases." Trends Mol. Med. (2001) 7: 479-482.

Marzolini et al., "A common polymorphism in the bile acid receptor farnesoid X receptor is associated with decreased hepatic target gene expression." Mol Endocrinol (2007) 21(8): 1769-1780.

McWhinney et al., "Intronic single nucleotide polymorphisms in the RET protooncogene are associated with a subset of apparently sporadic pheochromocytoma and may modulate age of onset" J. Clin. Endocrinol. Metab. (2003) 88(10):4911-4916.

Mishra et al., "Improved leishmanicidal effect of phosphorotioate antisense oligonucleotides by LDL-mediated delivery" Biochim. Biophys. Acta (1995) 1264:229-237.

Morita et al., "2'-O,4'-C-ethylene-bridged nucleic acids (ENA): highly nuclease-resistant and thermodynamically stable oligonucleotides for antisense drug" Bioorganic & Medicinal Chemistry Letters (2002) 12(1): 73-76.

Murray et al., "TricycloDNA-modified oligo-20-deoxyribonucleotides reduce scavenger receptor B1 mRNA in hepatic and extra-hepatic tissues—a comparative study of oligonucleotide length, design and chemistry" Nucleic Acids Res (2012) 40(13): 6135-6143.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Olie et al., "Analysis of ribosyl-modified, mixed backbone analogs of a bcl-2/bcl-xL antisense oligonucleotide" Biochemica et Biophysica Acta (2002) 1576: 101-109.

Ostergaard et al. "Rational design of antisense oligonucleotides targeting single nucleotide polymorphisms for potent and allele selective suppression of mutant Huntingtin in the CNS." Nucleic Acids Res. (2013) 41:9634-50.

Orum et al., "Locked nucleic acids: A promising molecular family for gene-function analysis and antisense drug development" Curr. Opinion Mol. Ther. (2001) 3:239-243.

Owen et al., "4'-Substituted nucleosides. 3. Synthesis of some 4'-fluorouridine derivatives" J. Org. Chem. (1976) 41(18): 3010-3017.

Palazzolo et al., "The role of the polyglutamine tract in androgen receptor" J Steroid Biochem Mol Biol (2008) 108(3-5): 245-252.

Persichetti et al., "Differential expression of normal and mutant Huntington's disease gene alleles." Neurobiol Dis (1996) 3(3): 183-190.

Pfister et al., "Five siRNAs targeting three SNPs may provide therapy for three-quarters of Huntington's Disease patients," Current Biology (2009) 19:774-778.

Rajasekaran et al., "Human alpha B-crystallin mutation causes oxido-reductive stress and protein aggregation cardiomyopathy in mice" Cell (2007) 130(3): 427-439.

Robertson et al., "Localized mutations in the gene encoding the cytoskeletal protein filamin A cause diverse malformations in humans." Nat Genet (2003) 33(4): 487-491.

(56) References Cited

OTHER PUBLICATIONS

Saison-Behmoaras et al., "Short modified antisense oligonucleotides directed against Ha-ras point mutation induce selective cleavage of the mRNA and inhibit T24 cells proliferation" Embo J. (1991) 10(5):1111-1118.

Sanghvi et al., "Heterocyclic Base Modifications in Nucleic Acids and Their Applications in Antisense Oligonucleotides" Antisense Research and Applications (1993) pp. 273-288.

Scholefield et al., "Design of RNAi hairpins for mutation-specific silencing of ataxin-7 and correction of a SCA7 phenotype." PLoS One (2009) 4(9): e7232.

Schwarz et al., "Designing siRNA that distinguish between genes that differ by a single nucleotide" PLoS Genetics (2006) 2(9): p. e140.

Sen et al., "Role of histidine interruption in mitigating the pathological effects of long polyglutamine stretches in SCA1: A molecular approach," Protein Sci. (2003) 12(5): 953-962.

Shashidharan etal., "TorsinA accumulation in Lewy bodies in sporadic Parkinson's disease" Brain Res. (2000) 877: 379-381.

Shea et al., "Synthesis, hybridization properties and antiviral activity of lipid-oligodeoxy nucleotide conjugates" Nucl. Acids Res. (1990) 18(13):3777-3783.

Shiels et al., "CHMP4B, a Novel Gene for Autosomal Dominant Cataracts Linked to Chromosome 20q" Am J Hum Genet (2007) 81(3): 596-606.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Confonnationally Restricted High-Affinity Oligonucleotide Analogue with a Handle" J. Org. Chem. (1998) 63:10035-10039.

Southwell et al. "Antisense oligonuceltide therapeutics for inherited neurodegenerative diseases" Trends Mol Med (2012) 18:634-43.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Takagi-Sato et al., "Fine-tuning of ENA gapmers as antisense oligonucleotides for sequence-specific inhibition" Oligonucleotides (2007) 17(3): 291-301.

Tang et al., "2'-C-Branched Ribonucleosides: Synthesis of the Phosphoramidite Derivatives of 2'-C-beta-Methylcytidine and Their Incorporation into Oligonucleotides." J Org Chem (1999) 64(3) 747-754.

Van Bilsen et al., "Identification and allele-specific silencing of the mutant huntingtin allele in Huntington's disease patient-derived fibroblasts" Human Gene Therapy (2008) 19:710-718.

Vezzoli et al., "R990G polymorphism of calcium-sensing receptor does produce a gain-of-function and predispose to primaiy hyperealciuria" Kidney Int. (2007) 71: 1155-1162.

Wahlesiedt et al., "Potent and nontoxic antisense oligonucleotides containing locked nucleic acids" PNAS (2000) 97:5633-5638.

Warby et al., "CAG expansion in the Huntington disease gene is associated with a specific and targetable predisposing haplogroup" The American Journal of Human Genetics (2009) 84(3):351-366.

Webster et al., "Mutation in the AChR ion channel gate underlies a fast channel congenital myasthenic syndrome." Neurology (2004) 62(7): 1090-1096.

Weinstein et al., "Genetic diseases associated with heterotrimeric G proteins" Trends Pharmacol Sci (2006) 27(5): 260-266.

Yen et al., "Sequence-specific cleavage of Huntingtin mRNA by catalytic DNA" Annals of Neurology (1999) 46(3):366-373.

Yu et al., "Structure, inhibitor, and regulatory mechanism of Lyp, a lymphoid-specific tyrosine phosphatase implicated in autoimmune diseases" PNAS (2007) 104(50): 19767-19772.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

European Search report for application EP 09741640.8 dated Dec. 11, 2012.

European Search Report for application EP 11186113.4 dated Nov. 30, 2011.

European Search report for application EP 11740542.3 dated Aug. 14, 2014.

European Search report for application EP 11740543 dated Sep. 18, 2013.

Extended European Search report for application EP 17206749.8 dated Feb. 13, 2018.

Extended European Search report for EP 19161655.6 dated Aug. 29, 2019.

Extended European Search report for EP 19164928.4 dated Sep. 17, 2019.

Extended European Search report for EP 19191293.0 dated Feb. 24, 2020.

International Search Report for application PCT/CA2009/000645 dated Aug. 25, 2009.

International Search Report for application PCT/US11/24103 dated Jul. 15, 2011.

International Search Report for application PCT/US11/24104 dated Jul. 20, 2011.

International Search Report for application PCT/US12/50015 dated Nov. 2, 2012.

International Search Report for application PCT/US12/50023 dated Oct. 16, 2012.

International Search Report for application PCT/US13/064666 dated Apr. 23, 2014.

International Search Report for application PCT/US14/14722 dated Aug. 25, 2014.

SELECTIVE ANTISENSE COMPOUNDS AND USES THEREOF

SEQUENCE LISTING

The present application is being filed along with a Sequence Listing in electronic format. The Sequence Listing is provided as a file entitled CORE0109USC2SEQ.txt, created Sep. 24, 2018, which is 392 Kb in size. The information in the electronic format of the sequence listing is incorporated herein by reference in its entirety.

BACKGROUND

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

SUMMARY

In certain embodiments, the present invention provides oligomeric compounds comprising oligonucleotides. In certain embodiments, such oligonucleotides comprise a region having a gapmer motif. In certain embodiments, such oligonucleotides consist of a region having a gapmer motif.

The present disclosure provides the following non-limiting numbered embodiments:

Embodiment 1: A compound comprising a modified oligonucleotide consisting of 12 to 30 linked nucleosides, wherein the linked nucleosides comprise at least 8 contiguous nucleobases of a nucleobase sequence recited in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165, 166, 167, 168, 169, 170, 171, 172, 173, or 174-573.

Embodiment 2: The compound of embodiment 1, wherein the modified oligonucleotide comprises at least 10 contiguous nucleobases of a nucleobase sequence recited in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165, 166, 167, 168, 169, 170, 171, 172, 173, or 174-573.

Embodiment 3: The compound of embodiment 1, wherein the modified oligonucleotide comprises at least 12 contiguous nucleobases of a nucleobase sequence recited in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165, 166, 167, 168, 169, 170, 171, 172, 173, or 174-573.

Embodiment 4: The compound of embodiment 1, wherein the modified oligonucleotide comprises at least 14 contiguous nucleobases of a nucleobase sequence recited in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165, 166, 167, 168, 169, 170, 171, 172, 173, or 174-573.

Embodiment 5: The compound of embodiment 1, wherein the modified oligonucleotide comprises at least 16 contiguous nucleobases of a nucleobase sequence recited in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165, 166, 167, 168, 169, 170, 171, 172, 173, or 174-573.

Embodiment 6: The compound of embodiment 1, wherein the modified oligonucleotide comprises a nucleobase sequence selected from among SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165, 166, 167, 168, 169, 170, 171, 172, 173, or 174-573.

Embodiment 7: The compound of embodiment 1, wherein the modified oligonucleotide consists of a nucleobase sequence selected from among SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163,1 64, 165, 166, 167, 168, 169, 170, 171, 172, 173, or 174-573.

Embodiment 8: The compound of any of embodiments 1 to 7, wherein the modified oligonucleotide consists of 14 to 26 linked nucleosides.

Embodiment 9: The compound of any of embodiments 1 to 7, wherein the modified oligonucleotide consists of 15 to 25 linked nucleosides.

Embodiment 10: The compound of any of embodiments 1 to 7, wherein the modified oligonucleotide consists of 16 to 25 linked nucleosides.

Embodiment 11: The compound of any of embodiments 1 to 7, wherein the modified oligonucleotide consists of 17 to 25 linked nucleosides.

Embodiment 12: The compound of any of embodiments 1 to 7, wherein the modified oligonucleotide consists of 15 to 22 linked nucleosides.

Embodiment 13: The compound of any of embodiments 1 to 7, wherein the modified oligonucleotide consists of 15 to 20 linked nucleosides.

Embodiment 14: The compound of any of embodiments 1 to 7, wherein the modified oligonucleotide consists of 16 to 20 linked nucleosides.

Embodiment 15: The compound of any of embodiments 1 to 7, wherein the modified oligonucleotide consists of 14 linked nucleosides.

Embodiment 16: The compound of any of embodiments 1 to 7, wherein the modified oligonucleotide consists of 15 linked nucleosides.

Embodiment 17: The compound of any of embodiments 1 to 7, wherein the modified oligonucleotide consists of 16 linked nucleosides.

Embodiment 18: The compound of any of embodiments 1 to 7, wherein the modified oligonucleotide consists of 17 linked nucleosides.

Embodiment 19: The compound of any of embodiments 1 to 7, wherein the modified oligonucleotide consists of 18 linked nucleosides.

Embodiment 20: The compound of any of embodiments 1 to 7, wherein the modified oligonucleotide consists of 19 linked nucleosides.

Embodiment 21: The compound of any of embodiments 1 to 7, wherein the modified oligonucleotide consists of 20 linked nucleosides.

Embodiment 22: The compound of any of embodiments 1 to 7, wherein the modified oligonucleotide consists of 21 linked nucleosides.

Embodiment 23: The compound of any of embodiments 1 to 7, wherein the modified oligonucleotide consists of 22 linked nucleosides.

Embodiment 24: The compound of any of embodiments 1 to 23, wherein the nucleobase sequence of the modified oligonucleotide is 90% complementary to SEQ ID NO. 1.

Embodiment 25: The compound of any of embodiments 1 to 23, wherein the nucleobase sequence of the modified oligonucleotide is 95% complementary to SEQ ID NO. 1.

Embodiment 26: The compound of any of embodiments 1 to 23, wherein the nucleobase sequence of the modified oligonucleotide is 100% complementary to SEQ ID NO. 1.

Embodiment 27: The compound of any of embodiments 1 to 26, wherein the oligonucleotide has an eeedk-d7-keee motif.

Embodiment 28: The compound of any of embodiments 1 to 26, wherein the oligonucleotide has an eeeedk-d7-eeee motif.

Embodiment 29: The compound of any of embodiments 1 to 26, wherein the oligonucleotide has an eeeedk-d7-keee motif.

Embodiment 30: The compound of any of embodiments 1 to 26, wherein the oligonucleotide has an eeeedk-d7-kkee motif Embodiment 31: The compound of any of embodiments 1 to 26, wherein the oligonucleotide has an eeeee-d9-eeeee motif.

Embodiment 32: The compound of any of embodiments 1 to 26, wherein the oligonucleotide has an eeeeedk-d7-eeeee motif.

Embodiment 33: The compound of any of embodiments 1 to 26, wherein the oligonucleotide has an eeeeeeek-d7-eee motif Embodiment 34: The compound of any of embodiments 1 to 26, wherein the oligonucleotide has an eeeeeeek-d7-eeee motif.

Embodiment 35: The compound of any of embodiments 1 to 26, wherein the oligonucleotide has an eeeeek-d7-eee motif.

Embodiment 36: The compound of any of embodiments 1 to 26, wherein the oligonucleotide has an eeeeek-d7-eeeeee motif.

Embodiment 37: The compound of any of embodiments 1 to 26, wherein the oligonucleotide has an eeeeek-d7-kee motif.

Embodiment 38: The compound of any of embodiments 1 to 26, wherein the oligonucleotide has an eeeeek-d7-kke motif Embodiment 39: The compound of any of embodiments 1 to 26, wherein the oligonucleotide has an eeeek-d7-eeee motif.

Embodiment 40: The compound of any of embodiments 1 to 26, wherein the oligonucleotide has an eeeek-d7-eeeeeee motif.

Embodiment 41: The compound of any of embodiments 1 to 26, wherein the oligonucleotide has an eeeek-d7-keee motif.

Embodiment 42: The compound of any of embodiments 1 to 26, wherein the oligonucleotide has an eeeek-d7-keeee motif.

Embodiment 43: The compound of any of embodiments 1 to 26, wherein the oligonucleotide has an eeeek-d7-kke motif Embodiment 44: The compound of any of embodiments 1 to 26, wherein the oligonucleotide has an eeeek-d7-kkee motif.

Embodiment 45: The compound of any of embodiments 1 to 26, wherein the oligonucleotide has an eeeekk-d3-k-d3-keke motif.

Embodiment 46: The compound of any of embodiments 1 to 26, wherein the oligonucleotide has an eeeekk-d7-kee motif.

Embodiment 47: The compound of any of embodiments 1 to 26, wherein the oligonucleotide has an eeeekk-d7-keke motif.

Embodiment 48: The compound of any of embodiments 1 to 26, wherein the oligonucleotide has an eeeekk-d7-kke motif Embodiment 49: The compound of any of embodiments 1 to 26, wherein the oligonucleotide has an eeeekk-d7-kkee motif.

Embodiment 50: The compound of any of embodiments 1 to 26, wherein the oligonucleotide has an eeek-d7-eeeeeeee motif Embodiment 51: The compound of any of embodiments 1 to 26, wherein the oligonucleotide has an eeek-d7-keeeee motif.

Embodiment 52: The compound of any of embodiments 1 to 26, wherein the oligonucleotide has an eeek-d7-kkee motif.

Embodiment 53: The compound of any of embodiments 1 to 26, wherein the oligonucleotide has an eeek-d7-kkeee motif.

Embodiment 54: The compound of any of embodiments 1 to 26, wherein the oligonucleotide has an eeek-d8-kee motif.

Embodiment 55: The compound of any of embodiments 1 to 26, wherein the oligonucleotide has an eeek-d9-keee motif Embodiment 56: The compound of any of embodiments 1 to 26, wherein the oligonucleotide has an eeek-d9-keke motif.

Embodiment 57: The compound of any of embodiments 1 to 26, wherein the oligonucleotide has an eeekk-d7-eeee motif.

Embodiment 58: The compound of any of embodiments 1 to 26, wherein the oligonucleotide has an eeekk-d7-keee motif.

Embodiment 59: The compound of any of embodiments 1 to 26, wherein the oligonucleotide has an eeekk-d7-kke motif.

Embodiment 60: The compound of any of embodiments 1 to 26, wherein the oligonucleotide has an eeekk-d7-kkee motif Embodiment 61: The compound of any of embodiments 1 to 26, wherein the oligonucleotide has an eeekk-d7-kkeee motif.

Embodiment 62: The compound of any of embodiments 1 to 26, wherein the oligonucleotide has an eek-d7-eeeeeeee motif.

Embodiment 63: The compound of any of embodiments 1 to 26, wherein the oligonucleotide has an eek-d7-keeeeee motif.

Embodiment 64: The compound of any of embodiments 1 to 26, wherein the oligonucleotide has an eek-d7-kkeee motif.

Embodiment 65: The compound of any of embodiments 1 to 26, wherein the oligonucleotide has an eek-d8-kkee motif Embodiment 66: The compound of any of embodiments 1 to 26, wherein the oligonucleotide has an eekk-d8-kee motif Embodiment 67: The compound of any of embodiments 1 to 26, wherein the oligonucleotide has an eekk-d8-kkee motif.

Embodiment 68: The compound of any of embodiments 1 to 26, wherein the oligonucleotide has an eekk-d8-kkeee motif Embodiment 69: The compound of any of embodiments 1 to 26, wherein the oligonucleotide has an ek-d7-eeeeeeeee motif.

Embodiment 70: The compound of any of embodiments 1 to 26, wherein the oligonucleotide has an ek-d8-kkeee motif.

Embodiment 71: The compound of any of embodiments 1 to 26, wherein the oligonucleotide has an ek-d9-kkke motif.

Embodiment 72: The compound of any of embodiments 1 to 26, wherein the oligonucleotide has an ekek-d6-k-dd-keke motif.

Embodiment 73: The compound of any of embodiments 1 to 26, wherein the oligonucleotide has an ekek-d8-kkeke motif Embodiment 74: The compound of any of embodiments 1 to 26, wherein the oligonucleotide has an ekek-d9-keee motif.

Embodiment 75: The compound of any of embodiments 1 to 26, wherein the oligonucleotide has an ekek-d9-keke motif.

Embodiment 76: The compound of any of embodiments 1 to 26, wherein the oligonucleotide has an ekekek-d7-keke motif.

Embodiment 77: The compound of any of embodiments 1 to 26, wherein the oligonucleotide has an ekekk-d8-keke motif.

Embodiment 78: The compound of any of embodiments 1 to 26, wherein the oligonucleotide has an ekk-d7-kkeee motif.

Embodiment 79: The compound of any of embodiments 1 to 26, wherein the oligonucleotide has an ekk-d7-kkeeeee motif.

Embodiment 80: The compound of any of embodiments 1 to 26, wherein the oligonucleotide has an ekk-d8-kkee motif.

Embodiment 81: The compound of any of embodiments 1 to 26, wherein the oligonucleotide has an ekk-d8-kkeee motif.

Embodiment 82: The compound of any of embodiments 1 to 26, wherein the oligonucleotide has an ekk-d8-kkeeee motif.

Embodiment 83: The compound of any of embodiments 1 to 26, wherein the oligonucleotide has an ekk-d8-kkke motif.

Embodiment 84: The compound of any of embodiments 1 to 26, wherein the oligonucleotide has an ekk-d9-kke motif.

Embodiment 85: The compound of any of embodiments 1 to 26, wherein the oligonucleotide has an ekkdk-d7-kke motif.

Embodiment 86: The compound of any of embodiments 1 to 26, wherein the oligonucleotide has an ekkk-d8-kke motif.

Embodiment 87: The compound of any of embodiments 1 to 26, wherein the oligonucleotide has an ekkk-d9-ke motif.

Embodiment 88: The compound of any of embodiments 1 to 26, wherein the oligonucleotide has an ekkkk-d7-kke motif.

Embodiment 89: The compound of any of embodiments 1 to 26, wherein the oligonucleotide has an ekkkk-d7-kkke motif.

Embodiment 90: The compound of any of embodiments 1 to 26, wherein the oligonucleotide has a kkekk-d9-kkekk motif.

Embodiment 91: The compound of any of embodiments 1 to 26, wherein the oligonucleotide has a kkkkk-d7-kkkkk motif Embodiment 92: The compound of any of embodiments 1 to 26, wherein the oligonucleotide has a ekkdk-d7-kke motif.

Embodiment 93: The compound of any of embodiments 1 to 26, wherein the oligonucleotide has a ekek-d8-kekee motif.

Embodiment 94: The compound of any of embodiments 1 to 26, wherein the oligonucleotide has a ekk-f-d8-kke motif.

Embodiment 95: The compound of any of embodiments 1 to 26, wherein the oligonucleotide has a ekk-z-d8-kke motif.

Embodiment 96: The compound of any of embodiments 1 to 26, wherein the oligonucleotide has a ekk-h-d8-kke motif Embodiment 97: The compound of any of embodiments 1 to 26, wherein the oligonucleotide has a ekk-d2-h-d6-kke motif.

Embodiment 98: The compound of any of embodiments 1 to 26, wherein the oligonucleotide has a ekk-d-h-d7-kke motif.

Embodiment 99: The compound of any of embodiments 1 to 26, wherein the oligonucleotide has a ekk-d3-f-d5-kke motif.

Embodiment 100: The compound of any of embodiments 1 to 26, wherein the oligonucleotide has a ekk-d3-z-d5-kke motif.

Embodiment 101: The compound of any of embodiments 1 to 26, wherein the oligonucleotide has a ekk-d3-h-d5-kke motif.

Embodiment 102: The compound of any of embodiments 1 to 26, wherein the oligonucleotide has a ekk-d4-h-d4-kke motif.

Embodiment 103: The compound of any of embodiments 1 to 26, wherein the oligonucleotide has a ekk-d5-f-d3-kke motif.

Embodiment 104: The compound of any of embodiments 1 to 26, wherein the oligonucleotide has a ekk-d5-z-d3-kke motif Embodiment 105: The compound of any of embodiments 1 to 26, wherein the oligonucleotide has a ekk-d5-h-d3-kke motif.

Embodiment 106: The compound of any of embodiments 1 to 26, wherein the oligonucleotide has a ekk-d6-f-d2-kke motif.

Embodiment 107: The compound of any of embodiments 1 to 26, wherein the oligonucleotide has a ekk-d6-z-d2-kke motif.

Embodiment 108: The compound of any of embodiments 1 to 26, wherein the oligonucleotide has a ekk-d6-h-d2-kke motif.

Embodiment 109: The compound of any of embodiments 1 to 26, wherein the oligonucleotide has a ekk-d7-f-d-kke motif Embodiment 110: The compound of any of embodiments 1 to 26, wherein the oligonucleotide has a ekk-d7-z-d-kke motif.

Embodiment 111: The compound of any of embodiments 1 to 26, wherein the oligonucleotide has a ekk-d7-h-d-kke motif.

Embodiment 112: The compound of any of embodiments 1 to 26, wherein the oligonucleotide has a ekk-d8-f-dkke motif.

Embodiment 113: The compound of any of embodiments 1 to 26, wherein the oligonucleotide has a ekk-d8-z-kke motif.

Embodiment 114: The compound of any of embodiments 1 to 26, wherein the oligonucleotide has a ekk-d8-h-kke motif Embodiment 115: The compound of any of embodiments 1 to 26, wherein the oligonucleotide has a ekk-d9-kke motif.

Embodiment 116: The oligomeric compound of any of embodiments 1 to 115 comprising at least one modified internucleoside linkage.

Embodiment 117: The oligomeric compound of embodiment 116, wherein each internucleoside linkage is a modified internucleoside linkage.

Embodiment 118: The oligomeric compound of embodiment 115 or 116 comprising at least one phosphorothioate internucleoside linkage.

Embodiment 119: The oligomeric compound of embodiment 117 wherein each internucleoside linkage is a phosphorothioate internucleoside linkage.

Embodiment 120: The oligomeric compound of any of embodiments 1 to 119 comprising at least one methylphosphonate internucleoside linkage.

Embodiment 121: The oligomeric compound of any of embodiments 1 to 119 comprising one methylphosphonate internucleoside linkage.

Embodiment 122: The oligomeric compound of any of embodiments 1 to 120 comprising two methylphosphonate internucleoside linkages.

Embodiment 123: The oligomeric compound of any of embodiments 1 to 120 comprising at least one modified nucleobase.

Embodiment 124: The oligomeric compound of embodiment 123, comprising at least one 2-thio-thymidine.

Embodiment 125: The oligomeric compound of embodiment 1, having an eeeekk-d7-kke motif and consisting of the nucleobase sequence of SEQ ID NO.: 24.

Embodiment 126: The oligomeric compound of any of embodiments 1 to 119 comprising at least one 5'-Me-DNA modification.

Embodiment 127: The oligomeric compound of any of embodiments 1 to 119 comprising one 5'-Me-DNA modification.

Embodiment 128: The oligomeric compound of embodiment 126 or 127, wherein the 5'-Me-DNA modification is an S-5'-Me-DNA.

Embodiment 129: The oligomeric compound of embodiment 126 or 127, wherein the 5'-Me-DNA modification is an R-5'-Me-DNA.

Embodiment 130: The oligomeric compound of any of embodiments 126 to 129, wherein the 5'-Me-DNA modification is at position 6 from the 5'-end.

Embodiment 131: The oligomeric compound of any of embodiments 126 to 129, wherein the 5'-Me-DNA modification is at position 7 from the 5'-end.

Embodiment 132: The oligomeric compound of any of embodiments 126 to 129, consisting of the nucleobase sequence of SEQ ID NO.: 3.

Embodiment 133: The oligomeric compound of any of embodiments 1 to 132, having an $EC_{50}$ for reduction of expression of target that is at least least two-fold lower than its $EC_{50}$ for reduction of expression of the non-target, when measured in cells.

Embodiment 134: The oligomeric compound of any of embodiments 1 to 132, having an $ED_{50}$ for reduction of expression of target that is at least least two-fold lower than its $ED_{50}$ for reduction of expression of the non-target, when measured in an animal.

Embodiment 135: A compound consisting of ISIS 572772.

Embodiment 136: A pharmaceutical composition comprising an oligomeric compound of any of embodiments 1-135 and a pharmaceutically acceptable carrier or diluent.

Embodiment 137: A method comprising contacting a cell with an oligomeric compound of any of embodiments 1-136.

Embodiment 138: The method of embodiment 137, wherein the cell is in vitro.

Embodiment 139: The method of embodiment 137, wherein the cell is in an animal.

Embodiment 140: The method of embodiment 137, wherein the animal is a human.

Embodiment 141: The method of embodiment 137, wherein the animal is a mouse.

Embodiment 142: A method of administering a pharmaceutical composition of embodiment 136 to an animal.

Embodiment 143: The method of embodiment 142, wherein the animal is a human.

Embodiment 144: The method of embodiment 143, wherein the animal is a mouse.

Embodiment 145: Use of an oligomeric compound of any of embodiments 1-136 for the preparation of a medicament for the treatment or amelioration of Huntington's disease.

Embodiment 146: A method of ameliorating a symptom of Huntington's disease, comprising administering an oligomeric compound of any of embodiments 1-136 to an animal in need thereof.

Embodiment 147: The method of embodiment 146, wherein the animal is a human.

Embodiment 148: The method of embodiment 147, wherein the animal is a mouse.

Embodiment 149: A method for reducing the rate of progression of a symptom associated with Huntington's Disease, comprising administering to a human in need thereof a compound of any of embodiments 1-136, and thereby reducing the rate of progression a symptom of Huntington's disease in the human.

Embodiment 150: A method for reversing degeneration indicated by a symptom associated with Huntington's disease, comprising administering to a human in need thereof a compound of any of embodiments 1-136, and thereby reversing degeneration indicated by a symptom of Huntington's disease in the human.

Embodiment 151: A method for treating a human with Huntington's disease comprising identifying the human with the disease and administering to the human a therapeutically effective amount of the compound of any of embodiments 1-136.

Embodiment 152: The method of embodiment 149, wherein the treatment reduces at least one of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy in the human.

Embodiment 153: A method for reducing the rate of progression of a symptom associated with Huntington's Disease, comprising administering to a human in need thereof ISIS 572772, and thereby reducing the rate of progression a symptom of Huntington's disease in the human.

Embodiment 154: A method for reversing degeneration indicated by a symptom associated with Huntington's disease, comprising administering to a human in need thereof ISIS 572772, and thereby reversing degeneration indicated by a symptom of Huntington's disease in the human.

Embodiment 155: A method for treating a human with Huntington's disease comprising identifying the human with the disease and administering to the human a therapeutically effective amount of ISIS 572772.

Embodiment 156: The method of embodiment 153, wherein the treatment reduces at least one of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy in the human.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means -OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase. As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limitied to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize.

As used herein, "non-target nucleic acid" means a nucleic acid molecule to which hybridization of an antisense compound is not intended or desired. In certain embodiments, antisense compounds do hybridize to a non-target, due to homology between the target (intended) and non-target (un-intended).

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "differentiating nucleobase" means a nucleobase that differs between two nucleic acids. In certain instances, a target region of a target nucleic acid differs by 1-4 nucleobases from a non-target nucleic acid. Each of those differences is refered to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino(=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "huntingtin transcript" means a transcript transcribed from a huntingtin gene.

As used herein, "Intracerebroventricular" or "ICV" means administration into the ventricular system of the brain.

B. Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonuleotides comprising at least one modified nucleoside. Such modified nucleosides comprise a modified sugar moeity, a modified nucleobase, or both a modifed sugar moiety and a modified nucleobase.

i. Certain Modified Sugar Moieties

In certain embodiments, oligomeric compounds of the invention comprise one or more modifed nucleosides comprising a modifed sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substitued sugar moieties. In certain embodiments, modified sugar moieties are bicyclic or tricyclic sugar moieties. In certain embodiments, modified sugar moieties are sugar surrogates. Such sugar surogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, $OCF_3$, $O(CH_2)_2SCH_3$, $O(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N(Rm)(Rn) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—N($R_m$)($R_n$), $O(CH_2)_2O(CH_2)_2N(CH_3)_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)_2$ $SCH_3$, O—$(CH_2)_2$—O—N$(CH_3)_2$, —$O(CH_2)_2O(CH_2)_2N(CH_3)_2$, and O—$CH_2$—C(=O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modifed sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_a R_b$)—N(R)—O— or, —C($R_a R_b$)—O—N(R)—; 4'- $CH_2$-2', 4'-$(CH_2)_2$-2', 4'-$(CH_2)$—O-2' (LNA); 4'-$(CH_2)$—S-2'; 4'-$(CH_2)_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issues on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$-0-N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.*,2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$, is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-$CH_2$—O-2') BNA, (B) β-D-Methyleneoxy (4'-$CH_2$—O-2') BNA (also referred to as locked nucleic acid or LNA), (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA (also referred to as constrained ethyl or cEt), (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-$(CH_2)_3$-2') BNA, and (M) 4'-$CH_2$—O—$CH_2$-2' as depicted below.

(A)

(B)

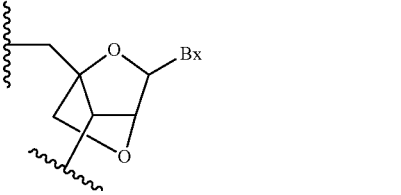

(C) 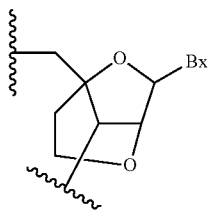

(D) 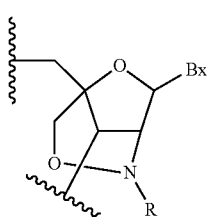

(E) 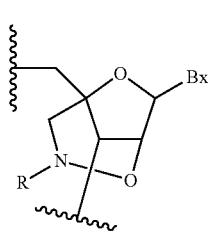

(F) 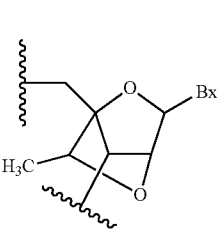

(G) 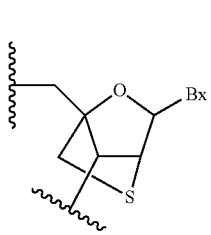

(H) 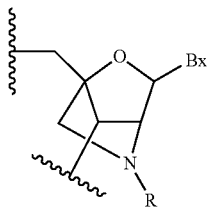

(I) 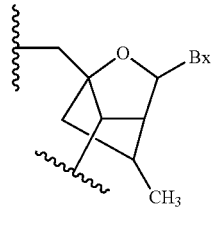

(M) 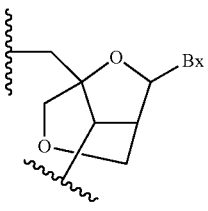

(J) 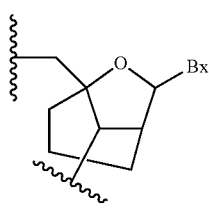

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occuring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, CJ. *Bioorg. & Med. Chem.* (2002) 10:841-854), fluoro HNA (F-HNA), and those compounds having Formula VII:

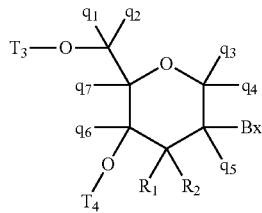

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

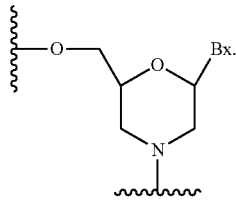

In certain embodiments, morpholinos may be modified, for example by adding or altering various substituent groups from the above morpholino structure. Such sugar surrogates are refered to herein as "modifed morpholinos."

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desireable characteristics. In certain embodmiments, oligonucleotides comprise one or more RNA-like nucleosides. In certain embodiments, oligonucleotides comprise one or more DNA-like nucleotides.

ii. Certain Modified Nucleobases

In certain embodiments, nucleosides of the present invention comprise one or more unmodified nucleobases. In certain embodiments, nucleosides of the present invention comprise one or more modifed nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C-$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

a. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

iii. 3'-Endo Modifications

In one aspect of the present disclosure, oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the C. elegans system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

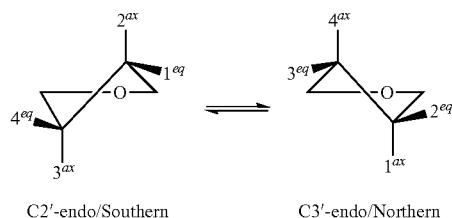

C2'-endo/Southern     C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as exemplified in Example 35, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

b. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

iv. Certain sugar motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

v. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2'deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

vi. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

vii. Certain 5'-wings

In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer has a nucleoside motif selected from among the following: ADDA; ABDAA; ABBA; ABB; ABAA; AABAA; AAABAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type, each C is a modified nucleoside of a third type, and each D is an unmodified deoxynucleoside.

In certain embodiments, the 5'-wing of a gapmer has a nucleoside motif selected from among the following: AB, ABB, AAA, BBB, BBBAA, AAB, BAA, BBAA, AABB, AAAB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, AAAAA, BBBBAA, and AAABW; wherein each A is a modified nucleoside of a first type, each B is a modified nucleoside of a second type, and each W is a modified nucleoside of either the first type, the second type or a third type.

In certain embodiments, the 5'-wing of a gapmer has a nucleoside motif selected from among the following: ABB; ABAA; AABAA; AAABAA; ABAB; ABADB; AAABB; AAAAA; AA; AAA; AAAA; AAAAB; ABBB; AB; and ABAB; wherein each A is a modified nucleoside of a first type, each B is a modified nucleoside of a second type, and each W is a modified nucleoside of either the first type, the second type or a third type.

In certain embodiments, an oligonucleotide comprises any 5'-wing motif provided herein. In certain such embodiments, the oligonucleotide is a 5'-hemimer (does not comprise a 3'-wing). In certain embodiments, such an oligonucleotide is a gapmer. In certain such embodiments, the 3'-wing of the gapmer may comprise any nucleoside motif.

In certain embodiments, the 5'-wing of a gapmer has a sugar motif selected from among those listed in the following non-limiting tables:

TABLE 1

Certain 5'-Wing Sugar Motifs
Certain 5'-Wing Sugar Motifs

| | | | | |
|---|---|---|---|---|
| AAAAA | ABCBB | BABCC | BCBBA | CBACC |
| ABBBB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAACB | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 2

Certain 5'-Wing Sugar Motifs
Certain 5'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |

TABLE 2-continued

Certain 5'-Wing Sugar Motifs
Certain 5'-Wing Sugar Motifs

| | | | | |
|---|---|---|---|---|
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |
| BABBB | ACBC | CAAB | BBC | |
| BBAAA | ACCA | CAAC | BCA | |
| BBAAB | ACCB | CABA | BCB | |
| BBABA | ACCC | CABB | BCC | |
| BBABB | BAAA | CABC | CAA | |
| BBBAA | BAAB | CACA | CAB | |
| BBBAB | BAAC | CACB | CAC | |
| BBBBA | BABA | CACC | CBA | |
| BBBBB | BABB | CBAA | CBB | |
| AAAA | AACC | CCCC | CBC | |
| AAAB | ABAA | AAAA | CCA | |
| AAAC | ABAB | AAAB | CCB | |
| AABA | ABAC | AABA | CCC | |
| AABB | ABBA | AABB | AAA | |
| AABC | ABBB | ABAA | AAB | |
| AACA | ABBC | ABAB | ABA | |
| AACB | ABCA | ABBA | ABB | |

In certain embodiments, each A, each B, and each C located at the 3'-most 5'-wing nucleoside is a modified nucleoside. For example, in certain embodiments the 5'-wing motif is selected from among A<u>B</u>B, B<u>B</u>B, and C<u>B</u>B, wherein the underlined nucleoside represents the 3'-most 5'-wing nucleoside and wherein the underlined nucleoside is a modified nucleoside. In certain embodiments, the the 3'-most 5'-wing nucleoside comprises a bicyclic sugar moiety selected from among cEt, cMOE, LNA, α-L-LNA, ENA and 2'-thio LNA. In certain embodiments, the the 3'-most 5'-wing nucleoside comprises a bicyclic sugar moiety selected from among cEt and LNA. In certain embodiments, the the 3'-most 5'-wing nucleoside comprises cEt. In certain embodiments, the the 3'-most 5'-wing nucleoside comprises LNA.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises a F-HNA. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$-$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises a F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, OCH$_3$ and O(CH$_2$)$_2$—OCH$_3$ and each B comprises a bicyclic sugar moiety selected from among cEt, cMOE, LNA, α-L-LNA, ENA and 2'-thio LNA. In certain embodiments, each A comprises O(CH$_2$)$_2$—OCH$_3$ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me DNA, and 5'-(R)-Me DNA. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

viii. Certain 3'-Wings

In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 inked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside.

In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

In certain embodiments, the 3'-wing of a gapmer has a nucleoside motif selected from among the following: ABB, ABAA, AAABAA, AAAABAA, AABAA, AAAABAA, AAABAA, ABAB, AAAAA, AAABB, AAAAAAAA, AAAAAAA, AAAAAA, AAAAB, AAAA, AAA, AA, AB, ABBB, ABAB, AABBB; wherein each A is a modified nucleoside of a first type, each B is a modified nucleoside of a second type. In certain embodiments, an oligonucleotide comprises any 3'-wing motif provided herein. In certain such embodiments, the oligonucleotide is a 3'-hemimer (does not comprise a 5'-wing). In certain embodiments, such an oligonucleotide is a gapmer. In certain such embodiments, the 5'-wing of the gapmer may comprise any nucleoside motif.

In certain embodiments, the 3'-wing of a gapmer has a nucleoside motif selected from among the following: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB, wherein each A is a modified nucleoside of a first type, each B is a modified nucleoside of a second type, and each W is a modified nucleoside of either the first type, the second type or a third type.

In certain embodiments, the 3'-wing of a gapmer has a nucleoside motif selected from among the following: ABB; AAABAA; AABAA; AAAABAA; AAAAA; AAABB; AAAAAAAA; AAAAAAA; AAAAAA; AAAAB; AB; ABBB; and ABAB, wherein each A is a modified nucleoside of a first type, each B is a modified nucleoside of a second type, and each W is a modified nucleoside of either the first type, the second type or a third type.

In certain embodiments, the 3'-wing of a gapmer has a sugar motif selected from among those listed in the following non-limiting tables:

TABLE 3

Certain 3'-Wing Sugar Motifs
Certain 3'-Wing Sugar Motifs

| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 4

Certain 3'-Wing Sugar Motifs
Certain 3'-Wing Sugar Motifs

| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |

TABLE 4-continued

Certain 3'-Wing Sugar Motifs
Certain 3'-Wing Sugar Motifs

| | | | | |
|---|---|---|---|---|
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |
| BABBB | ACBC | CAAB | BBC | |
| BBAAA | ACCA | CAAC | BCA | |
| BBAAB | ACCB | CABA | BCB | |
| BBABA | ACCC | CABB | BCC | |
| BBABB | BAAA | CABC | CAA | |
| BBBAA | BAAB | CACA | CAB | |
| BBBAB | BAAC | CACB | CAC | |
| BBBBA | BABA | CACC | CBA | |
| BBBBB | BABB | CBAA | CBB | |
| AAAA | AACC | CCCC | CBC | |
| AAAB | ABAA | AAAA | CCA | |
| AAAC | ABAB | AAAB | CCB | |
| AABA | ABAC | AABA | CCC | |
| AABB | ABBA | AABB | AAA | |
| AABC | ABBB | ABAA | AAB | |
| AACA | ABBC | ABAB | ABA | |
| AACB | ABCA | ABBA | ABB | |

In certain embodiments, each A, each B, and each C located at the 5'-most 3'-wing region nucleoside is a modified nucleoside. For example, in certain embodiments the 3'-wing motif is selected from among ABB, BBB, and CBB, wherein the underlined nucleoside represents the the 5'-most 3'-wing region nucleoside and wherein the underlined nucleoside is a modified nucleoside.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises an F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, $OCH_3$ and $O(CH_2)_2$—$OCH_3$ and each B comprises a bicyclic sugar moiety selected from among cEt, cMOE, LNA, α-L-LNA, ENA and 2'-thio LNA. In certain embodiments, each A comprises $O(CH_2)_2$—$OCH_3$ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, $OCH_3$ and $O(CH_2)_2$—$OCH_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

ix. Certain Central Regions (Gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleotides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

In certain embodiments, the gap comprises a nucleoside motif selected from among the following: DDDDXDDDDD; DDDDDXDDDD; DDDXDDDDD; DDDDXDDDDD; DDDDDXDDD; DDXDDDDDD; DDDXDDDDD; DXDDDDDD; DDXDDDDDD; DDXDDDDD; DDXDDDXDDD; DDDXDDDXDDD; DXDDDXDDD; DDXDDDXDD; DXDDDDXDDD; DDXDDDDXDD; DXDDDDXDDD; DDDDXDDD; DDDXDDD; DXDDDDDD; DDDDXXDDD; and DXXDXXDXX; wherein each D is an unmodified deoxynucleoside; and each X is a modified nucleoside or a substituted sugar moiety.

In certain embodiments, the gap comprises a nucleoside motif selected from among the following: DDDDDDDDD; DXDDDDDDD; DDXDDDDDD; DDDXDDDDD; DDDDXDDDD; DDDDDXDDD; DDDDDDXDD; DDDDDDDXD; DXXDDDDDD; DDDDDDXXD; DDXXDDDDD; DDDXXDDDD; DDDDXXDDD; DDDDDXXDD; DXDDDDXDD; DXDDDDXDD; DXDXDDDDD; DXDDDDXDD; DXDXDDDDD; DDXDDDXDD; DXDXDDDDD; DDXDDDDXD; DDXDXDDDD; DDXDDDXDD; DDXDDXDDD; DDXDXDDDD; DDDXDDDXD; DDXDXDDDD; DDXDXDDDD; DDDXDDDXD; DDDXDXDDD; DDDXDDXDD; DDDXDDXXD; DDDXXDDXD; DDDDXDDXD; DDDXDXXDD; DDDXXDDDD; DDDDXDDXD; DDDDXXDXD; DDDDXDDXD; DDDDXDXDD; and DDDDXDDXD; DDDDXDDXD; DDDDXXDXD; DDDDXDXDD; and DDDDDXDXD, wherein each D is an unmodified deoxynucleoside; and each X is a modified nucleoside or a substituted sugar moiety.

In certain embodiments, the gap comprises a nucleoside motif selected from among the following: DDDDXDDDD, DXDDDDDDD, DXXDDDDDD, DDXDDDDDD, DDDXDDDDD, DDDDXDDDD, DDDDDXDDD, DDDDDDXDD, DDDDDDDXD, and DDDDDDDXD, wherein each D is an unmodified deoxynucleoside; and each X is a modified nucleoside or a substituted sugar moiety.

In certain embodiments, the gap comprises a nucleoside motif selected from among the following: DDDDDDDD, DXDDDDDD, DDXDDDDD, DDDXDDDD, DDDDXDDD, DDDDDXDD, DDDDDDXD, DXDDDDXD, DXDDDXDD, DXDDXDDD, DXDXDDDD, DXXDDDDD, DDXXDDDD, DDXDXDDD, DDXDDXDD, DXDDDDXD, DDDXXDDD, DDDXDXDD, DDDXDDXD, DDDDXXDD, DDDDXDXD, and DDDDDXXD, wherein each D is an unmodified deoxynucleoside; and each X is a modified nucleoside or a substituted sugar moiety.

In certain embodiments, the gap comprises a nucleoside motif selected from among the following: DXDDDDD, DDXDDDD, DDDXDDD, DDDDXDD, DDDDDXD, DXDDDXD, DXDDXDD, DXDXDDD, DXXDDDD, DDXXDDD, DDXDXDD, DDXDDXD, DDDXXDD, DDDXDXD, and DDDDXXD, wherein each D is an unmodified deoxynucleoside; and each X is a modified nucleoside or a substituted sugar moiety.

In certain embodiments, the gap comprises a nucleoside motif selected from among the following: DXDDDD, DDXDDD, DDDXDD, DDDDXD, DDDDDX, DXDDDDD, DXDDDDX, DDXDDDD, DDXDDDDD, DDDXDDD, DDDXDDX, DDDDXDD, DDDDDXD, DXDDDDDD, DDXDDDDD, DDDXDDDD, DDDDXDDD, DDDDDXDD, DDDDDDXD, DXDDDDDD; DDXDDDDDD, DDDXDDDDD, DDDDXDDDD, DDDDDXDDD, DDDDDDXDD, DDDDDDDXD, DXDDDDDDD, DDXDDDDDD, DDDXDDDDD, DDDDXDDDD, DDDDDXDDD, DDDDDDXDD, DDDDDDDXD, and DDDDDDDDX, wherein each D is an unmodified deoxynucleoside; and each X is a modified nucleoside or a substituted sugar moiety.

In certain embodiments, each X comprises an unmodified 2'-deoxyfuranose sugar moiety. In certain embodiments, each X comprises a modified sugar moiety. In certain embodiments, each X comprises a 2'-substituted sugar moiety. In certain embodiments, each X comprises a 2'-substituted sugar moiety selected from among F, (ara)-F, OCH$_3$ and O(CH$_2$)$_2$—OCH$_3$. In certain embodiments, each X comprises a 5'-substituted sugar moiety. In certain embodiments, each X comprises a 5'-substituted sugar moiety selected from among 5'-Me, and 5'-(R)-Me. In certain embodiments, each X comprises a bicyclic sugar moiety. In certain embodiments, each X comprises a bicyclic sugar moiety selected from among cEt, cMOE, LNA, α-L-LNA, ENA and 2'-thio LNA. In certain embodiments, each X comprises a modified nucleobase. In certain embodiments, each X comprises a modified nucleobase selected from among 2-thio-thymidine and 5-propyne uridine. In certain embodiments, each X comprises a 2-thio-thymidine nucleoside. In certain embodiments, each X comprises an HNA. In certain embodiments, each C comprises an F-HNA. In certain embodiments, X represents the location of a single differentiating nucleobase.

x. Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among any of those listed in the tables above and any 5'-wing may be paired with any gap and any 3'-wing. For example, in certain embodiments, a 5'-wing may comprise AAABB, a 3'-wing may comprise BBA, and the gap may comprise DDDDDDD. For example, in certain embodiments, a gapmer has a 5'-wing, a gap, and a 3'-wing having features selected from among those listed in the following non-limiting table, wherein each motif is represented as (5'-wing)-(gap)-(3'-wing), wherein each number represents the number of linked nucleosides in each portion of the motif, for example, a 5-10-5 motif would have a 5'-wing comprising 5 nucleosides, a gap comprising 10 nucleosides, and a 3'-wing comprising 5 nucleosides:

TABLE 5

Certain Gapmer Sugar Motifs
Certain Gapmer Sugar Motifs

| | | | |
|---|---|---|---|
| 2-10-2 | 3-10-2 | 4-10-2 | 5-10-2 |
| 2-10-3 | 3-10-3 | 4-10-3 | 5-10-3 |
| 2-10-4 | 3-10-4 | 4-10-4 | 5-10-4 |
| 2-10-5 | 3-10-5 | 4-10-5 | 5-10-5 |
| 2-9-2 | 3-9-2 | 4-9-2 | 5-9-2 |
| 2-9-3 | 3-9-3 | 4-9-3 | 5-9-3 |
| 2-9-4 | 3-9-4 | 4-9-4 | 5-9-4 |
| 2-9-5 | 3-9-5 | 4-9-5 | 5-9-5 |
| 2-11-2 | 3-11-2 | 4-11-2 | 5-11-2 |
| 2-11-3 | 3-11-3 | 4-11-3 | 5-11-3 |
| 2-11-4 | 3-11-4 | 4-11-4 | 5-11-4 |
| 2-11-5 | 3-11-5 | 4-11-5 | 5-11-5 |
| 2-8-2 | 3-8-2 | 4-8-2 | 5-8-2 |
| 2-8-3 | 3-8-3 | 4-8-3 | 5-8-3 |
| 2-8-4 | 3-8-4 | 4-8-4 | 5-8-4 |
| 2-8-5 | 3-8-5 | 4-8-5 | 5-8-5 |

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting tables:

TABLE 6

Certain Gapmer Nucleoside Motifs

| 5'-wing region | Central gap region | 3'-wing region |
|---|---|---|
| ADDA | DDDDDD | ABB |
| ABBA | DDDADDD | ABAA |
| AAAAAAA | DDDDDDDDD | AAA |
| AAAAABB | DDDDDDDD | BBAAAAA |
| ABB | DDDDADDD | ABB |
| ABB | DDDDBDDD | BBA |
| ABB | DDDDDDDD | BBA |
| AABAA | DDDDDDDD | AABAA |
| ABB | DDDDDD | AABAA |
| AAABAA | DDDDDDDD | AAABAA |
| AAABAA | DDDDDDDD | AAB |
| ABAB | DDDDDDDD | ABAB |
| AAABB | DDDDDDD | BBA |
| ABADB | DDDDDDD | BBA |

TABLE 6-continued

Certain Gapmer Nucleoside Motifs

| 5'-wing region | Central gap region | 3'-wing region |
|---|---|---|
| ABA | DBDDDDDDD | BBA |
| ABA | DADDDDDDD | BBA |
| ABAB | DDDDDDDD | BBA |
| AA | DDDDDDDD | BBBBBBBB |
| ABB | DDDDDD | ABADB |
| AAAAB | DDDDDDD | BAAAA |
| ABBB | DDDDDDDD | AB |
| AB | DDDDDDDD | BBBA |
| ABBB | DDDDDDDD | BBBA |
| AB | DDDDDDDD | ABA |
| ABB | DDDDWDDDD | BBA |
| AAABB | DDDWDDD | BBAAA |
| ABB | DDDDWWDDD | BBA |
| ABADB | DDDDDDD | BBA |
| ABBDC | DDDDDDD | BBA |
| ABBDDC | DDDDDD | BBA |
| ABBDCC | DDDDDD | BBA |
| ABB | DWWDWWDWW | BBA |
| ABB | DWDDDDDDD | BBA |
| ABB | DDWDDDDDD | BBA |
| ABB | DWWDDDDDD | BBA |
| AAABB | DDWDDDDDD | AA |
| BB | DDWDWDDDD | BBABBBB |
| ABB | DDDD($^N$D)DDDD | BBA |
| AAABB | DDD($^N$D)DDD | BBAAA |
| ABB | DDDD($^N$D)($^N$D)DDD | BBA |
| ABB | D($^N$D)($^N$D)D($^N$D)($^N$D)D($^N$D)($^N$D) | BBA |
| ABB | D($^N$D)DDDDDDD | BBA |
| ABB | DD($^N$D)DDDDDD | BBA |
| ABB | D($^N$D)($^N$D)DDDDDD | BBA |
| AAABB | DD($^N$D)DDDDDD | AA |
| BB | DD($^N$D)D($^N$D)DDDD | BBABBBB |
| ABAB | DDDDDDDD | BABA |

TABLE 7

Certain Gapmer Nucleoside Motifs

| 5'-wing region | Central gap region | 3'-wing region |
|---|---|---|
| ABBW | DDDDDDDD | BBA |
| ABB | DWDDDDDDD | BBA |
| ABB | DDWDDDDDD | BBA |
| ABB | DDDWDDDDD | BBA |
| ABB | DDDDWDDDD | BBA |
| ABB | DDDDDWDDD | BBA |
| ABB | DDDDDDWDD | BBA |
| ABB | DDDDDDDWD | BBA |
| ABB | DDDDDDDD | WBBA |
| ABBWW | DDDDDDD | BBA |
| ABB | DWWDDDDDD | BBA |
| ABB | DDWWDDDDD | BBA |
| ABB | DDDWWDDDD | BBA |
| ABB | DDDDWWDDD | BBA |
| ABB | DDDDDWWD | BBA |
| ABB | DDDDDDD | WWBBA |
| ABBW | DDDDDDD | WBBA |
| ABBW | DDDDDWD | BBA |
| ABBW | DDDDDWDD | BBA |
| ABBW | DDDDWDDD | BBA |
| ABBW | DDDWDDDD | BBA |
| ABBW | DDWDDDDD | BBA |
| ABBW | DWDDDDDD | BBA |
| ABB | DWDDDDDD | WBBA |
| ABB | DWDDDDWD | BBA |
| ABB | DWDDDWDD | BBA |
| ABB | DWDDWDDD | BBA |
| ABB | DWDWDDDD | BBA |
| ABB | DDWDDDDD | WBBA |
| ABB | DDWDDDWD | BBA |
| ABB | DDWDDDWDD | BBA |

TABLE 7-continued

Certain Gapmer Nucleoside Motifs

| 5'-wing region | Central gap region | 3'-wing region |
|---|---|---|
| ABB | DDWDDWDDD | BBA |
| ABB | DDWDDDDD | BBA |
| ABB | DDWWDDDDD | BBA |
| ABB | DDDWDDDD | WBBA |
| ABB | DDDWDDDWD | BBA |
| ABB | DDDWDDWDD | BBA |
| ABB | DDDWDWDDD | BBA |
| ABB | DDDWWDDDD | BBA |
| ABB | DDDDWDDD | WBBA |
| ABB | DDDDWDDWD | BBA |
| ABB | DDDDWDWDD | BBA |
| ABB | DDDDWWDDD | BBA |
| ABB | DDDDDWDD | WBBA |
| ABB | DDDDDWDWD | BBA |
| ABB | DDDDDWWDD | BBA |
| ABB | DDDDDDWD | WBBA |

TABLE 8

Certain Gapmer Nucleoside Motifs

| 5'-wing region | Central gap region | 3'-wing region |
|---|---|---|
| ABBB | DDDDDDDD | BBA |
| ABB | DBDDDDDD | BBA |
| ABB | DDBDDDDD | BBA |
| ABB | DDDBDDDD | BBA |
| ABB | DDDDBDDD | BBA |
| ABB | DDDDDBDD | BBA |
| ABB | DDDDDDBD | BBA |
| ABB | DDDDDDDD | BBBA |
| ABBBB | DDDDDDD | BBA |
| ABB | DBBDDDDD | BBA |
| ABB | DDBBDDDD | BBA |
| ABB | DDDBBDDD | BBA |
| ABB | DDDDBBDD | BBA |
| ABB | DDDDDBBD | BBA |
| ABB | DDDDDDD | BBBBA |
| ABBB | DDDDDDD | BBBA |
| ABB | DDDDDBD | BBA |
| ABBB | DDDDDBDD | BBA |
| ABBB | DDDBDDDD | BBA |
| ABBB | DDDBDDDD | BBA |
| ABBB | DDBDDDDD | BBA |
| ABBB | DBDDDDDD | BBA |
| ABB | DBDDDDDD | BBBA |
| ABB | DBDDDDBD | BBA |
| ABB | DBDDDDBDD | BBA |
| ABB | DBDDDBDDD | BBA |
| ABB | DBDDBDDDD | BBA |
| ABB | DBDBDDDDD | BBA |
| ABB | DBBDDDDD | BBA |
| ABB | DDBDDDDD | BBBA |
| ABB | DDBDDDBD | BBA |
| ABB | DDBDDDDBD | BBA |
| ABB | DDBDDBDDD | BBA |
| ABB | DDBDBDDDD | BBA |
| ABB | DDBBDDDDD | BBA |
| ABB | DDDBDDDD | BBBA |
| ABB | DDDBDDDBD | BBA |
| ABB | DDDBDDBDD | BBA |
| ABB | DDDBDBDDD | BBA |
| ABB | DDDBBDDDD | BBA |
| ABB | DDDDBDDD | BBBA |
| ABB | DDDDBDDBD | BBA |
| ABB | DDDDBDBDD | BBA |
| ABB | DDDDBBDDD | BBA |
| ABB | DDDDDBDD | BBBA |
| ABB | DDDDDBDBD | BBA |
| ABB | DDDDDBBDD | BBA |
| ABB | DDDDDDBD | BBBA |
| ABB | DDDDDBDBD | BBA |
| ABB | DDDDDBBBD | BBA |
| ABB | DDDDDDDBD | BBBA |

TABLE 9

Certain Gapmer Nucleoside Motifs

| 5'-wing region | Central gap region | 3'-wing region |
|---|---|---|
| ABB | DDDDDDDD | BBA |
| AB | DBDDDDDD | BBA |
| AB | DDBDDDDD | BBA |
| AB | DDDBDDDD | BBA |
| AB | DDDDBDDD | BBA |
| AB | DDDDDBDD | BBA |
| AB | DDDDDDBD | BBA |
| AB | DDDDDDDBD | BBA |
| AB | DDDDDDDD | BBBA |
| ABBB | DDDDDDD | BBA |
| AB | DBBDDDDD | BBA |
| AB | DDBBDDDD | BBA |
| AB | DDDBBDDD | BBA |
| AB | DDDDBBDD | BBA |
| AB | DDDDDBBD | BBA |
| AB | DDDDDDBBD | BBA |
| AB | DDDDDDD | BBBBA |
| ABBBB | DDDDDDD | BBA |
| AB | DBBBDDDD | BBA |
| AB | DDBBBDDD | BBA |
| AB | DDDBBBDD | BBA |
| AB | DDDDBBBD | BBA |
| AB | DDDDDBBBD | BBA |
| AB | DDDDDDBBBD | BBA |
| AB | DDDDDDD | BBBBBA |
| AB | DDDDDDDD | BBBA |
| AB | DDDDDDBD | BBBA |
| AB | DDDDBDDD | BBBA |
| AB | DDDDBDDD | BBBA |
| AB | DDBDDDD | BBBA |
| AB | DBDDDDD | BBBA |
| AB | DDDDDBD | BBBBA |
| AB | DDDDBDD | BBBBA |
| AB | DDDDBDD | BBBBA |
| AB | DDBDDDD | BBBBA |
| AB | DBDDDDD | BBBBA |
| AB | DDDDBD | BBBBBA |
| AB | DDDDBD | BBBBBA |
| AB | DDBDDD | BBBBBA |
| AB | DBDDDD | BBBBBA |

TABLE 10

Certain Gapmer Nucleoside Motifs

| 5'-wing region | Central gap region | 3'-wing region |
|---|---|---|
| AAAAAA | DDDDDDD | BABA |
| AAAAAB | DDDDDDD | BABA |
| AAAABA | DDDDDDD | BABA |
| AAABAA | DDDDDDD | BABA |
| AABAAA | DDDDDDD | BABA |
| ABAAAA | DDDDDDD | BABA |
| BAAAAA | DDDDDDD | BABA |
| ABAAAB | DDDDDDD | BABA |
| ABAABA | DDDDDDD | BABA |
| ABABAA | DDDDDDD | BABA |
| ABBAAA | DDDDDDD | BABA |
| AABAAB | DDDDDDD | BABA |
| AABABA | DDDDDDD | BABA |
| AABBAA | DDDDDDD | BABA |
| AAABAB | DDDDDDD | BABA |
| AAABBA | DDDDDDD | BABA |
| AAAABB | DDDDDDD | BABA |
| BAAAAB | DDDDDDD | BABA |
| BAAABA | DDDDDDD | BABA |
| BAABAA | DDDDDDD | BABA |
| BABAAA | DDDDDDD | BABA |
| BBAAAA | DDDDDDD | BABA |
| BBBAAA | DDDDDDD | BABA |

TABLE 10-continued

Certain Gapmer Nucleoside Motifs

| 5'-wing region | Central gap region | 3'-wing region |
|---|---|---|
| BBABAA | DDDDDDD | BABA |
| BBAABA | DDDDDDD | BABA |
| BBAAAB | DDDDDDD | BABA |
| ABABAB | DDDDDDD | BABA |
| BBBBAA | DDDDDDD | BABA |
| BBBABA | DDDDDDD | BABA |
| BBBAAB | DDDDDDD | BABA |
| BBBBBA | DDDDDDD | BABA |
| BBBBAB | DDDDDDD | BABA |
| AAABBB | DDDDDDD | BABA |
| AABABB | DDDDDDD | BABA |
| ABAABB | DDDDDDD | BABA |
| BAAABB | DDDDDDD | BABA |
| AABBBB | DDDDDDD | BABA |
| ABABBB | DDDDDDD | BABA |
| BAABBB | DDDDDDD | BABA |
| ABBBBB | DDDDDDD | BABA |
| BABBBB | DDDDDDD | BABA |
| BBBBBB | DDDDDDD | BABA |

TABLE 11

Certain Gapmer Nucleoside Motifs

| 5'-wing region | Central gap region | 3'-wing region |
|---|---|---|
| AAAAA | DDDDDDD | AAAAA |
| AAAAB | DDDDDDD | AAAAA |
| AAABA | DDDDDDD | AAAAA |
| AAABB | DDDDDDD | AAAAA |
| AABAA | DDDDDDD | AAAAA |
| AABAB | DDDDDDD | AAAAA |
| AABBA | DDDDDDD | AAAAA |
| AABBB | DDDDDDD | AAAAA |
| ABAAA | DDDDDDD | AAAAA |
| ABAAB | DDDDDDD | AAAAA |
| ABABA | DDDDDDD | AAAAA |
| ABABB | DDDDDDD | AAAAA |
| ABBAA | DDDDDDD | AAAAA |
| ABBAB | DDDDDDD | AAAAA |
| ABBBA | DDDDDDD | AAAAA |
| ABBBB | DDDDDDD | AAAAA |
| BAAAA | DDDDDDD | AAAAA |
| BAAAB | DDDDDDD | AAAAA |
| BAABA | DDDDDDD | AAAAA |
| BAABB | DDDDDDD | AAAAA |
| BABAA | DDDDDDD | AAAAA |
| BABAB | DDDDDDD | AAAAA |
| BABBA | DDDDDDD | AAAAA |
| BABBB | DDDDDDD | AAAAA |
| BBAAA | DDDDDDD | AAAAA |
| BBAAB | DDDDDDD | AAAAA |
| BBABA | DDDDDDD | AAAAA |
| BBABB | DDDDDDD | AAAAA |
| BBBAA | DDDDDDD | AAAAA |
| BBBAB | DDDDDDD | AAAAA |
| BBBBA | DDDDDDD | AAAAA |
| BBBBB | DDDDDDD | AAAAA |
| AAAAA | DDDDDDD | BAAAA |
| AAAAB | DDDDDDD | BAAAA |
| AAABA | DDDDDDD | BAAAA |
| AAABB | DDDDDDD | BAAAA |
| AABAA | DDDDDDD | BAAAA |
| AABAB | DDDDDDD | BAAAA |
| AABBA | DDDDDDD | BAAAA |
| AABBB | DDDDDDD | BAAAA |
| ABAAA | DDDDDDD | BAAAA |
| ABAAB | DDDDDDD | BAAAA |
| ABABA | DDDDDDD | BAAAA |
| ABABB | DDDDDDD | BAAAA |
| ABBAA | DDDDDDD | BAAAA |
| ABBAB | DDDDDDD | BAAAA |
| ABBBA | DDDDDDD | BAAAA |

TABLE 11-continued

Certain Gapmer Nucleoside Motifs

| 5'-wing region | Central gap region | 3'-wing region |
|---|---|---|
| ABBBB | DDDDDDD | BAAAA |
| BAAAA | DDDDDDD | BAAAA |
| BAAAB | DDDDDDD | BAAAA |
| BAABA | DDDDDDD | BAAAA |
| BAABB | DDDDDDD | BAAAA |
| BABAA | DDDDDDD | BAAAA |
| BABAB | DDDDDDD | BAAAA |
| BABBA | DDDDDDD | BAAAA |
| BABBB | DDDDDDD | BAAAA |
| BBAAA | DDDDDDD | BAAAA |
| BBAAB | DDDDDDD | BAAAA |
| BBABA | DDDDDDD | BAAAA |
| BBABB | DDDDDDD | BAAAA |
| BBBAA | DDDDDDD | BAAAA |
| BBBAB | DDDDDDD | BAAAA |
| BBBBA | DDDDDDD | BAAAA |
| BBBBB | DDDDDDD | BAAAA |
| AAAAA | DDDDDDD | BBAAA |
| AAAAB | DDDDDDD | BBAAA |
| AAABA | DDDDDDD | BBAAA |
| AAABB | DDDDDDD | BBAAA |
| AABAA | DDDDDDD | BBAAA |
| AABAB | DDDDDDD | BBAAA |
| AABBA | DDDDDDD | BBAAA |
| AABBB | DDDDDDD | BBAAA |
| ABAAA | DDDDDDD | BBAAA |
| ABAAB | DDDDDDD | BBAAA |
| ABABA | DDDDDDD | BBAAA |
| ABABB | DDDDDDD | BBAAA |
| ABBAA | DDDDDDD | BBAAA |
| ABBAB | DDDDDDD | BBAAA |
| ABBBA | DDDDDDD | BBAAA |
| ABBBB | DDDDDDD | BBAAA |
| BAAAA | DDDDDDD | BBAAA |
| BAAAB | DDDDDDD | BBAAA |
| BAABA | DDDDDDD | BBAAA |
| BAABB | DDDDDDD | BBAAA |
| BABAA | DDDDDDD | BBAAA |
| BABAB | DDDDDDD | BBAAA |
| BABBA | DDDDDDD | BBAAA |
| BABBB | DDDDDDD | BBAAA |
| BBAAA | DDDDDDD | BBAAA |
| BBAAB | DDDDDDD | BBAAA |
| BBABA | DDDDDDD | BBAAA |
| BBABB | DDDDDDD | BBAAA |
| BBBAA | DDDDDDD | BBAAA |
| BBBAB | DDDDDDD | BBAAA |
| BBBBA | DDDDDDD | BBAAA |
| BBBBB | DDDDDDD | BBAAA |
| AAAAA | DDDDDDD | BBBAA |
| AAAAB | DDDDDDD | BBBAA |
| AAABA | DDDDDDD | BBBAA |
| AAABB | DDDDDDD | BBBAA |
| AABAA | DDDDDDD | BBBAA |
| AABAB | DDDDDDD | BBBAA |
| AABBA | DDDDDDD | BBBAA |
| AABBB | DDDDDDD | BBBAA |
| ABAAA | DDDDDDD | BBBAA |
| ABAAB | DDDDDDD | BBBAA |
| ABABA | DDDDDDD | BBBAA |
| ABABB | DDDDDDD | BBBAA |
| ABBAA | DDDDDDD | BBBAA |
| ABBAB | DDDDDDD | BBBAA |
| ABBBA | DDDDDDD | BBBAA |
| ABBBB | DDDDDDD | BBBAA |
| BAAAA | DDDDDDD | BBBAA |
| BAAAB | DDDDDDD | BBBAA |
| BAABA | DDDDDDD | BBBAA |
| BAABB | DDDDDDD | BBBAA |
| BABAA | DDDDDDD | BBBAA |
| BABAB | DDDDDDD | BBBAA |
| BABBA | DDDDDDD | BBBAA |
| BABBB | DDDDDDD | BBBAA |
| BBAAA | DDDDDDD | BBBAA |
| BBAAB | DDDDDDD | BBBAA |
| BBABA | DDDDDDD | BBBAA |

TABLE 11-continued

Certain Gapmer Nucleoside Motifs

| 5'-wing region | Central gap region | 3'-wing region |
|---|---|---|
| BBABB | DDDDDDD | BBBAA |
| BBBAA | DDDDDDD | BBBAA |
| BBBAB | DDDDDDD | BBBAA |
| BBBBA | DDDDDDD | BBBAA |
| BBBBB | DDDDDDD | BBBAA |
| AAAAA | DDDDDDD | BBBBA |
| AAAAB | DDDDDDD | BBBBA |
| AAABA | DDDDDDD | BBBBA |
| AAABB | DDDDDDD | BBBBA |
| AABAA | DDDDDDD | BBBBA |
| AABAB | DDDDDDD | BBBBA |
| AABBA | DDDDDDD | BBBBA |
| AABBB | DDDDDDD | BBBBA |
| ABAAA | DDDDDDD | BBBBA |
| ABAAB | DDDDDDD | BBBBA |
| ABABA | DDDDDDD | BBBBA |
| ABABB | DDDDDDD | BBBBA |
| ABBAA | DDDDDDD | BBBBA |
| ABBAB | DDDDDDD | BBBBA |
| ABBBA | DDDDDDD | BBBBA |
| ABBBB | DDDDDDD | BBBBA |
| BAAAA | DDDDDDD | BBBBA |
| BAAAB | DDDDDDD | BBBBA |
| BAABA | DDDDDDD | BBBBA |
| BAABB | DDDDDDD | BBBBA |
| BABAA | DDDDDDD | BBBBA |
| BABAB | DDDDDDD | BBBBA |
| BABBA | DDDDDDD | BBBBA |
| BABBB | DDDDDDD | BBBBA |
| BBAAA | DDDDDDD | BBBBA |
| BBAAB | DDDDDDD | BBBBA |
| BBABA | DDDDDDD | BBBBA |
| BBABB | DDDDDDD | BBBBA |
| BBBAA | DDDDDDD | BBBBA |
| BBBAB | DDDDDDD | BBBBA |
| BBBBA | DDDDDDD | BBBBA |
| BBBBB | DDDDDDD | BBBBA |
| AAAAA | DDDDDDD | BBBBB |
| AAAAB | DDDDDDD | BBBBB |
| AAABA | DDDDDDD | BBBBB |
| AAABB | DDDDDDD | BBBBB |
| AABAA | DDDDDDD | BBBBB |
| AABAB | DDDDDDD | BBBBB |
| AABBA | DDDDDDD | BBBBB |
| AABBB | DDDDDDD | BBBBB |
| ABAAA | DDDDDDD | BBBBB |
| ABAAB | DDDDDDD | BBBBB |
| ABABA | DDDDDDD | BBBBB |
| ABABB | DDDDDDD | BBBBB |
| ABBAA | DDDDDDD | BBBBB |
| ABBAB | DDDDDDD | BBBBB |
| ABBBA | DDDDDDD | BBBBB |
| ABBBB | DDDDDDD | BBBBB |
| BAAAA | DDDDDDD | BBBBB |
| BAAAB | DDDDDDD | BBBBB |
| BAABA | DDDDDDD | BBBBB |
| BAABB | DDDDDDD | BBBBB |
| BABAA | DDDDDDD | BBBBB |
| BABAB | DDDDDDD | BBBBB |
| BABBA | DDDDDDD | BBBBB |
| BABBB | DDDDDDD | BBBBB |
| BBAAA | DDDDDDD | BBBBB |
| BBAAB | DDDDDDD | BBBBB |
| BBABA | DDDDDDD | BBBBB |
| BBABB | DDDDDDD | BBBBB |
| BBBAA | DDDDDDD | BBBBB |
| BBBAB | DDDDDDD | BBBBB |
| BBBBA | DDDDDDD | BBBBB |
| BBBBB | DDDDDDD | BBBBB |

TABLE 12

Certain Gapmer Nucleoside Motifs

| 5'-wing region | Central gap region | 3'-wing region |
|---|---|---|
| AAAW | DDDDDDD | BBA |
| AABW | DDDDDDD | BBA |
| ABAW | DDDDDDD | BBA |
| ABBW | DDDDDDD | BBA |
| BAAW | DDDDDDD | BBA |
| BABW | DDDDDDD | BBA |
| BBAW | DDDDDDD | BBA |
| BBBW | DDDDDDD | BBA |
| ABB | DDDDDDD | WAAA |
| ABB | DDDDDDD | WAAB |
| ABB | DDDDDDD | WABA |
| ABB | DDDDDDD | WABB |
| ABB | DDDDDDD | WBAA |
| ABB | DDDDDDD | WBAB |
| ABB | DDDDDDD | WBBA |
| ABB | DDDDDDD | WBBB |
| AAAWW | DDDDDDD | BBA |
| AABWW | DDDDDDD | BBA |
| ABAWW | DDDDDDD | BBA |
| ABBWW | DDDDDDD | BBA |
| BAAWW | DDDDDDD | BBA |
| BABWW | DDDDDDD | BBA |
| BBAWW | DDDDDDD | BBA |
| BBBWW | DDDDDDD | BBA |
| ABB | DDDDDDD | WWAAA |
| ABB | DDDDDDD | WWAAB |
| ABB | DDDDDDD | WWABA |
| ABB | DDDDDDD | WWABB |
| ABB | DDDDDDD | WWBAA |
| ABB | DDDDDDD | WWBAB |
| ABB | DDDDDDD | WWBBA |
| ABB | DDDDDDD | WWBBB |
| AAAAW | DDDDDDD | BBA |
| AAABW | DDDDDDD | BBA |
| AABAW | DDDDDDD | BBA |
| AABBW | DDDDDDD | BBA |
| ABAAW | DDDDDDD | BBA |
| ABABW | DDDDDDD | BBA |
| ABBAW | DDDDDDD | BBA |
| ABBBW | DDDDDDD | BBA |
| BAAAW | DDDDDDD | BBA |
| BAABW | DDDDDDD | BBA |
| BABAW | DDDDDDD | BBA |
| BABBW | DDDDDDD | BBA |
| BBAAW | DDDDDDD | BBA |
| BBABW | DDDDDDD | BBA |
| BBBAW | DDDDDDD | BBA |
| BBBBW | DDDDDDD | WAAAA |
| ABB | DDDDDDD | WAAAB |
| ABB | DDDDDDD | WAABA |
| ABB | DDDDDDD | WAABB |
| ABB | DDDDDDD | WABAA |
| ABB | DDDDDDD | WABAB |
| ABB | DDDDDDD | WABBA |
| ABB | DDDDDDD | WABBB |
| ABB | DDDDDDD | WBAAA |
| ABB | DDDDDDD | WBAAB |
| ABB | DDDDDDD | WBABA |
| ABB | DDDDDDD | WBABB |
| ABB | DDDDDDD | WBBAA |
| ABB | DDDDDDD | WBBAB |
| ABB | DDDDDDD | WBBBA |
| ABB | DDDDDDD | WBBBB | wherein each A is a modified nucleoside of a first type, each B is a modified nucleoside of a second type and each W is a modified nucleoside or nucleobase of either the first type, the second type or a third type, each D is a nucleoside comprising an unmodified 2'deoxy sugar moiety and unmodified nucleobase, and $^{N}$D is modified nucleoside comprising a modified nucleobase and an unmodified 2'deoxy sugar moiety.

In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises an F-HNA. In certain embodiments, each A comprises a 5'-substituted sugar moiety selected from among 5'-Me, and 5'-(R)-Me.

In certain embodiments, each B comprises a modified sugar moiety. In certain embodiments, each B comprises a 2'-substituted sugar moiety. In certain embodiments, each B comprises a 2'-subsituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises an F-HNA. In certain embodiments, each B comprises a 5'-substituted sugar moiety selected from among 5'-Me, and 5'-(R)-Me.

In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, OCH$_3$ and O(CH$_2$)$_2$—OCH$_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA. In certain embodiments, each W comprises a 2-thio-thymidine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety. In certain embodiments, a gapmer has a sugar motif other than: E-K-K-$(D)_9$-K-K-E; E-E-E-E-K-$(D)_9$-E-E-E-E-E; E-K-K-K-$(D)_9$-K-K-K-E; K-E-E-E-K-$(D)_9$-K-E-E-E-K; K-D-D-K-$(D)_9$-K-D-D-K; K-E-K-E-K-$(D)_9$-K-E-K-E-K; K-D-K-D-K-$(D)_9$-K-D-K-D-K; E-K-E-K-$(D)_9$-K-E-K-E; E-E-E-E-K-$(D)_8$-E-E-E-E; or E-K-E-K-E-$(D)_9$-E-K-E-K-E, E-E-E-K-E-$(D)_7$-E-E-K, E-K-E-K-K-$(D)_7$-K-E-K-E, E-K-E-K-E-K-$(D)_7$-K-E-K-E, wherein K is a nucleoside comprising a cEt sugar moiety and E is a nucleoside comprising a 2'-MOE sugar moiety.

In certain embodiments a gapmer comprises a A-$(D)_4$-A-$(D)_4$-A-$(D)_4$-AA motif. In certain embodiments a gapmer comprises a B-$(D)_4$-A-$(D)_4$-A-$(D)_4$-AA motif. In certain embodiments a gapmer comprises a A-$(D)_4$-B-$(D)_4$-A-$(D)_4$-AA motif. In certain embodiments a gapmer comprises a A-$(D)_4$-A-$(D)_4$-B-$(D)_4$-AA motif. In certain embodiments a gapmer comprises a A-$(D)_4$-A-$(D)_4$-A-$(D)_4$-BA motif. In certain embodiments a gapmer comprises a A-$(D)_4$-A-$(D)_4$-A-$(D)_4$-BB motif. In certain embodiments a gapmer comprises a K-$(D)_4$-K-$(D)_4$-K-$(D)_4$-K-E motif.

xi. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif xii. Certain Modification Motifs Modification motifs define oligonucleotides by nucleoside motif (sugar motif and nucleobase motif) and linkage motif. For example, certain oligonucleotides have the following modification motif:

A$_s$A$_s$A$_s$D$_s$D$_s$D$_s$D$_s$($^N$D)$_s$D$_s$D$_s$D$_s$D$_s$B$_s$B$_s$B;
wherein each A is a modified nucleoside comprising a 2'-substituted sugar moiety; each D is an unmodified 2'-deoxynucleoside; each B is a modified nucleoside comprising a bicyclic sugar moiety; $^N$D is a modified nucleoside comprising a modified nucleobase; and s is a phosphorothioate internucleoside linkage. Thus, the sugar motif is a gapmer motif The nucleobase modification motif is a single modified nucleobase at 8$^{th}$ nucleoside from the 5'-end. Combining the sugar motif and the nucleobase modification motif, the nucleoside motif is an interrupted gapmer where the gap of the sugar modified gapmer is interrupted by a nucleoside comprising a modified nucleobase. The linkage motif is uniform phosphorothioate. The following non-limiting Table further illustrates certain modification motifs:

TABLE 13

Certain Modification Motifs

| 5'-wing region | Central gap region | 3'-wing region |
|---|---|---|
| B$_s$B$_s$ | $_s$D$_s$D$_s$D$_s$D$_s$D$_s$D$_s$D$_s$D$_s$ | A$_s$A$_s$A$_s$A$_s$A$_s$A$_s$A$_s$A |
| AsBsBs | DsDsDsDsDsDsDsDs | BsBsA |
| AsBsBs | DsDsDsDs($^N$D)sDsDsDs | BsBsA |
| AsBsBs | DsDsDsAsDsDsDs | BsBsA |
| AsBsBs | DsDsDsBsDsDsDs | BsBsA |
| AsBsBs | DsDsDsWsDsDsDs | BsBsA |
| AsBsBsBs | DsDsDsDsDsDsDs | BsBsAsBsB |
| AsBsBs | DsDsDsDsDsDsDs | BsBsAsBsB |
| BsBsAsBsBs | DsDsDsDsDsDsDs | BsBsA |
| AsBsBs | DsDsDsDsDsDsDs | BsBsAsBsBsBsB |
| AsAsBsAsAs | DsDsDsDsDsDsDs | BsBsA |
| AsAsAsBsAsAs | DsDsDsDsDsDsDs | BsBsA |
| AsAsBsAsAs | DsDsDsDsDsDsDs | AsAsBsAsA |
| AsAsAsBsAsAs | DsDsDsDsDsDsDs | AsAsBsAsAsA |
| AsAsAsAsBsAsAs | DsDsDsDsDsDsDs | BsBsA |
| AsBsAsBs | DsDsDsDsDsDsDs | BsAsBsA |
| AsBsAsBs | DsDsDsDsDsDsDs | AsAsBsAsAs |
| AsBsBs | DsDsDsDsDsDsDs | BsAsBsA |
| BsBsAsBsBsB | DsDsDsDsDsDsDs | BsAsBsA |
| AsAsAsAs | DsDsDsDsDsDsDs | AsAsAsA |
| AsAsAsAs | DsDsDsDsDsDs | AsAsAsA |
| AsAsAsAs | DsDsDsDsDsDsDs | BsBsAsBsBsBsB |
| AsAsBsBs | DsDsDsDsDsDs | BsBsA |
| AsBsAsBs | DsDsDsDsDsDs | BsBsA |
| AsBsAsBs | DsDsDsDsDsDs | AsAsBsBs |
| AsAsAsBs | DsDsDsDsDsDs | BsAsAsA |
| BsBs | DsDsDsDsDsDs | AsA |
| AsAs | DsDsDsDsDs | AsAsAsAsAsAsA |
| AsAs | DsDsDsDsDs | AsAsAsAsAsA |
| AsAsAs | DsDsDsDsDs | AsAsAsAsA |
| AsBs | DsDsDsDsDs | BsBsBsA |
| AsBsBsBs | DsDsDsDsDsDsDs | BsA |
| AsBs | DsDsDsDsDsDsDs | BsBsBsA |
| AsAsAsBsBs | DsDsDs($^N$D)sDsDsDs | BsBsAsAsA |
| AsAsAsBsBs | DsDsDsAsDsDs | BsBsAsAsA |
| AsAsAsBsBs | DsDsDsBsDsDs | BsBsAsAsA |
| AsAsAsAsBs | DsDsDsDsDs | BsAsAsAsA |
| AsAsBsBsBs | DsDsDsDsDs | BsBsBsAsA |
| AsAsAsBs | DsDsDsDsDs | AsAsAsAs |
| AsAsAsBs | DsDsDsDsDs | AsAsAsAs |
| AsBsBsBs | DsDsDsDsDs | AsAsAsAs |
| AsAsAsAs | DsDsDsDsDs | BsAsAsAs |
| AsAsAsAs | DsDsDsDsDs | BsBsAsAs |
| AsAsAsAs | DsDsDsDsDs | BsBsBsAsAs |
| AsBsBs | DsDsDs($^N$D)s($^N$D)sDsDsDs | BsBsA |
| AsBsBs | Ds($^N$D)s($^N$D)sDs($^N$D)s($^N$D)sDs($^N$D)s($^N$D)s | BsBsA |
| AsBsBs | Ds($^N$D)sDsDsDsDsDs | BsBsA |
| AsBsBs | DsDs($^N$D)sDsDsDsDsDs | BsBsA |
| AsBsBs | Ds($^N$D)s($^N$D)sDsDsDsDsDs | BsBsA |
| AsBsBs | DsDs(D)zDsDsDsDsDs | BsBsA |
| AsBsBs | Ds(D)zDsDsDsDsDs | BsBsA |
| AsBsBs | (D)zDsDsDsDsDsDs | BsBsA |
| AsBsBs | DsDsAsDsDsDsDsDs | BsBsA |
| AsBsBs | DsDsBsDsDsDsDs | BsBsA |
| AsBsBs | AsDsDsDsDsDsDs | BsBsA |
| AsBsBs | BsDsDsDsDsDsDs | BsBsA |
| AsBsAsBs | DsDs(D)zDsDsDsDs | BsBsBsAsAs |
| AsAsAsBsBs | DsDs($^N$D)sDsDsDsDsDs | AsA |
| AsBsBsBs | Ds(D)zDsDsDsDsDs | AsAsAsBsBs |
| AsBsBs | DsDsDsDsDsDsDs(D)z | BsBsA |
| AsAsBsBsBs | DsDsDsAsDsDsDs | BsBsBsAsA |
| AsAsBsBsBs | DsDsDsBsDsDsDs | BsBsBsAsA |
| AsBsAsBs | DsDsAsDsDsDs | BsBsAsBsBsBsB |
| AsBsBsBs | DsDsDs(D)zDsDsDs | BsA |
| AsAsBsBsBs | DsDsAsAsDsDsDs | BsBsA |

TABLE 13-continued

Certain Modification Motifs

| 5'-wing region | Central gap region | 3'-wing region |
| --- | --- | --- |
| AsBsBs | DsDsDsDs(D)zDsDsDsDs | BsBsBsA |
| BsBs | DsDs($^N$D)sDs($^N$D)sDsDsDsDs | BsBsAsBsBsBsB | wherein each A and B are nucleosides comprising differently modified sugar moieties, each D is a nucleoside comprising an unmodified 2'deoxy sugar moiety, each W is a modified nucleoside of either the first type, the second type or a third type, each $^N$D is a modified nucleoside comprising a modified nucleobase, s is a phosphorothioate internucleoside linkage, and z is a non-phosphorothioate internucleoside linkage.

In certain embodiments, each A comprises a modified sugar moiety. In certain embodiments, each A comprises a 2'-substituted sugar moiety. In certain embodiments, each A comprises a 2'-substituted sugar moiety selected from among F, (ara)-F, $OCH_3$ and $O(CH_2)_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each B comprises a modified sugar moiety. In certain embodiments, each B comprises a 2'-substituted sugar moiety. In certain embodiments, each B comprises a 2'-subsituted sugar moiety selected from among F, (ara)-F, $OCH_3$ and $O(CH_2)_2$—$OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each A comprises an HNA. In certain embodiments, each A comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, $OCH_3$ and $O(CH_2)_2$—$OCH_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety.

c. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

d. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

e. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

C. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

b. Certain Selective Antisense Compounds

In certain embodiments, antisense compounds provided are selective for a target relative to a non-target nucleic acid. In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the target and non-target nucleic acids are transcripts from different genes. In certain embodiments, the target and non-target nucleic acids are different alleles for the same gene. In certain embodiments, the introduction of a mismatch between an antisense compound and a non-target nucleic acid may alter the RNase H cleavage site of a target nucleic acid compared to a non-target nucleic acid. In certain embodiments, the target and non-target nucleic acids are not functionally related to one another (e.g., are transcripts from different genes). In certain embodiments, the target and not-target nucleic acids are allelic variants of one another. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (i.e. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNase H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

In certain embodiments, an antisense compound binds its intended target to form a target duplex. In certain embodiments, RNase H cleaves the target nucleic acid of the target duplex. In certain such embodiments, there is a primary cleavage site between two particular nucleosides of the target nucleic acid (the primary target cleavage site), which accounts for the largest amount of cleavage of the target nucleic acid. In certain embodiments, there are one or more secondary target cleavage sites. In certain embodiments, the same antisence compound hybridizes to a non-target to form a non-target duplex. In certain such embodiments, the non-target differs from the target by a single nucleobase within the target region, and so the antisense compound hybridizes with a single mismatch. Because of the mismatch, in certain embodiments, RNase H cleavage of the non-target may be reduced compared to cleavage of the target, but still occurs. In certain embodiments, though, the primary site of that cleavage of the non-target nucleic acid (primary non-target cleavage site) is different from that of the target. That is; the primary site is shifted due to the mismatch. In such a circumstance, one may use a modification placed in the antisense compound to disrupt RNase H cleavage at the primary non-target cleavage site. Such modification will result in reduced cleavage of the non-target, but will result little or no decrease in cleavage of the target. In certain embodiments, the modification is a modified sugar, nucleobase and/or linkage.

In certain embodiments, the primary non-target cleavage site is towards the 5'-end of the antisense compound, and the 5'-end of an antisense compound may be modified to prevent RNaseH cleavage. In this manner, it is thought that one having skill in the art may modify the 5'-end of an antisense compound, or modify the nucleosides in the gap region of the 5'-end of the antisense compound, or modify the the 3'-most 5'-region nucleosides of the antisense compound to selectively inhibit RNaseH cleavage of the non-target nucleic acid duplex while retaining RNase H cleavage of the target nucleic acid duplex. In certain embodiments, 1-3 of the 3'-most 5'-region nucleosides of the antisense compound comprises a bicyclic sugar moiety.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to the target nucleic acid. The mismatch between the antisense compound and the non-target nucleic acid may destabilize the antisense compound non-target nucleic acid duplex, and consequently the cleavage site of RNaseH may shift upstream towards the 5'-end of the antisense compound. Modification of the 5'-end of the antisense compound or the gap region near the 5'-end of the antisense compound, or one or more of the 3'-most nucleosides of the 5'-wing region, will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more downstream, towards the 3' end of the antisense compound. Accordingly, modifications at the 5'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 3'-most nucleosides of the 5'-wing region comprises a bicyclic sugar moiety. In certain embodiments, one or more of the 3'-most nucleosides of the 5'-wing region comprises a bicyclic sugar moiety selected from cEt and LNA. In certain embodiments, one or more of the 3'-most nucleosides of the 5'-wing region comprises cEt. In certain embodiments, one or more of the 3'-most nucleosides of the 5'-wing region comprises LNA.

In certain embodiments, the introduction of a mismatch between an antisense compound and a target nucleic acid may alter the RNase H cleavage site of a target nucleic acid compared to a non-target nucleic acid by shifting the RNaseH cleavage site downstream from the mismatch site and towards the 3'-end of the antisense compound. In certain embodiments where the cleavage site of a target nucleic acid compared to a non-target nucleic acid has shifted downstream towards the 3'-end of the antisense compound, the 3'-end of an antisense compound may be modified to prevent RNaseH cleavage. In this manner, it is thought that one having skill in the art may modify the 3'-end of an antisense compound, or modify the nucleosides in the gap region near the 3'-end of antisense compound, to selectively inhibit RNaseH cleavage of the non-target nucleic acid while retaining RNase H cleavage of the target nucleic acid.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to target nucleic acid. The mismatch between the antisense compound and the non-target nucleic acid may destabilize the antisense compound-non-target nucleic acid duplex, and consequently the cleavage site of RNaseH may shift downstream towards the 3'-end of the antisense compound. Modification of the 3'-end of the antisense compound, or one or more of the the 5'-most nucleosides of the 3'-wing region, or the gap region of the antisense compound near the 3'-end will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more upstream, towards the 5' end of the antisense compound. Accordingly, modifications at the 3'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 5'-most nucleosides of the 3'-wing region comprises a bicyclic sugar moiety. In certain embodiments, one or more of the 5'-most nucleosides of the 3'-wing region comprises a bicyclic sugar moiety selected from cEt and LNA. In certain embodiments, one or more of the 5'-most nucleosides of the 3'-wing region comprises cEt. In certain embodiments, one or more of the 5'-most nucleosides of the 3'-wing region comprises LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside. In certain embodiments, the selectivity of antisense compounds having certain gaps, e.g. gaps of 7 nucleosides or longer, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicylic nucleosides at the 5'-most 3'-wing nucleoside.

In certain embodiments, the selectivity of antisense compounds having certain gaps, e.g. gaps of 7 nucleosides or shorter, may be improved by the addition of one or more bicyclic nucleosides at the 3'-most 5'-wing nucleoside. In certain embodiments, the selectivity of antisense compounds having certain gaps, e.g. gaps of 7 nucleosides or shorter, may be improved by the addition of two or more bicyclic nucleosides at the 3'-most 5'-wing nucleoside. In certain embodiments, the selectivity of antisense compounds having certain gaps, e.g. gaps of 7 nucleosides or shorter, may be improved by the addition of one bicyclic nucleoside at the 3'-most 5'-wing nucleoside. In certain embodiments, the selectivity of antisense compounds having certain gaps, e.g. gaps of 7 nucleosides or shorter, may be improved by the addition of two bicyclic nucleosides at the 3'-most 5'-wing nucleoside. In certain embodiments, the selectivity of antisense compounds having certain gaps, e.g. gaps of 7 nucleosides or shorter, may be improved by the addition of three bicyclic nucleosides at the 3'-most 5'-wing nucleoside. In certain embodiments, the selectivity of antisense compounds having certain gaps, e.g. gaps of 7 nucleosides or shorter, may be improved by the addition of four bicyclic nucleosides at the 3'-most 5'-wing nucleoside. In certain embodiments, the selectivity of antisense compounds having certain gaps, e.g. gaps of 7 nucleosides or shorter, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);

a modification motif comprising a long 3'-wing (longer than 5, 6, or 7 nucleosides);

a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

i. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

ii. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{th}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

In certain embodiments, a target-selective nucleoside comprises a modified nucleoside. In certain embodiments, a target-selective nucleoside comprises a modified sugar. In certain embodiments, a target-selective nucleoside comprises a sugar surrogate. In certain embodiments, a target-selective nucleoside comprises a sugar surrogate selected from among HNA and F-HNA. In certain embodiments, a target-selective nucleoside comprises a sugar surrogate selected from among F-CeNA, FRNA, and FANA. In certain embodiments, a target-selective nucleoside comprises a 2'-substituted sugar moiety. In certain embodiments, a target-selective nucleoside comprises a 2'-substituted sugar moiety selected from among MOE, F and (ara)-F. In certain embodiments, a target-selective nucleoside comprises a 5'-substituted sugar moiety. In certain embodiments, a target-selective nucleoside comprises a 5'-substituted sugar moiety selected from 5'-(R)-Me DNA. In certain embodiments, a target-selective nucleoside comprises a 5'-substituted sugar moiety selected from 5'-(S)-Me DNA. In certain embodiments, a target-selective nucleoside comprises a bicyclic sugar moiety. In certain embodiments, a target-selective nucleoside comprises a bicyclic sugar moiety selected from among cEt, and α-L-LNA. In certain embodiments, a target-selective nucleoside comprises a modified nucleobase. In certain embodiments, a target-selective nucleoside comprises a modified nucleobase selected from among 2-thio-thymidine and 5-propyne uridine.

In certain embodiments, a modification at position 4 from the 5'-end increases selectivity. In certain embodiments, a modification at position 5 from the 5'-end increases selectivity. In certain embodiments, a modification at position 7 from the 5'-end increases selectivity. In certain embodiments, a modification at position 8 from the 5'-end increases potency and selectivity. In certain embodiments, a modification at position 9 from the 5'-end increases potency. In certain embodiments, a modification at position 10 from the 5'-end increases selectivity. In certain embodiments, a modification at position 11 from the 5'-end increases selectivity. In certain embodiments, a modification at position 12 from the 5'-end increases potency. In certain embodiments, an S-5'-Me-DNA modification increases allele selectivity.

iii. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif.

In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleid acid is at positions 1, 2, 3, or 4 of the antisense compounds from the 5'-end of the wing region. In certain embodiments, a mismatch relative to the target nucleid acid is at positions 4, 3, 2, or 1 of the antisense compounds from the 3'-end of the wing region.

iv. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

ABCXXXXXXXXXXC'B'A';
ABCXXXXXXXX(X/C')(X/B')(X/A');
(X/A)(X/B)(X/C)XXXXXXXXXC'B'A' where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

v. Combinations of features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

D. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments, the target nucleic acid is a Huntingtin gene transcript. In certain embodiments, the target nucleic acid is a single-nucleotide polymorphism-containing-target nucleic acid of a Huntingtin gene transcript. In certain embodiments, the target nucleic acid is not a Huntingtin gene transcript. In certain embodiments, the target nucleic acid is a single-nucleotide polymorphism-containing-target nucleic acid of a gene transcript other than Huntingtin. In certain embodiments, the target nucleic acid is any nucleic acid other than a Huntingtin gene transcript.

a. Single-Nucleotide Polymorphism

In certain embodiments, the invention provides selective antisense compounds that have greater activity for a target nucleic acid than for a homologous or partially homologous non-target nucleic acid. In certain such embodiments, the target and non-target nucleic acids are not functionally related to one another (e.g., are transcripts from different genes). In certain embodiments, the target and not-target nucleic acids are allelic variants of one another. Certain embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCL5 gene encoding the chemokine CCL5 involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry 2006, 11: 76); TGF-beta1 gene encoding TGF-beta1 protein involved in breast cancer and prostate cancer (Cancer Epidemiol. Biomarkers Prey. 2004, 13: 759); AChR gene encoding acetylcholine receptor involved in congenital myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Gene.t 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med Biol. 2008, 613:203)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

i. Certain Huntingtin Targets

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 (replaced by GENBANK Accession No. NT_006051), incorporated herein as SEQ ID NO: 1, and NM_002111.6, incorporated herein as SEQ ID NO: 574.

Table 14 provides SNPs found in the GM04022, GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM04022 cell line is heterozygous TC, the GM02171 cell line is homozygous CC, the GM02173 cell line is heterozygous TC, and the GM04281 cell line is homozygous TT. Fifty percent of HD patients have a Tat SNP position rs6446723.

TABLE 14

Allelic Variations for SNPs Associated with HD

| SNP | Variation | GM04022 | GM02171 | GM02173 | GM04281 | TargetPOP | allele |
|---|---|---|---|---|---|---|---|
| rs6446723 | T/C | TC | CC | TC | TT | 0.50 | T |
| rs3856973 | A/G | AG | AA | AG | GG | 0.50 | G |
| rs2285086 | A/G | AG | GG | AG | AA | 0.50 | A |
| rs363092 | A/C | AC | AA | AC | CC | 0.49 | C |
| rs916171 | C/G | GC | GG | GC | CC | 0.49 | C |
| rs6844859 | T/C | TC | CC | TC | TT | 0.49 | T |
| rs7691627 | A/G | AG | AA | AG | GG | 0.49 | G |
| rs4690073 | A/G | AG | AA | AG | GG | 0.49 | G |
| rs2024115 | A/G | AG | GG | AG | AA | 0.48 | A |
| rs11731237 | T/C | CC | CC | TC | TT | 0.43 | T |
| rs362296 | A/C | CC | AC | AC | AC | 0.42 | C |
| rs10015979 | A/G | AA | AA | AG | GG | 0.42 | G |
| rs7659144 | C/G | CG | CG | CG | CC | 0.41 | C |
| rs363096 | T/C | CC | CC | TC | TT | 0.40 | T |
| rs362273 | A/G | AA | AG | AG | AA | 0.39 | A |
| rs16843804 | T/C | CC | TC | TC | CC | 0.38 | C |
| rs362271 | A/G | GG | AG | AG | GG | 0.38 | G |
| rs362275 | T/C | CC | TC | TC | CC | 0.38 | C |
| rs3121419 | T/C | CC | TC | TC | CC | 0.38 | C |
| rs362272 | A/G | GG | — | AG | GG | 0.38 | G |
| rs3775061 | A/G | AA | AG | AG | AA | 0.38 | A |
| rs34315806 | T/C | CC | TC | TC | CC | 0.38 | C |
| rs363099 | T/C | CC | TC | TC | CC | 0.38 | C |
| rs2298967 | T/C | TT | TC | TC | TT | 0.38 | T |
| rs363088 | A/T | AA | TA | TA | AA | 0.38 | A |
| rs363064 | T/C | CC | TC | TC | CC | 0.35 | C |
| rs363102 | A/G | AG | AA | AA | AA | 0.23 | G |

TABLE 14-continued

Allelic Variations for SNPs Associated with HD

| SNP | Variation | GM04022 | GM02171 | GM02173 | GM04281 | TargetPOP | allele |
|---|---|---|---|---|---|---|---|
| rs2798235 | A/G | AG | GG | GG | GG | 0.21 | A |
| rs363080 | T/C | TC | CC | CC | CC | 0.21 | T |
| rs363072 | A/T | TA | TA | AA | AA | 0.13 | A |
| rs363125 | A/C | AC | AC | CC | CC | 0.12 | C |
| rs362303 | T/C | TC | TC | CC | CC | 0.12 | C |
| rs362310 | T/C | TC | TC | CC | CC | 0.12 | C |
| rs10488840 | A/G | AG | AG | GG | GG | 0.12 | G |
| rs362325 | T/C | TC | TC | TT | TT | 0.11 | T |
| rs35892913 | A/G | GG | GG | GG | GG | 0.10 | A |
| rs363102 | A/G | AG | AA | AA | AA | 0.09 | A |
| rs363096 | T/C | CC | CC | TC | TT | 0.09 | C |
| rs11731237 | T/C | CC | CC | TC | TT | 0.09 | C |
| rs10015979 | A/G | AA | AA | AG | GG | 0.08 | A |
| rs363080 | T/C | TC | CC | CC | CC | 0.07 | C |
| rs2798235 | A/G | AG | GG | GG | GG | 0.07 | G |
| rs1936032 | C/G | GC | CC | CC | CC | 0.06 | C |
| rs2276881 | A/G | GG | GG | GG | GG | 0.06 | G |
| rs363070 | A/G | AA | AA | AA | AA | 0.06 | A |
| rs35892913 | A/G | GG | GG | GG | GG | 0.04 | G |
| rs12502045 | T/C | CC | CC | CC | CC | 0.04 | C |
| rs6446723 | T/C | TC | CC | TC | TT | 0.04 | C |
| rs7685686 | A/G | AG | GG | AG | AA | 0.04 | G |
| rs3733217 | T/C | CC | CC | CC | CC | 0.03 | C |
| rs6844859 | T/C | TC | CC | TC | TT | 0.03 | C |
| rs362331 | T/C | TC | CC | TC | TT | 0.03 | C |

E. Certain Indications

In certain embodiments, provided herein are methods of treating an animal or individual comprising administering one or more pharmaceutical compositions as described herein. In certain embodiments, the individual or animal has Huntington's disease.

In certain embodiments, compounds targeted to huntingtin as described herein may be administered to reduce the severity of physiological symptoms of Huntington's disease. In certain embodiments, compounds targeted to huntingtin as described herein may be administered to reduce the rate of degeneration in an individual or an animal having Huntington's disease. In certain embodiments, compounds targeted to huntingtin as described herein may be administered regeneration function in an individual or an animal having Huntington's disease. In certain embodiments, symptoms of Huntingtin's disease may be reversed by treatment with a compound as described herein.

In certain embodiments, compounds targeted to huntingtin as described herein may be administered to ameliorate one or more symptoms of Huntington's disease. In certain embodiments administration of compounds targeted to huntingtin as described herein may improve the symptoms of Huntington's disease as measured by any metric known to those having skill in the art. In certain embodiments, administration of compounds targeted to huntingtin as described herein may improve a rodent's rotaraod assay performance. In certain embodiments, administration of compounds targeted to huntingtin as described herein may improve a rodent's plus maze assay. In certain embodiments, administration of compounds targeted to huntingtin as described herein may improve a rodent's open field assay performance.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual or animal in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

F. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

G. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

H. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Single Nucleotide Polymorphisms (SNPs) in the Huntingtin (HTT) Gene Sequence

SNP positions (identified by Hayden et al, WO/2009/1135322) associated with the HTT gene were mapped to the HTT genomic sequence, designated herein as SEQ ID NO: 1 (NT_006081.18 truncated from nucleotides 1566000 to 1768000). Table 15 provides SNP positions associated with the HTT gene. Table 15 provides a reference SNP ID number from the Entrez SNP database at the National Center for Biotechnology Information (NCBI, http://www.ncbi.nlm.nih.gov/sites/entrez?db=snp), incorporated herein by reference. Table 15 furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 1. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

TABLE 15

Single Nuclear Polymorphisms (SNPs) and their positions on SEQ ID NO: 1

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | A | G |
| rs363099 | 101709 | T/C | C | T |
| rs363096 | 119674 | T/C | T | c |
| rs2298967 | 125400 | C/T | T | c |
| rs2298969 | 125897 | A/G | G | A |
| rs6844859 | 130139 | C/T | T | c |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |

TABLE 15-continued

Single Nuclear Polymorphisms (SNPs) and their positions on SEQ ID NO: 1

| RS No. | SNP position | Polymorphism | Major allele | Minor allele |
|---|---|---|---|---|
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G |

Example 2

Modified Oligonucleotides Targeting Huntingtin (HTT) Single Nucleotide Polymorphisms (SNP)

A series of modified oligonucleotides were designed. These modified oligonucleotides were designed to target SNP positions associated with the HTT gene. In the tables, the 'k' subscript indicates an (S)-cEt modification; 'e' subscript indicates MOE modification; 'g' subscript indicates a 3'-fluoro-HNA modification; 'f' subscript indicates 2'-alpha-fluoro-2'-deoxyribose; 'm' before the cytosine residue indicates a 5-methylcytosine; 'x' before the thymine residue indicates a 2-thiothymine; number along with 'd' indicates a the number of deoxyribose nucleosides; the 'o' subscript after the sugar modification subscripts indicates a phosphate ester linkage; 'mp' subscript after the nucleoside indicates a methylphosphonate full linker; 's' subscript after the nucleoside indicates a phosphorothioate internucleoside linkages. The underlined nucleoside indicates the position on the modified oligonucleotide opposite to the SNP position.

TABLE 16

Modified oligonucleotides targeting Huntingtin (HTT) SNP rs2024115

| Isis No. | SEQUENCE | SNP | Motif | SEQ ID. NO. |
|---|---|---|---|---|
| 589567 | $T_{es}$ $mC_{es}$ $A_{ks}$ $A_{ks}$ $G_{ds}$ $mC_{ds}$ $\underline{T_{ds}}$ $A_{ds}$ $G_{ds}$ $T_{ds}$ $A_{ds}$ $A_{ds}$ $mC_{ks}$ $G_{ks}$ $A_{es}$ $T_{es}$ $G_e$ | rs2024115 | eekk-d8-kkeee | 37 |
| 607448 | $mC_{es}$ $A_{ks}$ $A_{ks}$ $G_{ds}$ $mC_{ds}$ $\underline{T_{ds}}$ $A_{ds}$ $G_{ds}$ $T_{ds}$ $A_{ds}$ $A_{ds}$ $mC_{ks}$ $G_{ks}$ $A_{es}$ $T_{es}$ $G_e$ | rs2024115 | ekk-d8-kkeee | 102 |
| 607441 | $T_{es}$ $mC_{es}$ $A_{ks}$ $A_{ks}$ $G_{ds}$ $mC_{ds}$ $\underline{T_{ds}}$ $A_{ds}$ $G_{ds}$ $T_{ds}$ $A_{ds}$ $A_{ds}$ $mC_{ks}$ $G_{ks}$ $A_{es}$ $T_e$ | rs2024115 | eekk-d8-kkee | 103 |
| 607455 | $A_{es}$ $A_{ks}$ $G_{ds}$ $mC_{ds}$ $\underline{T_{ds}}$ $A_{ds}$ $G_{ds}$ $T_{ds}$ $A_{ds}$ $A_{ds}$ $mC_{ks}$ $G_{ks}$ $A_{es}$ $T_{es}$ $G_e$ | rs2024115 | ek-d8-kkeee | 104 |
| 607462 | $mC_{es}$ $A_{es}$ $A_{ks}$ $G_{ds}$ $mC_{ds}$ $\underline{T_{ds}}$ $A_{ds}$ $G_{ds}$ $T_{ds}$ $A_{ds}$ $A_{ds}$ $mC_{ks}$ $G_{ks}$ $A_{es}$ $T_e$ | rs2024115 | eek-d8-kkee | 105 |
| 607469 | $T_{es}$ $mC_{es}$ $A_{es}$ $A_{ks}$ $G_{ds}$ $mC_{ds}$ $\underline{T_{ds}}$ $A_{ds}$ $G_{ds}$ $T_{ds}$ $A_{ds}$ $A_{ds}$ $mC_{ks}$ $G_{es}$ $A_e$ | rs2024115 | eeek-d8-kee | 106 |

TABLE 17

Modified oligonucleotides targeting Huntingtin (HTT) SNP rs6446723

| Isis No. | SEQUENCE | SNP | Motif | SEQ ID. NO. |
|---|---|---|---|---|
| 589450 | $T_{es}$ $A_{es}$ $A_{es}$ $T_{ks}$ $T_{ks}$ $T_{ds}$ $T_{ds}$ $mC_{ds}$ $T_{ds}$ $\underline{A}_{ds}$ $G_{ds}$ $A_{ds}$ $mC_{ks}$ $T_{ks}$ $T_{es}$ $T_{es}$ $A_{e}$ | rs6446723 | eeekk-d7-kkeee | 32 |
| 589546 | $T_{es}$ $A_{es}$ $A_{ks}$ $T_{ks}$ $T_{ds}$ $T_{ds}$ $T_{ds}$ $mC_{ds}$ $T_{ds}$ $\underline{A}_{ds}$ $G_{ds}$ $A_{ds}$ $mC_{ks}$ $T_{ks}$ $T_{es}$ $T_{es}$ $A_{e}$ | rs6446723 | eekk-d8-kkeee | 35 |
| 589547 | $A_{es}$ $A_{es}$ $T_{ks}$ $T_{ks}$ $T_{ds}$ $T_{ds}$ $mC_{ds}$ $T_{ds}$ $\underline{A}_{ds}$ $G_{ds}$ $A_{ds}$ $mC_{ds}$ $T_{ks}$ $T_{ks}$ $T_{es}$ $A_{es}$ $T_{e}$ | rs6446723 | eekk-d8-kkeee | 36 |
| 589718 | $T_{es}$ $A_{ks}$ $A_{es}$ $T_{ks}$ $T_{ds}$ $T_{ds}$ $T_{ds}$ $mC_{ds}$ $T_{ds}$ $\underline{A}_{ds}$ $G_{ds}$ $A_{ds}$ $mC_{ks}$ $T_{es}$ $T_{ks}$ $T_{es}$ $A_{e}$ | rs6446723 | ekek-d8-kekee | 44 |
| 617104 | $T_{es}$ $A_{es}$ $A_{eo}$ $T_{ko}$ $T_{ks}$ $T_{ds}$ $T_{ds}$ $mC_{ds}$ $T_{ds}$ $A_{ds}$ $G_{ds}$ $A_{ds}$ $mC_{ko}$ $T_{ko}$ $T_{es}$ $T_{es}$ $A_{e}$ | rs6446723 | eeekk-d7-kkeee | 84 |
| 617106 | $T_{es}$ $A_{eo}$ $A_{ko}$ $T_{ks}$ $T_{ds}$ $T_{ds}$ $mC_{ds}$ $T_{ds}$ $mC_{ds}$ $T_{ds}$ $A_{ds}$ $G_{ds}$ $A_{ds}$ $mC_{ko}$ $T_{ko}$ $T_{es}$ $T_{es}$ $A_{e}$ | rs6446723 | eekk-d8-kkeee | 85 |
| 617108 | $T_{es}$ $A_{ko}$ $A_{eo}$ $T_{ks}$ $T_{ds}$ $T_{ds}$ $mC_{ds}$ $T_{ds}$ $mC_{ds}$ $T_{ds}$ $A_{ds}$ $G_{ds}$ $A_{ds}$ $mC_{ko}$ $T_{eo}$ $T_{ks}$ $T_{es}$ $A_{e}$ | rs6446723 | ekek-d8-kekee | 86 |
| 617109 | $A_{es}$ $A_{eo}$ $T_{ko}$ $T_{ks}$ $T_{ds}$ $T_{ds}$ $mC_{ds}$ $T_{ds}$ $mC_{ds}$ $T_{ds}$ $A_{ds}$ $G_{ds}$ $A_{ds}$ $T_{ko}$ $T_{ko}$ $T_{es}$ $A_{es}$ $T_{e}$ | rs6446723 | eekk-d8-kkeee | 87 |
| 607446 | $A_{es}$ $A_{ks}$ $T_{ks}$ $T_{ds}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{es}$ $T_{es}$ $A_{e}$ | rs6446723 | ekk-d8-kkeee | 92 |
| 607439 | $T_{es}$ $A_{es}$ $A_{ks}$ $T_{ks}$ $T_{ds}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{es}$ $T_{e}$ | rs6446723 | eekk-d8-kkee | 93 |
| 607453 | $A_{es}$ $T_{ks}$ $T_{ds}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{es}$ $T_{es}$ $A_{e}$ | rs6446723 | ek-d8-kkeee | 94 |
| 607460 | $A_{es}$ $A_{ks}$ $T_{ks}$ $T_{ds}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{es}$ $T_{e}$ | rs6446723 | ekk-d8-kkee | 95 |
| 607467 | $T_{es}$ $A_{es}$ $A_{ks}$ $T_{ks}$ $T_{ds}$ $T_{ds}$ $T_{ds}$ $mC_{ds}$ $T_{ds}$ $A_{ds}$ $G_{ds}$ $A_{ds}$ $mC_{ks}$ $T_{es}$ $T_{e}$ | rs6446723 | eekk-d8-kee | 96 |
| 607447 | $A_{es}$ $T_{ks}$ $T_{ks}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{ks}$ $T_{es}$ $A_{es}$ $T_{e}$ | rs6446723 | ekk-d8-kkeee | 97 |
| 607440 | $A_{es}$ $A_{es}$ $T_{ks}$ $T_{ks}$ $T_{ds}$ $T_{ds}$ $mC_{ds}$ $T_{ds}$ $A_{ds}$ $G_{ds}$ $A_{ds}$ $mC_{ds}$ $T_{ks}$ $T_{ks}$ $T_{es}$ $A_{e}$ | rs6446723 | eekk-d8-kkee | 98 |
| 607454 | $T_{es}$ $T_{ks}$ $T_{ds}$ $T_{ds}$ $mC_{ds}$ $T_{ds}$ $A_{ds}$ $G_{ds}$ $A_{ds}$ $mC_{ds}$ $T_{ks}$ $T_{ks}$ $T_{es}$ $A_{es}$ $T_{e}$ | rs6446723 | ek-d8-kkeee | 99 |
| 607461 | $A_{es}$ $T_{ks}$ $T_{ks}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{ks}$ $T_{es}$ $A_{e}$ | rs6446723 | ekk-d8-kkee | 100 |
| 607468 | $A_{es}$ $A_{es}$ $T_{es}$ $T_{ks}$ $T_{ds}$ $T_{ds}$ $mC_{ds}$ $T_{ds}$ $A_{ds}$ $G_{ds}$ $A_{ds}$ $mC_{ds}$ $T_{ks}$ $T_{es}$ $T_{e}$ | rs6446723 | eeek-d8-kee | 101 |
| 607474 | $A_{es}$ $A_{es}$ $T_{es}$ $T_{ks}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{es}$ $T_{es}$ $A_{e}$ | rs6446723 | eeek-d7-kkeee | 127 |
| 607475 | $T_{es}$ $A_{es}$ $A_{es}$ $T_{ks}$ $T_{ds}$ $T_{ds}$ $T_{ds}$ $mC_{ds}$ $T_{ds}$ $A_{ds}$ $G_{ds}$ $A_{ks}$ $mC_{ks}$ $T_{es}$ $T_{es}$ $T_{e}$ | rs6446723 | eeek-d7-kkeee | 128 |
| 607476 | $A_{es}$ $T_{es}$ $T_{ks}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{es}$ $T_{es}$ $A_{e}$ | rs6446723 | eek-d7-kkeee | 129 |
| 607477 | $A_{es}$ $A_{es}$ $T_{es}$ $T_{ks}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{es}$ $T_{e}$ | rs6446723 | eeek-d7-kkee | 130 |
| 607478 | $T_{es}$ $A_{es}$ $A_{es}$ $T_{es}$ $T_{ks}$ $T_{ds}$ $T_{ds}$ $mC_{ds}$ $T_{ds}$ $A_{ds}$ $G_{ds}$ $A_{ds}$ $mC_{ks}$ $T_{ks}$ $T_{e}$ | rs6446723 | eeeek-d7-kke | 131 |

TABLE 18

Modified oligonucleotides targeting
Huntingtin (H77) SNP rs363080

| Isis No. | SEQUENCE | SNP | Motif | SEQ ID NO |
|---|---|---|---|---|
| 609234 | $A_{es}$ $G_{ks}$ $A_{ks}$ $G_{ds}$ $A_{ds}$ $A_{ds}$ $mC_{ds}$ $A_{ds}$ $A_{ds}$ $G_{ds}$ $A_{ds}$ $A_{le}$ $G_{ks}$ $G_{es}$ $mC_e$ | rs363080 | ekk-d8-kkee | 156 |
| 609235 | $G_{es}$ $A_{ks}$ $G_{ks}$ $A_{ds}$ $A_{ds}$ $mC_{ds}$ $A_{ds}$ $A_{ds}$ $G_{ds}$ $A_{ds}$ $A_{ds}$ $G_{ks}$ $G_{ks}$ $mC_{es}$ $T_e$ | rs363080 | ekk-d8-kkee | 157 |
| 609236 | $A_{es}$ $G_{ks}$ $A_{ks}$ $A_{ds}$ $mC_{ds}$ $A_{ds}$ $A_{ds}$ $G_{ds}$ $A_{ds}$ $A_{ds}$ $G_{ds}$ $G_{ds}$ $mC_{ks}$ $T_{es}$ $mC_e$ | rs363080 | ekk-d8-kkee | 158 |
| 609237 | $G_{es}$ $A_{ks}$ $A_{ks}$ $mC_{ds}$ $A_{ds}$ $A_{ds}$ $G_{ds}$ $A_{ds}$ $A_{ds}$ $G_{ds}$ $G_{ds}$ $mC_{ks}$ $T_{ks}$ $mC_{es}$ $mC_e$ | rs363080 | ekk-d8-kkee | 159 |
| 609238 | $A_{es}$ $G_{ks}$ $A_{ks}$ $G_{ds}$ $A_{ds}$ $A_{ds}$ $mC_{ds}$ $A_{ds}$ $A_{ds}$ $G_{ds}$ $A_{ds}$ $A_{ks}$ $G_{ks}$ $G_{es}$ $mC_{es}$ $T_e$ | rs363080 | ekk-d8-kkeee | 160 |
| 609239 | $G_{es}$ $A_{ks}$ $G_{ks}$ $A_{ds}$ $A_{ds}$ $mC_{ds}$ $A_{ds}$ $A_{ds}$ $G_{ds}$ $A_{ds}$ $A_{ds}$ $G_{ks}$ $G_{ks}$ $mC_{es}$ $T_{es}$ $mC_e$ | rs363080 | ekk-d8-kkeee | 161 |
| 609240 | $A_{es}$ $G_{ks}$ $A_{ks}$ $A_{ds}$ $mC_{ds}$ $A_{ds}$ $A_{ds}$ $G_{ds}$ $A_{ds}$ $A_{ds}$ $G_{ds}$ $G_{ks}$ $mC_{ks}$ $T_{es}$ $mC_{es}$ $mC_e$ | rs363080 | ekk-d8-kkeee | 162 |
| 609241 | $G_{es}$ $A_{ks}$ $A_{ks}$ $mC_{ds}$ $A_{ds}$ $A_{ds}$ $G_{ds}$ $A_{ds}$ $A_{ds}$ $G_{ds}$ $G_{ds}$ $mC_{ks}$ $T_{ks}$ $mC_{es}$ $mC_{es}$ $A_e$ | rs363080 | ekk-d8-kkeee | 163 |

TABLE 19

Modified oligonucleotides targeting
Huntingtin (HTT) SNP rs363064

| Isis No. | SEQUENCE | SNP | Motif | SEQ ID NO |
|---|---|---|---|---|
| 589532 | $G_{es}$ $A_{es}$ $A_{es}$ $T_{ks}$ $A_{ks}$ $mC_{ds}$ $\underline{G}_{ds}$ $G_{ds}$ $G_{ds}$ $T_{ds}$ $A_{ds}$ $A_{ds}$ $mC_{ks}$ $A_{ks}$ $T_{es}$ $T_{es}$ $T_e$ | rs363064 | eeekk-d7-kkeee | 33 |
| 589645 | $G_{es}$ $A_{es}$ $A_{ks}$ $T_{ks}$ $A_{ds}$ $mC_{ds}$ $\underline{G}_{ds}$ $G_{ds}$ $G_{ds}$ $T_{ds}$ $A_{ds}$ $A_{ds}$ $mC_{ks}$ $A_{ks}$ $T_{es}$ $T_{es}$ $T_e$ | rs363064 | eekk-d8-kkeee | 42 |
| 589646 | $A_{es}$ $A_{es}$ $T_{ks}$ $A_{ks}$ $mC_{ds}$ $\underline{G}_{ds}$ $G_{ds}$ $G_{ds}$ $T_{ds}$ $A_{ds}$ $A_{ds}$ $mC_{ds}$ $A_{ks}$ $T_{ks}$ $T_{es}$ $T_{es}$ $T_e$ | rs363064 | eekk-d8-kkeee | 43 |
| 617107 | $A_{es}$ $A_{e}o$ $T_{ko}$ $A_{ks}$ $mC_{ds}$ $\underline{G}_{ds}$ $G_{ds}$ $G_{ds}$ $T_{ds}$ $A_{ds}$ $A_{ds}$ $mC_{ds}$ $A_{ko}$ $T_{ko}$ $T_{es}$ $T_{es}$ $T_e$ | rs363064 | eekk-d8-kkeee | 88 |
| 617110 | $G_{es}$ $A_{es}$ $A_{e}o$ $T_{ko}$ $A_{ks}$ $mC_{ds}$ $\underline{G}_{ds}$ $G_{ds}$ $G_{ds}$ $T_{ds}$ $A_{ds}$ $A_{ds}$ $mC_{ko}$ $T_{ko}$ $T_{es}$ $T_{es}$ $T_e$ | rs363064 | eeekk-d7-kkeee | 89 |
| 607449 | $A_{es}$ $T_{ks}$ $A_{ks}$ $mC_{ds}$ $\underline{G}_{ds}$ $G_{ds}$ $G_{ds}$ $T_{ds}$ $A_{ds}$ $A_{ds}$ $mC_{ds}$ $A_{ks}$ $T_{ks}$ $T_{es}$ $T_{es}$ $T_e$ | rs363064 | ekk-d8-kkeee | 107 |
| 607442 | $A_{es}$ $A_{es}$ $T_{ks}$ $A_{ks}$ $mC_{ds}$ $\underline{G}_{ds}$ $G_{ds}$ $G_{ds}$ $T_{ds}$ $A_{ds}$ $A_{ds}$ $m_{ds}$ $A_{ks}$ $T_{ks}$ $T_{es}$ $T_e$ | rs363064 | eekk-d8-kkee | 108 |
| 607456 | $T_{es}$ $A_{ks}$ $mC_{ds}$ $\underline{G}_{ds}$ $G_{ds}$ $G_{ds}$ $T_{ds}$ $A_{ds}$ $A_{ds}$ $A_{ds}$ $mC_{ds}$ $A_{ks}$ $T_{ks}$ $T_{es}$ $T_{es}$ $T_e$ | rs363064 | ek-d8-kkeee | 109 |
| 607463 | $A_{es}$ $T_{es}$ $A_{ks}$ $mC_{ds}$ $\underline{G}_{ds}$ $G_{ds}$ $G_{ds}$ $T_{ds}$ $A_{ds}$ $A_{ds}$ $mC_{ds}$ $A_{ks}$ $T_{ks}$ $T_{es}$ $T_e$ | rs363064 | eek-d8-kkeee | 110 |
| 607470 | $A_{es}$ $A_{es}$ $T_{es}$ $A_{ks}$ $mC_{ds}$ $\underline{G}_{ds}$ $G_{ds}$ $G_{ds}$ $T_{ds}$ $A_{ds}$ $A_{ds}$ $m_{ds}$ $A_{ks}$ $T_{es}$ $T_e$ | rs363064 | eeek-d8-kee | 111 |
| 607450 | $A_{es}$ $A_{ks}$ $T_{ks}$ $A_{ds}$ $mC_{ds}$ $\underline{G}_{ds}$ $G_{ds}$ $G_{ds}$ $T_{ds}$ $A_{ds}$ $A_{ds}$ $mC_{ks}$ $A_{ks}$ $T_{es}$ $T_{es}$ $T_e$ | rs363064 | ekk-d8-kkeee | 112 |
| 607443 | $G_{es}$ $A_{es}$ $A_{ks}$ $T_{ks}$ $A_{ds}$ $mC_{ds}$ $\underline{G}_{ds}$ $G_{ds}$ $G_{ds}$ $T_{ds}$ $A_{ds}$ $A_{ds}$ $m_{ks}$ $A_{ks}$ $T_{es}$ $T_e$ | rs363064 | eekk-d8-kkee | 113 |
| 607457 | $A_{es}$ $T_{ks}$ $A_{ks}$ $mC_{ds}$ $\underline{G}_{ds}$ $G_{ds}$ $G_{ds}$ $T_{ds}$ $A_{ds}$ $A_{ds}$ $m_{ks}$ $A_{ks}$ $T_{es}$ $T_{es}$ $T_e$ | rs363064 | ek-d8-kkeee | 114 |

TABLE 19-continued

Modified oligonucleotides targeting Huntingtin (HTT) SNP rs363064

| Isis No. | SEQUENCE | SNP | Motif | SEQ ID NO |
|---|---|---|---|---|
| 607464 | $A_{es}$ $A_{ks}$ $T_{ks}$ $A_{ds}$ $mC_{ds}$ $\underline{G}_{ds}$ $G_{ds}$ $G_{ds}$ $T_{ds}$ $A_{ds}$ $A_{ds}$ $m_{ks}$ $A_{ks}$ $T_{es}$ $T_{e}$ | rs363064 | ekk-d8-kkee | 115 |
| 607471 | $G_{es}$ $A_{es}$ $A_{es}$ $T_{ks}$ $A_{ds}$ $mC_{ds}$ $\underline{G}_{ds}$ $G_{ds}$ $G_{ds}$ $T_{ds}$ $A_{ds}$ $A_{ds}$ $m_{ks}$ $AC_{s}$ $T_{e}$ | rs363064 | eeek-d8-kee | 116 |

Table 20

Modified oligonucleotides targeting Huntingtin (HTT) SNP rs7685686

| Isis No. | SEQUENCE | SNP | Motif | SEQ ID. NO |
|---|---|---|---|---|
| 460209 | $T_{es}$ $A_{ks}$ $A_{ks}$ $A_{ds}$ $T_{ds}$ $T_{ds}$ $G_{ds}$ $\underline{T}_{ds}$ $m_{ds}$ $A_{ds}$ $T_{ds}$ $mC_{ds}$ $A_{ks}$ $mC_{ks}$ $mC_{e}$ | rs7685686 | ekk-d9-kke | 3 |
| 476333 | $A_{es}$ $T_{ks}$ $A_{es}$ $A_{ks}$ $T_{ds}$ $T_{ds}$ $G_{ds}$ $\underline{T}_{ds}$ $m_{ds}$ $A_{ds}$ $T_{ds}$ $mC_{ds}$ $A_{ks}$ $mC_{es}$ $mC_{ks}$ $A_{e}$ | rs7685686 | ekek-d9-keke | 4 |
| 540083 | $A_{es}$ $A_{ks}$ $T_{ks}$ $T_{ks}$ $G_{ds}$ $\underline{T}_{ds}$ $m_{ds}$ $A_{ds}$ $T_{ds}$ $mC_{ds}$ $A_{ds}$ $mC_{ds}$ $m_{ds}$ $A_{ks}$ $G_{e}$ | rs7685686 | ekkk-d9-ke | 7 |
| 540094 | $T_{es}$ $T_{ks}$ $G_{ds}$ $\underline{T}_{ds}$ $mC_{ds}$ $A_{ds}$ $T_{ds}$ $mC_{ds}$ $A_{ds}$ $mC_{ds}$ $mC_{ds}$ $A_{ks}$ $G_{ks}$ $A_{e}$ | rs7685686 | ek-d9-kkke | 8 |
| 540095 | $A_{es}$ $T_{ks}$ $T_{ds}$ $G_{ds}$ $T_{ds}$ $mC_{ds}$ $A_{ds}$ $\underline{T}_{ds}$ $mC_{ds}$ $A_{ds}$ $mC_{ds}$ $mC_{ks}$ $A_{ks}$ $G_{ks}$ $A_{e}$ | rs7685686 | ek-d9-kkke | 9 |
| 540096 | $A_{es}$ $A_{ks}$ $T_{ds}$ $T_{ds}$ $G_{ds}$ $\underline{T}_{ds}$ $mC_{ds}$ $A_{ds}$ $T_{ds}$ $mC_{ds}$ $A_{ds}$ $mC_{ks}$ $mC_{ks}$ $A_{ks}$ $G_{e}$ | rs7685686 | ek-d9-kkke | 10 |
| 540108 | $A_{es}$ $T_{es}$ $A_{es}$ $A_{ks}$ $A_{ks}$ $T_{ds}$ $T_{ds}$ $G_{ds}$ $\underline{T}_{ds}$ $mC_{ds}$ $A_{ds}$ $T_{ds}$ $m_{ks}$ $A_{ks}$ $mC_{es}$ $mC_{es}$ $A_{e}$ | rs7685686 | eeekk-d7-kkeee | 11 |
| 550913 | $A_{ks}$ $A_{ks}$ $T_{es}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{es}$ $T_{ks}$ $T_{k}$ | rs7685686 | kkekk-d9-kkekk | 12 |
| 551429 | $T_{es}$ $A_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{e}$ | rs7685686 | eeekk-d7-kke | 13 |
| 556845 | $T_{es}$ $A_{ks}$ $A_{ks}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ks}$ $mC_{ks}$ $m_{e}$ | rs7685686 | ekk-d9-kke | 14 |
| 558257 | $T_{es}$ $A_{ks}$ $A_{ks}$ $A_{ds}$ $T_{ds}$ $Tdmp$ $G_{ds}$ $\underline{T}_{ds}$ $mC_{ds}$ $A_{ds}$ $T_{ds}$ $mC_{ds}$ $A_{ks}$ $mC_{ks}$ $m_{e}$ | rs7685686 | ekk-d9-kke | 15 |
| 566267 | $T_{es}$ $A_{ks}$ $A_{ks}$ $A_{es}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{e}$ | rs7685686 | ekkdk-d7-kke | 16 |
| 568876 | $A_{ks}$ $T_{ks}$ $A_{ks}$ $A_{ks}$ $A_{ks}$ $T_{ds}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{ks}$ $A_{k}$ | rs7685686 | kkkkk-d7-kkkkk | 17 |
| 571036 | $A_{es}$ $T_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{ks}$ $A_{e}$ | rs7685686 | ekekek-d7-keke | 18 |
| 571037 | $A_{es}$ $T_{es}$ $A_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{ks}$ $A_{e}$ | rs7685686 | eeeekk-d7-keke | 19 |
| 571039 | $A_{es}$ $T_{ks}$ $A_{es}$ $A_{ks}$ $A_{ds}$ $xT_{ds}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{ks}$ $A_{e}$ | rs7685686 | ekek-d9-keke | 20 |
| 571069 | $A_{es}$ $T_{es}$ $A_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{es}$ $A_{e}$ | rs7685686 | eeeekk-d7-kkee | 21 |
| 571171 | $A_{es}$ $T_{ks}$ $A_{es}$ $A_{ks}$ $A_{ds}$ $T_{ds}$ $T_{dmp}$ $G_{ds}$ $\underline{T}_{ds}$ $mC_{ds}$ $A_{ds}$ $T_{ds}$ $mC_{ds}$ $A_{ks}$ $mC_{es}$ $mC_{ks}$ $A_{e}$ | rs7685686 | ekek-d9-keke | 22 |
| 572771 | $T_{es}$ $A_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{es}$ $A_{e}$ | rs7685686 | eeekk-d7-kkee | 23 |
| 572772 | $A_{es}$ $T_{es}$ $A_{es}$ $A_{es}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{e}$ | rs7685686 | eeeekk-d7-kke | 24 |
| 575007 | $T_{es}$ $A_{ks}$ $A_{ks}$ $A_{ds}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{e}$ | rs7685686 | ekkdk-d7-kke | 25 |
| 575008 | $T_{es}$ $A_{ks}$ $A_{ks}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $m_{e}$ | rs7685686 | ekkkk-d7-kke | 26 |
| 585246 | $T_{es}$ $A_{es}$ $A_{es}$ $A_{ks}$ $T_{ks}$ $T_{ds}$ $G_{ds}$ $T_{ds}$ $mC_{ds}$ $A_{ds}$ $T_{ds}$ $mC_{ds}$ $A_{ks}$ $mC_{ks}$ $mC_{es}$ $A_{es}$ $G_{e}$ | rs7685686 | eeekk-d7-kkeee | 31 |
| 589537 | $A_{es}$ $A_{es}$ $A_{ks}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ks}$ $mC_{ks}$ $A_{es}$ $G_{es}$ $A_{e}$ | rs7685686 | eekk-d8-kkeee | 34 |
| 593199 | $T_{es}$ $A_{es}$ $A_{eo}$ $A_{ko}$ $T_{ks}$ $T_{ds}$ $G_{ds}$ $\underline{T}_{ds}$ $mC_{ds}$ $A_{ds}$ $T_{ds}$ $mC_{ds}$ $A_{ko}$ $C_{ks}$ $C_{e}$ | rs7685686 | eeekk-d7-kke | 47 |
| 593200 | $A_{es}$ $T_{ks}$ $T_{ds}$ $G_{ds}$ $\underline{T}_{ds}$ $mCA_{ds}$ $T_{ds}$ $mC_{ds}$ $A_{ds}$ $mC_{ds}$ $mC_{ko}$ $A_{ko}$ $G_{ks}$ $A_{e}$ | rs7685686 | ek-d9-kkke | 48 |
| 593201 | $A_{es}$ $T_{ko}$ $A_{es}$ $A_{ko}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{ko}$ $mC_{es}$ $mC_{ks}$ $A_{e}$ | rs7685686 | ekekek-d7-keke | 49 |
| 593202 | $A_{es}$ $T_{ko}$ $A_{ko}$ $A_{ko}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ko}$ $mC_{ko}$ $mC_{ks}$ $A_{e}$ | rs7685686 | ekkkk-d7-kkke | 50 |

TABLE 20-continued

Modified oligonucleotides targeting Huntingtin (HTT) SNP rs7685686

| Isis No. | SEQUENCE | SNP | Motif | SEQ ID. NO |
|---|---|---|---|---|
| 593203 | $T_{ks}$ $A_{ko}$ $A_{ko}$ $A_{ko}$ $T_{ks}$ $T_{ds}$ $G_{ds}$ $\underline{T}_{ds}$ $mC_{ds}$ $A_{ds}$ $T_{ds}$ $mC_{ds}$ $A_{ko}$ $mC_{ko}$ $mC_{ks}$ $A_{ks}$ $G_k$ | rs7685686 | kkkkk-d7-kkkkk | 51 |
| 593204 | $A_{ks}$ $T_{ko}$ $A_{ko}$ $A_{ko}$ $A_{ko}$ $T_{ds}$ $T_{ds}$ $G_{ds}$ $T_{dsm}$ $C_{ds}$ $A_{ds}$ $T_{ds}$ $mC_{ko}$ $A_{ko}$ $mC_{ko}$ $mC_{ko}$ $A_k$ | rs7685686 | kkkkk-d7-kkkkk | 52 |
| 598229 | $A_{es}$ $T_{es}$ $A_{es}$ $A_{es}$ $A_{ks}$ $T_{ks}$ $T_{ds}$ $G_{ds}$ $\underline{T}_{ds}$ $mC_{ks}$ $A_{ds}$ $T_{ds}$ $m_{ds}$ $A_{ks}$ $mC_{es}$ $mC_{ks}$ $A_e$ | rs7685686 | eeeekk-d3-k-d3-keke | 53 |
| 598299 | $T_{es}$ $A_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{es}$ $A_e$ | rs7685686 | eeekk-d7-keee | 54 |
| 598300 | $T_{es}$ $A_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{es}$ $mC_{es}$ $mC_{es}$ $A_e$ | rs7685686 | eeekk-d7-eeee | 55 |
| 598301 | $T_{es}$ $A_{es}$ $A_{es}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{es}$ $A_e$ | rs7685686 | eeeek-d7-kkee | 56 |
| 598302 | $T_{es}$ $A_{es}$ $A_{es}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{es}$ $A_e$ | rs7685686 | eeeek-d7-keee | 57 |
| 598303 | $T_{es}$ $A_{es}$ $A_{es}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{es}$ $mC_{es}$ $mC_{es}$ $A_e$ | rs7685686 | eeeek-d7-eeee | 58 |
| 598304 | $T_{es}$ $A_{es}$ $A_{es}$ $A_{ds}$ $T_{ks}$ $T_{ds}$ $G_{ds}$ $\underline{T}_{ds}$ $mC_{ds}$ $A_{ds}$ $T_{ds}$ $m_{ds}$ $A_{ks}$ $mC_{es}$ $mC_{es}$ $A_e$ | rs7685686 | eeedk-d7-keee | 59 |
| 598305 | $A_{es}$ $T_{es}$ $A_{es}$ $A_{es}$ $A_{ds}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $m_{ks}$ $mC_{es}$ $A_e$ | rs7685686 | eeeedk-d7-kkee | 60 |
| 598306 | $A_{es}$ $T_{es}$ $A_{es}$ $A_{es}$ $A_{ds}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $m_{es}$ $A_e$ | rs7685686 | eeeedk-d7-keee | 61 |
| 598307 | $A_{es}$ $T_{es}$ $A_{es}$ $A_{es}$ $A_{ds}$ $T_{ks}$ $T_{ds}$ $G_{ds}$ $\underline{T}_{ds}$ $mC_{ds}$ $A_{ds}$ $T_{ds}$ $mC_{ds}$ $A_{es}$ $mC_{es}$ $mC_{es}$ $A_e$ | rs7685686 | eeeedk-d7-eeee | 62 |
| 598308 | $T_{es}$ $A_{eo}$ $A_{eo}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{eo}$ $mC_{eo}$ $A_{es}$ $G_e$ | rs7685686 | eeeek-d7-keeee | 63 |
| 598309 | $A_{es}$ $A_{eo}$ $A_{eo}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{eo}$ $A_{eo}$ $G_{es}$ $A_e$ | rs7685686 | eeek-d7-keeeee | 64 |
| 598310 | $A_{es}$ $A_{eo}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{es}$ $A_{eo}$ $G_{eo}$ $A_{es}$ $A_e$ | rs7685686 | eek-d7-keeeeee | 65 |
| 606560 | $A_{es}$ $T_{es}$ $A_{es}$ $A_{ks}$ $A_{ds}$ $xT_{ds}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_{ks}$ $A_e$ | rs7685686 | eeek-d9-keke | 66 |
| 606561 | $A_{es}$ $T_{ks}$ $A_{es}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ks}$ $mC_{es}$ $mC_{es}$ $A_e$ | rs7685686 | ekek-d9-keee | 67 |
| 606562 | $A_{es}$ $T_{es}$ $A_{es}$ $A_{ks}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ks}$ $mC_{es}$ $mC_{es}$ $A_e$ | rs7685686 | eeek-d9-keee | 68 |
| 606578 | $A_{es}$ $T_{ks}$ $A_{es}$ $A_{ks}$ $A_{ds}$ $T_{ds}$ $T_{ds}$ $G_{ds}$ $\underline{T}_{ds}$ $mC_{ds}$ $A_{ks}$ $T_{ds}$ $mC_{ds}$ $A_{ks}$ $mC_{es}$ $mC_{ks}$ $A_e$ | rs7685686 | ekek-d6-k-dd-keke | 69 |
| 617115 | $A_{es}$ $T_{es}$ $A_{es}$ $A_{es}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_e$ | rs7685686 | eeeeek-d7-kke | 70 |
| 617116 | $A_{es}$ $T_{es}$ $A_{es}$ $A_{es}$ $A_{ks}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_e$ | rs7685686 | eeeekk-d7-kee | 71 |
| 617117 | $A_{es}$ $T_{es}$ $A_{es}$ $A_{es}$ $A_{es}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_e$ | rs7685686 | eeeeek-d7-kee | 72 |
| 617118 | $A_{es}$ $T_{eo}$ $A_{eo}$ $A_{eo}$ $A_{eo}$ $T_{ks}$ $T_{ds}$ $G_{ds}$ $\underline{T}_{ds}$ $mC_{ds}$ $A_{ds}$ $T_{ds}$ $mC_{ds}$ $A_{ks}$ $mC_{es}$ $mC_e$ | rs7685686 | eeeeek-d7-kee | 73 |
| 617119 | $A_{es}$ $T_{eo}$ $A_{eo}$ $A_{eo}$ $A_{eo}$ $T_{ks}$ $T_{ds}$ $G_{ds}$ $\underline{T}_{ds}$ $mC_{ds}$ $A_{ds}$ $T_{ds}$ $m_{ds}$ $A_{es}$ $mC_{es}$ $mC_e$ | rs7685686 | eeeeek-d7-eee | 74 |
| 617425 | $A_{es}$ $T_{es}$ $A_{es}$ $A_{es}$ $A_{es}$ $T_{ks}$ $T_{ds}$ $G_{ds}$ $\underline{T}_{ds}$ $m_{ds}$ $A_{ds}$ $T_{ds}$ $mC_{ds}$ $A_{es}$ $mC_{es}$ $mC_e$ | rs7685686 | eeeeek-d7-eee | 75 |
| 613581 | $A_{es}$ $A_{eo}$ $T_{eo}$ $A_{eo}$ $A_{es}$ $A_{ds}$ $T_{ks}$ $T_{ds}$ $G_{ds}$ $T_{ds}$ $mC_{ds}$ $A_{ds}$ $T_{ds}$ $mC_{ds}$ $A_{eo}$ $mC_{eo}$ $mC_{es}$ $A_{es}$ $G_e$ | rs7685686 | eeeeedk-d7-eeeee | 76 |
| 613582 | $A_{es}$ $T_{es}$ $A_{eo}$ $A_{eo}$ $A_{es}$ $T_{ks}$ $T_{ds}$ $G_{ds}$ $T_{ds}$ $m_{ds}$ $A_{ds}$ $T_{ds}$ $mC_{ds}$ $A_{eo}$ $mC_{eo}$ $mC_{eo}$ $A_{es}$ $G_{es}$ $A_e$ | rs7685686 | eeeeek-d7-eeeeee | 77 |
| 613583 | $T_{es}$ $A_{eo}$ $A_{eo}$ $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{eo}$ $mC_{eo}$ $A_{eo}$ $G_{es}$ $A_{es}$ $A_e$ | rs7685686 | eeeek-d7-eeeeeee | 78 |
| 613584 | $A_{es}$ $A_{eo}$ $A_{eo}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{eo}$ $mC_{eo}$ $A_{eo}$ $G_{eo}$ $A_{es}$ $A_{es}$ $A_e$ | rs7685686 | eeek-d7-eeeeeeee | 79 |
| 613585 | $A_{es}$ $A_{eo}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{eo}$ $A_{eo}$ $G_{eo}$ $A_{eo}$ $A_{es}$ $A_{es}$ $A_e$ | rs7685686 | eek-d7-eeeeeeeee | 80 |
| 613586 | $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_{eo}$ $A_{eo}$ $G_{eo}$ $A_{eo}$ $A_{eo}$ $A_{es}$ $A_e$ | rs7685686 | ek-d7-eeeeeeeee | 81 |
| 613588 | $T_{es}$ $A_{es}$ $A_{eo}$ $T_{eo}$ $A_{eo}$ $A_{eo}$ $A_{es}$ $T_{ks}$ $T_{ds}$ $G_{ds}$ $T_{ds}$ $mC_{ds}$ $A_{ds}$ $T_{ds}$ $mC_{ds}$ $A_{eo}$ $mC_{es}$ $mC_{es}$ $A_e$ | rs7685686 | eeeeeeek-d7-eee | 82 |
| 613589 | $T_{es}$ $T_{es}$ $A_{eo}$ $A_{eo}$ $T_{eo}$ $A_{eo}$ $A_{eo}$ $A_{es}$ $T_{ks}$ $T_{ds}$ $G_{ds}$ $T_{ds}$ $mC_{ds}$ $A_{ds}$ $T_{ds}$ $mC_{ds}$ $A_{es}$ $mC_{es}$ $mC_e$ | rs7685686 | eeeeeeeek-d7-eee | 83 |

Table 20-continued

Modified oligonucleotides targeting Huntingtin (HTT) SNP rs7685686

| Isis No. | SEQUENCE | SNP | Motif | SEQ ID. NO |
|---|---|---|---|---|
| 617105 | $A_{es}$ $A_{eo}$ $A_{ko}$ $T_{ks}$ $T_{ds}$ $G_{ds}$ $T_{ds}$ $mC_{ds}$ $A_{ds}$ $T_{ds}$ $mC_{ds}$ $A_{ds}$ $mC_{ko}$ $mC_{ko}$ $A_{es}$ $G_{es}$ $A_{e}$ | rs7685686 | eekk-d8-kkeee | 90 |
| 617111 | $A_{es}$ $T_{ko}$ $A_{eo}$ $A_{ks}$ $A_{ds}$ $xT_{ds}$ $T_{ds}$ $G_{ds}$ $T_{ds}$ $mC_{ds}$ $A_{ds}$ $T_{ds}$ $mC_{ds}$ $A_{ko}$ $mC_{es}$ $mC_{ks}$ $A_{e}$ | rs7685686 | ekek-d9-keke | 91 |

TABLE 21

Modified oligonucleotides targeting Huntingtin (HTT) SNP rs363088

| Isis No. | SEQUENCE | SNP | Motif | SEQ ID. NO |
|---|---|---|---|---|
| 435871 | $T_{es}$ $mC_{es}$ $A_{es}$ $mC_{es}$ $A_{es}$ $G_{ds}$ $mC_{ds}$ $T_{ds}$ $A_{ds}$ $\underline{T_{ds}}$ $mC_{ds}$ $T_{ds}$ $T_{ds}$ $mC_{es}$ $T_{es}$ $mC_{es}$ $A_{es}$ $T_{es}$ $mC_{e}$ | rs363088 | eeeee-d9-eeeee | 2 |
| 525366 | $mC_{es}$ $A_{ks}$ $mC_{es}$ $A_{ks}$ $G_{ds}$ $mC_{ds}$ $T_{ds}$ $A_{ds}$ $\underline{T_{ds}}$ $mC_{ds}$ $T_{ds}$ $mC_{ds}$ $T_{ks}$ $mC_{es}$ $A_{ds}$ $T_{e}$ | rs363088 | ekek-d9-keke | 5 |
| 525368 | $A_{ks}$ $mC_{es}$ $A_{ks}$ $G_{ds}$ $mC_{ds}$ $T_{ds}$ $A_{ds}$ $\underline{T_{ds}}$ $mC_{ds}$ $T_{ds}$ $mC_{ds}$ $T_{ks}$ $mC_{es}$ $A_{ks}$ $T_{e}$ | rs363088 | kekk-d8-keke | 6 |
| 575172 | $A_{es}$ $mC_{ks}$ $A_{ks}$ $G_{ds}$ $mC_{ds}$ $T_{ds}$ $A_{ds}$ $\underline{T_{ds}}$ $mC_{ds}$ $T_{ds}$ $T_{ds}$ $mC_{ds}$ $T_{ks}$ $mC_{ks}$ $A_{e}$ | rs363088 | ekkk-d8-kke | 27 |
| 575175 | $A_{es}$ $mC_{ks}$ $A_{ks}$ $G_{ds}$ $mC_{ds}$ $T_{ds}$ $A_{ds}$ $\underline{T_{ds}}$ $mC_{ds}$ $T_{ds}$ $T_{ds}$ $mC_{ks}$ $T_{ks}$ $mC_{ks}$ $A_{e}$ | rs363088 | ekk-d8-kkke | 28 |
| 582658 | $mC_{es}$ $A_{ks}$ $mC_{es}$ $A_{ks}$ $G_{ds}$ $mC_{ds}$ $T_{ds}$ $A_{ds}$ $\underline{T_{ds}}$ $mC_{ds}$ $T_{ds}$ $T_{ds}$ $mC_{ds}$ $T_{ks}$ $mC_{es}$ $A_{ks}$ $T_{e}$ | rs363088 | ekekk-d8-keke | 29 |
| 582661 | $C_{es}$ $A_{ks}$ $mC_{es}$ $A_{ks}$ $G_{ds}$ $mC_{ds}$ $T_{ds}$ $A_{ds}$ $\underline{T_{ds}}$ $mC_{ds}$ $T_{ds}$ $T_{ek}$ $mC_{ks}$ $T_{ks}$ $mC_{ks}$ $A_{ks}$ $T_{e}$ | rs363088 | ekek-d8-kkeke | 30 |
| 589595 | $mC_{es}$ $A_{es}$ $mC_{ks}$ $A_{ks}$ $G_{ds}$ $mC_{ds}$ $T_{ds}$ $A_{ds}$ $\underline{T_{ds}}$ $mC_{ds}$ $T_{ds}$ $T_{ds}$ $mC_{ks}$ $T_{ks}$ $mC_{es}$ $A_{es}$ $T_{e}$ | rs363088 | eekk-d8-kkeee | 38 |
| 589596 | $A_{es}$ $mC_{es}$ $A_{ks}$ $G_{ks}$ $mC_{ds}$ $T_{ds}$ $A_{ds}$ $\underline{T_{ds}}$ $mC_{ds}$ $T_{ds}$ $T_{ds}$ $mC_{ds}$ $T_{ks}$ $mC_{ks}$ $A_{es}$ $T_{es}$ $mC_{e}$ | rs363088 | eekk-d8-kkeee | 39 |
| 591416 | $mC_{es}$ $A_{es}$ $mC_{es}$ $A_{ks}$ $G_{ks}$ $mC_{ds}$ $T_{ds}$ $A_{ds}$ $\underline{T_{ds}}$ $mC_{ds}$ $T_{ds}$ $T_{ds}$ $mC_{ds}$ $T_{ks}$ $mC_{ks}$ $A_{es}$ $T_{e}$ | rs363088 | eeekk-d8-kkee | 46 |

TABLE 22

Modified oligonucleotides targeting Huntingtin (HTT) SNP rs362307

| Isis No. | SEQUENCE | SNP | Motif | SEQ ID NO |
|---|---|---|---|---|
| 609230 | $G_{es}$ $G_{ks}$ $G_{ks}$ $mC_{ds}$ $A_{ds}$ $mC_{ds}$ $G_{ds}$ $mC_{ds}$ $T_{ds}$ $T_{ks}$ $mC_{ks}$ $mC_{es}$ $A_{e}$ | rs362307 | ekk-d8-kkee | 148 |
| 609231 | $A_{es}$ $G_{ks}$ $G_{ks}$ $G_{ds}$ $mC_{ds}$ $A_{ds}$ $mC_{ds}$ $A_{ds}$ $G_{ds}$ $A_{ds}$ $mC_{ds}$ $T_{ks}$ $T_{ks}$ $mC_{es}$ $mC_{e}$ | rs362307 | ekk-d8-kkee | 149 |
| 609232 | $A_{es}$ $A_{ks}$ $G_{ks}$ $G_{ds}$ $G_{ds}$ $mC_{ds}$ $A_{ds}$ $mC_{ds}$ $A_{ds}$ $G_{ds}$ $A_{ds}$ $mC_{ks}$ $T_{ks}$ $T_{es}$ $mC_{e}$ | rs362307 | ekk-d8-kkee | 150 |
| 609233 | $mC_{es}$ $A_{ks}$ $A_{ks}$ $G_{ds}$ $G_{ds}$ $G_{ds}$ $mC_{ds}$ $A_{ds}$ $mC_{ds}$ $A_{ds}$ $G_{ds}$ $A_{ks}$ $mC_{ks}$ $T_{es}$ $T_{e}$ | rs362307 | ekk-d8-kkee | 151 |
| 609242 | $G_{es}$ $G_{ks}$ $G_{ks}$ $mC_{ds}$ $A_{ds}$ $mC_{ds}$ $A_{ds}$ $G_{ds}$ $A_{ds}$ $mC_{ds}$ $T_{ds}$ $T_{ks}$ $mC_{ks}$ $mC_{es}$ $A_{es}$ $A_{e}$ | rs362307 | ekk-d8-kkeee | 152 |

TABLE 22-continued

Modified oligonucleotides targeting
Huntingtin (HTT) SNP rs362307

| Isis No. | SEQUENCE | SNP | Motif | SEQ ID NO |
|---|---|---|---|---|
| 609243 | A$_{es}$ G$_{ks}$ G$_{ks}$ G$_{ds}$ mC$_{ds}$ A$_{ds}$ mC$_{ds}$ A$_{ds}$ G$_{ds}$ A$_{ds}$ mC$_{ds}$ T$_{ks}$ T$_{ks}$ mC$_{es}$ mC$_{es}$ A$_e$ | rs362307 | ekk-d8-kkeee | 153 |
| 609244 | A$_{es}$ A$_{ks}$ G$_{ks}$ G$_{ds}$ G$_{ds}$ mC$_{ds}$ A$_{ds}$ mC$_{ds}$ A$_{ds}$ G$_{ds}$ A$_{ds}$ mC$_{ks}$ T$_{ks}$ T$_{es}$ mC$_{es}$ mC$_e$ | rs362307 | ekk-d8-kkeee | 154 |
| 609245 | mC$_{es}$ A$_{ks}$ A$_{ks}$ G$_{ds}$ G$_{ds}$ G$_{ds}$ mC$_{ds}$ A$_{ds}$ mC$_{ds}$ A$_{ds}$ G$_{ds}$ A$_{ks}$ mC$_{ks}$ T$_{es}$ T$_{es}$ mC$_e$ | rs362307 | ekk-d8-kkeee | 155 |

TABLE 22

Modified oligonucleotides targeting
Huntingtin (HT1) SNP rs7685686 (G)

| Isis No. | SEQUENCE | SNP | Motif | SEQ ID. NO. |
|---|---|---|---|---|
| 609274 | T$_{es}$ A$_{ks}$ A$_{ks}$ A$_{ds}$ T$_{ds}$ T$_{ds}$ G$_{ds}$ m$\underline{C}_{ds}$ mC$_{ds}$ A$_{ds}$ T$_{ks}$ mC$_{ks}$ A$_{es}$ mC$_{es}$ mC$_e$ | rs7685686 (G) | ekk-d7-kkeee | 132 |
| 609226 | T$_{es}$ A$_{ks}$ A$_{ks}$ A$_{ds}$ T$_{ds}$ T$_{ds}$ G$_{ds}$ m$\underline{C}_{ds}$ mC$_{ds}$ A$_{ds}$ T$_{ds}$ mC$_{ks}$ A$_{ks}$ mC$_{es}$ mC$_{es}$ | rs7685686 (G) | ekk-d8-kkee | 136 |
| 609266 | T$_{es}$ A$_{ks}$ A$_{ks}$ A$_{ds}$ T$_{ds}$ T$_{ds}$ G$_{ds}$ m$\underline{C}_{ds}$ mC$_{ds}$ A$_{ds}$ T$_{ks}$ mC$_{ks}$ A$_{es}$ mC$_{es}$ mC$_{es}$ A$_{es}$ G$_e$ | rs7685686 (G) | ekk-d7-kkeeeee | 140 |
| 609270 | T$_{es}$ A$_{ks}$ A$_{ks}$ A$_{ds}$ T$_{ds}$ T$_{ds}$ G$_{ds}$ m$\underline{C}_{ds}$ mC$_{ds}$ A$_{ds}$ T$_{ds}$ mC$_{ks}$ A$_{ks}$ mC$_{es}$ mC$_{es}$ A$_{es}$ G$_e$ | rs7685686 (G) | ekk-d8-kkeeee | 144 |
| 611714 | T$_{es}$ A$_{es}$ A$_{es}$ A$_{ks}$ T$_{ks}$ T$_{ds}$ G$_{ds}$ m$\underline{C}_{ds}$ mC$_{ds}$ A$_{ds}$ T$_{ds}$ mC$_{ds}$ A$_{ks}$ mC$_{ks}$ mC$_e$ | rs7685686 (G) | eeekk-d7-kke | 164 |
| 611715 | A$_{es}$ T$_{ks}$ A$_{es}$ A$_{ks}$ A$_{ds}$ xT$_{ds}$ T$_{ds}$ G$_{ds}$ m$\underline{C}_{ds}$ mC$_{ds}$ A$_{ds}$ T$_{ds}$ mC$_{ds}$ A$_{ks}$ mC$_{es}$ mC$_{ks}$ A$_e$ | rs7685686 (G) | ekek-d9-keke | 165 |
| 611716 | A$_{es}$ T$_{ks}$ A$_{es}$ A$_{ks}$ A$_{ds}$ T$_{ds}$ T$_d$x G$_{ds}$ m$\underline{C}_{ds}$ mC$_{ds}$ A$_{ds}$ T$_{ds}$ mC$_{ds}$ A$_{ks}$ mC$_{es}$ mC$_{ks}$ A$_e$ | rs7685686 (G) | ekek-d9-keke | 166 |
| 611717 | A$_{es}$ T$_{es}$ A$_{es}$ Ap$_s$ A$_{ke}$ T$_{ks}$ T$_{ds}$ G$_{ds}$ m$\underline{C}_{ds}$ mC$_{ds}$ A$_{ds}$ T$_{ds}$ mC$_{ds}$ A$_{ks}$ mC$_{ks}$ mC$_e$ | rs7685686 (G) | eeeekk-d7-kke | 167 |
| 611718 | T$_e$ A$_{ks}$ A$_{ks}$ A$_{ds}$ T$_{ks}$ T$_{ds}$ G$_{ds}$ m$\underline{C}_{ds}$ mC$_{ds}$ A$_{ds}$ T$_{ds}$ mC$_{ds}$ A$_{ks}$ mC$_{ks}$ mC$_e$ | rs7685686 (G) | ekk-d-k-d7-kke | 168 |
| 611719 | T$_e$ A$_{ks}$ A$_{ks}$ A$_{ks}$ T$_{ks}$ T$_{ds}$ G$_{ds}$ m$\underline{C}_{ds}$ mC$_{ds}$ A$_{ds}$ T$_{ds}$ mC$_{ds}$ A$_{ks}$ mC$_{ks}$ mC$_e$ | rs7685686 (G) | ekkkk-d7-kke | 169 |
| 611720 | A$_e$ T$_{ks}$ T$_{ds}$ G$_{ds}$ m$\underline{C}_{ds}$ mC$_{ds}$ A$_{ds}$ T$_{ds}$ mC$_{ds}$ A$_{ds}$ T$_{ds}$ mC$_{ds}$ mC$_{ko}$ A$_{ko}$ G$_{ks}$ A$_e$ | rs7685686 (G) | ek-d9-kkke | 170 |
| 611721 | T$_{es}$ A$_{es}$ A$_{es}$ A$_{es}$ T$_{ks}$ T$_{ds}$ G$_{ds}$ m$\underline{C}_{ds}$ mC$_{ds}$ A$_{ds}$ T$_{ds}$ mC$_{ds}$ A$_{ks}$ mC$_{es}$ mC$_{es}$ A$_{es}$ | rs7685686 (G) | eeeek-d7-keee | 171 |
| 611722 | A$_{es}$ T$_{es}$ A$_{es}$ A$_{es}$ A$_{ds}$ T$_{ks}$ T$_{ds}$ G$_{ds}$ mC$_{ds}$ mC$_{ds}$ T$_{ds}$ mC$_{ds}$ A$_{ks}$ mC$_{es}$ mC$_{es}$ A$_e$ | rs7685686 (G) | eeee-d-k-d7-keee | 172 |
| 611723 | T$_{es}$ A$_{eo}$ A$_{eo}$ A$_{es}$ T$_{ks}$ T$_{ds}$ G$_{ds}$ m$\underline{C}_{ds}$ mC$_{ds}$ A$_{ds}$ T$_{ds}$ mC$_{ds}$ A$_{ks}$ mC$_{eo}$ mC$_{eo}$ A$_{es}$ G$_e$ | rs7685686 (G) | eeeek-d7-keeee | 173 |
| 609275 | A$_{es}$ A$_{ks}$ A$_{ks}$ T$_{ds}$ T$_{ds}$ G$_{ds}$ m$\underline{C}_{ds}$ mC$_{ds}$ A$_{ds}$ T$_{ds}$ mC$_{ks}$ A$_{ks}$ mC$_{es}$ mC$_{es}$ A$_e$ | rs7685686 (G) | ekk-d7-kkeee | 133 |
| 609227 | A$_{es}$ A$_{ks}$ A$_{ks}$ T$_{ds}$ T$_{ds}$ G$_{ds}$ m$\underline{C}_{ds}$ mC$_{ds}$ A$_{ds}$ T$_{ds}$ mC$_{ds}$ A$_{ks}$ mC$_{ks}$ mC$_{es}$ A$_e$ | rs7685686 (G) | ekk-d8-kkee | 137 |
| 609267 | A$_{es}$ A$_{ks}$ A$_{ks}$ T$_{ds}$ T$_{ds}$ G$_{ds}$ m$\underline{C}_{ds}$ mC$_{ds}$ A$_{ds}$ T$_{ds}$ mC$_{ks}$ A$_{ks}$ mC$_{es}$ mC$_s$ A$_{es}$ G$_{es}$ A$_e$ | rs7685686 (G) | ekk-d7-kkeeeee | 141 |
| 609271 | A$_{es}$ A$_{ks}$ A$_{ks}$ T$_{ds}$ T$_{ds}$ G$_{ds}$ m$\underline{C}_{ds}$ mC$_{ds}$ A$_{ds}$ T$_{ds}$ mC$_{ds}$ A$_{ks}$ mC$_{ks}$ mC$_s$ A$_{es}$ G$_{es}$ A$_e$ | rs7685686 (G) | ekk-d8-kkeeee | 145 |

TABLE 22-continued

Modified oligonucleotides targeting
Huntingtin (HT1) SNP rs7685686 (G)

| Isis No. | SEQUENCE | SNP | Motif | SEQ ID. NO. |
|---|---|---|---|---|
| 609276 | $A_{es}$ $A_{ks}$ $T_{ks}$ $T_{ds}$ $G_{ds}$ m$\underline{C}_{ds}$ m$C_{ds}$ $A_{ds}$ $T_{ds}$ m$C_{ds}$ $A_{ks}$ m$C_{ks}$ m$C_{es}$ $A_{es}$ $G_e$ | rs7685686 (G) | ekk-d7-kkeee | 134 |
| 609228 | $A_{es}$ $A_{ks}$ $T_{ks}$ $T_{ds}$ $G_{ds}$ m$\underline{C}_{ds}$ m$C_{ds}$ $A_{ds}$ $T_{ds}$ m$C_{ds}$ $A_{ds}$ m$C_{ks}$ m$C_{ks}$ $A_{es}$ $G_e$ | rs7685686 (G) | ekk-d8-kkee | 138 |
| 609268 | $A_{es}$ $A_{ks}$ $T_{ks}$ $T_{ds}$ $G_{ds}$ m$\underline{C}_{ds}$ m$C_{ds}$ $A_{ds}$ $T_{ds}$ m$C_{ds}$ $A_{ks}$ m$C_{ks}$ m$C_{es}$ $A_{es}$ $G_{es}$ $A_{es}$ $A_e$ | rs7685686 (G) | ekk-d7-kkeeee | 142 |
| 609272 | $A_{es}$ $A_{ks}$ $T_{ks}$ $T_{ds}$ $G_{ds}$ m$\underline{C}_{ds}$ m$C_{ds}$ $A_{ds}$ $T_{ds}$ m$C_{ds}$ $A_{ds}$ m$C_{ks}$ m$C_{ks}$ $AC_s$ $G_{es}$ $AC_s$ $A_e$ | rs7685686 (G) | ekk-d8-kkeeee | 146 |
| 609277 | $A_{es}$ $T_{ks}$ $T_{ks}$ $G_{ds}$ m$C_{ds}$ m$\underline{C}_{ds}$ $A_{ds}$ $T_{ds}$ m$C_{ds}$ $A_{ds}$ m$C_{ks}$ m$C_{ks}$ $A_{es}$ $G_{es}$ $A_e$ | rs7685686 (G) | ekk-d7-kkeee | 135 |
| 609229 | $A_{es}$ $T_{ks}$ $T_{ks}$ $G_{ds}$ m$C_{ds}$ m$\underline{C}_{ds}$ $A_{ds}$ $T_{ds}$ m$C_{ds}$ $A_{ds}$ m$C_{ds}$ m$C_{ks}$ $A_{ks}$ $GC_s$ $A_e$ | rs7685686 (G) | ekk-d8-kkee | 139 |
| 609269 | $A_{es}$ $T_{ks}$ $T_{ks}$ $G_{ds}$ m$\underline{C}_{ds}$ m$C_{ds}$ $A_{ds}$ $T_{ds}$ m$C_{ds}$ $A_{ds}$ m$C_{ks}$ m$C_{ks}$ $A_{es}$ $G_{es}$ $A_{es}$ $A_{es}$ $A_e$ | rs7685686 (G) | ekk-d7-kkeeee | 143 |
| 609273 | $A_{es}$ $T_{ks}$ $T_{ks}$ $G_{ds}$ m$\underline{C}_{ds}$ m$C_{ds}$ $A_{ds}$ $T_{ds}$ m$C_{ds}$ $A_{ds}$ m$C_{ds}$ m$C_{ks}$ $A_{ks}$ $G_{es}$ $A_{es}$ $A_{es}$ $A_e$ | rs7685686 (G) | ekk-d8-kkeeee | 147 |

As described above in Example 1, certain SNPs may have two or more allelic variants. For example, the two allelic variants for SNP rs7685686 are A and G. In certain embodiments, antisense oligonucleotides can be designed that target either allelic variant. In certain embodiments, a higher percentage of the population may have a particular allelic variant. Modified oligonucleotides were designed to target the G allelic variant of rs7685686. These modified oligonucleotides are described further in Table 22 below.

TABLE 23

Modified oligonucleotides targeting
Huntingtin (HTT) SNP rs362273

| Isis No. | SEQUENCE | SNP | Motif | SEQ ID NO |
|---|---|---|---|---|
| 589601 | $T_{es}$ $T_{es}$ $G_{ks}$ $A_{ks}$ $T_{ds}$ m$C_{ds}$ $T_{ds}$ $G_{ds}$ $\underline{T}_{ds}$ $A_{ds}$ $G_{ds}$ m$C_{ds}$ $A_{ks}$ $G_{ks}$ m$C_{es}$ $A_{es}$ $G_e$ | rs362273 | eekk-d8-kkeee | 40 |
| 589602 | $TC_s$ $G_{es}$ $A_{ks}$ $T_{ks}$ m$C_{ds}$ $T_{ds}$ $G_{ds}$ $\underline{T}_{ds}$ $A_{ds}$ $G_{ds}$ m$C_{ds}$ $A_{ds}$ $G_{ks}$ m$C_{ks}$ $A_{es}$ $G_{es}$ m$C_e$ | rs362273 | eekk-d8-kkeee | 41 |
| 589737 | $T_{es}$ $T_{ks}$ $G_{es}$ $A_{ks}$ $T_{ds}$ m$C_{ds}$ $T_{ds}$ $G_{ds}$ $\underline{T}_{ds}$ $A_{ds}$ $G_{ds}$ m$C_{ds}$ $A_{ks}$ $G_{es}$ m$C_{ks}$ $A_{es}$ $G_e$ | rs362273 | ekek-d8-kekee | 45 |
| 607451 | $G_{es}$ $A_{ks}$ $T_{ks}$ m$C_{ds}$ $T_{ds}$ $G_{ds}$ $T_{ds}$ $A_{ds}$ $G_{ds}$ m$C_{ds}$ $A_{ds}$ $G_{ks}$ m$C_{ks}$ $A_{es}$ $G_{es}$ m$C_e$ | rs362273 | ekk-d8-kkeee | 117 |
| 607452 | $T_{es}$ $G_{ks}$ $A_{ks}$ $T_{ds}$ m$C_{ds}$ $T_{ds}$ $G_{ds}$ $T_{ds}$ $A_{ds}$ $G_{ds}$ m$C_{ds}$ $A_{ks}$ $G_{ks}$ m$C_{es}$ $A_{es}$ $G_e$ | rs362273 | ekk-d8-kkeee | 122 |

TABLE 24

Modified oligonucleotides targeting
Huntingtin (HTT) SNP rs362274

| Isis No. | SEQUENCE | SNP | Motif | SEQ ID. NO. |
|---|---|---|---|---|
| 607444 | $T_{es}$ $G_{es}$ $A_{ks}$ $T_{ks}$ m$C_{ds}$ $T_{ds}$ $G_{ds}$ $T_{ds}$ $A_{ds}$ $G_{ds}$ m$C_{ds}$ $A_{ds}$ $G_{ks}$ m$C_{ks}$ $A_{es}$ $G_e$ | rs362274 | eekk-d8-kkee | 118 |
| 607445 | $T_{es}$ $T_{es}$ $G_{ks}$ $A_{ks}$ $T_{ds}$ m$C_{ds}$ $T_{ds}$ $G_{ds}$ $T_{ds}$ $A_{ds}$ $G_{ds}$ m$C_{ds}$ $A_{ks}$ $G_{ks}$ m$C_{es}$ $A_e$ | rs362274 | eekk-d8-kkee | 123 |

TABLE 25

Modified oligonucleotides targeting
Huntingtin (HTT) SNP rs362275

| Isis No. | SEQUENCE | SNP | Motif | SEQ ID. NO. |
|---|---|---|---|---|
| 607458 | $A_{es}$ $T_{ks}$ $mC_{ds}$ $T_{ds}$ $G_{ds}$ $T_{ds}$ $A_{ds}$ $G_{ds}$ $mC_{ds}$ $A_{ds}$ $G_{ks}$ $mC_{ks}$ $A_{es}$ $G_{es}$ $mC_e$ | rs362275 | ek-d8-kkeee | 119 |
| 607459 | $G_{es}$ $A_{ks}$ $T_{ds}$ $mC_{ds}$ $T_{ds}$ $G_{ds}$ $T_{ds}$ $A_{ds}$ $G_{ds}$ $mC_{ds}$ $A_{ks}$ $G_{ks}$ $mC_{es}$ $A_{es}$ $G_e$ | rs362275 | ek-d8-kkeee | 124 |

TABLE 25

Modified oligonucleotides targeting
Huntingtin (HTT) SNP rs362276

| Isis No. | SEQUENCE | SNP | Motif | SEQ ID. NO. |
|---|---|---|---|---|
| 607465 | $G_{es}$ $A_{es}$ $T_{ks}$ $mC_{ds}$ $T_{ds}$ $G_{ds}$ $T_{ds}$ $A_{ds}$ $G_{ds}$ $mC_{ds}$ $A_{ds}$ $G_{ks}$ $mC_{ks}$ $A_{es}$ $G_e$ | rs362276 | eek-d8-kkee | 120 |
| 607466 | $T_{es}$ $G_{es}$ $A_{ks}$ $T_{ds}$ $mC_{ds}$ $T_{ds}$ $G_{ds}$ $T_{ds}$ $A_{ds}$ $G_{ds}$ $mC_{ds}$ $A_{ks}$ $G_{ks}$ $mC_{es}$ $A_e$ | rs362276 | eek-d8-kkee | 125 |

TABLE 26

Modified oligonucleotides targeting
Huntingtin (HTT) SNP rs362277

| Isis No. | SEQUENCE | SNP | Motif | SEQ ID NO |
|---|---|---|---|---|
| 607472 | $T_{es}$ $G_{es}$ $A_{es}$ $T_{ks}$ $mC_{ds}$ $T_{ds}$ $G_{ds}$ $T_{ds}$ $A_{ds}$ $G_{ds}$ $mC_{ds}$ $A_{ds}$ $G_{ks}$ $mC_{es}$ $A_e$ | rs362276 | eeek-d8-kee | 121 |
| 607473 | $T_{es}$ $T_{es}$ $G_{es}$ $A_{ks}$ $T_{ds}$ $mC_{ds}$ $T_{ds}$ $G_{ds}$ $T_{ds}$ $A_{ds}$ $G_{ds}$ $mC_{ds}$ $A_{ks}$ $G_{es}$ $mC_e$ | rs362276 | eeek-d8-kee | 126 |

Example 3

Modified Oigonucleotides Targeting Huntingtin (HTT) Single Nucleotide Polymorphisms (SNP)

A series of modified oligonucleotides targeting Huntingtin (HTT) were designed. These modified oligonucleotides were designed to target SNP positions associated with the HTT gene. The table below provides the sequence and motif for each modified oligonucleotide. The motifs indicate certain 2'-modifications to the nucleobases in the nucleobase sequences. In the table below, 'k' indicates an (S)-cEt modification; 'e' indicates a MOE modification; a number along with 'd' indicates the number of deoxyribose nucleosides. For example, a compound having an ekk-d9-kke motif would have the following structure: $N_eN_kN_kN_dN_dN_dN_dN_dN_dN_dN_dN_dN_kN_kN_e$, wherein each N represents a nucleobase and wherein each subscript represents a nucleobase modification according to the examples described above. All interncleoside linkages are phosphorothioate unless otherwise indicated.

| Isis No. | SNP | SEQUENCE (5' to 3') | MOTIF (5' to 3') | SEQ ID NO. |
|---|---|---|---|---|
| 460207 | rs362332 | ACACAGTAGATGAGG | ekk-d9-kke | 174 |
| 460218 | rs362332 | GCACACAGTAGATGAGGGA | eeeee-d3-k-d5-eeeee | 175 |
| 460026 | rs2298969 | AAGGGATGCTGACTTGGGC | eeee-d9-eeeee | 176 |
| 460208 | rs4690072 | CAGTGCTACCCAACC | ekk-d9-kke | 177 |
| 525364 | rs4690072 | ACAGTGCTACCCAACCT | ekek-d9-keke | 178 |
| 435331 | rs2024115 | TTCAAGCTAGTAACGATGC | eeeee-d9-eeeee | 179 |
| 525365 | rs2024115 | CTTCAAGCTAGTAACGA | ekek-d9-keke | 180 |
| 525368 | rs363088 | ACAGCTATCTTCTCA | ekk-d9-kke | 181 |

-continued

| Isis No. | SNP | SEQUENCE (5' to 3') | MOTIF (5' to 3') | SEQ ID NO. |
|---|---|---|---|---|
| 460065 | rs7685686 | ATAAATTGTCATCACCAG | eeee-d9-eeeee | 182 |
| 435879 | rs7685686 | AATAAATTGTCATCACCAG | eeeee-d9-eeeee | 183 |
| 460085 | rs7685686 | ATAAATTGTCATCACCA | eeeee-d7-eeeee | 184 |
| 435870 | rs362331 | GCACACAGTAGATGAGGGA | eeeee-d9-eeeee | 185 |
| 460071 | rs362331 | GCACACAGTAGATGAGGGA | eeeee-d10-eeee | 186 |
| 460212 | rs362331 | GCACACAGTAGATGAGGGA | eeeee-d4-k-d4-eeeee | 187 |
| 460231 | rs362331 | ACAGTAGATGAGGGAGCAG | eeeee-k-d8-eeeee | 188 |
| 474892 | rs362331 | CACACAGTAGATGAGGG | kekk-d9-kkek | 189 |
| 435890 | rs2298969 | AAGGGATGCTGACTTGGGC | eeeee-d9-eeeee | 190 |
| 460210 | rs2298969 | GGGATGCTGACTTGG | ekk-d9-kke | 191 |
| 474871 | rs7685686 | ATAAATTGTCATCACCA | ekkk-d9-kkke | 192 |
| 474891 | rs7685686 | ATAAATTGTCATCACCA | kekk-d9-kkek | 193 |
| 474919 | rs7685686 | AATAAATTGTCATCACCAG | kekek-d9-kekek | 194 |
| 474923 | rs7685686 | AATAAATTGTCATCACCAG | kdkdk-d9-kdkdk | 195 |
| 476337 | rs7685686 | AATAAATTGTCATCACCAG | ekeke-d9-ekeke | 196 |
| 460012 | rs4690072 | ACAGTGCTACCCAACCT | eee-d9-eeeee | 197 |
| 525367 | rs2024115 | TTCAAGCTAGTAACG | ekk-d9-kke | 198 |
| 435869 | rs362306 | GAGCAGCTGCAACCTGGCA | eeeee-d9-eeeee | 199 |
| 460069 | rs362306 | GAGCAGCTGCAACCTGGCA | eeeee-d10-eeee | 200 |
| 460206 | rs362306 | GCAGCTGCAACCTGG | ekk-d9-kke | 201 |
| 463571 | rs362273 | TTGATCTGTAGCAGCAGCT | eeeee-d9-eeeee | 202 |
| 476444 | rs6844859 | CCTTCCTCACTGAGGATGA | eeeee-d9-eeeee | 203 |
| 435330 | rs3856973 | TAACACTCGATTAACCCTG | eeeee-d9-eeeee | 204 |
| 435868 | rs362275 | AAGAAGCCTGATAAAATCT | eeeee-d9-eeeee | 205 |
| 491416 | rs7685686 | TGCTTCAGAGCTGAGCAGAA | eeeee-d10-eeeee | 206 |
| 553748 | | ACCACAACGGCGATT | ekk-d9-kke | 207 |
| 553751 | | TACCTAAGAGCACAT | ekk-d9-kke | 208 |
| 553752 | rs2285086 | TAGTTCATCCCAGTG | ekk-d9-kke | 209 |
| 553754 | rs2798235 | GAGGAGGTATACTGT | ekk-d9-kke | 210 |
| 553762 | rs362303 | TGGTGCCGGGTGTCT | ekk-d9-kke | 211 |
| 553764 | rs362310 | AAACGGCGCAGCGGG | ekk-d9-kke | 212 |
| 553765 | | CGCCTATACCATACA | ekk-d9-kke | 213 |
| 553767 | | GATAATATCCTATCA | ekk-d9-kke | 214 |
| 553768 | rs363080 | AGAGAACAAGAAGGC | ekk-d9-kke | 215 |
| 553769 | rs363092 | AACCACTGTGGGATG | ekk-d9-kke | 216 |
| 553772 | rs363102 | CTAAAACTAACTTGA | ekk-d9-kke | 217 |
| 553773 | | CGTTGAAGTACTGTC | ekk-d9-kke | 218 |
| 553775 | rs3856973 | TAACACTCGATTAAC | ekk-d9-kke | 219 |

-continued

| Isis No. | SNP | SEQUENCE (5' to 3') | MOTIF (5' to 3') | SEQ ID NO. |
|---|---|---|---|---|
| 553776 | rs4690073 | CCTAAATCAATCTAC | ekk-d9-kke | 220 |
| 553777 | rs6446723 | ATTTTCTAGACTTTA | ekk-d9-kke | 221 |
| 553778 | rs6844859 | CTTCCTCACTGAGGA | ekk-d9-kke | 222 |
| 553779 | rs7659144 | GAAATGGGTTTTCC | ekk-d9-kke | 223 |
| 553780 | rs7691627 | TAAGAAACACAATCA | ekk-d9-kke | 224 |
| 553781 | rs916171 | GAACAAACAGAAGAA | ekk-d9-kke | 225 |
| 553782 | rs362303 | TGGTGCCAGGTGTCT | ekk-d9-kke | 226 |
| 553784 | rs362310 | AAACGGCACAGCGGG | ekk-d9-kke | 227 |
| 435295 | rs2024115 | ACTTCAAGCTAGTAACGAT | eeeee-d9-eeeee | 228 |
| 553742 | | ACACCACAACGGCGATTTG | eeeee-d9-eeeee | 229 |
| 553743 | | CTTACCTAAGAGCACATTT | eeeee-d9-eeeee | 230 |
| 435864 | rs2285086 | GCTAGTTCATCCCAGTGAG | eeeee-d9-eeeee | 231 |
| 435910 | rs2798235 | CAGAGGAGGTATACTGTAT | eeeee-d9-eeeee | 232 |
| 435311 | rs362303 | AATGGTGCCGGGTGTCTAG | eeeee-d9-eeeee | 233 |
| 435309 | rs362310 | AGAAACGGCGCAGCGGGAA | eeeee-d9-eeeee | 234 |
| 553744 | | TCCGCCTATACCATACAAT | eeeee-d9-eeeee | 235 |
| 553745 | | ATGATAATATCCTATCAAA | eeeee-d9-eeeee | 236 |
| 435911 | rs363080 | AGAGAGAACAAGAAGGCTC | eeeee-d9-eeeee | 237 |
| 435872 | rs363092 | CAAACCACTGTGGGATGAA | eeeee-d9-eeeee | 238 |
| 435300 | rs363102 | ATCTAAAACTAACTTGAGA | eeeee-d9-eeeee | 239 |
| 553746 | | AGCGTTGAAGTACTGTCCC | eeeee-d9-eeeee | 240 |
| 435294 | rs3856973 | GTTAACACTCGATTAACCC | eeeee-d9-eeeee | 241 |
| 435301 | rs4690073 | TCCCTAAATCAATCTACAA | eeeee-d9-eeeee | 242 |
| 435875 | rs6446723 | TAATTTTCTAGACTTTATG | eeeee-d9-eeeee | 243 |
| 435876 | rs6844859 | ACCTTCCTCACTGAGGATG | eeeee-d9-eeeee | 244 |
| 435878 | rs7659144 | TGGAAATGGGTTTTCCAC | eeeee-d9-eeeee | 245 |
| 435880 | rs7691627 | AATAAGAAACACAATCAAA | eeeee-d9-eeeee | 246 |
| 435906 | rs916171 | CAGAACAAACAGAAGAATT | eeeee-d9-eeeee | 247 |
| 435329 | rs362303 | AATGGTGCCAGGTGTCTAG | eeeee-d9-eeeee | 248 |
| 435327 | rs362310 | AGAAACGGCACAGCGGGAA | eeeee-d9-eeeee | 249 |
| 553766 | rs363064 | AGAATACGGGTAACA | ekk-d9-kke | 250 |
| 553771 | rs363099 | CTGAGCGGAGAAACC | ekk-d9-kke | 251 |
| 553770 | rs363096 | TTCCCTAAAAACAAA | ekk-d9-kke | 252 |
| 553753 | rs2298967 | CTTTTCTATTGTCTG | ekk-d9-kke | 253 |
| 553758 | rs362272 | TAGAGGACGCCGTGC | ekk-d9-kke | 254 |
| 553783 | rs363096 | TTCCCTAGAAACAAA | ekk-d9-kke | 255 |
| 553763 | rs362307 | CAAGGGCACAGACTT | ekk-d9-kke | 256 |
| 553750 | rs16843804 | TAACCGTGGCATGGG | ekk-d9-kke | 257 |

-continued

| Isis No. | SNP | SEQUENCE (5' to 3') | MOTIF (5' to 3') | SEQ ID NO. |
|---|---|---|---|---|
| 553755 | rs3121419 | GACTATAGCACCCAG | ekk-d9-kke | 258 |
| 553757 | rs362271 | GTGTGTACAGAACCT | ekk-d9-kke | 259 |
| 553760 | rs362275 | GAAGCCTGATAAAAT | ekk-d9-kke | 260 |
| 553774 | rs3775061 | TTCAGAATGCCTCAT | ekk-d9-kke | 261 |
| 553761 | rs362296 | GGACAGGGTGTGCTC | ekk-d9-kke | 262 |
| 553747 | rs10015979 | AGCTAGGCTAAAGAG | ekk-d9-kke | 263 |
| 553749 | rs11731237 | TGGGCAGAAAGGACT | ekk-d9-kke | 264 |
| 553759 | rs362273 | TGATCTGTAGCAGCA | ekk-d9-kke | 265 |
| 553756 | rs34315806 | CTTTTCCGTGCTGTT | ekk-d9-kke | 266 |
| 435298 | rs363064 | GGAGAATACGGGTAACATT | eeeee-d9-eeeee | 267 |
| 435303 | rs363099 | GGCTGAGCGGAGAAACCCT | eeeee-d9-eeeee | 268 |
| 435304 | rs363096 | GATTCCTAAAAACAAAAA | eeeee-d9-eeeee | 269 |
| 435305 | rs2298967 | TGCTTTTCTATTGTCTGTC | eeeee-d9-eeeee | 270 |
| 435308 | rs362272 | CATAGAGGACGCCGTGCAG | eeeee-d9-eeeee | 271 |
| 435322 | rs363096 | GATTCCCTAGAAACAAAAA | eeeee-d9-eeeee | 272 |
| 435328 | rs362307 | CACAAGGGCACAGACTTCC | eeeee-d9-eeeee | 273 |
| 435863 | rs16843804 | TTTAACCGTGGCATGGGCA | eeeee-d9-eeeee | 274 |
| 435866 | rs3121419 | GAGACTATAGCACCCAGAT | eeeee-d9-eeeee | 275 |
| 435867 | rs362271 | ACGTGTGTACAGAACCTGC | eeeee-d9-eeeee | 276 |
| 435873 | rs3775061 | TGTTCAGAATGCCTCATCT | eeeee-d9-eeeee | 277 |
| 435882 | rs362296 | GGGGACAGGGTGTGCTCTC | eeeee-d9-eeeee | 278 |
| 435887 | rs10015979 | GCAGCTAGGCTAAAGAGTC | eeeee-d9-eeeee | 279 |
| 435909 | rs11731237 | GGTGGGCAGAAAGGACTGA | eeeee-d9-eeeee | 280 |
| 463566 | rs362273 | GTTGATCTGTAGCAGCAGC | eeeee-d9-eeeee | 281 |
| 463567 | rs34315806 | AACTTTTCCGTGCTGTTCT | eeeee-d9-eeeee | 282 |
| 589448 | rs3856973 | AACACTCGATTAACCCT | eeekk-d7-kkeee | 283 |
| 589447 | rs3856973 | TAACACTCGATTAACCC | eeekk-d7-kkeee | 284 |
| 589163 | rs3856973 | TTAACACTCGATTAACC | eeekk-d7-kkeee | 285 |
| 589446 | rs3856973 | GTTAACACTCGATTAAC | eeekk-d7-kkeee | 286 |
| 589445 | rs3856973 | AGTTAACACTCGATTAA | eeekk-d7-kkeee | 287 |
| 589669 | rs3856973 | AACACTCGATTAACCCT | eekek-d7-kekee | 288 |
| 589668 | rs3856973 | TAACACTCGATTAACCC | eekek-d7-kekee | 289 |
| 589667 | rs3856973 | TTAACACTCGATTAACC | eekek-d7-kekee | 290 |
| 589666 | rs3856973 | GTTAACACTCGATTAAC | eekek-d7-kekee | 291 |
| 589665 | rs3856973 | AGTTAACACTCGATTAA | eekek-d7-kekee | 292 |
| 589544 | rs3856973 | ACACTCGATTAACCCTG | eekk-d8-kkeee | 293 |
| 589543 | rs3856973 | AACACTCGATTAACCCT | eekk-d8-kkeee | 294 |
| 589542 | rs3856973 | TAACACTCGATTAACCC | eekk-d8-kkeee | 295 |

-continued

| Isis No. | SNP | SEQUENCE (5' to 3') | MOTIF (5' to 3') | SEQ ID NO. |
|---|---|---|---|---|
| 589541 | rs3856973 | TTAACACTCGATTAACC | eekk-d8-kkeee | 296 |
| 589540 | rs3856973 | GTTAACACTCGATTAAC | eekk-d8-kkeee | 297 |
| 589539 | rs3856973 | AGTTAACACTCGATTAA | eekk-d8-kkeee | 298 |
| 589716 | rs3856973 | ACACTCGATTAACCCTG | ekek-d8-kekee | 299 |
| 589715 | rs3856973 | AACACTCGATTAACCCT | ekek-d8-kekee | 300 |
| 589714 | rs3856973 | TAACACTCGATTAACCC | ekek-d8-kekee | 301 |
| 589713 | rs3856973 | TTAACACTCGATTAACC | ekek-d8-kekee | 302 |
| 589712 | rs3856973 | GTTAACACTCGATTAAC | ekek-d8-kekee | 303 |
| 589711 | rs3856973 | AGTTAACACTCGATTAA | ekek-d8-kekee | 304 |
| 589444 | rs7685686 | AAATTGTCATCACCAGA | eeekk-d7-kkeee | 305 |
| 589443 | rs7685686 | AATAAATTGTCATCACC | eeekk-d7-kkeee | 306 |
| 589442 | rs7685686 | TAATAAATTGTCATCAC | eeekk-d7-kkeee | 307 |
| 589664 | rs7685686 | AAATTGTCATCACCAGA | eekek-d7-kekee | 308 |
| 589663 | rs7685686 | TAAATTGTCATCACCAG | eekek-d7-kekee | 309 |
| 589662 | rs7685686 | ATAAATTGTCATCACCA | eekek-d7-kekee | 310 |
| 589661 | rs7685686 | AATAAATTGTCATCACC | eekek-d7-kekee | 311 |
| 589660 | rs7685686 | TAATAAATTGTCATCAC | eekek-d7-kekee | 312 |
| 589538 | rs7685686 | AATTGTCATCACCAGAA | eekk-d8-kkeee | 313 |
| 589536 | rs7685686 | TAAATTGTCATCACCAG | eekk-d8-kkeee | 314 |
| 589535 | rs7685686 | ATAAATTGTCATCACCA | eekk-d8-kkeee | 315 |
| 589534 | rs7685686 | AATAAATTGTCATCACC | eekk-d8-kkeee | 316 |
| 589533 | rs7685686 | TAATAAATTGTCATCAC | eekk-d8-kkeee | 317 |
| 589710 | rs7685686 | AATTGTCATCACCAGAA | ekek-d8-kekee | 318 |
| 589709 | rs7685686 | AAATTGTCATCACCAGA | ekek-d8-kekee | 319 |
| 589708 | rs7685686 | TAAATTGTCATCACCAG | ekek-d8-kekee | 320 |
| 589707 | rs7685686 | ATAAATTGTCATCACCA | ekek-d8-kekee | 321 |
| 589706 | rs7685686 | AATAAATTGTCATCACC | ekek-d8-kekee | 322 |
| 589705 | rs7685686 | TAATAAATTGTCATCAC | ekek-d8-kekee | 323 |
| 589468 | rs2024115 | TCAAGCTAGTAACGATG | eeekk-d7-kkeee | 324 |
| 589467 | rs2024115 | TTCAAGCTAGTAACGAT | eeekk-d7-kkeee | 325 |
| 589466 | rs2024115 | CTTCAAGCTAGTAACGA | eeekk-d7-kkeee | 326 |
| 589465 | rs2024115 | ACTTCAAGCTAGTAACG | eeekk-d7-kkeee | 327 |
| 589464 | rs2024115 | AACTTCAAGCTAGTAAC | eeekk-d7-kkeee | 328 |
| 589568 | rs2024115 | CAAGCTAGTAACGATGC | eekk-d8-kkeee | 329 |
| 589566 | rs2024115 | TTCAAGCTAGTAACGAT | eekk-d8-kkeee | 330 |
| 589565 | rs2024115 | CTTCAAGCTAGTAACGA | eekk-d8-kkeee | 331 |
| 589564 | rs2024115 | ACTTCAAGCTAGTAACG | eekk-d8-kkeee | 332 |
| 589563 | rs2024115 | AACTTCAAGCTAGTAAC | eekk-d8-kkeee | 333 |

-continued

| Isis No. | SNP | SEQUENCE (5' to 3') | MOTIF (5' to 3') | SEQ ID NO. |
|---|---|---|---|---|
| 589453 | rs6446723 | TTTTCTAGACTTTATGA | eeekk-d7-kkeee | 334 |
| 589452 | rs6446723 | ATTTTCTAGACTTTATG | eeekk-d7-kkeee | 335 |
| 589451 | rs6446723 | AATTTTCTAGACTTTAT | eeekk-d7-kkeee | 336 |
| 589449 | rs6446723 | TTAATTTTCTAGACTTT | eeekk-d7-kkeee | 337 |
| 589674 | rs6446723 | TTTTCTAGACTTTATGA | eekek-d7-kekee | 338 |
| 589673 | rs6446723 | ATTTTCTAGACTTTATG | eekek-d7-kekee | 339 |
| 589672 | rs6446723 | AATTTTCTAGACTTTAT | eekek-d7-kekee | 340 |
| 589671 | rs6446723 | TAATTTTCTAGACTTTA | eekek-d7-kekee | 341 |
| 589670 | rs6446723 | TTAATTTTCTAGACTTT | eekek-d7-kekee | 342 |
| 589550 | rs6446723 | TTTCTAGACTTTATGAT | eekk-d8-kkeee | 343 |
| 589549 | rs6446723 | TTTTCTAGACTTTATGA | eekk-d8-kkeee | 344 |
| 589548 | rs6446723 | ATTTTCTAGACTTTATG | eekk-d8-kkeee | 345 |
| 589545 | rs6446723 | TTAATTTTCTAGACTTT | eekk-d8-kkeee | 346 |
| 589722 | rs6446723 | TTTCTAGACTTTATGAT | ekek-d8-kekee | 347 |
| 589721 | rs6446723 | TTTTCTAGACTTTATGA | ekek-d8-kekee | 348 |
| 589720 | rs6446723 | ATTTTCTAGACTTTATG | ekek-d8-kekee | 349 |
| 589719 | rs6446723 | AATTTTCTAGACTTTAT | ekek-d8-kekee | 350 |
| 589717 | rs6446723 | TTAATTTTCTAGACTTT | ekek-d8-kekee | 351 |
| 589463 | rs6844859 | TTCCTCACTGAGGATGA | eeekk-d7-kkeee | 352 |
| 589462 | rs6844859 | CTTCCTCACTGAGGATG | eeekk-d7-kkeee | 353 |
| 589461 | rs6844859 | CCTTCCTCACTGAGGAT | eeekk-d7-kkeee | 354 |
| 589460 | rs6844859 | ACCTTCCTCACTGAGGA | eeekk-d7-kkeee | 355 |
| 589459 | rs6844859 | CACCTTCCTCACTGAGG | eeekk-d7-kkeee | 356 |
| 590761 | rs6844859 | TTCCTCACTGAGGATGA | eekek-d7-kekee | 357 |
| 590760 | rs6844859 | CTTCCTCACTGAGGATG | eekek-d7-kekee | 358 |
| 590759 | rs6844859 | CCTTCCTCACTGAGGAT | eekek-d7-kekee | 359 |
| 590758 | rs6844859 | ACCTTCCTCACTGAGGA | eekek-d7-kekee | 360 |
| 590757 | rs6844859 | CACCTTCCTCACTGAGG | eekek-d7-kekee | 361 |
| 589562 | rs6844859 | TCCTCACTGAGGATGAA | eekk-d8-kkeee | 362 |
| 589561 | rs6844859 | TTCCTCACTGAGGATGA | eekk-d8-kkeee | 363 |
| 589560 | rs6844859 | CTTCCTCACTGAGGATG | eekk-d8-kkeee | 364 |
| 589559 | rs6844859 | CCTTCCTCACTGAGGAT | eekk-d8-kkeee | 365 |
| 589558 | rs6844859 | ACCTTCCTCACTGAGGA | eekk-d8-kkeee | 366 |
| 589557 | rs6844859 | CACCTTCCTCACTGAGG | eekk-d8-kkeee | 367 |
| 590767 | rs6844859 | TCCTCACTGAGGATGAA | ekek-d8-kekee | 368 |
| 590766 | rs6844859 | TTCCTCACTGAGGATGA | ekek-d8-kekee | 369 |
| 590765 | rs6844859 | CTTCCTCACTGAGGATG | ekek-d8-kekee | 370 |
| 590764 | rs6844859 | CCTTCCTCACTGAGGAT | ekek-d8-kekee | 371 |

-continued

| Isis No. | SNP | SEQUENCE (5' to 3') | MOTIF (5' to 3') | SEQ ID NO. |
|---|---|---|---|---|
| 590763 | rs6844859 | ACCTTCCTCACTGAGGA | ekek-d8-kekee | 372 |
| 590762 | rs6844859 | CACCTTCCTCACTGAGG | ekek-d8-kekee | 373 |
| 589483 | rs363092 | ACCACTTTGGGATGAAT | eeekk-d7-kkeee | 374 |
| 589482 | rs363092 | AACCACTTTGGGATGAA | eeekk-d7-kkeee | 375 |
| 589481 | rs363092 | AAACCACTTTGGGATGA | eeekk-d7-kkeee | 376 |
| 589480 | rs363092 | CAAACCACTTTGGGATG | eeekk-d7-kkeee | 377 |
| 589479 | rs363092 | GCAAACCACTTTGGGAT | eeekk-d7-kkeee | 378 |
| 589586 | rs363092 | CCACTTTGGGATGAATA | eekk-d8-kkeee | 379 |
| 589585 | rs363092 | ACCACTTTGGGATGAAT | eekk-d8-kkeee | 380 |
| 589584 | rs363092 | AACCACTTTGGGATGAA | eekk-d8-kkeee | 381 |
| 589583 | rs363092 | AAACCACTTTGGGATGA | eekk-d8-kkeee | 382 |
| 589582 | rs363092 | CAAACCACTTTGGGATG | eekk-d8-kkeee | 383 |
| 589581 | rs363092 | GCAAACCACTTTGGGAT | eekk-d8-kkeee | 384 |
| 589458 | rs2285086 | AGTTCATCCCAGTGAGA | eeekk-d7-kkeee | 385 |
| 589457 | rs2285086 | TAGTTCATCCCAGTGAG | eeekk-d7-kkeee | 386 |
| 589456 | rs2285086 | CTAGTTCATCCCAGTGA | eeekk-d7-kkeee | 387 |
| 589455 | rs2285086 | GCTAGTTCATCCCAGTG | eeekk-d7-kkeee | 388 |
| 589454 | rs2285086 | TGCTAGTTCATCCCAGT | eeekk-d7-kkeee | 389 |
| 589679 | rs2285086 | AGTTCATCCCAGTGAGA | eekek-d7-kekee | 390 |
| 589678 | rs2285086 | TAGTTCATCCCAGTGAG | eekek-d7-kekee | 391 |
| 589677 | rs2285086 | CTAGTTCATCCCAGTGA | eekek-d7-kekee | 392 |
| 589676 | rs2285086 | GCTAGTTCATCCCAGTG | eekek-d7-kekee | 393 |
| 589675 | rs2285086 | TGCTAGTTCATCCCAGT | eekek-d7-kekee | 394 |
| 589556 | rs2285086 | GTTCATCCCAGTGAGAA | eekk-d8-kkeee | 395 |
| 589555 | rs2285086 | AGTTCATCCCAGTGAGA | eekk-d8-kkeee | 396 |
| 589554 | rs2285086 | TAGTTCATCCCAGTGAG | eekk-d8-kkeee | 397 |
| 589553 | rs2285086 | CTAGTTCATCCCAGTGA | eekk-d8-kkeee | 398 |
| 589552 | rs2285086 | GCTAGTTCATCCCAGTG | eekk-d8-kkeee | 399 |
| 589551 | rs2285086 | TGCTAGTTCATCCCAGT | eekk-d8-kkeee | 400 |
| 589728 | rs2285086 | GTTCATCCCAGTGAGAA | ekek-d8-kekee | 401 |
| 589727 | rs2285086 | AGTTCATCCCAGTGAGA | ekek-d8-kekee | 402 |
| 589726 | rs2285086 | TAGTTCATCCCAGTGAG | ekek-d8-kekee | 403 |
| 589725 | rs2285086 | CTAGTTCATCCCAGTGA | ekek-d8-kekee | 404 |
| 589724 | rs2285086 | GCTAGTTCATCCCAGTG | ekek-d8-kekee | 405 |
| 589723 | rs2285086 | TGCTAGTTCATCCCAGT | ekek-d8-kekee | 406 |
| 589473 | rs2798235 | AGGAGGCATACTGTATT | eeekk-d7-kkeee | 407 |
| 589472 | rs2798235 | GAGGAGGCATACTGTAT | eeekk-d7-kkeee | 408 |
| 589471 | rs2798235 | AGAGGAGGCATACTGTA | eeekk-d7-kkeee | 409 |

-continued

| Isis No. | SNP | SEQUENCE (5' to 3') | MOTIF (5' to 3') | SEQ ID NO. |
|---|---|---|---|---|
| 589470 | rs2798235 | CAGAGGAGGCATACTGT | eeekk-d7-kkeee | 410 |
| 589469 | rs2798235 | ACAGAGGAGGCATACTG | eeekk-d7-kkeee | 411 |
| 589574 | rs2798235 | GGAGGCATACTGTATTT | eekk-d8-kkeee | 412 |
| 589573 | rs2798235 | AGGAGGCATACTGTATT | eekk-d8-kkeee | 413 |
| 589572 | rs2798235 | GAGGAGGCATACTGTAT | eekk-d8-kkeee | 414 |
| 589571 | rs2798235 | AGAGGAGGCATACTGTA | eekk-d8-kkeee | 415 |
| 589570 | rs2798235 | CAGAGGAGGCATACTGT | eekk-d8-kkeee | 416 |
| 589569 | rs2798235 | ACAGAGGAGGCATACTG | eekk-d8-kkeee | 417 |
| 589478 | rs363080 | GAGAACGAGAAGGCTCC | eeekk-d7-kkeee | 418 |
| 589477 | rs363080 | AGAGAACGAGAAGGCTC | eeekk-d7-kkeee | 419 |
| 589476 | rs363080 | GAGAGAACGAGAAGGCT | eeekk-d7-kkeee | 420 |
| 589475 | rs363080 | AGAGAGAACGAGAAGGC | eeekk-d7-kkeee | 421 |
| 589474 | rs363080 | AAGAGAGAACGAGAAGG | eeekk-d7-kkeee | 422 |
| 589580 | rs363080 | AGAACGAGAAGGCTCCA | eekk-d8-kkeee | 423 |
| 589579 | rs363080 | GAGAACGAGAAGGCTCC | eekk-d8-kkeee | 424 |
| 589578 | rs363080 | AGAGAACGAGAAGGCTC | eekk-d8-kkeee | 425 |
| 589577 | rs363080 | GAGAGAACGAGAAGGCT | eekk-d8-kkeee | 426 |
| 589576 | rs363080 | AGAGAGAACGAGAAGGC | eekk-d8-kkeee | 427 |
| 589575 | rs363080 | AAGAGAGAACGAGAAGG | eekk-d8-kkeee | 428 |
| 589497 | rs362273 | GATCTGTAGCAGCAGCT | eeekk-d7-kkeee | 429 |
| 589496 | rs362273 | TGATCTGTAGCAGCAGC | eeekk-d7-kkeee | 430 |
| 589495 | rs362273 | TTGATCTGTAGCAGCAG | eeekk-d7-kkeee | 431 |
| 589494 | rs362273 | GTTGATCTGTAGCAGCA | eeekk-d7-kkeee | 432 |
| 589493 | rs362273 | GGTTGATCTGTAGCAGC | eeekk-d7-kkeee | 433 |
| 589689 | rs362273 | GATCTGTAGCAGCAGCT | eekek-d7-kekee | 434 |
| 589688 | rs362273 | TGATCTGTAGCAGCAGC | eekek-d7-kekee | 435 |
| 589687 | rs362273 | TTGATCTGTAGCAGCAG | eekek-d7-kekee | 436 |
| 589686 | rs362273 | GTTGATCTGTAGCAGCA | eekek-d7-kekee | 437 |
| 589685 | rs362273 | GGTTGATCTGTAGCAGC | eekek-d7-kekee | 438 |
| 589604 | rs362273 | ATCTGTAGCAGCAGCTT | eekk-d8-kkeee | 439 |
| 589603 | rs362273 | GATCTGTAGCAGCAGCT | eekk-d8-kkeee | 440 |
| 589600 | rs362273 | GTTGATCTGTAGCAGCA | eekk-d8-kkeee | 441 |
| 589599 | rs362273 | GGTTGATCTGTAGCAGC | eekk-d8-kkeee | 442 |
| 589740 | rs362273 | ATCTGTAGCAGCAGCTT | ekek-d8-kekee | 443 |
| 589739 | rs362273 | GATCTGTAGCAGCAGCT | ekek-d8-kekee | 444 |
| 589738 | rs362273 | TGATCTGTAGCAGCAGC | ekek-d8-kekee | 445 |
| 589736 | rs362273 | GTTGATCTGTAGCAGCA | ekek-d8-kekee | 446 |
| 589735 | rs362273 | GGTTGATCTGTAGCAGC | ekek-d8-kekee | 447 |

-continued

| Isis No. | SNP | SEQUENCE (5' to 3') | MOTIF (5' to 3') | SEQ ID NO. |
|---|---|---|---|---|
| 589492 | rs363088 | CAGCTATCTTCTCATCA | eeekk-d7-kkeee | 448 |
| 589491 | rs363088 | ACAGCTATCTTCTCATC | eeekk-d7-kkeee | 449 |
| 575481 | rs363088 | CACAGCTATCTTCTCAT | eeekk-d7-kkeee | 450 |
| 589490 | rs363088 | TCACAGCTATCTTCTCA | eeekk-d7-kkeee | 451 |
| 589489 | rs363088 | TTCACAGCTATCTTCTC | eeekk-d7-kkeee | 452 |
| 589684 | rs363088 | CAGCTATCTTCTCATCA | eekek-d7-kekee | 453 |
| 589683 | rs363088 | ACAGCTATCTTCTCATC | eekek-d7-kekee | 454 |
| 589682 | rs363088 | CACAGCTATCTTCTCAT | eekek-d7-kekee | 455 |
| 589681 | rs363088 | TCACAGCTATCTTCTCA | eekek-d7-kekee | 456 |
| 589680 | rs363088 | TTCACAGCTATCTTCTC | eekek-d7-kekee | 457 |
| 589598 | rs363088 | AGCTATCTTCTCATCAA | eekk-d8-kkeee | 458 |
| 589597 | rs363088 | CAGCTATCTTCTCATCA | eekk-d8-kkeee | 459 |
| 589594 | rs363088 | TCACAGCTATCTTCTCA | eekk-d8-kkeee | 460 |
| 589593 | rs363088 | TTCACAGCTATCTTCTC | eekk-d8-kkeee | 461 |
| 589734 | rs363088 | AGCTATCTTCTCATCAA | ekek-d8-kekee | 462 |
| 589733 | rs363088 | CAGCTATCTTCTCATCA | ekek-d8-kekee | 463 |
| 589732 | rs363088 | ACAGCTATCTTCTCATC | ekek-d8-kekee | 464 |
| 589731 | rs363088 | CACAGCTATCTTCTCAT | ekek-d8-kekee | 465 |
| 589730 | rs363088 | TCACAGCTATCTTCTCA | ekek-d8-kekee | 466 |
| 589729 | rs363088 | TTCACAGCTATCTTCTC | ekek-d8-kekee | 467 |
| 589502 | rs362271 | TGTGTACAGAACCTGCC | eeekk-d7-kkeee | 468 |
| 589501 | rs362271 | GTGTGTACAGAACCTGC | eeekk-d7-kkeee | 469 |
| 589500 | rs362271 | CGTGTGTACAGAACCTG | eeekk-d7-kkeee | 470 |
| 589499 | rs362271 | ACGTGTGTACAGAACCT | eeekk-d7-kkeee | 471 |
| 589498 | rs362271 | CACGTGTGTACAGAACC | eeekk-d7-kkeee | 472 |
| 589694 | rs362271 | TGTGTACAGAACCTGCC | eekek-d7-kekee | 473 |
| 589693 | rs362271 | GTGTGTACAGAACCTGC | eekek-d7-kekee | 474 |
| 589692 | rs362271 | CGTGTGTACAGAACCTG | eekek-d7-kekee | 475 |
| 589691 | rs362271 | ACGTGTGTACAGAACCT | eekek-d7-kekee | 476 |
| 589690 | rs362271 | CACGTGTGTACAGAACC | eekek-d7-kekee | 477 |
| 589610 | rs362271 | GTGTACAGAACCTGCCG | eekk-d8-kkeee | 478 |
| 589609 | rs362271 | TGTGTACAGAACCTGCC | eekk-d8-kkeee | 479 |
| 589608 | rs362271 | GTGTGTACAGAACCTGC | eekk-d8-kkeee | 480 |
| 589607 | rs362271 | CGTGTGTACAGAACCTG | eekk-d8-kkeee | 481 |
| 589606 | rs362271 | ACGTGTGTACAGAACCT | eekk-d8-kkeee | 482 |
| 589605 | rs362271 | CACGTGTGTACAGAACC | eekk-d8-kkeee | 483 |
| 589746 | rs362271 | GTGTACAGAACCTGCCG | ekek-d8-kekee | 484 |
| 589745 | rs362271 | TGTGTACAGAACCTGCC | ekek-d8-kekee | 485 |

-continued

| Isis No. | SNP | SEQUENCE (5' to 3') | MOTIF (5' to 3') | SEQ ID NO. |
|---|---|---|---|---|
| 589744 | rs362271 | GTGTGTACAGAACCTGC | ekek-d8-kekee | 486 |
| 589743 | rs362271 | CGTGTGTACAGAACCTG | ekek-d8-kekee | 487 |
| 589742 | rs362271 | ACGTGTGTACAGAACCT | ekek-d8-kekee | 488 |
| 589741 | rs362271 | CACGTGTGTACAGAACC | ekek-d8-kekee | 489 |
| 589517 | rs363099 | TGAGCGGAGAAACCCTC | eeekk-d7-kkeee | 490 |
| 589516 | rs363099 | CTGAGCGGAGAAACCCT | eeekk-d7-kkeee | 491 |
| 589515 | rs363099 | GCTGAGCGGAGAAACCC | eeekk-d7-kkeee | 492 |
| 589514 | rs363099 | GGCTGAGCGGAGAAACC | eeekk-d7-kkeee | 493 |
| 589513 | rs363099 | AGGCTGAGCGGAGAAAC | eeekk-d7-kkeee | 494 |
| 589628 | rs363099 | GAGCGGAGAAACCCTCC | eekk-d8-kkeee | 495 |
| 589627 | rs363099 | TGAGCGGAGAAACCCTC | eekk-d8-kkeee | 496 |
| 589626 | rs363099 | CTGAGCGGAGAAACCCT | eekk-d8-kkeee | 497 |
| 589625 | rs363099 | GCTGAGCGGAGAAACCC | eekk-d8-kkeee | 498 |
| 589624 | rs363099 | GGCTGAGCGGAGAAACC | eekk-d8-kkeee | 499 |
| 589623 | rs363099 | AGGCTGAGCGGAGAAAC | eekk-d8-kkeee | 500 |
| 589531 | rs363064 | AGAATACGGGTAACATT | eeekk-d7-kkeee | 501 |
| 589530 | rs363064 | GAGAATACGGGTAACAT | eeekk-d7-kkeee | 502 |
| 589529 | rs363064 | GGAGAATACGGGTAACA | eeekk-d7-kkeee | 503 |
| 589528 | rs363064 | TGGAGAATACGGGTAAC | eeekk-d7-kkeee | 504 |
| 589644 | rs363064 | AGAATACGGGTAACATT | eekk-d8-kkeee | 505 |
| 589643 | rs363064 | GAGAATACGGGTAACAT | eekk-d8-kkeee | 506 |
| 589642 | rs363064 | GGAGAATACGGGTAACA | eekk-d8-kkeee | 507 |
| 589522 | rs16843804 | AACCGTGGCATGGGCAG | eeekk-d7-kkeee | 508 |
| 589521 | rs16843804 | TAACCGTGGCATGGGCA | eeekk-d7-kkeee | 509 |
| 589520 | rs16843804 | TTAACCGTGGCATGGGC | eeekk-d7-kkeee | 510 |
| 589519 | rs16843804 | TTTAACCGTGGCATGGG | eeekk-d7-kkeee | 511 |
| 589518 | rs16843804 | CTTTAACCGTGGCATGG | eeekk-d7-kkeee | 512 |
| 589634 | rs16843804 | ACCGTGGCATGGGCAGT | eekk-d8-kkeee | 513 |
| 589633 | rs16843804 | AACCGTGGCATGGGCAG | eekk-d8-kkeee | 514 |
| 589632 | rs16843804 | TAACCGTGGCATGGGCA | eekk-d8-kkeee | 515 |
| 589631 | rs16843804 | TTAACCGTGGCATGGGC | eekk-d8-kkeee | 516 |
| 589630 | rs16843804 | TTTAACCGTGGCATGGG | eekk-d8-kkeee | 517 |
| 589629 | rs16843804 | CTTTAACCGTGGCATGG | eekk-d8-kkeee | 518 |
| 589512 | rs3121419 | ACTATAGCACCCAGATT | eeekk-d7-kkeee | 519 |
| 589511 | rs3121419 | GACTATAGCACCCAGAT | eeekk-d7-kkeee | 520 |
| 589510 | rs3121419 | AGACTATAGCACCCAGA | eeekk-d7-kkeee | 521 |
| 589509 | rs3121419 | GAGACTATAGCACCCAG | eeekk-d7-kkeee | 522 |
| 589508 | rs3121419 | AGAGACTATAGCACCCA | eeekk-d7-kkeee | 523 |

-continued

| Isis No. | SNP | SEQUENCE (5' to 3') | MOTIF (5' to 3') | SEQ ID NO. |
|---|---|---|---|---|
| 589704 | rs3121419 | ACTATAGCACCCAGATT | eekek-d7-kekee | 524 |
| 589703 | rs3121419 | GACTATAGCACCCAGAT | eekek-d7-kekee | 525 |
| 589702 | rs3121419 | AGACTATAGCACCCAGA | eekek-d7-kekee | 526 |
| 589701 | rs3121419 | GAGACTATAGCACCCAG | eekek-d7-kekee | 527 |
| 589700 | rs3121419 | AGAGACTATAGCACCCA | eekek-d7-kekee | 528 |
| 589622 | rs3121419 | CTATAGCACCCAGATTT | eekk-d8-kkeee | 529 |
| 589621 | rs3121419 | ACTATAGCACCCAGATT | eekk-d8-kkeee | 530 |
| 589620 | rs3121419 | GACTATAGCACCCAGAT | eekk-d8-kkeee | 531 |
| 589619 | rs3121419 | AGACTATAGCACCCAGA | eekk-d8-kkeee | 532 |
| 589618 | rs3121419 | GAGACTATAGCACCCAG | eekk-d8-kkeee | 533 |
| 589617 | rs3121419 | AGAGACTATAGCACCCA | eekk-d8-kkeee | 534 |
| 589758 | rs3121419 | CTATAGCACCCAGATTT | ekek-d8-kekee | 535 |
| 589757 | rs3121419 | ACTATAGCACCCAGATT | ekek-d8-kekee | 536 |
| 589756 | rs3121419 | GACTATAGCACCCAGAT | ekek-d8-kekee | 537 |
| 589755 | rs3121419 | AGACTATAGCACCCAGA | ekek-d8-kekee | 538 |
| 589754 | rs3121419 | GAGACTATAGCACCCAG | ekek-d8-kekee | 539 |
| 589753 | rs3121419 | AGAGACTATAGCACCCA | ekek-d8-kekee | 540 |
| 589527 | rs2298967 | TTTTCTATTGTCTGTCC | eeekk-d7-kkeee | 541 |
| 589526 | rs2298967 | CTTTTCTATTGTCTGTC | eeekk-d7-kkeee | 542 |
| 589525 | rs2298967 | GCTTTTCTATTGTCTGT | eeekk-d7-kkeee | 543 |
| 589524 | rs2298967 | TGCTTTTCTATTGTCTG | eeekk-d7-kkeee | 544 |
| 589523 | rs2298967 | TTGCTTTTCTATTGTCT | eeekk-d7-kkeee | 545 |
| 589640 | rs2298967 | TTTCTATTGTCTGTCCC | eekk-d8-kkeee | 546 |
| 589639 | rs2298967 | TTTTCTATTGTCTGTCC | eekk-d8-kkeee | 547 |
| 589638 | rs2298967 | CTTTTCTATTGTCTGTC | eekk-d8-kkeee | 548 |
| 589637 | rs2298967 | GCTTTTCTATTGTCTGT | eekk-d8-kkeee | 549 |
| 589636 | rs2298967 | TGCTTTTCTATTGTCTG | eekk-d8-kkeee | 550 |
| 589635 | rs2298967 | TTGCTTTTCTATTGTCT | eekk-d8-kkeee | 551 |
| 589507 | rs34315806 | TTTTCCGTGCTGTTCTG | eeekk-d7-kkeee | 552 |
| 589506 | rs34315806 | CTTTTCCGTGCTGTTCT | eeekk-d7-kkeee | 553 |
| 589505 | rs34315806 | ACTTTTCCGTGCTGTTC | eeekk-d7-kkeee | 554 |
| 589504 | rs34315806 | AACTTTTCCGTGCTGTT | eeekk-d7-kkeee | 555 |
| 589503 | rs34315806 | AAACTTTTCCGTGCTGT | eeekk-d7-kkeee | 556 |
| 589699 | rs34315806 | TTTTCCGTGCTGTTCTG | eekek-d7-kekee | 557 |
| 589698 | rs34315806 | CTTTTCCGTGCTGTTCT | eekek-d7-kekee | 558 |
| 589697 | rs34315806 | ACTTTTCCGTGCTGTTC | eekek-d7-kekee | 559 |
| 589696 | rs34315806 | AACTTTTCCGTGCTGTT | eekek-d7-kekee | 560 |
| 589695 | rs34315806 | AAACTTTTCCGTGCTGT | eekek-d7-kekee | 561 |

-continued

| Isis No. | SNP | SEQUENCE (5' to 3') | MOTIF (5' to 3') | SEQ ID NO. |
|---|---|---|---|---|
| 589616 | rs34315806 | TTTCCGTGCTGTTCTGA | eekk-d8-kkeee | 562 |
| 589615 | rs34315806 | TTTTCCGTGCTGTTCTG | eekk-d8-kkeee | 563 |
| 589614 | rs34315806 | CTTTTCCGTGCTGTTCT | eekk-d8-kkeee | 564 |
| 589613 | rs34315806 | ACTTTTCCGTGCTGTTC | eekk-d8-kkeee | 565 |
| 589612 | rs34315806 | AACTTTTCCGTGCTGTT | eekk-d8-kkeee | 566 |
| 589611 | rs34315806 | AAACTTTTCCGTGCTGT | eekk-d8-kkeee | 567 |
| 589752 | rs34315806 | TTTCCGTGCTGTTCTGA | ekek-d8-kekee | 568 |
| 589751 | rs34315806 | TTTTCCGTGCTGTTCTG | ekek-d8-kekee | 569 |
| 589750 | rs34315806 | CTTTTCCGTGCTGTTCT | ekek-d8-kekee | 570 |
| 589749 | rs34315806 | ACTTTTCCGTGCTGTTC | ekek-d8-kekee | 571 |
| 589748 | rs34315806 | AACTTTTCCGTGCTGTT | ekek-d8-kekee | 572 |
| 589747 | rs34315806 | AAACTTTTCCGTGCTGT | ekek-d8-kekee | 573 |

Example 4

300 µg ICV Bolus 8 Week Study With Mice

Oligos were screened in human patient fibroblasts (either GM4022 or GM2173B) at 4 µM with electroporation (2 mm multiwell, 115V, 6 mS, 1 pulse, 3.5 e5 cells per well). Target message was measured with an allele specific ABI primer probe set 24-hours post electroporation. Results were normalized to Ribogreen. The half maximal inhibitory concentration ($IC_{50}$) of each oligonucleotide is presented in the Table below and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. "ND" means data not available.

Mice were separated into groups of 4 mice. Each mouse in each group of mice was administered a single 300 µg ICV dose of each of the oligonucleotides in the table below. At 3 hours post injection, each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after it is lifted; (5) the mouse demonstrates any movement after it is lifted; (6) the mouse responds to a tail pinch; (7) the mouse has a regular respiratory rate. For each of the 7 different criteria, each mouse was given a sub-score of 0 if it met the criteria or 1 if it did not. After each of the 7 criteria were evaluated, the sub-scores were summed for each mouse and then averaged for each group. For example, if a mouse was bright, alert, and responsive 3 hours after the 300 µg ICV dose, and met all other other criteria, it would get a summed score of 0. If another mouse was not bright, alert, and responsive 3 hours after the 300 µg ICV dose but met all other criteria, it would receive a score of 1. Saline treated mice generally receive a score of 0. A score of at the top end of the range would be suggestive of acute toxicity. In the table below, a subscript 'k' indicates an (S)-cEt modification; a subscript 'e' indicates a MOE modification; a subscript 'd' indicates a 2-deoxynucleoside and an "N" without a subscript also indicates a 2'-deoxynucleoside. In the table below, an "x" represents a 2-thiothymine. Subscripts "s" and "o" refer to phosphorothioate and phosphodiester internucleoside bonds, respectively.

Each mouse was then evaluated weekly by a trained observer for 8 weeks and examined for adverse events. Adverse events are defined as any behavior not typical in a naive matched control animal. Animals were evaluated for adverse events including, but not limited to: limb clasping, abnormal limb splay, abnormal gait, tremors, abnormal respiration, paralysis, spasticity, impaired righting reflex, hyperactivity and lethargy. For each group, the number of animals that exhibited any adverse events during any of the 8 weekly observations was calculated. For example, a group of animals where no animals exhibited any adverse events is given a score of 0.

TABLE 28

300 µg ICV Bolus 8 Week Study With Mice

| Isis No. | SNP | Mut $IC_{50}$ (µM) | Wt $IC_{50}$ (µM) | Score at 3 hours post injection | # of Mice in group with one or more adverse events for 8 weeks |
|---|---|---|---|---|---|
| 540083 | rs7685686 | ND | ND | ND | 4 |
| 540094 | rs7685686 | 0.31 | 4.8 | 4.3 | 2 |
| 540095 | rs7685686 | 0.69 | 8.3 | 6 | 4 |
| 540096 | rs7685686 | 0.65 | 10 | 3.5 | 2 |
| 540108 | rs7685686 | 0.41 | >10 | 0.8 | 4 |
| 550913 | rs7685686 | 0.12 | 0.6 | 2 | 3 |
| 551429 | rs7685686 | 0.24 | >10 | 0.3 | 0 |
| 566267 | rs7685686 | 0.34 | >15 | 1.5 | 0 |
| 568876 | rs7685686 | 0.1 | >10 | 1.3 | 4 |
| 571036 | rs7685686 | 0.17 | >10 | 1 | 4 |
| 571037 | rs7685686 | 0.11 | >10 | 0 | 4 |
| 575007 | rs7685686 | 0.67 | >10 | 1.8 | 0 |
| 585246 | rs7685686 | 0.6 | >10 | 4.5 | 4 |
| 571069 | rs7685686 | 0.29 | >10 | 0 | 4 |
| 572771 | rs7685686 | 0.54 | >10 | 0 | 3 |
| 572772 | rs7685686 | 0.57 | >10 | 0 | 0 |
| 575008 | rs7685686 | 0.18 | >10 | 0 | 1 |

TABLE 28-continued

300 μg ICV Bolus 8 Week Study With Mice

| Isis No. | SNP | Mut IC$_{50}$ (μM) | Wt IC$_{50}$ (μM) | Score at 3 hours post injection | # of Mice in group with one or more adverse events for 8 weeks |
|---|---|---|---|---|---|
| 460209 | rs7685686 | 0.34 | 1.7 | 1.3 | 0 |
| 476333 | rs7685686 | 0.32 | 1.6 | 0 | 1 |
| 540108 | rs7685686 | 0.41 | >10 | 0.3 | 2 |
| 593199 | rs7685686 | ND | ND | 0 | 3 |
| 593200 | rs7685686 | ND | ND | 0.5 | 0 |
| 593201 | rs7685686 | ND | ND | 0 | 4 |
| 593202 | rs7685686 | ND | ND | 0 | 4 |
| 593203 | rs7685686 | ND | ND | 0 | 3 |
| 593204 | rs7685686 | ND | ND | 0 | 4 |
| 558257 | rs7685686 | 0.6 | >10 | 0 | ND |
| 571039 | rs7685686 | 0.34 | >10 | 2.5 | ND |
| 598229 | rs7685686 | ND | ND | 0 | ND |
| 598300 | rs7685686 | ND | ND | 1.3 | ND |
| 598301 | rs7685686 | ND | ND | 2.3 | ND |
| 598302 | rs7685686 | ND | ND | 0.3 | ND |
| 598303 | rs7685686 | ND | ND | 1.5 | ND |
| 598304 | rs7685686 | ND | ND | 1.5 | ND |
| 598305 | rs7685686 | ND | ND | 0 | ND |
| 598306 | rs7685686 | ND | ND | 0.5 | ND |
| 598307 | rs7685686 | ND | ND | 0.8 | ND |
| 598308 | rs7685686 | ND | ND | 1.8 | ND |
| 606560 | rs7685686 | ND | ND | 1.5 | ND |
| 606578 | rs7685686 | ND | ND | 2.8 | ND |
| 435871 | rs363088 | ND | ND | 4.8 | 3 |
| 525366 | rs363088 | 0.6 | 2.88 | ND | 4 |
| 525368 | rs363088 | 0.8 | 6.88 | .3 | 4 |
| 575172 | rs363088 | 0.9 | 5.0 | 0 | 4 |
| 575175 | rs363088 | 0.4 | 2.64 | 0 | 4 |
| 582658 | rs363088 | 0.8 | 6.9 | 0 | 4 |
| 582661 | rs363088 | 0.4 | 3.0 | 0 | 4 |
| 589595 | rs363088 | 1.2 | 9.6 | 0 | 4 |
| 589596 | rs363088 | 1.4 | >10 | 0 | 4 |
| 591416 | rs363088 | ND | ND | 0 | 3 |
| 589450 | rs6446723 | 1.3 | >10 | 3.8 | 0 |
| 589532 | rs363064 | 2.5 | >10 | 5.8 | 2 |
| 589537 | rs7685686 | 0.8 | 4.8 | 2.8 | 2 |
| 589546 | rs6446723 | 1.3 | >10 | 1.8 | 0 |
| 589547 | rs6446723 | 1.5 | >10 | 2.3 | 1 |
| 589567 | rs6446723 | 0.8 | 9.6 | 6 | 3 |
| 589601 | rs362273 | 1.3 | 7 | 6 | 4 |
| 589602 | rs362273 | 1.4 | >10 | 6 | 3 |
| 589645 | rs363088 | 1.5 | >10 | 5.7 | 2 |
| 589646 | rs363088 | 3.2 | >10 | 4.3 | 0 |
| 589718 | rs6446723 | 1.4 | >10 | 3.3 | 1 |
| 589737 | rs363088 | 1.3 | 4.8 | 5.8 | 4 |
| 556845 | rs7685686 | ND | ND | 3 | ND |
| 598309 | rs7685686 | ND | ND | 0.5 | ND |
| 598310 | rs7685686 | ND | ND | 0.3 | ND |
| 606561 | rs7685686 | ND | ND | 1.5 | ND |
| 606562 | rs7685686 | ND | ND | 2.3 | ND |
| 598299 | rs7685686 | ND | ND | 1 | ND |

Example 5

300 μg ICV Bolus Study with Mice

Additional oligonucleotides, shown in the table below, were administered to mice at a single 300 μg ICV dose. The mice were evaluated according to the procedures in Example 4 above.

TABLE 29

300 μg ICV Bolus Study With Mice

| ISIS NO. | SNP | Sequence (5' to 3') | Sugar Motif | Score at 3 hours post injection | SEQ ID NO |
|---|---|---|---|---|---|
| 551429 | rs7685686 | T$_e$A$_e$A$_e$A$_k$T$_k$TGTCATCA$_k$C$_k$C$_e$ | 5-7-3 | .3 | 3 |
| 571037 | rs7685686 | A$_e$T$_e$A$_e$A$_k$A$_e$T$_k$TGT$^m$CAT$^m$CA$_k$$^m$C$_e$$^m$C$_k$$^m$C$_e$A$_e$ | 6-7-4 | 0 | 11 |
| 540108 | rs7685686 | A$_e$T$_e$A$_e$A$_k$A$_e$TTGT$^m$CAT$^m$C$_k$A$_k$$^m$C$_e$$^m$C$_k$$^m$C$_e$A$_e$ | 5-7-5 | .3 | 11 |
| 571036 | rs7685686 | A$_e$T$_e$A$_e$A$_k$A$_e$T$_k$TGT$^m$CAT$^m$CA$_k$$^m$C$_e$$^m$C$_k$$^m$C$_e$A$_e$ | 6-7-4 | 1 | 11 |
| 568876 | rs7685686 | A$_k$T$_k$A$_k$A$_k$A$_k$TIGTCATC$_k$A$_k$C$_k$C$_k$A$_k$ | 5-7-5 | 1.3 | 11 |
| 566267 | rs7685686 | T$_e$A$_k$A$_k$ATzTGT$^m$CAT$^m$CA$_k$$^m$C$_k$$^m$C$_e$ | 3-9-3 or 5-7-3 | 1.5 | 3 |
| 575007 | rs7685686 | T$_e$A$_k$A$_k$AT$_k$TGT$^m$CAT$^m$CA$_k$$^m$C$_k$$^m$C$_e$ | 3-9-3 or 5-7-3 | 1.8 | 3 |
| 550913 | rs7685686 | A$_k$A$_k$T$_e$A$_k$A$_k$ATTGTCATCA$_k$C$_k$C$_e$T$_k$T$_k$ | 5-9-5 | 2 | 12 |
| 540096 | rs7685686 | A$_k$A$_k$TTGTCATCAC$_k$C$_k$A$_k$G$_e$ | 2-9-4 | 3.5 | 7 |
| 585246 | rs7685686 | T$_e$A$_e$A$_e$A$_k$T$_k$TGTCATCA$_k$C$_k$C$_e$A$_e$G$_e$ | 5-7-5 | 4.5 | 31 |
| 540094 | rs7685686 | T$_e$T$_k$GT$^m$CAT$^m$CA$^m$C$^m$CA$_k$G$_k$A$_k$A$_e$ | 2-9-4 | 4.3 | 8 |
| 540095 | rs7685686 | A$_e$T$_k$TGTCATCACC$_k$A$_k$G$_k$A$_e$ | 2-9-4 | 6 | 48 |
| 540083 | rs7685686 | A$_k$A$_k$T$_k$T$_k$GTCATCACCA$_k$G$_e$ | 4-9-2 | ND | 7 |
| 593200 | rs7685686 | A$_{es}$T$_{ks}$T$_{ds}$G$_{ds}$T$_{ds}$mCA$_{ds}$T$_{ds}$mC$_{ds}$A$_{ds}$mC$_{ds}$ | 2-9-4 | 0.5 | 48 |

TABLE 29-continued

300 µg ICV Bolus Study With Mice

| ISIS NO. | SNP | Sequence (5' to 3') | Sugar Motif | Score at 3 hours post injection | SEQ ID NO |
|---|---|---|---|---|---|
| | | mC$_{ke}$A$_{ke}$G$_{ks}$A$_e$ | | | |
| 593202 | rs7685686 | A$_{es}$T$_{ko}$A$_{ko}$A$_{ko}$A$_{ks}$T$_{ks}$T$_{ds}$G$_{ds}$T$_{ds}$mC$_{ds}$A$_{ds}$ T$_{ds}$mC$_{ds}$A$_{ko}$mC$_{ko}$mC$_{ks}$A$_e$ | 6-7-4 | 0 | 4 |
| 476333 | rs7685686 | A$_{es}$T$_{ks}$A$_{es}$A$_{ks}$A$_{ds}$T$_{ds}$T$_{ds}$G$_{ds}$T$_{ds}$mC$_{ds}$A$_{ds}$ T$_{ds}$mC$_{ds}$A$_{ks}$mC$_{es}$mC$_{ks}$A$_e$ | 4-9-4 | 0 | 4 |
| 571039 | rs7685686 | A$_{es}$T$_{ks}$A$_{es}$A$_{ks}$A$_{ds}$XT$_{ds}$T$_{ds}$G$_{ds}$T$_{ds}$mC$_{ds}$A$_{ds}$ T$_{ds}$mC$_{ds}$A$_{ks}$mC$_{es}$mC$_{ks}$A$_e$ | 4-9-4 | 2.5 | 4 |
| 598229 | rs7685686 | A$_{es}$T$_{es}$A$_{es}$A$_{es}$A$_{ks}$T$_{ks}$T$_{ds}$G$_{ds}$T$_{ds}$mC$_{ks}$A$_{ds}$ T$_{ds}$mC$_{ds}$A$_{ks}$mC$_{es}$mC$_{ks}$A$_e$ | 6-7-4 | 0 | 4 |
| 593203 | rs7685686 | T$_{ks}$A$_{ko}$A$_{ko}$A$_{ko}$T$_{ks}$T$_{ds}$G$_{ds}$I$_{ds}$mC$_{ds}$A$_{ds}$T$_{ds}$ mC$_{ds}$A$_{ko}$mC$_{ko}$mC$_{ko}$A$_{ks}$G$_k$ | 5-7-5 | 0 | 31 |
| 593204 | rs7685686 | A$_{ks}$T$_{ko}$A$_{ko}$A$_{ko}$A$_{ko}$T$_{ds}$T$_{ds}$G$_{ds}$T$_{ds}$mC$_{ds}$A$_{ds}$ T$_{ds}$mC$_{ko}$A$_{ko}$mC$_{ko}$mC$_{ko}$A$_k$ | 5-7-5 | 0 | 4 |
| 598305 | rs7685686 | A$_{es}$T$_{es}$A$_{es}$A$_{es}$A$_{ds}$T$_{ks}$T$_{ds}$G$_{ds}$T$_{ds}$mC$_{ds}$A$_{ds}$ T$_{ds}$mC$_{ds}$A$_{ks}$mC$_{ks}$mC$_{es}$A$_e$ | 4-9-4 or 6-7-4 | 0 | 4 |
| 598306 | rs7685686 | A$_{es}$T$_{es}$A$_{es}$A$_{es}$A$_{ds}$T$_{ks}$T$_{ds}$G$_{ds}$T$_{ds}$mC$_{ds}$A$_{ds}$ T$_{ds}$mC$_{ds}$A$_{ks}$mC$_{es}$mC$_{es}$A$_e$ | 4-9-4 or 6-7-4 | 0.5 | 4 |
| 598307 | rs7685686 | A$_{es}$T$_{es}$A$_{es}$A$_{es}$A$_{ds}$T$_{ks}$T$_{ds}$G$_{ds}$T$_{ds}$mC$_{ds}$A$_{ds}$ T$_{ds}$mC$_{ds}$A$_{es}$mC$_{es}$mC$_{es}$A$_e$ | 4-9-4 or 6-7-4 | 0.8 | 4 |
| 606560 | rs7685686 | A$_{es}$T$_{es}$A$_{es}$A$_{ks}$A$_{ds}$XT$_{ds}$T$_{ds}$G$_{ds}$T$_{ds}$mC$_{ds}$A$_{ds}$ T$_{ds}$mC$_{ds}$A$_{ks}$mC$_{es}$mC$_{ks}$A$_e$ | 4-9-4 | 1.5 | 4 |
| 606561 | rs7685686 | A$_{es}$T$_{ks}$A$_{es}$A$_{ks}$A$_{ds}$XT$_{ds}$T$_{ds}$G$_{ds}$T$_{ds}$mC$_{ds}$A$_{ds}$ T$_{ds}$mC$_{ds}$A$_{ks}$mC$_{es}$mC$_{es}$A$_e$ | 4-9-4 | 1.5 | 4 |
| 606562 | rs7685686 | A$_{es}$T$_{es}$A$_{es}$A$_{ks}$A$_{ds}$XT$_{ds}$T$_{ds}$G$_{ds}$T$_{ds}$mC$_{ds}$A$_{ds}$ T$_{ds}$mC$_{ds}$A$_{ks}$mC$_{es}$mC$_{es}$A$_e$ | 4-9-4 | 2.3 | 4 |
| 606578 | rs7685686 | A$_{es}$T$_{ks}$A$_{es}$A$_{ks}$A$_{ds}$T$_{ds}$T$_{ds}$G$_{ds}$T$_{ds}$mC$_{ds}$A$_{fs}$ T$_{ds}$mC$_{ds}$A$_{ks}$mC$_{es}$mC$_{ks}$A$_e$ | 4-9-4 | 2.8 | 4 |
| 617107 | rs363064 | A$_{es}$A$_{eo}$T$_{ko}$A$_{ks}$mC$_{ds}$G$_{ds}$G$_{ds}$G$_{ds}$T$_{ds}$A$_{ds}$A$_{ds}$ mC$_{ds}$A$_{ke}$T$_{ko}$T$_{es}$T$_{es}$T$_e$ | 4-8-5 | 1.25 | 108 |
| 617110 | rs363064 | G$_{es}$A$_{es}$A$_{eo}$T$_{ko}$A$_{ks}$mC$_{ds}$G$_{ds}$G$_{ds}$G$_{ds}$T$_{ds}$A$_{ds}$ A$_{ds}$mC$_{ke}$T$_{ko}$T$_{es}$T$_{es}$T$_e$ | 5-7-5 | 1.75 | 89 |

Example 6

Modified Oligonucleotides Targeting HTT SNP rs7685686 or rs6446723

The modified oligonucleotides described in the previous examples were tested in vitro targeting HTT SNP rs7685686 or rs6446723. Human patient fibroblasts GM04022 cell line was used. Cultured GM04022 cells at a density of 35,000 cells per well were transfected using electroporation at 130V with 0.37, 1.1, 3.3 and 10 µM concentrations of modified oligonucleotides. After a treatment period of approximately 24 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 30.

The IC$_{50}$ of each modified oligonucleotide is presented in the table below and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

ISIS 141923 (C$_e$C$_e$T$_e$T$_e$C$_e$CCTGAAGGTTC$_e$C$_e$T$_e$C$_e$C$_e$, 5-10-5 MOE (SEQ ID NO: 575)) was included in the study as a negative control and is denoted as "neg control". A non-allele specific antisense oligonucleotide, ISIS 387916 (T$_e$C$_e$T$_e$C$_e$T$_e$ATTGCACATTC$_e$C$_e$A$_e$A$_e$G$_e$, 5-10-5 MOE (SEQ ID NO: 576)) was used as a positive control and is denoted as "pos control". ISIS 460209 or 572772 was also included in the study for comparison.

TABLE 30

Modified oligonucleotides targeting Huntingtin (HTT) SNP rs7685686 or rs6446723

| Isis No. | SNP | IC$_{50}$ (μM) Mut | Wt | Selectivity (wt vs mut) | Motif | SEQ ID. NO. |
|---|---|---|---|---|---|---|
| 460209[1] | rs7685686 | <0.4 | 2.25 | 5.6 | ekk-d9-kke | 3 |
| 572772[2] | rs7685686 | 0.27 | >10 | >37 | eeeekk-d7-kke | 24 |
| 551429 | rs7685686 | <0.4 | >10 | >25 | eeekk-d7-kke | 13 |
| 556845 | rs7685686 | <0.4 | >10 | >25 | ekk-d9-kke | 14 |
| 617425 | rs7685686 | 1.3 | >10 | >8 | eeeeek-d7-eee | 75 |
| 617115 | rs7685686 | <0.4 | >10 | >25 | eeeeek-d7-kke | 70 |
| 617116 | rs7685686 | <0.4 | >10 | >25 | eeeekk-d7-kee | 71 |
| 617117 | rs7685686 | 0.7 | >10 | >14 | eeeeek-d7-kee | 72 |
| 617118 | rs7685686 | 0.4 | >10 | >25 | eeeeek-d7-kee | 73 |
| 617119 | rs7685686 | 0.8 | >10 | >13 | eeeeek-d7-eee | 74 |
| 617111 | rs7685686 | <0.4 | >10 | >25 | ekek-d9-keke | 91 |
| 613581 | rs7685686 | 0.9 | >10 | >11 | eeeeedk-d7-eeeee | 76 |
| 613582 | rs7685686 | 0.4 | >10 | >25 | eeeeek-d7-eeeee | 77 |
| 613583 | rs7685686 | 0.7 | >10 | >14 | eeeek-d7-eeeeee | 78 |
| 613584 | rs7685686 | 0.4 | >10 | >25 | eeek-d7-eeeeeee | 79 |
| 613585 | rs7685686 | 0.4 | >10 | >25 | eek-d7-eeeeeeee | 80 |
| 613586 | rs7685686 | 0.7 | >10 | >14 | ek-d7-eeeeeeeee | 81 |
| 613588 | rs7685686 | 0.7 | >10 | >14 | eeeeeeek-d7-eee | 82 |
| 613589 | rs7685686 | 1.2 | >10 | >8 | eeeeeeeek-d7-eee | 83 |
| 617105 | rs7685686 | <0.4 | 5.9 | 15 | eekk-d8-kkeee | 90 |
| 606561 | rs7685686 | <4 | >10 | 25 | ekek-d9-keee | 67 |
| 606562 | rs7685686 | 0.7 | >10 | 25 | eeek-d9-keee | 68 |
| 611714 | rs7685686 (G) | 0.6 | 4.7 | 8 | eeeekk-d7-kke | 164 |
| 611715 | rs7685686 (G) | 0.6 | 5.6 | 9 | ekek-d9-keke | 165 |
| 611717 | rs7685686 (G) | 0.8 | 4.7 | 6 | eeeekk-d7-kke | 167 |
| 611718 | rs7685686 (G) | 0.8 | 7.0 | 9 | ekk-d-k-d7-kke | 168 |
| 611719 | rs7685686 (G) | 0.9 | 3.2 | 4 | ekkkk-d7-kke | 169 |
| 611720 | rs7685686 (G) | <0.4 | 2.5 | 6 | ek-d9-kkke | 170 |
| 611721 | rs7685686 (G) | 0.9 | >10 | >11 | eeeek-d7-keee | 171 |
| 611722 | rs7685686 (G) | 1.5 | >10 | >7 | eeee-d-k-d7-keee | 172 |
| 611723 | rs7685686 (G) | 2.7 | 9.6 | 4 | eeeek-d7-keeee | 173 |
| 617104 | rs6446723 | <0.4 | 6.8 | 17 | eeekk-d7-kkeee | 84 |
| 617106 | rs6446723 | <0.4 | 5.7 | 14 | eekk-d8-kkeee | 85 |
| 617108 | rs6446723 | <0.4 | 5.8 | 14 | ekek-d8-kekee | 86 |
| 617109 | rs6446723 | <0.4 | 3.6 | 9 | eekk-d8-kkeee | 87 |
| 387916 (pos control) | | <0.4 | 0.6 | 2 | eeeee-d10- eeeee | 575 |
| 141923 (neg control) | | >10 | >10 | 1 | eeeee-d10- eeeee | 576 |

[1]IC$_{50}$ measured from average of 2 independent assays
[2]IC$_{50}$ measured from average of 3 independent assays

Example 7

Modified Oligonucleotides Targeting HTT SNP rs7685686

The modified oligonucleotides were designed to target SNP positions associated with the HTT gene. In Table 31, the 'k' subscript indicates an (S)-cEt modification; 'e' subscript indicates MOE modification; the 'y' subscript indicates a tricyclo DNA (tcDNA) modification; the 'z' subscript indicates a 2'-(ara)-F modification; the 'f' subscript indicates a 2'-F modification; 'm' before the cytosine residue indicates a 5-methylcytosine; number along with 'd' indicates the number of deoxyribose nucleosides; 's' subscript after the nucleoside indicates a phosphorothioate internucleoside linkage. The underlined nucleoside indicates the position on the modified oligonucleotide opposite to the SNP position.

TABLE 31

Modified oligonucleotides targeting HTT SNP rs7685686

| Isis No. | SNP | Sequence (5' to 3') | Gap Chemistry | Motif | SEQ ID NO |
|---|---|---|---|---|---|
| 460209 | rs7685686 | T$_{es}$ A$_{ks}$ A$_{ks}$ A$_{ds}$ T$_{ds}$ T$_{ds}$ G$_{ds}$ T$_{ds}$ mC$_{ds}$ A$_{ds}$ T$_{ds}$ mC$_{ds}$ A$_{ks}$ mC$_{ks}$ mC$_e$ | Full deoxy | ekk-d9-kke | 3 |
| 582670 | rs7685686 | T$_{es}$ A$_{ks}$ A$_{ks}$ A$_{ds}$ T$_{ds}$ T$_{ds}$ G$_{ds}$ T$_{ds}$ mC$_{ds}$ A$_{ds}$ T$_{ks}$ mC$_{ks}$ A$_{es}$ mC$_{es}$ mC$_e$ | Full deoxy | ekk-d7-kkeee | 3 |
| 566270 | rs7685686 | T$_{es}$ A$_{ks}$ A$_{ks}$ A$_{ds}$ T$_{zs}$ T$_{ds}$ G$_{ds}$ T$_{ds}$ mC$_{ds}$ A$_{ds}$ T$_{ds}$ mC$_{ds}$ A$_{ks}$ mC$_{ks}$ mC$_e$ | Deoxy/2'-(ara)-F | ekk-d-z-d7-kke | 3 |
| 566271 | rs7685686 | T$_{es}$ A$_{ks}$ A$_{ks}$ A$_{ds}$ T$_{ds}$ T$_{zs}$ G$_{ds}$ T$_{ds}$ mC$_{ds}$ A$_{ds}$ T$_{ds}$ mC$_{ds}$ A$_{ks}$ mC$_{ks}$ mC$_e$ | Deoxy/2'-(ara)-F | ekk-d2-z-d6-kke | 3 |

TABLE 31-continued

Modified oligonucleotides targeting HTT SNP rs7685686

| Isis No. | SNP | Sequence (5' to 3') | Gap Chemistry | Motif | SEQ ID NO |
|---|---|---|---|---|---|
| 581400 | rs7685686 | $T_{es}$ $A_{ks}$ $A_{ks}$ $A_{ds}$ $U_{fs}$ $T_{ds}$ $G_{ds}$ $\underline{T_{ds}}$ $mC_{ds}$ $A_{ds}$ $T_{ds}$ $mC_{ds}$ $A_{ks}$ $mC_{ks}$ $mC_e$ | Deoxy/2'-F | ekk-d-f-d7-kke | 577 |
| 581401 | rs7685686 | $T_{es}$ $A_{ks}$ $A_{ks}$ $A_{ds}$ $T_{ds}$ $U_{fs}$ $G_{ds}$ $\underline{T_{ds}}$ $mC_{ds}$ $A_{ds}$ $T_{ds}$ $mC_{ds}$ $A_{ks}$ $mC_{ks}$ $mC_e$ | Deoxy/2'-F | ekk-d2-f-d6-kke | 578 |
| 539557 | rs7685686 | $T_{es}$ $A_{ks}$ $A_{ks}$ $A_{ds}$ $T_{ds}$ $T_{ds}$ $G_{ds}$ $\underline{T_{ys}}$ $mC_{ds}$ $A_{ds}$ $T_{ds}$ $mC_{ds}$ $A_{ks}$ $mC_{ks}$ $mC_e$ | Deoxy/Tricyclo DNA (tcDNA) | ekk-d4-y-d4-kke | 3 |

Example 8

Selectivity of Modified Oligonucleotides Targeting HTT SNP rs7685686

Several modified oligonucleotides presented in Table 31 were tested in vitro targeting HTT SNP rs7685686. Heterozygous fibroblast GM04022 cell line was used (from Coriell Institute). Cultured GM04022 cells at a density of 400,000 cells per well were transfected using electroporation (Harvard Apparatus ECM830, 115 V, 6 ms) with 0.06, 0.19, 0.56, 1.7, 5.0 and 15 μM concentrations of ISIS 460209, 566270, 566271, 581400, or 581401 or 0.027, 0.082, 0.25, 0.7, 2.2, 6.7 and 20 μM concentrations of ISIS 582670. Treated cells were maintained at 37° C. and 5% $CO_2$ in minimal essential medium containing 15% fetal bovine serum, non-essential amino acids and penicillin/streptomycin. Approximately 24 hours post-transfection, the cells were washed with DPBS buffer and lysed. RNA was extracted using the Qiagen RNeasy96 kit and levels of the human HTT mRNA alleles were determined using the qPCR assay C_2231945_10 at SNP rs362331 from Life Technologies. The mutant and wild-type HTT mRNA levels were measured simultaneously by using two different fluorophores, FAM for mutant allele and VIC for wild-type allele. Quantitative RT-PCR reactions were run on the ABI 7900HT instrument using the Quantitect Probe RT-PCR kit following the manufacturer's instructions. The HTT mRNA levels were normalized to total RNA content, as measured by RIBOGREEN. The $IC_{50}$ and selectivity were calculated using methods described previously in Example 6 and the results are presented in Table 32. ISIS 460209 was included in the study for comparison.

TABLE 32

Selectivity of modified oligonucleotides targeting Huntingtin (HTT) SNP rs7685686

| Isis No. | SNP | Mut $IC_{50}$ (μM) | Selectivity (wt vs mut) | Motif | SEQ ID No. |
|---|---|---|---|---|---|
| 460209 | rs7685686 | 0.29 | 6.9 | ekk-d9-kke | 3 |
| 566270 | rs7685686 | 0.14 | 7.4 | ekk-d7-kkeee | 3 |
| 566271 | rs7685686 | 0.11 | 7.1 | ekk-d-z-d7-kke | 3 |
| 581400 | rs7685686 | 0.6 | >25 | ekk-d2-z-d6-kke | 577 |
| 581401 | rs7685686 | 0.77 | >19 | ekk-d-f-d7-kke | 3 |
| 582670 | rs7685686 | 0.42 | >47 | ekk-d7-kkeee | 3 |

Example 9

Tm and Selectivity of Modified Oligonucleotide Containing Tricyclo DNA (tcDNA) Modification Targeting HTT SNP rs7685686

ISIS 539557 from Table 31 was tested for thermal stability. Its potency and selectivity targeting HTT SNP rs7685686 were also evaluated in vitro. ISIS 460209 was included in the study for comparison.

Thermal Stability Assay

The $T_m$ for ISIS 539557 was measured using the method described herein. The modified oligonucleotide and RNA was mixed in a 1:1 ratio (4 μM duplex) in buffer containing 10 mM phosphate, 100 mM NaCl and 10 mM EDTA at pH 7.0. The duplex was denatured at 85 ° C. and slowly cooled to the starting temperature of the experiment (15 ° C.). Thermal denaturation temperatures ($T_m$ values) were measured in quartz cuvettes (pathlength 1.0 cm) on a Cary 100 UV/VIS spectrophotometer equipped with a Peltier temperature controller. Absorbance at 260 nm was measured as a function of temperature using a temperature ramp of 0.5 ° C. per min. $T_m$ value was determined using the hyperchromicity method incorporated into the instrument software. The results for $T_m$ versus matched and mismatched RNA are presented in Table 33.

Cell Culture, Transfection and Selectivity Analysis

Heterozygous fibroblast GM04022 cell line was used (from Coriell Institute). Cultured GM04022 cells at a density of 400,000 cells per well were transfected using electroporation (Harvard Apparatus ECM830, 115 V, 6 ms) with 2 μM concentrations of ISIS 460209 or 539557. Treated cells were maintained at 37° C. and 5% $CO_2$ in minimal essential medium containing 15% fetal bovine serum, non-essential amino acids and penicillin/streptomycin. Approximately 24 hours post-transfection, the cells were washed with DPBS buffer and lysed. RNA was extracted using the Qiagen RNeasy96 kit and levels of the human HTT mRNA alleles were determined using the qPCR assay C_2231945_10 at SNP rs362331 from Life Technologies. The mutant and wild-type HTT mRNA levels were measured simultaneously by using two different fluorophores, FAM for mutant allele and VIC for wild-type allele. Quantitative RT-PCR reactions were run on the ABI 7900HT instrument using the Quantitect Probe RT-PCR kit following the manufacturer's instructions. The HTT mRNA levels were normalized to total RNA content, as measured by RIBOGREEN. The percent of HTT mRNA reduction, relative to untreated control levels was measured. The results for selectivity in Table 33 are presented as the ratio of wt HTT/mut HTT mRNA reduction in GM4022 fibroblasts.

TABLE 33

T$_m$ and selectivity of ISIS 582670 targeting HTT SNP rs7685686 in GM4022 cells

| Isis No. | SNP | mut T$_m$ (° C.) | wt T$_m$ (° C.) | Δ T$_m$ mut-wt | Ratio (wt vs mut) | Motif | SEQ ID NO |
|---|---|---|---|---|---|---|---|
| 460209 | rs7685686 | 53.7 | 52.2 | 1.5 | 2.6 | ekk-d9-kke | 3 |
| 582670 | rs7685686 | 53.8 | 51.7 | 2.1 | 3.3 | ekk-d7-kkeee | 3 |

Example 10

Duration of Action of Modified Oligonucleotides

Mice were given a single ICV injection of modified oligonucleotides targeted to mutant HTT nucleic acid transcripts. The modified oligonucleotides had either 2'-MOE modifications or cEt modifications. After the initial ICV injection, mice from each group were sacrificed at 1, 2, 4, 8, 12, and 16 weeks and the amoung of mutant HTT protein was analyzed. It was found that the modified oligonucleotides having cEt modifications reduced mutant HTT protein for up to 16 weeks after a single ICV dose. It was found that 2'-MOE modified oligonucleotides reduced mutant HTT protein for 4-8 weeks, after which point in time mutant HTT levels began to rise and approach mutant HTT levels found in animals treated with PBS control. This example shows that a single dose of modified oligonucleotides targeted to mutant huntingtin transcript can inhibit mutant HTT protein expression for greater than 16 weeks.

Example 11

Modified Oligonucleotides Targeting HTT SNP rs7685686

The modified oligonucleotides were designed to target SNP positions associated with the HTT gene. In Table 31, the 'k' subscript indicates an (S)-cEt modification; 'e' subscript indicates MOE modification; the 'y' subscript indicates a tricyclo DNA (tcDNA) modification; the 'z' subscript indicates a 2'-(ara)-F modification (shown below); the 'f' subscript indicates a 2'-F modification in the ribo orientation (shown below); the 'h' subscript indicates a F-CeNA modification; 'm' before the cytosine residue indicates a 5-methylcytosine; number along with 'd' indicates the number of deoxyribose nucleosides; 's' subscript after the nucleoside indicates a phosphorothioate internucleoside linkage; '$^{s5'}$' before a residue indicates an S-5'-Me-DNA modification, e.g. "$^{s5}$T'"; '$^{r5'}$' before a residue indicates an S-5'-Me-DNA modification, e.g. "$^{r5}$T." The underlined nucleoside indicates the position on the modified oligonucleotide opposite to the SNP position.

Examples of the 2'-(ribo)-flouro (f), 2'-(ara)-fluor (z), and F-CeNA (h) modifications are provided below:

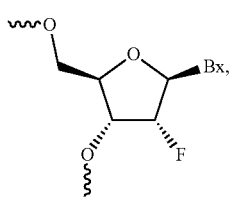

f

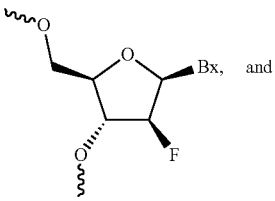

z and

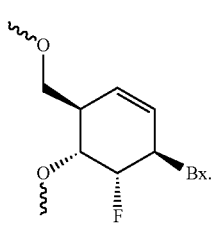

h

Examples of R-5'-Me-DNA and S-5'-Me-DNA modifications are provided below:

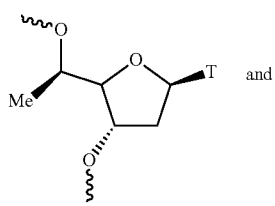

R-5'-Me-DNA and

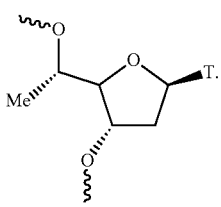

S-5'-Me-DNA

TABLE 34

Modified oligonucleotides targeting HTT SNP rs7685686

| Isis No. | SNP | Sequence (5' to 3') | Gap Chemistry | Motif | SEQ ID NO |
|---|---|---|---|---|---|
| 460209 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Full deoxy | ekk-d9-kke | 3 |
| 582670 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ks}$ $mC_{ks}$ $A_{es}$ $mC_{es}$ $mC_e$ | Full deoxy | ekk-d7-kkeee | 3 |
| 566270 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/2'-(ara)-F | ekk-d-z-d7-kke | 3 |
| 566271 | rs7685686 | $T_{es}$ $A_{ks}$ $A_{ks}$ $A_{ds}$ $T_{ds}$ $T_{zs}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/2'-(ara)-F | ekk-d2-z-d6-kke | 3 |
| 581400 | rs7685686 | $T_{es}$ $A_{ks}$ $A_{ks}$ $A_{ds}$ $U_{fs}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/2'-F | ekk-d-f-d7-kke | 577 |
| 581401 | rs7685686 | $T_{es}$ $A_{ks}$ $A_{ks}$ $A_{ds}$ $T_{ds}$ $U_{fs}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/2'-F | ekk-d2-f-d6-kke | 578 |
| 539557 | rs7685686 | $T_{es}$ $A_{ks}$ $A_{ks}$ $A_{ds}$ $T_{ds}$ $T_{ds}$ $G_{ds}$ $\underline{T}_{ys}$ $mC_{ds}$ $A_{ds}$ $T_{ds}$ $mC_{ds}A_{ks}$ $mC_{ks}$ $mC_e$ | Deoxy/Tricyclo DNA (tcDNA) | ekk-d4-y-d4-kke | 3 |
| 575837 | rs7685686 | $T_{es}$ $A_{ks}$ $A_{ks}$ $A_{fs}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/2'-F | ekk-f-d8-kke | 3 |
| 575831 | rs7685686 | $T_{es}$ $A_{ks}$ $A_{ks}$ $A_{zs}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/2'-(ara)-F | ekk-z-d8-kke | 3 |
| XXXX1 | rs7685686 | $T_{es}$ $A_{ks}$ $A_{ks}$ $A_{hs}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/F-CeNA | ekk-h-d8-kke | 3 |
| 582981 | rs7685686 | $T_{es}$ $A_{ks}$ $A_{ks}$ $A_{ds}$ $T_{ds}$ $T_{hs}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/F-CeNA | ekk-d2-h-d6-kke | 3 |
| 582980 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/F-CeNA | ekk-d-h-d7-kke | 3 |
| 575840 | rs7685686 | $T_{es}$ $A_{ks}$ $A_{ks}$ $A_{ds}$ $T_{ds}$ $T_{ds}$ $G_{fs}$ $\underline{T}_{ds}$ $mC_{ds}$ $A_{ds}$ $T_{ds}$ $mC_{ds}A_{ks}$ $mC_{ks}$ $mC_e$ | Deoxy/2'-F | ekk-d3-f-d5-kke | 3 |
| 566272 | rs7685686 | $T_{es}$ $A_{ks}$ $A_{ks}$ $A_{ds}$ $T_{ds}$ $T_{ds}$ $G_{zs}$ $\underline{T}_{ds}$ $mC_{ds}$ $A_{ds}$ $T_{ds}$ $mC_{ds}A_{ks}$ $mC_{ks}$ $mC_e$ | Deoxy/2'-(ara)-F | ekk-d3-z-d5-kke | 3 |
| XXXX2 | rs7685686 | $T_{es}$ $A_{ks}$ $A_{ks}$ $A_{ds}$ $T_{ds}$ $T_{ds}$ $G_{hs}$ $\underline{T}_{ds}$ $mC_{ds}$ $A_{ds}$ $T_{ds}$ $mC_{ds}A_{ks}$ $mC_{ks}$ $mC_e$ | Deoxy/F-CeNA | ekk-d3-h-d5-kke | 3 |
| 586156 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_e$ | Deoxy/F-CeNA | ekk-d4-h-d4-kke | 3 |
| 581402 | rs7685686 | $T_{es}$ $A_{ks}$ $A_{ks}$ $A_{ds}$ $T_{ds}$ $T_{ds}$ $G_{ds}$ $\underline{T}_{hs}$ $mC_{ds}$ $A_{ds}$ $T_{ds}$ $mC_{ds}A_{ks}$ $mC_{ks}$ $mC_e$ | Deoxy/2'-F | ekk-d5-f-d3-kke | 3 |
| 566273 | rs7685686 | $T_{es}$ $A_{ks}$ $A_{ks}$ $A_{ds}$ $T_{ds}$ $T_{ds}$ $G_{ds}$ $\underline{T}_{zs}$ $mC_{ds}$ $A_{ds}$ $T_{ds}$ $mC_{ds}A_{ks}$ $mC_{ks}$ $mC_e$ | Deoxy/2'-(ara)-F | ekk-d5-z-d3-kke | 3 |
| 582982 | rs7685686 | $T_{es}$ $A_{ks}$ $A_{ks}$ $A_{ds}$ $T_{ds}$ $T_{ds}$ $G_{ds}$ $\underline{T}_{hs}$ $mC_{ds}$ $A_{ds}$ $T_{ds}$ $mCd_{s}A_{ks}$ $mC_{ks}$ $mC_e$ | Deoxy/F-CeNA | ekk-d5-h-d3-kke | 3 |
| 575842 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{fs}$ $T_{ds}$ $mC_{ds}A_{ks}$ $mC_{ks}$ $mC_e$ | Deoxy/2'-F | ekk-d6-f-d2-kke | 3 |
| 566274 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{zs}$ $T_{ds}$ $mC_{ds}A_{ks}$ $mC_{ks}$ $mC_e$ | Deoxy/2'-(ara)-F | ekk-d6-z-d2-kke | 3 |
| XXXX3 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{hs}$ $T_{ds}$ $mC_{ds}A_{ks}$ $mC_{ks}$ $mC_e$ | Deoxy/F-CeNA | ekk-d6-h-d2-kke | 3 |
| 581403 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $U_{fs}$ $mC_{ds}A_{ks}$ $mC_{ks}$ $mC_e$ | Deox>/2'-F | ekk-d7-f-d-kke | 579 |
| 566275 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{zs}$ $mC_{ds}A_{ks}$ $mC_{ks}$ $mC_e$ | Deoxy/2'-(ara)-F | ekk-d7-z-d-kke | 3 |
| 582983 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{hs}$ $mC_{ds}A_{ks}$ $mC_{ks}$ $mC_e$ | Deoxy/F-CeNA | ekk-d7-h-d-kke | 3 |

TABLE 34-continued

Modified oligonucleotides targeting HTT SNP rs7685686

| Isis No. | SNP | Sequence(5' to 3') | Gap Chemistry | Motif | SEQ ID NO |
|---|---|---|---|---|---|
| 581404 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{fs}$ $A_{ks}$ $mC_{ks}$ $mC_{e}$ | Deoxy/2'-F | ekk-d8-f-dkke | 3 |
| 578228 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{ks}$ $A_{ks}$ $mC_{ks}$ $mC_{e}$ | Deoxy/2'-(ara)-F | ekk-d8-z-kke | 3 |
| 582984 | rs7685686 | $T_{es}$ $A_{ks}$ $A_{ks}$ $A_{ds}$ $T_{ds}$ $T_{ds}$ $G_{ds}$ $\underline{T}_{ds}$ $mC_{ds}$ $A_{ds}$ $T_{ds}$ $mC_{hs}$ $A_{ks}$ $mC_{ks}$ $mC_{e}$ | Deoxy/F-CeNA | ekk-d8-h-kke | 3 |
| XXXX4 | rs7685686 | $T_{es}$ $A_{ks}$ $A_{ks}$ $A_{ds}^{r5}$ $T_{ds}$ $T_{ds}$ $G_{ds}$ $\underline{T}_{ds}$ $mC_{ds}$ $A_{ds}$ $T_{ds}$ $mC_{ds}A_{ks}$ $mC_{ks}$ $mC_{e}$ | Deoxy/K-5'-Me DNA | ekk-d9-kke | 3 |
| XXXX5 | rs7685686 | $T_{es}$ $A_{ks}$ $A_{ks}$ $A_{dss}^{5}$ $G_{ds}$ $\underline{T}_{ds}$ $mC_{ds}$ $A_{ds}$ $T_{ds}$ $mC_{ds}$ $A_{ks}$ $mC_{ks}$ $mC_{e}$ | Deoxy/S-5'-Me DNA | ekk-d9-kke | 3 |
| XXXX6 | rs7685686 | $TC_{s}$ $A_{ks}$ $A_{ks}$ $A_{ds}$ $T_{ds}^{r5}$ $G_{ds}$ $\underline{T}_{ds}$ $mC_{ds}$ $A_{ds}$ $T_{ds}$ $mC_{ds}$ $A_{ks}$ $mC_{ks}$ $mC_{e}$ | Deoxy/R-5'-Me DNA | ekk-d9-kke | 3 |
| XXXX7 | rs7685686 | $T_{es}$ $A_{ks}$ $A_{ks}$ $A_{ds}$ $T_{dss}^{5}$ $T_{ds}$ $G_{ds}$ $\underline{T}_{ds}$ $mC_{ds}$ $A_{ds}$ $T_{ds}$ $mC_{ds}$ $A_{ks}$ $mC_{ks}$ $mC_{e}$ | Deoxy/S-5'-Me DNA | ekk-d9-kke | 3 |

Example 12

Selectivity of Modified Oligonucleotides Targeting HTT SNP rs7685686

Several modified oligonucleotides presented in Table 31 were tested in vitro targeting HTT SNP rs7685686. Heterozygous fibroblast GM04022 cell line was used (from Coriell Institute). Cultured GM04022 cells at a density of 400,000 cells per well or 450,000 cells per well were transfected using electroporation (Harvard Apparatus ECM830, 115 V, 6 ms) with 0.06, 0.19, 0.56, 1.7, 5.0 and 15 µM concentrations of the modified oligonucleotides presented in Table 31, except for ISIS 582670, in which concentrations of 0.027, 0.082, 0.25, 0.7, 2.2, 6.7 and 20 µM were used. Treated cells were maintained at 37° C. and 5% $CO_2$ in minimal essential medium containing 15% fetal bovine serum, non-essential amino acids and penicillin/streptomycin. Approximately 24 hours post-transfection, the cells were washed with DPB S buffer and lysed. RNA was extracted using the Qiagen RNeasy96 kit and levels of the human HTT mRNA alleles were determined using the qPCR assay C_2231945_10 at SNP rs362331 from Life Technologies. The mutant and wild-type HTT mRNA levels were measured simultaneously by using two different fluorophores, FAM for mutant allele and VIC for wild-type allele. Quantitative RT-PCR reactions were run on the ABI 7900HT instrument using the Quantitect Probe RT-PCR kit following the manufacturer's instructions. The HTT mRNA levels were normalized to total RNA content, as measured by RIBOGREEN. The $IC_{50}$ and selectivity were calculated using methods described previously in Example 6 and the results are presented in Table 32. ISIS 460209 was included in the study for comparison.

In certain embodiments, a modification at position 4 from the 5'-end increases selectivity. In certain embodiments, a modification at position 5 from the 5'-end increases selectivity. In certain embodiments, a modification at position 7 from the 5'-end increases selectivity. In certain embodiments, a modification at position 8 from the 5'-end increases potency and selectivity. In certain embodiments, a modification at position 9 from the 5'-end increases potency. In certain embodiments, a modification at position 10 from the 5'-end increases selectivity. In certain embodiments, a modification at position 11 from the 5'-end increases selectivity. In certain embodiments, a modification at position 12 from the 5'-end increases potency. In certain embodiments, an S-5'-Me-DNA modification increases allele selectivity.

TABLE 35

Selectivity of modified oligonucleotides targeting Huntingtin (HT7) SNP rs7685686

| Isis No. | SNP | Mut $IC_{50}$ (µM) | Selectivity (wt vs mut) | Motif | SEQ ID No. |
|---|---|---|---|---|---|
| 460209 | rs7685686 | .31 | 9 | ekk-d9-kke | 3 |
| 575837 | rs7685686 | .28 | 15 | ekk-f-d8-kke | 3 |
| 575831 | rs7685686 | .21 | 19 | ekk-z-d8-kke | 3 |
| XXXX1 | rs7685686 | ND | ND | ekk-h-d8-kke | 3 |
| 582981 | rs7685686 | .35 | >29 | ekk-d2-h-d6-kke | 3 |
| 582980 | rs7685686 | .34 | 7 | ekk-d-h-d7-kke | 3 |
| 575840 | rs7685686 | .94 | >11 | ekk-d3-f-d5-kke | 3 |
| 566272 | rs7685686 | .07 | 27 | ekk-d3-z-d5-kke | 3 |
| XXXX2 | rs7685686 | ND | ND | ekk-d3-h-d5-kke | 3 |
| 586156 | rs7685686 | .39 | 5 | ekk-d4-h-d4-kke | 3 |
| 581402 | rs7685686 | .16 | 5 | ekk-d5-f-d3-kke | 3 |
| 566273 | rs7685686 | .09 | 18 | ekk-d5-z-d3-kke | 3 |
| 582982 | rs7685686 | .23 | 13 | ekk-d5-h-d3-kke | 3 |
| 575842 | rs7685686 | .20 | 50 | ekk-d6-f-d2-kke | 3 |
| 566274 | rs7685686 | .20 | >50 | ekk-d6-z-d2-kke | 3 |
| XXXX3 | rs7685686 | ND | ND | ekk-d6-h-d2-kke | 3 |
| 581403 | rs7685686 | .35 | 18 | ekk-d7-f-d-kke | 579 |
| 566275 | rs7685686 | .22 | 28 | ekk-d7-z-d-kke | 3 |
| 582983 | rs7685686 | .30 | 17 | ekk-d7-h-d-kke | 3 |
| 581404 | rs7685686 | .07 | 18 | ekk-d8-f-dkke | 3 |
| 578228 | rs7685686 | .10 | 32 | ekk-d8-z-kke | 3 |
| 582984 | rs7685686 | .06 | 10 | ekk-d8-h-kke | 3 |
| XXXX4 | rs7685686 | .15 | 6.9 | ekk-d9-kke | 3 |
| XXXX5 | rs7685686 | .38 | 16.3 | ekk-d9-kke | 3 |
| XXXX6 | rs7685686 | .31 | 5.7 | ekk-d9-kke | 3 |
| XXXX7 | rs7685686 | .40 | >38 | ekk-d9-kke | 3 |

What is claimed is:

1. A compound comprising a modified oligonucleotide consisting of 12 to 30 linked nucleosides, wherein the nucleobase sequence of the modified oligonucleotide comprises at least 8 contiguous nucleobases of the nucleobase sequence recited in SEQ ID NO: 2, wherein the modified oligonucleotide has a sugar motif selected from ekek-d9-keke, kekk-d8-keke, ekkk-d8-kke, ekk-d8-kkke, ekekk-d8-keke, ekek-d8-kkeke, eekk-d8-kkeee, and eeekk-d8-kkee, wherein k is a cEt sugar moiety, e is a 2'-OCH$_2$CH$_2$OCH$_3$ ribosyl sugar moiety, and d is a 2'-deoxyribosyl sugar moiety.

2. The compound of claim 1, wherein the nucleobase sequence of the modified oligonucleotide is 100% complementary to SEQ ID NO. 1.

3. The compound of claim 1, wherein the modified oligonucleotide has the nucleobase sequence recited in SEQ ID NO: 5.

4. The compound of claim 1, wherein the modified oligonucleotide has the nucleobase sequence recited in SEQ ID NO: 6.

5. The compound of claim 1, wherein the modified oligonucleotide has the nucleobase sequence recited in SEQ ID NO: 27.

6. The compound of claim 1, wherein the modified oligonucleotide has the nucleobase sequence recited in SEQ ID NO: 28.

7. The compound of claim 1, wherein the modified oligonucleotide has the nucleobase sequence recited in SEQ ID NO: 29.

8. The compound of claim 1, wherein the modified oligonucleotide has the nucleobase sequence recited in SEQ ID NO: 30.

9. The compound of claim 1, wherein the modified oligonucleotide has the nucleobase sequence recited in SEQ ID NO: 38.

10. The compound of claim 1, wherein the modified oligonucleotide has the nucleobase sequence recited in SEQ ID NO: 39.

11. The compound of claim 1, wherein the modified oligonucleotide has the nucleobase sequence recited in SEQ ID NO: 46.

12. The compound of claim 3, wherein the modified oligonucleotide has a ekek-d9-keke sugar motif.

13. The compound of claim 4, wherein the modified oligonucleotide has a kekk-d8-keke sugar motif.

14. The compound of claim 5, wherein the modified oligonucleotide has a ekkk-d8-kke sugar motif.

15. The compound of claim 6, wherein the modified oligonucleotide has a ekk-d8-kkke sugar motif.

16. The compound of claim 7, wherein the modified oligonucleotide has a ekekk-d8-keke sugar motif.

17. The compound of claim 8, wherein the modified oligonucleotide has a ekek-d8-kkeke sugar motif.

18. The compound of claim 9, wherein the modified oligonucleotide has a eekk-d8-kkeee sugar motif.

19. The compound of claim 10, wherein the modified oligonucleotide has a eekk-d8-kkeee sugar motif.

20. The compound of claim 11, wherein the modified oligonucleotide has a eeekk-d8-kkee sugar motif.

21. The compound of claim 1, comprising at least one phosphorothioate internucleoside linkage.

22. A method of ameliorating a symptom of Huntington's disease, comprising administering the compound of claim 1 to a subject in need thereof.

23. The compound of claim 1, wherein the compound is conjugated.

24. A pharmaceutical composition comprising the compound of claim 1 and a pharmaceutically acceptable carrier or diluent.

\* \* \* \* \*

SEQUENCE LISTING

<160> NUMBER OF SEQ ID NOS: 579

<210> SEQ ID NO 1
<211> LENGTH: 202001
<212> TYPE: DNA
<213> ORGANISM: Homo sapien

<400> SEQUENCE: 1

| | | | | | |
|---|---|---|---|---|---:|
| gcccagcagg | tgtcagcctc | attttacccc | gccccctattc | aagatgaagt | tgttctggtt | 60 |
| ccaacgcctc | tgacatatta | gctgcatcat | tttacatttc | tttttttttt | ttcctttttaa | 120 |
| atgggtcttt | gctctgtcac | ccaggctgga | gtgctgtggt | atgatctcgg | ctcactgcaa | 180 |
| tctccacctc | cgaggttcca | gcgattctct | tgcctcagcc | tcccgagtag | ctgggactac | 240 |
| aggcacccac | catcatactg | gctaattttt | tgtgttttta | gtagagatgg | ggtttcccca | 300 |
| tgttgcccag | gctgatctca | aactcctggg | cttaagcaat | acagccgcgt | tggcctccca | 360 |
| aagtgttggg | attacaagca | tgagctaccc | cacccagctc | attttacatt | tccacttgtt | 420 |
| aaactgaaaa | ctggcccgag | aaagcttctg | tactgccatc | cttgcgtcct | tgcagatgaa | 480 |
| tcgtaaccta | gcatagtagg | taggcagact | gaaaacctaa | cttagcagta | ggcttctgta | 540 |
| acaacagctg | tgtctcagcc | agttcctgca | gccagacttc | aaccactcac | aggccgcaaa | 600 |
| ctgttcaaac | tgtgttcgga | gaaggcgaat | tcatctggct | gttaacgtgc | ctcacttctg | 660 |
| ctttctgtgg | ccactttccc | ttttctgtcc | ataaatttgc | tttgaccaca | cagcatccct | 720 |
| agagtctccc | tgaatctgct | gtgattctgg | gacctgcacc | atttgtgaat | tgttttttttt | 780 |
| ttccttgatc | agctaaactc | tgttcaattc | aatttgttgg | aagtttttaa | cataccaatg | 840 |
| gtgcaccaag | gttccaattt | ctccacttcc | tcataaataa | gtcattttaa | atggcttttc | 900 |
| agtattccaa | tatttggaag | tattaatgtt | tctaccaatt | ttctattttt | ggacattgag | 960 |
| gttgtttcat | tttttttttc | ttttttgag | acagagtctc | gctccgtcac | ccaggctgga | 1020 |
| gtgcagtggc | ctgatcccgg | cccactgcaa | cctccacctc | cctcctcagc | ctcctgagta | 1080 |
| gctgggatta | caggtgcatg | caccaccaca | cccagctaat | ttttgtattt | ttagtagaga | 1140 |
| tggggtttca | ccatgttggt | caggctggtc | tcaaactcct | gacctcaggt | ggtccacctg | 1200 |
| ccttggcctc | ccaaaatgct | gggattacag | gcctgagcca | ctgcgcctgg | cctcatcttc | 1260 |
| ttgatattaa | tgttgcttta | acatctttgt | ccctgtgttt | tttgttttt | ttttgagac | 1320 |
| ggagtctcat | tcattctgtc | acccaggctg | gagttcagtg | gcgtgatctc | agctcactgc | 1380 |
| aacctctgtc | tcctgggttc | cagtgattct | cctgcgtcgg | tctcctgagt | agctgtgttc | 1440 |
| ctgggtcttt | cgatggttat | ttaatacttc | cctacagtaa | tgccctgtgc | gtacatgcta | 1500 |
| agtgtgatga | aatggttggc | acagttaaat | cttttgaaag | acattgccaa | gtcactcttc | 1560 |
| agaaaagtga | taggaggtca | tagcaatttt | aagaagtcct | catttctaca | tttccttact | 1620 |
| aatctcggtt | ggtgtctctt | caatctttcc | tcacactttt | cttgggtttt | tcctgaatca | 1680 |
| tgagtctact | acatttacac | attttaaagc | atctttagaa | acaggatctc | attttgttgc | 1740 |
| ccaggctaga | gtttggtggc | atgattatag | ctcctcatac | tcctgggctc | aagtgatcct | 1800 |
| tccacctctg | aaaccccaaa | atttgagaaa | ggtctcattt | aatttagaaa | gtttatttg | 1860 |
| ccaaggttga | gggtgcacac | ctgtgatgat | atacgagtta | aaagaaatt | atttaggcag | 1920 |
| atactgaggg | taagaaagtc | ctcggtaagg | ttttcttttc | aatgaaaagc | agccccaag | 1980 |
| cattttcttt | tctaacaaag | agcagcctgt | aaaatcgagc | tgcagacata | cacaagcaag | 2040 |
| ctggaagctt | gcacaggtga | atgctggcag | ctgtgccaat | aagaaaggc | tacctggggc | 2100 |

```
caggcagatc caacatggcg gctccatctt ccctttcctt gtcaaccatg tgcacagtaa    2160
ggagcaggca acatagtgtc ccccgagtag agaccaattt gcataataaa aggtgagggt    2220
agggtgggca gcttctttgc atgctatgta acattatgc ctggtccaac caatctttgg     2280
gccctgtgta aattagacac cacctcctca agcctgtcta taaaaccctg tccattctgc    2340
cgcaggctgg aagacccact ggggcacccc tctctctcta taggagacag ctattcattt    2400
ttctctttct ttcacctatt aaagctccac tcttaaccc actccgtgtg tatctatgtt     2460
cttgatttcc ttggcatgag gcaatgaacc ttgggtatta ccccagaacc ttgggtatta    2520
tgccacttca gtgacacagc ctcaggaaat cctgatgaca tgttcccaag atggtcgggg    2580
cacagcttgg ttttatacat tttagggaga catgagacgt caattcatat atgtaagaag    2640
tacattggtt ccgtccagaa aggcggggac aacttgaggc aggagagag cttctaggtc      2700 acaggtagac aaatggttgc attcttttga atctccgata agcctttcca aaggaggcaa    2760
tcagaatatg cgtctattga ctgggcgcag tggctcatgc ctgtaatgcc agcactttgg    2820
gaggcggagg tgggtggatc acctgaggtc aggagtttga gagcagcccg gccaacatgg    2880
tgaaaccctg tctctactaa aaatacaaaa aattagctgg gcgtggtggc gggcgcctgt    2940
aatcccagct actcgggagg ctgaggcagg agaatagctt gaacccagaa ggaagaggtt    3000
gcagtgagct gagatggtgc cattgcactc cagcctgggc aacaagagtg aaactccatc    3060
tcagaaaaaa aaaaaaaagg cctgggcaaa gtggctcacg cctgtaatcc cagcactttg    3120
ggaagccgag gcgggcaggt cacaaagtca ggagattgag accatcctgg ctaacatgat    3180
gaaaccccat ctctactaaa aaatacaaaa aactagctgg gtgtggtggc gagcacctgt    3240
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaa aaaaaaaaa aagagagag agaatatgca tctatctcag       3420
tgagcagaag gatgactttg aatggaatgg gagcagttcc tagcttgaac ttcccctta     3480 gcttcagtga tttgggggct caaggtatgt tcctttcaca tacctcagcc tcccaagtag    3540
ctgggaccac aagtgcatgc caccacacgt ggctaatgtt ttattttttt tgtaggaata    3600
gggtctcact atgtgtccag gctggtctaa aaccctgag ctcaaatggt cctcccgcct     3660
cagcctcccg aaatgctggg attacaggca tgagccagca tgcccggcct agtctacatt    3720
tttataaatt gctaattcaa agttccctct ccaaaacctc atggttttcc ctgttctcat    3780
cccctgcacc ctcccttccc ctggagtact cacctggcct tggaggtctg gtgtgagccc    3840
ggacttcgat tctaggcaca gcatgtgatg agcgccccca ggtcaaacac ctcccctctg    3900
cggcctgtgc ttcaccgcct tgacagtgag aaaggtctcc cttcggctca ttctcgaagt    3960
ctcaaacttc acttctcctg tgcgctgatt ctgaattcag ccccgtcca aggtcctggc     4020 cccttctct tctgcttggc gtgttgttca tcaccactgt gcactgctga gggtaagtgc     4080
ggttctctgg acctctgctt tatcattaga acagactctt gcggtttccc acgacattcc    4140
tttcacttct cacttggaag atgagccgtg aggaaatcct gtgttgtgtg gtatgtgggc    4200
tgtgcttctg cttgacttga gggccaagca gcattgcaag ccatggtttt aaataagaaa    4260
gaacatttct aaccttcatc ttctagtaag gaaacaagtg ggctttagag ttcttgctca    4320
ggaaagacct atgtcccagt ccaaccggac ctttttactaa agagatcttc ctgatcctcc    4380
tccccaggcc aggggagggg tcctccctgg ggttggagcc tttagtaggg ggtcggagac    4440
```

```
acgacgtagc cttcatgaca ttcatagtct agttacacga tccctgtaag ggtcagttga    4500
agtaagtgct acaaaggaag ggaggtgctc agtggagagg gctctctttt atgtattata    4560
tttctttcat ggggagggat atggatcagg gatcagcaga ggtgtttcag tcccgaggga    4620
aagaaagtca gcgtggcttg ggagttggga gcagcaagac agtggctcaa gatatcttaa    4680
gactagtgga gtacaccttg catgttaaaa gccttgctca gggctgcctg gttcttgtag    4740
gacgacagag atggcctagc tctgcatact gcaccccag gggctcagaa cagtgcaaat    4800
gtcagtctat ctgtcagtgg cagagccagc cttggagcag gggtgcaagg aggtctctgc    4860
actggccagg catgcagaac attctgttca gtagcactgg acagaaggcc ccatctagat    4920
gagacagagc tggtggggca ggacaaagac tcctggcagc tcaaacggcc tggcagatgc    4980
ttggagagag ggggcttctt gagacagcac catttctggg aagagagtca cctgggaggg    5040
atgaggccac gctccggctt ggaggtgaag agaggggctg ctgcaagaaa gaattagaga    5100
catgccagcc tttgctgtgt tgcccaggct ggtcatgaac tcttggcctc aagcaatctt    5160
cccacctcag cctcccaag cgctgggatt atagacatga gcccccatgc tggccaataa    5220
aagatgattt tatggagggg atggtggtga aggttgtggg tggtatgaaa tagtaagaaa    5280
tatatattgg tctgcaccca gttcctgcca cagagctcct aaaatcctga aacttcctg    5340 ggtgagcatc ttttgttcta atgaggtgac tcttggtggc tcctggatag gagtgaatca    5400
ccagaaagat caagccagag ttagaagcag aaagtgctgg ctataacaca ggaaagctgt    5460
aacacaaata ataaagtttt ttttttttt tttgagatgg agcctcactc tgttgcccag    5520
gctggagtgc aatggtgcaa tctcagctca ctacaagctc tgcctccag gttcaagtga    5580 ttctcctgcc tcagcctcct gagcagttgg gactacaggt gtgtgccacc acatctggct    5640 aattttgta ttttagcag agacggggtt tcaccatatt aaccaggctg gcctcaaact    5700
ccttaccttg tgatccgcct gcctcagcct cccaaagtgc tgggattaca ggcatgagcc    5760
accgtgcctg gccaaaagac attgttctta aagaatcaa ctaactaacc aaataaataa    5820
aaatctaacc taattaagaa actaaaaata cacaaaaatt aatttcaagg ggagaaaat    5880 catgtaaaga gagaaagata atgaatactt tgcagaaatt tatgaacata acataaaac    5940 ttggatgaaa tgcatttcta ggaaaacata atttatcaaa actaaccaca agtaaaatag    6000
aagcctaaat aggatatttt caagagaaga agtaaagttg tcaaagtgct acccttcaaa    6060
aaaacaccag gctcaaacaa tctgacatgg gaatgttagc acaccttaga gagcaaataa    6120
aactttgaat gggcttgaaa tattccagac tctagaaaaa caaaacttcc caattctttt    6180
tataaagcaa gtataaattg ataccaaaat cttataaaga ccttatacaa aacttcatac    6240
caatctcttt tatgaataca aaaccttaa taaagtatta ccagacagaa cccaacaata    6300
cataaaaatg tcacatcata acatagtggg gtttatttca ataatgcatg gatggttcaa    6360
tacaaggaaa ttcagtaaca caatataata gatcatgtga atatacccaa agaaaaaata    6420
gattattttc atagatgctg taaaggcatt tgaccaaatt caacacctac tttttaggtg    6480
gtcaataaaa taaattagtt actccttctt tagcatgata aaatatattt atcagcccag    6540
aaggcatcat tttacccgat aagggcacac gctggaggga ataatgttaa aattaggaat    6600
aagaggatag ctagtttctt tcttctttt tttttttgag acggagtctt gctctgttgc    6660
caggctggag tgcagtggtg caatgttggc tcactgcacg ccccccgcct cccaggttca    6720
agcgattctc ctgcctcagc ctcccgagta gctgggacta caggcgcgca ccaccatgcc    6780
cggctaattt tttttttgtat tttagtagag atggggtttc accatgttgg tcaggctggt    6840
```

```
cttgaactcc caacctcacg tactgggatt accggtgtga gccaccacgc cagcccaact   6900
actttcaaca ttatccttaa tactgatgct tattgactta ctatggggtt acctctagat   6960
aaatccataa taagttgaaa atataagtaa aaaatgccct taatacacct aacctaccaa   7020
acatcatagc tgagcccagc ctgccttagc tatgctcaga cactgacgtc agcctacaat   7080
tggcaaaatc acacagcagc acagtctact gcagagcatc tgctgtttgc ccttgtgact   7140
gcgtggctgc ctgggagctt cccagcttca caagacagta ttacgtagca catcactagc   7200
ctggggaaag atcaaagttg aaaatttgaa gtgtggtttc cattgaatgt gtactgcttt   7260
tgcaccatca tcaagtcaaa aattttagt tgaaccagcc taagtttggg accatcttta   7320
ttttcaggag gaacttccat gtacattgat gacggacgat agaatccgtt tctatcatcc   7380
taatgaacat aatgaataaa tccagacaaa cataaacatt aacagagtaa gcagctttcg   7440
gggctggaag ccagaagagg gtgggagcgc agagagagag gccaaacacc agggctgctt   7500
ctgctttgcg ggtatttgct gatctggaca aggtatctgg aaggctgagc taagcctcct   7560
tttttttga ggtggcgtct cactctgttg ccaggctgga gtgcaatggt gcgatctcag   7620
ctcactgcaa cctccacctc cctggttcaa gcgattctcc tgcctcagcc tcccgagtag   7680
ctgggattac aggctcccgc cactacaccc agctgatttt tgtaatttta gtagagacgg   7740
ggtttcacca tgttggccag gatggtctcg atctcttgac gtcatgatct gtccacctcg   7800
gcctcccaaa gtgctgggat tataggcgtg acccaccgtg ccccgtctga gctaagcctc   7860
ttgagcatag gggactaaaa atgaaatcta gcgcatgcca agtttagggt cccaggcaat   7920
tcctttccac tttggggtcc actttgggt ccaccccacc caagaagaag gatgacttgg   7980
aagtaaacca gctctgaaat atggatggtc ctctgggacc ataccaatcc cttcatatca   8040
accacatcca gttcctcaaa actggaactt ggattaagat ggcctaggac ttctagtgtc   8100
ccaggagcct ggcattgcaa acaaaaatcc tctccggaag aagataatac cttaagcttc   8160
aaatgactct ctaataaatt tcaaatacaa tgtccagcac acaaacacaa attaccagga   8220
acgtgatatg aggcctgatg gatgggaatt agcagaaact tcaggcatga gaaacatacc   8280
ctcagaggcc tagaatctat ctagtgtcta gataatggag atatgaaata cagacactta   8340
aacaactatg tttcccatgt tcaaagagga aatttgcaaa acttgaaagt gttggcagga   8400
aatcagaaac tataaaatgt gacaacagca tactttagag tcagtataaa ttacggtccc   8460
gaaaactgca gaattccaga acttaatggt aaagcaaggg tttaacagca gaatagaaat   8520
agccagagag aactaggaag taagtcagat gacactaccc agaataaggc actgagaggc   8580
caaggaatgg aaaatgcaga agaaaggata tggtgagagg atctaatata catttatttg   8640
gagtaccagg gagagagaga aggagaagaa cagaagccgt gtttcaagga cggtgactga   8700
gaggcttcga aactgatgaa agccatcagt tcacaaattc aaagcccagt gaattccaag   8760
gagaaaaaaa gaaatcccata ctgtgaaagc aagtccagac aatgacaaac accatcaaca   8820
atacacagga caggcataag atgcatttaa tggggacact cagaggcaga gggttatcag   8880
aaggaggcac ttctctccca agttctcatc atcccagggc cagggacagc tggtcacacc   8940
ttagggagtt cactaggaga gggatctggc ttccttgtcat tctgggtatt tgtagggaaa   9000
ttggaaggga accgagagca cctagccaat cgcatagcaa tgggagattt caggctgtgg   9060
ggaatgtctt tgctggtgaa aagaacatcc tgacccttaga aatctttcac cgaggggggat   9120
ctgcgttcca gaacttctgg agctggtata ggtaaggctt tgagctttcc tactgagcca   9180
```

```
gcctgttgct aggttaccaa aggggacctc gagggccatc tggccaacaa gcagacttgt   9240
ctctccttac accccagac  gtatcactgc aaaactacag aaaaccaaag acagagaaaa   9300
tcttaaaagc agccagattt aaaaaatggc atattagttt caaagcagca gccatgaaat   9360
tgacagctga tgtctcaaca gcaagaatga aaagtggaag acaggccagg tgtggtggct   9420
caggcctgta atcccagcac tttgggaggc cgaggcgggt ggatcacgag gtcaggagac   9480
caagaccatc ctggctaaca tggtgaaacc ccgtctctac taaaaataca aaaaattag    9540 tcgggcatgg tggtgggtgc ctgtagtccc agctactcgg gaggctgagg caggagaatg   9600
gcgtgaaccc gggaggcgga gcttgcagtg agccgagatt gtgccactgc actccagcct   9660
gggtgacaga gcaagactct gtctcaaaaa aaaaaaaaa  aaaaaaaaa  aaagggtgac   9720 gaagcttcaa tctcctgaaa ggaagcaact gccgcctttg attcgatacc caccaaaatc   9780
cgtgaagaag aaggcaaaa  taaaaacact tcctgattga actggaaaga tttccgcaat   9840
agaagaccca ctgtccaagg aattctaaag gatgctttcc aggcagaaga aaatgacccc   9900
agaggaagat cagagattca ggaaagaaat ggagagtgat aaaaatgaa  aattcggggg   9960 ccaatttaaa caaagctga  ctgctctaca actgttgtgt ctctatcttt tgtaacatat  10020
atgtgtgtgt agctttttt  ttttttttg  tcaagatgga ttctcactct gtcgcccagg  10080
ctacagtgaa atggcacggt ctcggctcac tgcaacctct gccccttggg ctcaaatgat  10140
tctcttgcct cagcctcctg agtagctgag attacaggtg cctggcacaa tgcctggcta  10200 attttgtat  ttttactaga gatgggattt ctccatgttg gccaggctgg tcttgaacac  10260
ctgacctcag gtgatccacc tgcctgggcc tcccaaagtg ctaggattac aggcgcgagc  10320
cactgcatct ggcctatgtg tgtgtttata tggaattaaa acacatggca ataatccct   10380 ccaaattggg agaaaccaaa aatagcattt aaatgttgta agctccctgc ataatcaaga  10440
agagaataga tttacgttag attttgatac ctggaggatg aatgttgtaa tttctagggt  10500
gaccatgaaa agaggagaca acggtgtatg tttttttttt tttgagatgg agtctcactt  10560
tgtcacccag gctggagtgt gtggtgtga  tcttggctca ctgcaacctc ctcctcttgg  10620
gttcaggcca tcctcccacc taggcctcca gagtaggtgg gatcacaggc acctgccacc  10680
acacctggct aattttttt  tttttttaaa tatttagtag agatgggggtt tcaccatgtt  10740 ggccaggctg tcttgaact  cctgacctca ggcgatctgc ctacctctgc ctctcaaagt  10800
gctgggatta caggtgtgag ccatcgcgcc cggccaacag tgatcacttt caaactaaca  10860
gaggttcaaa aataaaatca gacttaacca aaaaccaggt aacagagctg gtaggatata  10920
cagaaagact gacctcacgt atatcaacga ttacagttaa tattaatgaa ggaaatgctc  10980
tagtttaaaa acgagggttg tcaaagaccc cacataagaa gctccttacc agcggtgcac  11040
ctagaaccta aggaaacagg acagatgaag gaggacgcgc cccgccgct  gtcctgcgcc  11100 tcagccatcc tatgagacgg gaaaggtttc tgtctgcagc tgggcccgtg ctctttacca  11160
gctcctggct ttcttctctg gaaggttcct gcctgttttg ccctcacacc tgctcctctc  11220
tcagccctct caggggtggg gctggaggcc accaaagagc ctcctctgct ctccagttgc  11280
tcgactgctc ctcatttccc cctggggtct gcgtcagggt ttccttcttt tccagcccca  11340
ccccgcgtgc atcccacctg gtctcgggtc ggggctgctc ccgcttactg ccccctgccc  11400
aggctggtgt gcacccccctc tggctgcttt caaggcctct tctctcttct cggcaggaca  11460
ggcacaggca ggtggccagg tgtcatgctt agctccccgc ccagtgagat tctttcatt   11520 aacaatcttc ccctgaatag ttcatgttca ttgctgaaaa tttgaaaaat atggaaaagc  11580
```

```
acaaagatta agatataaac cgccctcaat tcccctgccc agagagagtc actgctatga   11640
cttggtgact aggaacctta tttctctctc gctcttttt ttttttttga dacagagtct   11700
tgctctgtca cccaggctgg agtgcagtgg ctcgatctca gctcactgca acctccgcct   11760
cctgggttca agcgattctc ctgcctcagc ctcttgagta gctgggatta caggcacctg   11820
ccaccatgcc cggctaattt ttgtattttt agttgagaga gggtttcatc ttgttggtca   11880
ggcggacttg aactcctgac ctcaggtgat cagcccacct cggcctccca aagtgctggg   11940
attacaggtg tgagccactg cgccttcatc tctcttctgt gtatgtgtac gctgtttttt   12000 cttagaatg ggggacgtta tcaggctcta catggtgtgt agtcggctag catgttgtaa   12060
gcctttccct gtgtcacaag tgctcatctg aacaggatt ctaatgactg cctgtggcta   12120
tgttgggatt cctttaactc agctccttct gcccagcatc tatctttttt ccatcttttg   12180
tcctaagtgt tgctataata aatcattgat cacacatgcc tgactgtttg cataggataa   12240
attacgggaa atgttttgc tgttcaggga ctgtgcccat ttttaggcct cagagacacc   12300
atgccagact gcccagtatt gatctttact cttttagat gatgccaaac ttttctgtga   12360
actttaaaaa cctgtgtctt gacagtccat ttctgtaagt ctttcacatt agatttcctg   12420
tcaggatgat agtcaattct aggcagatga tgttttctca gccatggctg aagcagttgt   12480
gatttgttgt ggccatgtaa agtcccgatg atccattgcc tccctggatg ggttggaata   12540
atttggtttg ggagcatata acagaatgac ctggagtcac agcagctcag acggaagtgt   12600
atttctccct tacagatgaa agaattccag gccaggctgg aatgacaact gcacacagtc   12660
atctgggccc cctccttcca gctcccatca ccccaggatg tggcttttat gcagatgatc   12720
caaaatggct gctcaagtcc cagccaacac atcccattcc agggagcagg aaaaaggtgt   12780
gtctttccct tcattttatg tgattccttt ctagaagtac tactcattac ttctgcttgc   12840
atctccctgg ctagcactta cttagttata tggccatagc tagctgaagg aaggacaggg   12900
actgtcatac actagctaag aggcaaactg cttagataaa aaggtctcta aagaaggtca   12960
gagcggctgc tagggtgcaa ctctattact tattgttatg ggacgaactg tgtccctcat   13020
tcaggttgat gtcctaagcc ccagaacctc agaatgggat tgtatttgga dacaggttct   13080
ttaaggaggt aaggaggcta aaatgagatc attagggtgg gccataatcc gactgatgtc   13140
ttacaagaag agattaggac acggacatgc tcagagggac ggccacgtga ggacaccaag   13200
aaaggcagct gtctgcaagt caaggacagg gctcagggga aaccaacctt gccaacacct   13260
tcatctcgga cttctagcct ctaggaccat gagaagatac atttctgttg tttaagctgc   13320
ccggtctgtg gtactttgtt atggcagccc aagtaaacaa atacagtcat ctgctgctgg   13380
aacaaatcac cccagcactg tggcttggca gcacacatgt ctagtcatag agttatatgt   13440
agttacgtgt agagccatat gtatcgtcac acgttctgtg ggtcaggaat ttggacccag   13500
cttaaccagc tccacttctc gccagggttc agtcaaatac cagctgcctc ccacctgaga   13560
gctcagccgg ggaagggtcc cttttccaatc tcacgtggtg ttggcaggat ccagttcctc   13620
atggcctgct ggactgagaa cctcagttct cactgcctgt tggccagagg ccgcctttat   13680
gtcctcgcca tgtgggcctc tccaacatgg cagctgactt catcagagca tccatgccaa   13740
gaaggcaaca gagagggcca gggagactga agtcataccc ttttgcgacc tagtcatggg   13800
gtgacattcc atcacctttg cccattggtt agaagcaggc caccaggtac agcccaagct   13860
cacggggagg ggtcatacaa gggtgtcaat accaggaggt gaggggtgct ggggccatct   13920
```

```
tatgagtctg cccactgagg taactaacaa ccttgaggcc tgacacagtg gacaaaggcc  13980
cttattaaca gcagagaact gggaactttta tttatttatt tatttttgag acagagtctc  14040
actcttgtca cccaggctgg agtgcaatgg catgatcttg gctcactgca acctccacct  14100
cccaggttca gcaattctg cctcagcctc cggaatagct gggactacag gcatgcacca  14160
ctacacccgg ctaattttg tattttagt agagacaggg tttcgccatg ttggccaggc  14220
tggtctcgaa ctcctgacct ctggtgatct gcctgcctg gcctcccaaa gtgctgggat  14280
tacaggcgtg agccaccgca cctcgctgga acttaatttt tttagagaca gtgtcgctct  14340
atcacccaag ctggagtgca gtggtgcaat cctagctcac ttgcagcctc aaattcctgg  14400
gttcaggtga tcctcccaca tcagcctccc aagaactggg aactaacagc tgtttctctg  14460
ctgtccttct caagaaaagg gaggctactg ctaccccact ggggacaatg ctgggttccc  14520
ctttaggaca ggctctgaga caaggcggag gtgctgtttg tggccacaga gcaggggact  14580
ctgggttgca ggtgtggcct ggctaaagta ggctttactg ggctcctctc tgcctgcatc  14640 acccccggc tgggcggttg tctctgaggc caaccttact ccctgctggg caggctggac  14700
agctgccctc tccgtttgcc cctctaccac ccaaaaggca ggaggctctg gagaccagga  14760
ccctgcccgc cacggcctgt gtcccaggcg tgagggggtg ccccacagac ctctgctgag  14820
ctgctgctga atgacgcccc ttggggtcc tgccggaagg tcagagcagg ggtgcactcc  14880
cataaagaaa cgcccccagg tcgggactca ttcctgtggg cggcatcttg tggccatagc  14940
tgcttctcgc tgcactaatc acagtgcctc tgtgggcagc aggcgctgac cacccaggcc  15000
tgccccagac cctctcctcc cttccggggc gctgcgctgg gaccgatggg gggcgccagg  15060
cctgtggaca ccgccctgca ggggcctctc cagctcactg ggggtggggt ggggtcaca  15120 cttgggtcc tcaggtcgtg ccgaccacgc gcattctctg cgctctgcgc aggagctcgc  15180
ccaccctctc cccgtgcaga gagccccgca gctggctccc cgcagggctg tccgggtgag  15240
tatggctctg gccacgggcc agtgtggcgg gagggcaaac cccaaggcca cctcggctca  15300
gagtccacgg ccggctgtcg ccccgctcca ggcgtcggcg ggggatcctt tccgcatggg  15360
cctgcgcccg cgctcggcgc ccctccacg gccccgcccc gtccatggcc ccgtccttca  15420
tgggcgagcc cctccatggc cctgcccctc cgcgcccac ccctccctcg ccccacctct  15480
caccttcctg ccccgccccc agcctcccca ccctcaccg gccagtcccc tccctatcc  15540 cgctccgccc ctcagccgcc ccgcccctca gccggcctgc ctaatgtccc cgtccccagc  15600
atcgccccgc cccgccccg tctcgccccg ccctcaggc ggcctccctg ctgtgccccg  15660
ccccggcctc gccacgcccc tacctcacca cgccccccgc atcgccacgc ccccgcatc  15720 gccacgcctc ccttaccatg cagtcccgcc ccgtcccttc ctcgtcccgc ctcgccgcga  15780
cacttcacac acagcttcgc ctcaccccat tacagtctca ccacgccccg tccctctcc  15840 gttgagcccc cgcgccttcgc ccgggtgggg cgctgcgctg tcagcggcct tgctgtgtga  15900
ggcagaacct gcgggggcag gggcgggctg gttccctggc cagccattgg cagagtccgc  15960
aggctagggc tgtcaatcat gctggccggc gtggccccgc ctccgccggc gcggccccgc  16020
ctccgccggc gcagcgtctg ggacgcaagg cgccgtgggg gctgccggga cgggtccaag  16080
atggacggcc gctcaggttc tgcttttacc tgcggcccag agcccattc attgccccgg  16140 tgctgagcgg cgccgcgagt cggcccgagg cctccgggga ctgccgtgcc gggcgggaga  16200
ccgccatggc gaccctggaa aagctgatga aggccttcga gtccctcaag tccttccagc  16260
agcagcagca gcagcagcag cagcagcagc agcagcagca gcagcagcag cagcaacagc  16320
```

```
cgccaccgcc gccgccgccg ccgccgcctc ctcagcttcc tcagccgccg ccgcaggcac    16380
agccgctgct gcctcagccg cagccgcccc cgccgccgcc cccgccgcca cccggcccgg    16440
ctgtggctga ggagccgctg caccgaccgt gagtttgggc ccgctgcagc tccctgtccc    16500
ggcgggtccc aggctacggc ggggatggcg gtaaccctgc agcctgcggg ccggcgacac    16560
gaaccccgg ccccgcagag acagagtgac ccagcaaccc agagcccatg agggacaccc    16620
gccccctcct ggggcgaggc cttcccccac ttcagccccg ctccctcact tgggtcttcc    16680
cttgtcctct cgcgagggga ggcagagcct tgttgggccc tgtcctgaat tcaccgaggg    16740
gagtcacggc ctcagccctc tcgcccttcg caggatgcga agagttgggg cgagaacttg    16800
tttcttttta tttgcgagaa accagggcgg gggttctttt aactgcgttg tgaagagaac    16860
ttggaggagc cgagatttgc tcagtgccac ttccctcttc tagtctgaga gggaagaggg    16920
ctgggggcgc gggacacttc gagaggaggc ggggtttgga gctggagaga tgtgggggca    16980
gtggatgaca taatgctttt aggacgcctc ggcgggagtg gcggggcagg ggggggcgg    17040
ggagtgaggg cgcgtccaat gggagatttc ttttcctagt ggcacttaaa acagcctgag    17100
atttgaggct cttcctacat tgtcaggaca tttcatttag ttcatgatca cggtggtagt    17160
aacacgattt taagcaccac ctaagagatc tgctcatcta agcctaagtt ggtctgcagg    17220
cgtttgaatg agttgtggtt gccaagtaaa gtggtgaact tacgtggtga ttaatgaaat    17280
tatcttaaat attaggaaga gttgattgaa gttttttgcc tatgtgtgtt gggaataaaa    17340
ccaacacgtt gctgatgggg aggttaattg ccgagggatg aatgaggtgt acattttacc    17400
agtattccag tcaggcttgc cagaatacgg ggggtccgca gactccgtgg gcatctcaga    17460
tgtgccagtg aaagggtttc tgtttgcttc attgctgaca gcttgttact ttttggaagc    17520
tagggggtttc tgttgcttgt tcttggggag aattttttgaa acaggaaaag agagaccatt    17580
aaaacatcta gcggaacccc aggactttcc ctggaagtct gtgtgtcgag tgtacagtag    17640
gagttaggaa gtactctggt gcagttcagg cctttctctt acctctcagt attctatttc    17700
cgatctggat gtgtcccaga tggcatttgg taagaatatc tctgttaaga ctgattaatt    17760
tttagtaata tttcttgttc tttgtttctg ttatgatcct tgtctcgtct tcaaagttta    17820
attagaaaat gattcggaga gcagtgttag cttatttgtt ggaataaaat ttaggaataa    17880
attattctaa aggatggaaa aacttttttgg atatttggag aaattttaaa acaatttggc    17940
ttatctcttc agtaagtaat ttctcatcca gaaatttact gtagtgcttt tctaggaggt    18000
aggtgtcata aaagttcaca cattgcatgt atcttgtgta aacactaaac agggctcctg    18060
atgggaagga agacctttct gctgggctgc ttcagacact tgatcattct aaaaatatgc    18120
cttctctttc ttatgctgat ttgacagaac ctgcatttgc ttatcttcaa aatatgggta    18180
tcaagaaatt tcctttgctg ccttgacaaa ggagatagat tttgtttcat tactttaagg    18240
taatatatga ttaccttatt taaaaaattt aatcaggact ggcaaggtgg cttacacctt    18300
taatccgagc actttgggag gcctaggtgg acgaatcacc tgaggtcagg agtttgagac    18360
cagcctggct aacatggtga aaccctgtct ctactaaaaa tacaaaaatt agctggtcat    18420
ggtggcacgt gcctgtaatc caagctacct gggaggctga ggcaggaaaa tcgcttgaac    18480
ccgggaggca gagtctgcag tgagttgaga tcacgccact gcactccagc ctgggtgaca    18540
gagcgagact ctatctcaaa aaaaatttt tttaatgtat tattttttgca taagtaatac    18600
attgacatga tacaaattct gtaattacaa aagggcaata attaaaatat cttccttcca    18660
```

```
cccctttcct ctgagtacct aactttgtcc ccaagaacaa gcactatttc agttcctcat    18720
gtatcctgcc agatataacc tgttcatatt gtaagataga tttaaaatgc tctaaaaaca    18780
aaagtagttt agaataatat atatctatat attttttgag atgtagtctc acattgtcac    18840
ccaggctgga gtgcagtgat acaatctcgg ctcactgcag tctctgcctc ccaggttcaa    18900
atgcttctcc tgcctcagcc ttctgagtag ctgggattac aggcgccac caccatgtcc     18960 agctaatttt tgtattttta gtagagatgg ggtttcacca tgttggccag gctggtcttg    19020
aactcctgac cttgtgatct gtccacctcg gcctcccaaa gtgctgggat tacaggtgtg    19080
agccaccatg cctggctaga ataataactt ttaaaggttc ttagcatgct ctgaaatcaa    19140
ctgcattagg tttatttata gttttatagt tattttaaat aaaatgcata tttgtcatat    19200
ttctctgtat tttgctgttg agaaaggagg tattcactaa ttttgagtaa caaacactgc    19260
tcacaaagtt tggattttgg cagttctgtt cacgtgcttc agccaaaaaa tcctcttctc    19320
aaagtaagat tgatgaaagc aatttagaaa gtatctgttc tgttttatg gctcttgctc      19380 tttggtgtgg aactgtggtg tcacgccatg catgggcctc agtttatgag tgtttgtgct    19440
ctgctcagca tacaggatgc aggagttcct tatgggctg gctgcaggct cagcaaatct      19500
agcatgcttg ggagggtcct cacagtaatt aggaggcaat taatacttgc ttctggcagt    19560
ttcttattct ccttcagatt cctatctggt gtttccctga ctttattcat tcatcagtaa    19620
atatttacta aacatgtact atgtgcctgg cactgttata ggtgcagggc tcagcagtga    19680
gcagacaaag ctctgccctc gtgaagcttt cattctaatg aaggacatag acagtaagca    19740
agatagataa gtaaaatata cagtacgtta atacgtggag gaacttcaaa gcagggaagg    19800
ggatagggaa atgtcagggt taatcgagtg ttaacttatt tttattttta aaaaaattgt    19860
taagggcttt ccagcaaaac ccagaaagcc tgctagacaa attccaaaag agctgtagca    19920
ctaagtgttg acattttat tttatttttgt tttgttttgt ttttttgag acagttcttg       19980 ctctatcagc caggctggag tgcactagtg tgatcttggc tcactgcaac ctctgcctct    20040
tgggttcaag tgattctcat gcctcagcct cctgtttagc tgggattata gacatgcact    20100
gccatgcctg ggtaattttt ttttttttccc ccgagacgga gtcttgctct gtcgcccagg    20160
ctggagtgca gtggcgcgat ctcagctcac tgcaagctcc gcttcccgag ttcacgccat    20220
tctcctgcct cagtctccca gtagctggg actacaggcg cctgccacca cgtccagcta     20280 attttttttgt attttttaata gagacggggt ttcaccgtgt tagccaggat gatcttgatc    20340
tcctgacctc gtcatccgcc gaccttgtga tccgcccacc tcggcctccc aaagtgctgg    20400
gattacaggc atgagccact gtgcccggcc acgcctgggt aattttttgta tttttagtag    20460 agatggggtt ttgccatgat gagcaggctg gtctcgaact cccggcctca tgtgatctgc    20520
ctgccttggc ctcccaaagt gctaggatta caggcatgag ccaccatacc tggccagtgt    20580
tgatatttta aatacggtgt tcagggaagg tccactgaga agacagcttt tttttttttt    20640
tttttggggg ttgggggca aggtcttgct ctttaaccca ggctggaatg cagtatcact     20700
atcgtagctc acttcagcct tgaactcctg ggctcaagtg atcctcccac ctcaacctca    20760
caatgtgttg ggactatagg tgtgagccat cacacctggc cagatgatgg cttttgagta    20820
aagacctcaa gcgagttaag agtctagtgt aagggtgtat gaagtagtgg tattccagat    20880 gggggggaaca ggtccaaaat cttcctgttt caggaatagc aaggatgtca ttttagttgg    20940
gtgaattgag tgaggggggac atttgtagta agaagtaagg tccaagaggt caagggagtg    21000
ccatatcaga ccaatactac ttgccttgta gatggaataa agatattggc atttatgtga    21060
```

```
gtgagatggg atgtcactgg aggattagag cagaggagta gcatgatctg aatttcaatc   21120
ttaagtgaac tctggctgac aacagagtga aggggaacac cggcaaaagc agaaaccagt   21180
taggaagcca ctgcagtgct cagataagca tggtgggttc tgtcagggta ccggctgtcg   21240
gctgtgggca gtgtgaggaa tgactgactg gattttgaat gcggaaccaa ctgcacttgt   21300
tgaactctgc taagtataac aatttagcag tagcttgcgt tatcaggttt gtattcagct   21360
gcaagtaaca gaaaatcctg ctgcaatagc ttaaactggt aacaagcaag agcttatcag   21420
aagacaaaaa taagtctggg gaaattcaac aataagttaa ggaacccagg ctctttcttt   21480
tttttttttt tgaaacggag tttcgctctt gtcacccggg ctggagtgca atgatgtgat   21540
ctcagctcac taaaacctct acctcctggg ttcaagtgat tcttctgcct cagcctccca   21600
agtaactggg attacaggcg tataccacca tgcccagcta attttgtgt ttttagtaga   21660 gatggggttt caccatgttg gccaggctgg tctcgaactt ctgacctcag gtgatccact   21720
cgcctcagcc tgccaaagtg ctgggattac aggtttgggc cactgcaccc ggtcagaacc   21780
caggctcttt cttatactta ccttgcaaac ccttgttctc attttttccc tttgtatttt   21840
tattgttgaa ttgtaatagt tctttatata ttctggatac tggattctta tcagatagat   21900
gatttgtaaa aactctccct tcctttggat tgtcttttta cttcttgat agtgtctttt   21960 gaagtgtaaa agttttaat tttgatgaag tcgagtttat ctattttgtc tttggttgct   22020
gtgcttcaag tgtcatatct aagaaatcat tgtctaatcc aaagtcaaaa aggtttactc   22080
ctatgttttc ttctaagaat tttagagttt tacatttaag tctgatccat tttgagttaa   22140
tttttatata tggttcaggt agaagtccaa ctttattctt ttccatgtgg ttattcagtt   22200
gtcccagcac tgtttgttga agagactatt cttttcccat ggaattatct tagtacccttt   22260 gttgaaaatt aatcgtcctt aattgtataa atttatttct agactgtcag ttctacctgt   22320
tggtctttat gtcgatcctg tgccagtacc atacagtctt gattactgaa gtttgtgtca   22380
cagtttaaat tcatgaaatg tgagttctcc aactttgttc cttttcaaga ttgatttggc   22440
catgctgggt cccttgcatt tccgtacgaa ttgtaggatc agcttgtcag tttcaacaaa   22500
gaagccaagt aggattctga gagggattgt gttgaatctg tagatcaact tggggagtat   22560
tcgcatctta acaatattgt cttccaccta tgaacatggg caaactttgt gtaaatggtc   22620
agattgtaag tatttcgggc tgtgtgggca cagtgtctct gtcacagcta cgcggctctg   22680
ccattgtagc atgaaagtag ccataagcaa tatgtatgag tgtctgtgtt ccaatagaat   22740
tttattaatg acaaggaagt ttgaatttca tataattttc acctgtcatg agatagtatt   22800
tgattatttt ggtcaaccat ttaaaaatgt aaaaacattt cttagcttgt gaactagcca   22860
aaaatatgca ggttatagtt ttcccactcc taggttaaaa tatgatagga ccacatttgg   22920
aaagcatttc ttttttttt ttttttttt tttttgagac ggagtttcac tcttgttgcc   22980
caggctggag tgcagtggcg cgatctcggc tcactgcaac ctctgcctcc caggttcaag   23040
acattctcct gcacggcctc cctagtagct gggattacag gcatgcgcca ccacacccag   23100
ctaattttgt attttagta gagacggggt ttctccatgt tggtcaggct ggtcttgaac   23160
tcctgacctc aggtgatcca cccgcctcag cctcccaaag tgctgggatt acagggtgtg   23220
agccaccaca ccctgctgga aagcatttct ttttggctg ttttgtttt tttttaaac   23280 tagttttgaa aattataaaa gttacacata tacattataa aaatatcttc aagcagcaca   23340
gatgaaaaac aaagcccttc ttgcaagtct gtcatctttg tctaacttcc taagaacaaa   23400
```

```
agtgtttctt gtgtcttctt cccagatttt aatatgcata tacaagcatt taaatgtgtc    23460
attttttgtt tgcttgactg agatcacatt acatatgtat ttttttactt aacaatgtgt    23520
catagatatt gttccatagc agtacctgta attcttatta attgctatgt aatattttag    23580
aatttctttt taaaagagga cttttggaga tgtaaaggca aaggtctcac attttttgtgg   23640 ctgtagaatg tgctggtgac atattctctc taccttgaga agtccccatc cccatcacct    23700
ccatttcctg taaataagtc aaccacttga taaactacct ttgaatggat ccacactcaa    23760
aacatttagt cttattcaga caacaaggag gaaaaataaa ataccttata aagcactgtt    23820
taatattgta ttaaattgga tcaatttggg ggctagaatg tatgttagag acatgatatg    23880
tccataggtc cttgctatca cagtgaggtc tcaggacag tcgtttggta tcatttggga     23940
tctcataagc agactctctc tgcttgacct gacaaatcag agtctgtgtt ttaacaggtt    24000
cagtgagtga cttacatgca cattggagtt tgggaagctc cactgtaggt gcttagacct    24060 taccttttgtt gttgctaata acaatgcaag catttgggag gaagacctgt gttgctcata   24120
tgtgtccagg tgtagctgag gtggccttgc ttatctgctg tagggccgtt gagcatttct    24180
gtagctgtga tgagtgagct gaggtgagcc tgcggagagc tcccagccat tggtagtggg    24240
actcgcttag atgaactgga aggacccttt catctgagca gccactatgg agaaaaacaa    24300
ccgaatgagg ggagagacaa tgtgcaattt tatttagggc acaaaggaga gctgtggtta    24360
gaaggtgaca tttgagtgga aaggggggcaa gccatgtgta tagcgggaga agagaggtcc   24420
aggcagagtt aacagaaggc agaaatgctt tccatgtttg agaaccagta aggaggccag    24480
tggctgaagt aaggtgaagg gcagaaataa ggatgaggct gcgagagatg agaggttaga    24540
gacgagcgtc ttgtgcacca agataagctt gtgtggtcaa aacaagtagt ttaatttatg    24600 ttttttaaaag atcattttgg ctgggcacaa tggttcatgc ctgtaatacc agtagtttga   24660
gacggtgtgg tgggaggatt gcctgaggcc agacgaccag catagccaac atagcagcac    24720
ctataaggtc tctacaaaaa actttaaaaa attagctggg catagtggtg tgtgcctgta    24780
gtcccagcta ctcaggaggc tgaggaggct ggaggattgc ttgagtccag gagtttgagg    24840
ctgcagtgag ctatgattat gccactacac tacaacctgg gcaagagagt gagaccctgt    24900
ctctaaatat acacacacac acacacacac acacacacac acacacacac acacacacac    24960
acacacatat atatgtatat atatgcattt agatgaaaag atcactttga caataccaca    25020
tgctggtgag gatttagaaa aactaggtca cttattgctg gtgggaatat aatatagtac    25080
ggccactctg gaaaacagtt tggcagtttg tcataaaact gaacataccg ttagtataca    25140
gcccagcagc aactacaatc ctgggcatta atcctagaga aatgaaacct taatgttcac    25200
ataaaaacct atactcaagt atgcatagca gctttacccca taatatctaa gaactggaat   25260
cagctcagat gtccttcaac aggtgaatgg ttaaactact cagtaataaa aaggaatgag    25320
ctactgatag catgcaacag tttaggtgaa gttatgctaa tgaaaaaagc caatcccaaa    25380
aggttataca tactgtatga ttctatgttt ttttgcaatg gcacagtttt agggatggag    25440
aatagattag tggttgcctg gggttagaga tggggtagta gagtaggtta tggtggcag     25500 aggagagaaa agagagggag gtgaatgtgg ttataaaagg acaacacagg ggaatacttg    25560
taatggaaat gctttgtctt tttttttttt tttttttttt tggcgacaga gtcttgctct    25620
gttgcccagg ctggagtgca gtggcatgat cttttctcac tgcaacctct gcctcctggg    25680
ttcaagtgat acttgtgtct cagtctccca tgttcagagt gaaacaaacc agaggtaatg    25740
ttcatccaaa taatccaaca cacatgacat taaaacatca agatcaggtc ggacgtggtg    25800
```

```
gctcatgcct gtaatcccag cacttttggg aggccaaggt gggcagatca cttgaggtca   25860
ggagttcgag accagccggg ccaacatgat gaaaccccat cttgactaaa aatacaaaaa   25920
ttagccgggc atggtggtgt gcacctgtag tcccagctac ttgggaggct gaggcaagag   25980
aactgcttga acccgagggg cagaggttgc agtgagctga gagtgcgcca ttgcacttca   26040
gcctgtgtga cagagtaaga ctccatctcc aaaaaaaaaa aaccaagatc aattaaaata   26100
cagcattact gggccgggtg tggtggctca cacctgtaat cccagcactt tgggaggccg   26160
agatgggcag atcacgaggt caggagatcc agaccatccc ggctaacacg gtgaaacccc   26220
gtctctacta aaaatacaa aaaattagcc gggtatagtg gtgggtgcct gtagtcccag   26280
ctacttggga ggctgaagca ggagaatggt gtgaacccgg gaggcagagc tggcagtgag   26340
ctgagatcgc gccactgcac tccagcctgg gcgacagagc aagactccgt ctcgggggaa   26400
aaaaaaaaat aaataaatag aatgctgtag tgtccttgag tttacatgcc cctccttacg   26460
cttgtgtgcc cgtgcagatt gcttgattac acaattagag gaggctggcg gaggattgtt   26520
ttaatttttt ttttttgag acagtctggc tctgttcccc aggctagagt gcaatggcgc   26580
aatcttggtg cactgcaacc tctgcctcct gggttcaagc agttcttctg ccgcagcctc   26640
ccgagtagct gggattatag gcgcccgcca ccacgcccaa ctattttttg tattttagt    26700 agagcagcgt ttcaccatgc tggccaggct ggtctcgaac tcctgacctc agatgatctg   26760
ctgccccagc ctcccaaagt gctgggatta caggcgtgag ccacacctgg ccgtttgttt   26820
taattttgaa ggtgaagtga aagtgactac atttaccaaa agtgattgaa aagccaggac   26880
tgttcttacc ctgttttttcc agttcttgct cagagcaagg tggtttcttt ttcacttaat   26940
caccatactt acttttcatg tagaacaagt cagtttgagt tatcagttca tcatcttaac   27000
taaattccat gggggaagga attagtttta gtttcttaaa cttccaggtt tgcttattgg   27060
acaaaatgag atagcaaggc agtgttttta agttagattt tttatttctt tggtaataca   27120
attttctcag aaacttagta gtcttttagt ttagttgttt ttagttggtc ctatgttttg   27180
gatcacccct ctctacttta ttttgatagt gccaactgtg aagacatctg aagccatagg   27240
tttggatggg aaggaggcat ctttagcctg atcatcttcg ccaggctgtt tatctccttt   27300
tgcttggctg agaagtctta ataggaggct tattcccagc tatttgggga catagaagca   27360
gttagccatt gcttatattt tactgaggtc tgtgtggtat gttgattgta gtcagttaac   27420
gattttgaga actgaaggca gcctggtata tatagagtag gtattagact gtgtttcttc   27480
taattgaatt tcccatctct tgtaatctat gccatcatct tctgtactgc tgagaaagaa   27540
agaaagtttc taatcaaact ataccactgg ttgtaagatg cagtttggct ttagtgatgt   27600
taacacatga ttcaaacgtg aaattgattg agtattggtg aaatacagag gagatttaaa   27660
gccagaagac ctgggtttaa atgctggctg tatgacttca tatctgtgtg atcttgggca   27720
tgtcatggtt ggcacttcaa tttcttctct ctataatggg ggaagtgagg ccagtcatgg   27780
tggctcatac ctataatccc agtgctttgg gaggccaaga tgggaagatc gcttgaggcc   27840
aggagtttga gcaattgggc aacatcgtga ggccccgtct ctacaaaata tttgaaaaa    27900 attagccagg cccagtggtg cgtgcctgtg gtccgcgcca ctcaggaggc tgagacggga   27960
ggatcctttc agcctaggag tttaaggcta aagtgagcca tgattgtgct atcgtactcc   28020
agcctgggca gcagagcaag atcctgactc taaaaaaaag taaataaag taaaatggg    28080 gaaatgaact gctttagtaa catcatctgt ttttctgtg agcagcgtag cttgacagcc    28140
```

```
attggtgaac tcgtgccctg tgcttccctg tccagatccc cattctgccc gcaacatgga   28200
gtataacggt ttattcatag tagtcgagaa acactcactg aatgaatgaa tgaggtgtag   28260
aactaagtgg agtgggtaat tcaacacata ttaatttcct tctttttttt attttttagaa  28320 agaaagaact ttcagctacc aagaaagacc gtgtgaatca ttgtctgaca atatgtgaaa   28380
acatagtggc acagtctgtc aggtaattgc actttgaact gtctagagaa aataagaact   28440
ttgtatattt tcagtcttaa tgggctagaa tattctttgt gtcccagcta ttttaaatgg   28500
attcagaaat ccatttaaga tgaagaagga cccttttccc atatttctgg ctatatacaa   28560
ggatatccag acactgaaat gaataatgtt ccctttttgt aatctttat gcaaaaatta    28620 aaaccattat ggtaattgaa caacatgttt atgtttagtt aacaccctta gcaactatag   28680
ttattttaaa accatctatg gtttgatatt tttgcatttg ttgcaatagt aggaacagca   28740
caagacagtt cagtttgtct ctcttatttg cttttttcttg gcagtttgct gtcctattgt   28800
acctctgctc ctagcagtgg ctggagccca ctcctctgtg cttcgggatt agtggggatc   28860
gtggggcatt gactgtaggt cagctttcct tgcttgatct ttctcactgg gatgaactag   28920
cagcaccttc ttttgtagct gctttgcttt tgactatctt tctgaccgtt gttcctagta   28980
gctgtagatg gtaaatatat ttaggcctgt ttccaatggc tcagtaggag acatattcac   29040
ctatgatatc tgaattctgt tacccacatg ggcatgcgtg aaatagttgc cttgccttac    29100
tttcccttgg aataaataat tcatgttatt ctcctggtag aagctagaaa aagcctttat   29160
agtcagtcag aaaaaaattt ttagacaaat aatcttgatt ttagtactga caaaaacgtg   29220
tggtgattct ttttttaatt tttttttgag acggagtttc actcttgttg cccaggctgg   29280
agtgcaatgg cgtgatctcg gctcactgca acctctgcct cctgggttca agtgattctc   29340
ctgcctcagc ctcccaagta gctggagtta caggcatgtg ctactgtgcc cagctaattt   29400 tgtatttta gtagagatgt tggtcaggct gatctcgaac tcccaacctt aggtgatctg    29460
cccgcctcag cctcccaaag tgctgggatt acaggcgtga gccagggcgc ccggtgattc   29520
atttgttttt tcaaaaaatt tcctcttggc cattgctttt cacttttgtt tttttttttt    29580
ttttgagacg gagtcacgat ctgtcaccca ggctggagtg cagtggcatg atcttggctt   29640
actgcaagct ctgcctccca ggttcacgcc attctcctgc ttcagcctgg cgagtagctg   29700
ggactacagg tgctcgccac cacacccggc tatttttg tatttttagt agagatgggg     29760
tttcaccgtg gtcttgatct cctgacctca tgacccgctc aactcagcct cccaaagtgc   29820
tgggattaca ggcgtgagcc accgcgcccg gccctctctt gtcttttttat tgtggtaaaa    29880 tgcacataaa attgactgtc ttaaccattt ttaggggtac agttcagtat atatattcgt    29940
aatgttgtac agccatcact gccatctact tcataagttt ttcttctgtc aaaactgaac    30000
atctgtcttc attaaactcc ctatcatcca ttctttcctg tagtcccttt ctactttctg    30060
tctgtatgag tgtaactgct ctggagacct catgtaagtg gattcctaca ggatttgtgt    30120 ttttttttttg gtgatctgct tatttttaat gcctctgtgc atttgtatta tatactttca   30180
aagtgatttc acaaaaccgt ttcatttttag gttaactcat ttctgttgtt tgtgaaatac   30240
tgtgtatgat tctgttctgt ttctgtctaa tttgtggaaa tgttgtggga agaaaatgaa   30300
ataacaaatg agcatatgtc ctgaaaataa aaatataaaa attctaagtt agcatgctat   30360
tgtagaatac aacgctatga taaaagtagg aaaaaaaaag gtttgaattc tatctctgct   30420
acctgtgtaa gctgggtgac tttagataag ctgtaacgtg tttgagcctt actggctcat   30480
ttttgaaatg taatccctag ttacacagtt cttgtgggat cagatggtac atgtgaaaca   30540
```

```
ctgtgaaaaa gcaactgcat agatatgttc attagccacc tgagcgggaa gcgtatccca   30600
ttgcgatgcc catcatccaa agctatatgt tatctttact tttttttttt tgagacagag   30660
tcttgctctg ttgcccaggc tagagtgcag tggtgcaatc tcagctcact gcaagctcca   30720
cctcccgggt tcacgctatt ctcctgcccc agcctcccaa gtagctggga ctacaggcac   30780
ccgccaccat gcctggctaa attttgtat ttttagtaga gatggggttt caccgtgtta   30840
gccaggatgg tcttgatctc ctgacctcgt gatccgcccg cctcggcctc ccaaagtgct   30900
gggattacag gcgtgagcca ctgcccctgg ccatctttac ttttttttgtg aaatgacttt   30960 aaatacttgg caaacatttg gtcattgttc atctgatctc caccatccag gtctcagaga   31020
acataatttc tctctgaaag cttattgacc caggaaataa gatctctttc aatctgagtg   31080
cgtcaggctt tattcttgtc attttgtctt ttgataattt tcaaatggaa ttcatggaat   31140
gttggcttat attcatatat tagtaaagta tgttgagaca tcttaagatt gatttgtggt   31200
tctatatgcc atattaaatc aaaataatag ctgttaatgg ttttcacatt agtctgtctc   31260 ttgttttat ggagtaatgc tgagagttca ttatgcttgt tctacagaag agcatgttaa   31320
aaggagtttt tggagtcaga gaggttattc ttggtttcat aggatacact ctatactttt   31380
tagggatttc agagtatata gctgaaggtg atattttatg taaatatgtt ttatggaaac   31440
ttattgctca tcgctgtttc ctgttaactc tcctaaaata taattaaact tttgaacttt   31500
ttttatagct tttgtgctag actaattttt gtctctaatg aggttatata aatggcagct   31560
tctgacgttt tcaatgtagg aagtcattta aaacttcatg tatattgtga aaatgtagtc   31620
tgctttaagc tctctaaagt ggtctaagtt actggttcct aagtatggat gagcatcaaa   31680
atcatctgga aaatttgtta aaaatacagt aatgaaggca cctcactgtc ctttttccca   31740
aacatacttc tgcattctgt ttgagtaggt agggactaca cattttttcac aagtatcctc   31800 ttgggaatac ccaggaatgc ttacttgagc aacctcttac taatatgtac cttgataagg   31860
tggctaggta aacataaata tacaaaaatc catagatctc ccatatatta gcataaatca   31920
gctagaaaat ataacgttta aagatctagt tcacagtagc accaatatat cgaactctaa   31980
ggaatcgata aatatgcaaa aactttataa aaacttctgt taatgtttct gaaagatata   32040
ggtgaccact ttctagatag gaagatttta tattactaag ttgaattttc tctaaattaa   32100
cacagaaatt taaaataatc ttgatcaaaa ttctagtaga ggtattttg aacttgttca   32160 ctgcaagaat aaatacataa ttgcaaagaa tatctcaaaa tcatcaccag gcctggtgtg   32220
gtggcccatg cctgtaatcc cagcactttg ggaggctgag gcaggcagat cacctgaggt   32280
caagagtttg agaccagctg gaccagtgcg gtgaaacact gcctctacta aaaatacaaa   32340
aattagctgg gtgtggtggt gcatgcctgt agtcccagct acttgggagg ctgaggcagg   32400
agaattgctt gaacccagga ggtacaggtt gcggtgagcc tagatcgcac cactgcattc   32460
cagcctgggc gacaagagca aaattctgtc tcaagaaaaa agagaaaaaa gaaaagaaa   32520 tcaacactaa tatggtgaga cttaatgtat gtgacattaa aatagtgatt ggatgttaaa   32580
acaggtatag aacagaaaga agagtgtatg tgtgtatctg tatgaattta tgatgggtgt   32640
aacatatatg tattagggaa atgagggaaa tgatacattt ctctgacttt gggagaacat   32700
tatatctcta cctcatattg caaacaaaca taaagttcag attaattacc taaatgtgaa   32760
aaaatgaaat aatttctttta aaaatgtaa tcttagtttg aggaaggtta acattataaa   32820
ggaaaaaact gttttgagtg gaatatagtt caatatgtca aaatccacct tcaacaaaat   32880
```

```
tgaaagtaaa ttgaacttgg ggaaagtatt gacagcatat agatcaaagg ttactagcct   32940
gtgtaaagag cagttataaa tatcgttaag aaaaacactg tcgacctgtc ggcaccttgt   33000
tctccgactc ccagcctcca gaactgtgac gagtaagtgc ttattgttta aaccacccag   33060
tctgtatgtg gtattttgtt atagaaactc aagctgatta ggacactagt aatcagtaga   33120
ctgaaactga aacaaaaata agaacctttt ttacctgtca aattggcaaa cattaagaat   33180
attcagattt ttgtcagagg tgatacaacc ttctaagaag gcaatttggg aaatataaa    33240 gctttagatt attatatgtc tgacctagca gttttacctc tagggtgctt acccctagga   33300
aagtgtgtaa tgatattggt gcagtgccct tcatcccatt agaaaattaa aataaccctt   33360
aatggcctac cactaaaagg ggattgaaaa tttaagatat atttatttat gtgtttattg   33420
agatggagtc ttgcactgtc cgcctgggcc agagtgcaat ggtgcgatct cggctcactg   33480
caacctctgc ttcccgggtt catgtgattc tcctgcctca gcctcctgag tagctgggat   33540
tacaggctca caccaccgca cccggctaat ttttgtatt tttagtagag atggggtttc    33600
actgtgttgg ccagactggt ctcgaactcc tgacctcatg atccgcgccc ctcggcctcc   33660
cagtgttggg attacaggtg tgagccactg cgcctggcca gatacattta tacaagagaa   33720
tgttagttaa cattcataga tatttatatt ttgtttactt tttattaaaa aattttttt    33780 tagagacagg atcttactct gtcacccagg caggatgcag ttgcacaatc atagcccact   33840
gcagcctgaa ctcctgggct taagtgatcc ttctgcctca gccttttgag tacctggggg   33900
actttaggca gtgctactat acctggctaa ttttaaatg ttttatagat gagatcttgc     33960
tgtattgccc aggctggtct agaattcctg gcccaagtg atcctcccac cttggcctcc     34020
caaagcgctg agattacagg catgagccac cacttctgac caatagatat ttatatttgt   34080
gactggaaaa tatattaaca atgtgttaaa aaattcagtt aaaaaataat gaaagattt     34140 tgcttctggc taagatagaa taacaaggac agcatttatc ttcttgcctt gaaatagttg   34200
aaaacggaag aaatatatgt aacagtggtt ttcaagttat tgggcatcag gcaaagaaga   34260
atagttatcc caggaaaatg aatgtggaga gccctacaat ttccttacat tactgcctgg   34320
tcatggcaag aggaaaaact gagaggagac tgaggctgag ccagtggttt gctgggttga   34380
ggaggcagag ctgggagtgc agagatgcaa ggtggtgaga gcccatatgg aagaatacca   34440
gggaagagag ctgcagaggg agctccggag acctgcaccc tgccctctca gtaccctgtc   34500
atgtgtgtag ctgagtactg acgagcactt gcttgtgcgg aaatgaccca gggctggagg   34560
tagagccacc tgaaaggatt agaaggaaca gttgctgaaa gtcacacagg gccaggaaga   34620
atttctaatc acaccagttg gagtggaaaa cctcagctct catagagcag gtagggtact   34680
cagaagggtt tgcccaccta gccccagact aagtttcgtt actctgaccc tacctaatat   34740 taaaagaga ttaattaaat tgttcgcaac aaaaataata tatttcagtg tttgtaacac     34800
gtagaagtga attgtatgac aatagcataa aggctggaag agcagaaatt gacatgtatt   34860
tgcgctgggc agaataatgc tcccctcttt ccccaaaaga tatcaagtcc taatccctgg   34920
agcctgtaaa tattacttta tatggaaaat tgttttatga tgtgattaaa ttcaggatct   34980
tgagatgagg gggctatctt ggatgatctg ggtaggcact aaatgcaatc acatatatat   35040 aaaaggagg cagagggaga ttttacacac agagagaagg ccctgtgaag atggaacaga    35100
aagatttgaa ggtgctggcc ttgaaaattg gagtgatgaa gctataagcc aaggaatgca   35160
gcagccacca aagctggaag aggcacggag cagttctcat ttagagccta ctccagaggg   35220
aatgtggtgc tgccaattcc tttttttttt ttttttttaa gatatcattt accccttaa    35280
```

```
gttggttttt ttttttttttt ttttttttttta gtatttattg atcattcttg ggtgtttctt   35340
ggagaggggg atttggcagg gtcataggac aatagtggag ggaaggtcag cagataaaca      35400
tgtaaacaaa ggtctctggt tttcctaggc agagggccct gccacgttct gcagtgtttg      35460
tgtccctggg tacttgagat tagggagtgg tgatgactct taacgagtat gctgccttca      35520
agcatctgtt taacaaagca catcttgcac cgcccttaat ccatttaacc cttagtggac      35580
acagcacatg tttcagagag cacggggttg ggggtaaggt tatagattaa cagcatccca     35640
aggcagaaga attttctta gtacagaaca aaatggagtg tcctatgtct acttcttttct    35700
acgcagacac agtaacaatc tgatctctct ttcttttccc acatttcctc cttttctatt    35760
cgacaaaact gccaccgtca tcatggactg ttctcaatga gctattgggt acacctccca    35820
gatgggtgg cggccgggca gagggctcc tcacttccca gatggggcgg ccgggcagag     35880
gcgcccccca acctcccaga cggggcggcg gctgggcggg ggctgccccc cacctcccgg    35940
acggggcggg tggccgggcg ggggctgccc accacctccc ggacggggcg gctggccggg    36000
cggggggctgc ccccaccctc ccggacgggg cgggtggccg ggcgggggct gccccccacc   36060
tcccggacgg ggcggctggc cgggcggggg ctgcccccca cctcccggac ggagcggctg    36120
ccgggcggag gggctcctca cttcccggac ggggcggctg ctgggcggag gggctcctca    36180
cttctcagac ggggcggctg gtcagagacg ctcctcacct cccagacggg gtggcagtgg    36240
ggcagagaca ttcttaagtt cccagacgga gtcacggccg ggcagaggtg ctcttcacat    36300
ctcagacggg gcggcgggc agaggtgctc cccacttccc agacgatggg cggccgggca   36360
gagatgctcc tcacttccta gatgggatga cagccgggaa gaggcgctcc tcacttccca    36420
gactgggcag ccaggcagag gggctcctca catcccagac gatgggcggc caggcagaaa    36480
cgctcctcac ttcctagacg gggtggcggc tgggcagagg ccgcaatctt ggcactttgg    36540
gaggccaagg caggcggctg ggaggtgaag gttgtagtga cccgagatca cgccactgca    36600
ctccagcctg ggcaacactg agcactgagt gagcgagact ccgtctgcaa tcccggcacc    36660
tcgggaggcc gaggctggca gatcacttgc agtcaggagc tggagaccag cccggccaac    36720
acggcgaaac cccgtctcca ccaaaaaaca cgaaaaccag tcagacatgg cggtgcgtgc    36780
ctgcaatccc aggcacttgg caggctgagg caggagaatc aggtagggag gttgcagtga    36840
gtagagatgg tggcagtaca gtccagcctt ggctcggcat cagagggaga ctgtgcgagg    36900
gcgagggcga gggcgaggga attccttaat ttcagtttag tgatactaat tttggactct    36960
ggcctctaaa actgtgaaag aaaaaatttt ttgtttgttt gtttctttta agccacatag    37020
tttgtggtaa tttgttacag cagctgcagg aaactaattt atgctgcatg tgaaatggtg    37080
taataaggta gattgtgatg aagatacata gtataaacaa ttaagcaaca actaaaagca    37140
caacaaggaa ttatagctaa tgaaccaaaa aaggagatta gaataataaa aatggtgaat    37200
cccaaagaag ccagaaatag gggaagaggc aaataaagga aagaaagagc ttgatggtag    37260
atttcaacct aactatgtca aaaaggacat tacatgtaaa aggcagcgat ttttcagatt   37320
gaatggaaaa gtaagactcg gtatatgctg ctgcctgcaa gaaacacatt ctaaatataa    37380
aggcaaaaat aacctacagg taacagaacg gaaagaagtt cactgtgctt acaagaatta    37440
gatgcaagct agactggttc tgttaatatc agacaaagtg gatttcaaag caaaggctct    37500
tgcccaggat gagatggtca tttcataatg atgaagggga ttcgttcatc agcctggcat    37560
agcaagctga aatgttttatg caccggacta cagagctaaa atacatgaag caaagcctga   37620
```

```
cagaactaca agtagaaaca gacaaatcca cagtgataga gatttcagta gccgctctca    37680
atgatttgta gaacacgtag ccataatatc tggatctaga acacttgacc aacactgtcc    37740
cctgtgcaac ctcattggca tttacaggac actccaccca gcaccagcag aagagacact    37800
ctctcaagtg ctcacagaat gtttgccaag atagagcaga tgctgggcca taaaacaagt    37860
ctctaaatta aaagcattca aattattcag agtatgtttt ctgacctcag tatcattaag    37920
ttggaatata ttataggaag ataacctgga aaagcctcag atatgtggaa aaacccattt    37980
ccacatggcc catgggtcag aagtgaagtc aaaagggaaa tttgaaagtc ttttggattg    38040
actgatataa aaacaataga tttctaaact tgtggggtgc tgttacagca tagtaaatgg    38100
aaatttctag cattaaatgc ctgttttagg aaagaaagat ttcaaatcaa tgacctcagc    38160
ttctaccttt ggaaacttga aaatgacaag caaatggaat ccagagttac cagaagggcc    38220
aggtacggtg gcttatgcct gcagttctgc cactttggga ggccgaggca ggtggattgt    38280
ttgagactgg cagttgaaga ccagcctggg cagcctaggg agaccccata tctacaaaaa    38340
acaaaaaaat tagccaggtg tggtggcatg tgcctgtagt cccagctaac caggagtcta    38400
aggtgggagg attgcttgag tctgggaggt tgaggctgca gtgaactgtg attgtgccac    38460
tgtgttccat cctgggcaac agaatgagac cctgtctcaa aaacaaaaac agttactaga    38520
agaatggaca tcataaagat aggagcagaa gtcagtaaaa tagaaaacaa aaatacatag    38580
gaaatcaata aaaccaaaag ctggttcatc aagaacatca ataaattggt aaagctgata    38640
ggaaaaacag tgaagtcaca aattagcaat atcaggaatg agggagatga cagtagtata    38700
gattatatag atattaaaag gactgtatga ggcaggtgtg gtggttcacg cctgtaatcc    38760
cagcaccttg ggaggccgag gtggacagat cacctgaggt caggagtttg gaccagcct    38820 ggccaacatg gtgaaactct gtctctacta aaaatacaaa aattagttgg tcgtggtgct    38880
gtgtgcctgt aatcccagct acttgggagg ctgaggcagg agaattgctt gaacctggga    38940
ggcggaggtt gcagtgagct gagattgtgc cgttgcactc cagcctgggt gacagagcaa    39000
gactccatct caaaacaaat aaataaataa aaaggactat atggtaatat tatgaacaac    39060
tttatgccaa taaatttgac aacttataga tgaaatggat gagttccttg aaagacacag    39120
aaactattaa agctctctca agaagatata gataagctga ttagccctat atctatttta    39180
ttgaatttaa atgtaaaaat caatatttag ttactgaaaa acttttaagt gtggttggaa    39240
atggtatacg aacttttca actgaatttt atgaagtcta atcacaggta aaggttttct    39300
gatgaaaatt tagtgtctga attgagatat actgtaaaaa atgttatata tcttaattat    39360
ttcttcacat taattacatg ttgaaataat actttgggtg tattgggtta aattaaatat    39420
tatgaaaatc ttgcctgttt tcttttttact tttgatgcgt cagctaggaa atataaaagt    39480
gtagctcaca ttctgtttct gttgacagta ctgctttgga gcacagtgtt tgaatgatct    39540
atcatttcaa agacctttcc tcagttcgtt attcatggct gtctgtattc cacatagata    39600
aggtctgaaa tactgctaag tggcatgttt tgttttatgc ttttataagt ttgttgatca    39660
ttactgatgt ggacttttgg tgcctcttag gctcattgct atcttccaac cattgtttgc    39720 aattttttacc tagagataaa gagaaagaga catttggttt cagagtagtt agattgggat    39780
catgaaagag caacctcatt ttgatgcttc aaaaatagca catccccgt attactggga    39840 tttgctattc ttgggattac ttcaagaaca tccttgtgtt actggtttgg atgcttctga    39900
atgctgtgaa gtcagtttca tgtacatggc tcatcagttt agctctctct tggctttgtt    39960
tagacagttg gagcatgatg gcctaaacag cttcttcaa ttaaacattt taaaatagtt    40020
```

```
tacaaatagt aaacaaactc cagtttttgt gactctttgt ctcgcacaac aaaaacacaa   40080
tctgaccatg atcatctggc atcttagggt gaaatatgtg tatactttgg cccataccga   40140
aagcaagatt aaaaagggc aggagagata gactgctgaa ctgattttca aggttccaag    40200
aatattgtag gttaagagta aaagtaaact tttggtagaa agcagtgggt tgtctaggat   40260
tgaagtatct gaagttttta aacgaaaatt taaaagaaa aatgagaatt gccttacaag    40320
tacaatctct tcttttttaa aaaataaact ttattttgaa atagtttag atttatagaa    40380 aaaaattaga tagggtagga agttttcata taccctacat ccagttaccc cagttattat   40440
catcctaatt tagtgtgaga cattttcatg tttaatgaat caatattgat atgctattaa   40500
cttaagtcca gactttattc agattttctt aatttctatg taatgtcctt tttctgttcc   40560
agaattccat gcaggacacc ggatacctca ttacatttca ttgtcatgtc acctttaggct  40620 cctcttgaca gtttctcttc ttttttgct tagaaattct ccagaatttc agaaacttct    40680
gggcatcgct atggaacttt ttctgctgtg cagtgatgac gcagagtcag atgtcaggat   40740
ggtggctgac gaatgcctca acaaagttat caaagtaaga accgtgtgga tgatgttctc   40800
ctcagagcta tcattgttgt aggctgagag aagaagcgat cattgagtgt tcttctgttt   40860
tgagtccctg aggatgtctg cacttttttc ctttctgatg tatggtttgg aggtgctctg   40920
ttgtatggtt tggaggtgct ctgttgtatg gtttggaggt gctctattgt atggtttgga   40980
ggtgctctgt tgtatggttt ggaggtgctc ttgtatggtt tggaggtgct cttgtatggt   41040
ttggaggtgc tctgttgtat ggtttggagg tggtcttgta tggtttgcag gtgctctatt   41100
gcatggtttg caggtgctct attgtatggt ttggaagtgc tcttgtatgg tttggaggtg   41160
ctcttgtatg gtttggagat gctctattgt atggtttgca ggtgctctat tgtatggttt   41220
ggaagtgctc ttgtatggtt tggaggtgct cttgtatggt ttggaggtgc tctgttgtat   41280
ggtttggagg tgctctgttg tatggtttgg aggtgctctt gtatggtttg gaggtgctct   41340
attgtatggt ttggagatgc tctggtatct gcctgcattg cttgccacac ctgcccggtc   41400
agaaggcgct atgttgacaa ttgtgcctgc acggtgccta ggtcaatgaa gggaaccgat   41460
ggtagccact ggatgctcct gggaaaatgt cactacaggc accagagaag ccagagctat   41520
gcccaaattt ctatgagtct cagttttctt aaccataaaa tgggatcaat gttttgtgg    41580 catgtgtatg agtgtgtgtc tgtgtatgtg tgaggattaa attgtgtatg tgtgaggact   41640
aattgccact actggatcct caaagtggta agaagtgttc ttattaataa tgacatcctt   41700
acactcttac ccagcaagat tgatgggtgt ggcactgctt ctctttttcc atcacatggt   41760
ttccatggta tccttttgcc cagggaatct ttgctttgtg gctagcactt tgttgtttgg   41820
ctaatcacgc tttctgtggt caggacgctg gcttctctgg agccatggga ttctagctcc   41880
ctgtcttgtc cctagagtgg tcactgtctt ctctctccgc ttgcaattcc tgctttgctc   41940
gcatctcact tatgcagtga cgtatatcag tttcaccttg ttctccgtgc ctgctgatca   42000
ttggcaccac ttgcatggtg ccatttaggg cctgcttcca gttaagcttg cttctccaca   42060
ggcctaaata tccttgcttg cttcttttat tctcactggc aggaccaggg cggtctgtct   42120
ttgcatgaga cagggtctcg ctcagtcacc caggctggag tgcagtggct gatcacggct   42180
cattgcagcc ttgagctacc gggctcaagc tatcctcctg gcttggcccc ttgagtagct   42240
gggactacag gcgtgcacca ccatgcccag ctaattttta aaattatttg tagagatggg   42300
atctcgccag gttgcccagg ctggtcttga acgcctgggc tcaagtgatc ctccctcctt   42360
```

```
ggtttcccaa agtgctggga tcacaggtgt gagccactgt gcctggccct tgatgtttca   42420
gttcttgata tttgatcctc agagtcagaa atctaaaaa gagggctatc ccaggttgcc   42480
ttggttcatg gcaaatggga cgttaagagg gcagagagaa tatgaacaga aactgttcta   42540
atattggtca tttaatgtgt aagtattgtt ctttttaaa cctccttcat ttttttcca    42600 ggaattgctg gacacagtgg cttggtgtgt gtctgaggac tgtaggccat ggccctaggt   42660
tgtggtttta ggtctcaggt gctcttcctg gctgtctcct tgcttctttc ccatgtcctc   42720
ttctttgttt ccagccattt ctcccttatg cttaagtttg gtgcagcagg gtttggctgc   42780
tctcagattc ctgcttcctc agatgctgta gttgtcaggc ccagcgggct ggcagcggga   42840
tcaggatctg gctaggtttg ctctcactgt ggcagagtag ggggaggcgt gggagagcac   42900
gtgtgacccc aggccagctg tagggagcat aggcatggtc acgtagcctt caggtcctag   42960
actttgtctt ctcatgagta tggctgtgtg tgtatggtga aaactaggtt ctacttagcc   43020
caagaaaatg ggcacatttt gcatgtggtt tctgtagaga aatgcactgg gtatctgaca   43080
tagcctggca gcatgcctcc ctcaggtagg ttagtctcag gcggtgaagc acgtgtgtcc   43140
agcaagaact tcatatgtgg cataaagtct ccgttctgtg aggtgctggc aaatcaccac   43200
caccgtcaag aggctgaagt gattttttgtc tagggaggca ggaaaggctt cctggagtca   43260
gcagccagta ggtgaaagag tagattggag accttcttaa tcatcaccgc ctcttgtctc   43320
aaggggtgcc aggaagctgt ggaggctgaa cccatcttat gctgccagag agtgggacac   43380
catgagggtc aggtcaaggg gttgtacctt gtttggtaga gaattagggg ctcttgaaga   43440
ctttggatgt ggtcagggga gtgtatcatt taggaagagt gacccggtga ggacgtgggg   43500
tagaggagga caggtgggag ggagtccagg tgggagtgag tagacccagc aggagtgcag   43560
ggcctcgagc caggatggtg gcagggctgt gaggagaggc agccaccgt gtgtctgcgg    43620 aagcaggggc aagagggaag aggccagcag cgtgctgcca tcacccagcg actggcgtag   43680
attgtgagag accattccct gctcttagga ggggctgagt tttagttttc tcttgttata   43740
caataagctt ggtatttgtt tacaaaacat ttgtaaagct aaatcaaggt ttgataaggc   43800
ttctagtttt atttaagaag taatgttgaa ataaatgttt gtccaattcg ctttgctcat   43860
ttaaggactt tcagtacaaa ctgcaacaac aggattagga tttaaacgtt tctgagatgt   43920
ttttactcct cagaatttcc cagaatgtga tctggttttg atttttcaagc ttgctgaccc   43980 aataggttaa cccacaagtt ttacgaagac catctcagtc cacttacatc aactgcccat   44040
gccacggtta aagagatcat cgactgatgt ttggcacagc ttcctccctc ttgggtgggc   44100
aagcatttgg aagagaaggc tcctatgggt gagagtgggg caccaaagtc ttccctgtcc   44160
catcccctag cttgagaagc ccttctctaa tgtggacttt gtgccgttag catcgttact   44220
agcttgaagt tgaccatctg gacgtacttt ctggtttagc ctcacaagtg agcaaggagg   44280
gttgagagat gtgctgtgag gaatgtgggg ccccagctgg cagcaggctc tgggtcaggg   44340
gggcagggac cacgggcata cctgacagtg aggaggggcc acacctgcag aaaaggatgc   44400
aggactccgc cttgggaagt gttctaggcc agagcgaggg tctgtggttt ataagtacac   44460
ccacagtgct cgggaccctg cagatgtcca gggtgccgtc tgagcccgta tcatccaaca   44520
gaatgttctg ctagtgaaga ttaaagattt actccagggg ctttaggatt tattatatat   44580
atataaatcc tatatatata attttttttt tttttttttt tgagatggag tttcgctctt   44640
gttgcccagg ctggagtgca atggcgtgat cttggctcac tgcaacctcc gcctcccggg   44700
ttcaaactat tctcctgcct cagcctctcg agtagctggg attacaggcg cccaccacca   44760
```

```
cacccggcta attttttgtat tttttagtag agacggagtt tctccatgtt ggtcaggctg   44820
gtcttgaact cctgacctca ggtgatctgc ccgccttggc ctcccaaagt gctgggatta   44880
caggcatgag ccaccccacc tggccaggat ttattgtatt tgaaccatct accattttaa   44940
ttttgatgtt atgtagtatt tgatgataat gaaagttaaa ttgttttttct ttccattttt   45000
ctgtttaagt gaatgacctg tatctagttt attcagtaac ttcctgcata tatttgtttc   45060
tttcattctt aatgaatata ttcttaattt agttgctatt atgttttgct ttgccccaaa   45120
attgaaatct tagtttcctt ttagctcgtt ttagaactag tgatgggatg tgtcttccat   45180
aaatctcttg tgatttgttg taggctttga tggattctaa tcttccaagg ttacagctcg   45240
agctctataa ggaaattaaa aaggtgggcc ttgcttttct tttttaaaaa tgttttaaat   45300
tttaaatttt tataggtaca cgtattttgt aggtacatgt aaatgtatat atttatgggg   45360
tacatgagat atttttgatac aggtatacaa tacataataa tcacaccatg gaaagttgga   45420
tatccatgcc ctcaagcatt tatcctttgt gttacaaaca atccagttac atgctttact   45480
tatttttattt tatttttgag acagagtctt gctttcaccc atgctagagt acagtggcat   45540
gaccttggct cactgcaacc tccgcctccc gggttcaacc gaactttggg ctggtctcaa   45600
actcctgacc tcaggtgatc cgcccgcctc ggcctcccaa agtgttggga ttacaggcgt   45660
gagccactgt gccgggcctg attgtacatt ttaaaataac taaaacagtc agggcacagt   45720
ggctcatgcc tgtaatccca gcattttggg aggctgaggc aggtgatcac ctgagatcag   45780
gagttcgaga ccagcctggc caacatggag aaaccctgtc tctactaaaa atacaaaaat   45840
tagccaagtg tggtggcggg cgcctgtaat cctggctact cgggaggctg aggtagggga   45900
atcgcttgaa cctgggggtg gaggttgcag tgagccgaga tcacgccact gcattccagc   45960
ctgagcgaca gagtgagact ttgtctcaaa aaataaaaat gaaataaaat tgggccgggt   46020
gtggtggctc acaccttagt cccagcactt tgggaacctg aggcaggtgg atgcttgaga   46080
ccaggagttt gagaccagca tgggcaacat ggcaaaacgc tgtctgtaca gaaattagct   46140
gggtgtggtg gtgcacaact atagtctcag ctacttggga gattgaggtg ggaggattaa   46200
ttgagcctgg aaggttgaat ctataggtag ctgagattgt gccactgccc ttcagcctgg   46260
gcgaccaagt gagaccctgt ctcaaaagaa aacaaaaaa acaaaaaaca aaccactatt   46320
atcgactata tattattgtc tatgatccct ctgctgtgct gtcgaatacc aggtcttggg   46380
cccttatttc catcactgag caaacttcac tctgttaagc agcaggtgtg ggatttcatc   46440
gttattcagt aattcacaat gttagaagga atgctgtttt ggtagacgat tgctttactt   46500
ttcttcaaaa ggttactctt tattagatga gatgagaatt aaaaatggta acttacttta   46560
tatctttata attgaagccc actagacctt aaagtagtta ccagatgttt tatgcattta   46620
aatggccttt tctctaaaat tagaaagtaa caaggaaaga aaatgcttcg tttctatgca   46680
accctcttgg tgactagtat gtgactctta atgcaaccct cattgcaccc cctcagaatg   46740
gtgcccctcg gagtttgcgt gctgccctgt ggaggtttgc tgagctggct cacctggttc   46800
ggcctcagaa atgcaggtaa gttgtacact ctggatgttg gttttttgtcg ggggccagct   46860
gctactgatc ctttatgtct cagctcagat gtcatttcaa aagtctgctc tgccctctcc   46920
aaattgcagt cgaccttgcc ctgtttatgt ttccctcata gcactaatcc atgtcagaaa   46980
ttgtcacgta cagtctatct gtgtgcttgt ttattttcta tcccacccct ccgcaagaga   47040
cttatgggat gtgtgcccca ggacagcagg ggtcttactg tcttatgctc tgttgcagcc   47100
```

```
cagcagcgat aacagtgtct gcacatagta cttgcttaaa agatacttgc caaattgttg   47160
aaggttgagg taccaatttc attattgctg actataggag ttatagcaaa atatccattt   47220
gtctgttaca tgagttaaaa atatggttgt tgcactgtga atagtttggt ttagtcaaaa   47280
cagttgtatc ttaacggatt gagaaacaaa agcaggacca cttttcatca gctccctcct   47340
tctccttaac cagcaataca tgctgatgct gatatcccat agaccctcag ctccatcctg   47400
agtcactggg aatgtggtct aaaccctcac tattaatatg aactgagttt caataagaat   47460
cttatatggg tcgggcatag tggctcatac ctttgatccc agcacttcag gaggccaagg   47520
caggtggatt gcttgaccca gactaggcaa catggtgaaa cgccgcctct acaaaaaata   47580
caaaacttag ccaggcatgg tggtgcgtgc ctgtggtcac agccactcga gaggctgagg   47640
tgggaggatc acttgagcct gggaggtgga ggtcgtgttg agccaagatc gcaccactgc   47700
actccagcct gggcaacaga gtgagacctg tctcaaaaaa accaaaatcc agaaaagaac   47760
ttatatggct gcagaggtat aatcactaag gaaatttcct tttgtataat cttttttctt   47820
ttactatcat ttaaaaaaat gtgttatatt tctgaagcaa cacatccagg ttctgcacat   47880
agcagccaaa gtgaccttaa agaatataac tgggtcttgt cattcccta tttaaactct   47940 tgtacccatt tcccagtgcc gtttagatag agattccaga ctcgtcaatg gctctgtcac   48000
ctcagacacc ctgcattgac tcattagtct gattagagtc aggttttct tcctcctgat   48060 ggttttttt tccccttag ttctcagcgg aacagtcact tccttaggga ggtttcccca   48120
gccaccctct gaggccgtgc ttgttgccag actctgccac tagagggcag ggctgcacca   48180
ctcctggcac ctcgcacccg gcctgccctg tcactctgtg tgttgggtga attcctgtga   48240
tctgtgactc actgctctgt gtcctacaca ttcggctttt cttctctccc cacaacccca   48300
ttttataatt ctccttttc aggaaagctt tattcccatt taaaaatttt tgtttttaaa   48360
atggtatttt cttacactta ttttctaatt aaaaatgagt gttttaagaa gtattatgat   48420
ttactgcaaa taatttttaa acccagcctt ttagatcctc tgtgatcata agagaaatga   48480
aggatgtctc ccaacacttg agcttcatcc acatttcatc ctcctgttct ttcagctgag   48540
ttttccccat cccattaggg actgttggaa tataaaactg gcttttccct aacagggaat   48600
gaattgcttc tgtttctcct gaaggagagc tggaagaatg acttgcgttc ttttgcatac   48660
acaggcctta cctggtgaac cttctgccgt gcctgactcg aacaagcaag agacccgaag   48720
aatcagtcca ggagaccttg gctgcagctg ttcccaaaat tatggcttct tttggcaatt   48780
ttgcaaatga caatgaaatt aaggtatgat tgttgcctca ggtcacaaac atgcgagtga   48840
tgctgtgagt gagtctgtgg agggtgaggg cttctgaaca gggagtcctg tgggagtgct   48900 tcttgggta tgttgtatgt cgtaatttag actaccatca tttgtgttat ttttgaggca   48960
cctaaggact tctttccact tctcatttct tactgtgggg tgaagagttg aattgggaga   49020
tggtttctag atgcaaattg aaaaggcatt tttccagagc agatttgttt tcggcgtact   49080
agagtgactc tttaacctag ctgcgggaag atgactgtgc caagactgca ggtaggagaa   49140
agctcactga cgaggccttg tgggtctgaa cgtcctgcag ctatcagagc ctgttggctt   49200
cctgttgtgc attccaacaa atcatcttca aacccacttt agtgttttgt ttataatgtc   49260
cagaaatagt gaccctgtca catgctctac agattacagg attcttagcc tcttcctttt   49320
tggtaggtca gtcctgggtt tgagcccaag tgaccctcct gggaggtgat gatacacact   49380
gggtagagtg gaatcagatg gacttggatt agaattctgt cctctttact agttattttc   49440
ctctaggcaa actgcccaac agctctaagc tatttccttc gtattctgaa aaataagcct   49500
```

```
taatgggacc catatagggc aactctgaga gtaaaataaa ggaatatgtg ttagagtgta    49560
gcatagtcac ccacgggaag ggcttagatg ttagctgcta ctgctcttat tagctgaatg    49620
atttggaata aactgttagc ctctctcatg ttttttctct tgagcttcga agttttcttg    49680
ttaatactaa ggagatattc aaactagtca tggggttttg gaatgacgaa gggagatgat    49740
gaatctaaag aatttagtgt aatatttctt catgctcagt aaatggtagt ttctgctgct    49800
gttattttta ttaccatctc tttggaatgg gagtaggtgc tcctttgtgg tcagaggctg    49860
tgagagctcc acagcgccag tttgcccatc tgtacactgg ggtctgttga aggcagtccc    49920
ctctgtgata tctctggctg tcagagctca gatgatagat ggtattttg tactcttagt    49980 tctcatcatt ttcatgattt cgatcaccat ttgagtatga tgatgctaac actttgttga    50040
acgtagaatc cgttaattac ttccttcctg aacctttggc attaaaaaaa atctattctg    50100
ctacctctct gctcatttat ggttattcaa atttattatc aagagcctgg tacagtggct    50160
tgtgcctata attgtagcta cttgggaggc tgaggtagga ggattgcttg aggccaggag    50220
tttgagacca gcctgggcaa gatagtgaga ccctatctct aaaaaaactg aaaaaaaatt    50280
agctggacat gatggcatgt gcctgtggtc ctagctactc aggaggctga cacaggaggc    50340
tcggttgagc ccaggagttg gagttcgagg ctacactgag ctgtgattgt gccaccacac    50400
tccagcatgg gtggtaaaac aagatgccat ttcttaaaaa aaaaaaatat atatatat     50460 attatcaatg aaattcagta gtaccaacag gattataaac aaagatagta gttcccttcc    50520 tacttttct cttaatcctt gtgtctcaca ggcaaacata actcttagta tttcttccaa     50580
tatttacttt catgtttctt tctttctttc ttttttttc tttgagatgg agttttgctc     50640
ttgttgccaa ggctggagtg caatgacgca atcttggctc accacaacct ctgtctcccg    50700
ggttcaagcg attctcctgc ctcagcctcc tagtagctgg gattacaggc atgcatcacc    50760
acgctcggct aattttgtac ttttagtaga tggggttt ctccggggttg gtcaggctgg      50820 tctcgaactc ctgacctcag gtgatcctcc cacctcagcc tcccaaagtg ctgggattac    50880
aggcgtgagc cactgcgccc agcaacttcc acatttctaa ataacatgct tctactgcta    50940
tttttttttt caatttaga catttttta ctttcactat agttctatca gaattcagtg       51000
tgtacgttat tatgcctaag taaatagtca tggttgctta cgtattatat ttctttgatt    51060
gtgtttctta tttgatgaga aagctgtgtt ttttgctctg ggttgaaact ggagagagga    51120
cctggggagg aggaggagga cagatgaagt tggtgactgt accttcatgg ccatagctgg    51180
gttctcagca cccggggatc tgctgatcac ctactcatag gccaggcccc tatcgaagtt    51240
ctaggtgacc cagtgctggg gacggggggg ccacctgcaa ggtctaatca tggaggtggg    51300
ggctacagtg ttggcttgtg ctggggccag catccttagg aaggcatctt ggaggtggag    51360
gagacagccg cccacttctt gattgggggcc ttcagcagca ccagcttctt gggcaggctg    51420
gtgctggctt tcatcaccat gtcgtgttca atcttcttcc agatcctgac ttctaggttc    51480
agctttcctc agaccctggt tcctttcaga ggccattgct gctgccttgc tctttgctgg    51540
cttgtgcctt gattatatgt ctttgtacaa cttttttgttt tcctggagtt aatcttcaca    51600
tctgttttct tggagttaat cgttacctct atatcgcttg cttattattc tttggccttt    51660
ttgtcttctc acaccttcca acttctttgt aatatgtgtt tagtacaatt tttcatgaca    51720
ggtagtttac tgaatcagtt tttccccagt gtggtcatcc aacttgagtt atccagctct    51780
ctgccccagt ctgggcaggt tgatcttcag gtctgtagta cacttgtatc ctaggacttc    51840
```

```
tctttgccat tagcctggaa tttcctttgc agttctcccg ttggatgccc agttcctaga   51900
tgccatatgt ttttctatcg tctagtagct tcctgagaga agatgaatgg gagggaaatt   51960
gtatgaggtt ttgcattcat aaaaatgcca ttttttttcc tgtacacttg gctgggtatg   52020
gtgttctggg gtagaaatca ttttccctca gaaatgcaaa gtctttgccc tgttgtctta   52080
aaatctccaa cgtgacccga ttccttaacc tatgaatgta cttttctttg gaagctttcc   52140
atttttgggg aggtgaagtg ctaggtactt agtaggcctt ttaatttgga aacttacatc   52200
ccttcagttc tgggaaaatt ttcttaacat ttctctgaga agttcttgcc ttttatttc   52260 tgtgttctct cctgaaattg gttagttgga tgttggtcct cctagattga ctcacatctt   52320
acctttttct tttctttttc tggtacttt tagatatcca tctcaaactc ttctattcat   52380
tgttatgttt ttaacttctt tcttttctt gtctcttgat ggggtcttgc cctgttgccc   52440
aggttgtggt gcagtggtgc gatcatagct cactgcagcc tcaaattcct gggctcaagc   52500
agctgttctg cctcaccctc ccaagtagtt gggactacag gtatgcacca ccacgtccag   52560
ctattttctt tactttttt ttttttttt tgagatggag tcctactctg tcgcccaggc   52620
tagagtgcgg tggtgggatt ttggctcact taagcctctg cctcccaggt tcaagcagtt   52680
ctcctgcctc agcctctcaa gtagctggga ttacaggtgt gcaccaccat gcccggctaa   52740
tttttgtatt tttagtagag ccagagtttc accatgttgg ccaggctggt ctcgaacgcc   52800
tgacctcagg tgatccgcct gccttggcct ccgaaagtgc cgggattaca ggcgtgagcc   52860
catcattaga tctttaaata ccagtatcta taagtctttt cctcttgagt cagctagtat   52920
ccctggaagg aaaattactca ttttcctgct tggaggctat aagcttggct atgtttatcc   52980
tgcaaccggg gactggaagg gaggggactg acagtgttgc tggtcagggt gccctcttac   53040
tttttgtttt ctgtgtgcat ctcacgtctg tcctcagcct atgtaaacac ctcttgagat   53100
tatccctctc aatctttgcc ggaggtgggg gaggggctgc ttcctgggct gccttggatt   53160
ggagggaaga cctcaggtga gtgggtggga atttgcccaa ggagccatga gaccagccac   53220
tatttcaccc tctccatccc tccactttca gatgtatgtg gcgcctccaa agcccgagct   53280
cttcttggcg tctgtggctt caataagctt gcttttgct ggtatccctc ctaccctccc   53340
ctgtccccag caaagcttgc atttgaactt cttcctacgg gctaacaaat cagtcagtta   53400
tgtagctctt gttactttt agcttccgaa gttttgttga cacccgtagt ctgctaatgt   53460
ccctgttctg ttctttctgt tcgtgtaaat atatgcttta tacaacttct ttacatgatt   53520 tttgtgggg ttctgggtag cagagcttca caagttcaat ccagcgtgtt ggattagaaa   53580
tctcccaccc tctggtttat tcttattctc aaaattacct gccaaacact gatactccct   53640 tgttttttcct tttcctgaca ggaaatgtac ataccataca ggacagaaat cattagtgta   53700
tcccttggtg aataaccaca aagtgaactt aacccttgta accgccaccc aggtcaagac   53760
agaatattac caagcactca gaagcctctc ccctattccc ccgtcactgc tcctgccttc   53820
ctccccaagg tcatgactgc tggcttctaa ttccagagtc tgttttaaa ttctgtgtac   53880 atagaccatg gattaagtgt tcttttgtc tggtttattt tggtcgacat taagttcatg   53940
agagtcttct atattatcgt gtgtattagt attcctgtag ttttaggagc ttcatagcat   54000
tccattgtag ggatatacca cagtttattc attgtattat cactgggttg tttctagttc   54060
ttggctattg cgagcagtgc tactgtgacc actcttaggt gtgtcttttg gagtacatgt   54120
gcaggtttcc atcttgcaca gctagaggtg gagttgttgg gtgatagggt gtgtgcatct   54180
cagctgcagt agaaactgcc aaatagcttt ccttgagtgc ttgtaccagc tcacccttt    54240
```

```
gccactgtgt atggggattc caggagctct ggtcctcgct agcacttgga attgctgatg    54300
cttttactct tagccttcct gatgggtgtt ttctggaatc acattatgat tttaatttcc    54360
attccttaaa gtaccttgg ctctgaagtt taatgattca tgcatctctt cccttttgaa     54420
gtactcttac aggtatgttg tgcatgtgtt gaaaagtggc actatctatt ctaaaataca    54480
gtatgcctcc tctgtgtttg aacagttgta gcgtggcctt ggggcctcct gttagctggc    54540
ttggagaagg gattcttggg attgtagaga ttagacctga ggaggcccct tggagctctc    54600
tgactaaatt ttattcttta ttattccaaa ctatttaagc tcaccgtgtg ctgactcatc    54660
ataataatga gtagctctca ttgtgcttgt ctatttggac tcatacaatg attttttttt    54720
tttctttgag acagagtctt gctctgttgc ctaggctgga gtgcagtggc acaatctcgg    54780
ctcactgcag cctccacctc ccaggttcaa gtgattcttg tgcctcagct tctcaagtag    54840
ctgagactgc aggtgcgtac caccatgcct ggctaatgtt tgtattttta gtagagacgg    54900
ggtttcacca tgttggccag gttggtctca aactcctgac ctcaagtgat ctgccttctt    54960
cagcctccca aagtgctggg attacaggtg tgagccactg agcttggcca aagtagtttt    55020
ttaagatgtt agtatctttt cttgcagcta aaaaagtttg tcagagatga ttctactttg    55080
ttctccaggt gttttctcag ggagaaattg gaggcagtaa gccactgggg gagtcctgtg    55140 gctgggggg ggggtagtcc tgtggctcct tgtcagggag tcctgtggct ggcaaggaga     55200
gaagtcctgt ggctgggttg ggagggagtc ctgtggctgg ggtctcatcc tgtgcctaac    55260
agtgtccaga ggtgccgaga ccagctcagt cggggagacc ctaacccagc agcgctagag    55320
gaattaaaga cacacacaca gaaatataga ggtgtgaagt gggaaatcag gggtctcaca    55380
gcctttagag ctgagagccc tgaacagaga tttacccaca tatttattaa tagcaaacca    55440
gtcattagca ttgtttctat agatgttaaa ttaactaaaa gtatcccta tgggaaacga     55500 ggggatgggc cgaattaaaa gaagaggttg ggctagttaa ccgcagcagg agcatgtcct    55560
taaggcacag atcgctcatg ctattgtttg tggcttaaga atgcctttaa gcggttttcc    55620
accctgggtg ggccaggtgt tccttgccct cattcctgtc aacccacaac cttccagtgt    55680
gggcattagg gccattatga acatgttaca gtgcttcaga gattttgttt atggccagtt    55740
ttggggccag tttatggcca gattttgggg ggcctgctcc caatacagag gtctcgtgta    55800
aattccctgg gaggcgataa gcctctgaga aacagactat gctaaccacg ccatgaaaga    55860
gaaacttatt tataaatcag atgccagtta ctagtttact gcttatttgc ccaggcgtag    55920
ctctgacaga gtccccgact catagtgctt gctcagtgca tgctgaacaa tgattggaat    55980
caagtcatgg ctcagagcat agttttgaat aatgggaaat ggatgttctt aagtaacata    56040
gtcaccaaga taatgcgact agctgggtca cccctttca attttaggat attttttatca    56100 agatttaaat ggccatcatt agagttatag cactttctcc tttggattgt cctagaggcc    56160
catgagaaag tattccctaa tttcttagga aacagtttg tgggtagtat gcggtcatgt     56220
ccagttaaat tgcagatatt tccgatcgaa gatgttccag tcctgagaac ttcgtgacat    56280
tagcaggact tctacaagcc atctcttagg gtggggcatt tactgcagtt ggctagtact    56340
cttttctcct taactttgtc atttgttgat tttttttta ctgtcccaa atactgtggg      56400 cagagtgtat ctagaattga ggcctccacc attgcggaga ggacatggat gctgagcagt    56460
cccctgagtg aaggttataa agaagcaaat agactacaca tgtctgtaaa ctgctcttga    56520
gtgtcccaaa tttggggtac ttcagttcag ctgtaggaaa agcctcaaac tgtttatact    56580
```

```
ttgcaagaat tggaaacttc taattcacgt taagttttat gtaatacatg ataagcttca   56640
taggagcttc atcttttatc tacttggact tttgcttccg taggttttgt taaaggcctt   56700
catagcgaac ctgaagtcaa gctccccac cattcggcgg acagcggctg gatcagcagt    56760
gagcatctgc cagcactcaa gaaggacaca atatttctat agttggctac taaatgtgct   56820
cttaggtaag gtggaggcat atgagtggaa gagtctccag catgtactca agatagacct   56880
ttgaaataaa taaaaccaga tgatccctca gcttctagac caggctattt ggcactggtt   56940
gattgaatgt gaactgcact ggggctgctg tgagcccgca tgggtctctg tgaccctgca   57000
gatgcagccg tgcccaggga ctgggcagtg ggtgtgggct ggtgtgagcc ctgtctgcca   57060
cccagggcct ggccctctgt ctgtgtcggc catgactatg gtgagtcttg taggcttgag   57120
actgtgcctc gggttcctgc gggttctctg taggtcagtt gacagtttct cctgttgttt   57180
gggtaactgt ggaaacgaac actggcaagt gctgaagcga gcatgtggac gtgcgatatg   57240
aaataacgac ctggctttca aaggcagtga ggctctctgg aaaggacctt gctgagctag   57300
ggatgtgggt gtgtagccat tcccagtggg cctcatggcg tactcgttca tgatcatgtt   57360
tgtgccatct tgatctctca ggatctcttc tttttttaaca gattaagccg ggaatctcca   57420
aacagtgagt cagatgttaa gatgtcttgc ttccacccc acaggcttac tcgttcctgt    57480
cgaggatgaa cactccactc tgctgattct tggcgtgctg ctcaccctga ggtatttggt   57540
gcccttgctg cagcagcagg tcaaggacac aagcctgaaa ggcagcttcg gagtgacaag   57600
gaaagaaatg gaagtctctc cttctgcaga gcagcttgtc caggtaggag cacagggttt   57660
actctaggcc ctgcatgtga atgactgaca ttcaaagaac cgattaattt ggaagagaag   57720
cggcagaacc gagagttaga ggtgtggact ctggagctgc gctgctcgtt tccaacccta   57780
ggtgctgacc tctagctgtc ttccctctgt atgtccctgt caccgtgagt caaatgcggg   57840
tgatgcctcc tcaggtgccg tgttacctaa gcctctcaga gaccactgct accctgtttc   57900
taaaaccaga ggtcacgata tgtgttcatc cacccagtaa atactgattg agcacccact   57960
gtgtgctagg ctctgggata ggggctgggt atacaatggt gagtatttca gctgcagctt   58020 ctgcccgtg gaggctgtgg cctagcacac tggtctaggc acggtggtat atgctcactc    58080
aaggagatag ggacgtggtc gtttggggtg tcggaacaaa atgtcggaac ttctctttcc   58140
aatgcagaga aaccttgcag taattctaat gtactgtgat tggcagttga cttcagttct   58200
ttgtagcacg cttactcagg ttatttcact aactatgtaa ccatgcagcc tcattttaag   58260
caattggatt ttttgaactt tacttaaaat gttatgtcag ggttttttatt gtgcttaatg   58320 tgtgccattt agctaagttt tgtaggatac gaaattgtaa gtggcttaaa atgattctta   58380
atagaatcat gaattgaaga taatgctaat aatttaagca ctgagttagg tagtgtttgt   58440
aaaatgctta gaatgcttcc tggcacatgt taaggccatg taagtgctgc gtgttgataa   58500
acagctgagc aaaagtggac tcttaagaaa gtattgggc tgagagttct gttccaacca    58560 gctgccttt ggttattttt cagaataaaa gcagagtctc atgggatatg acatttatat    58620
ttccttcaca aaaaacactg ctgagtgttt tgttgagtaa aaagggtgta gccatggtaa   58680
taatacattt aaaatatagt ttatttcatc tttaccttgc cttgttttt tttaagcta     58740 gcttttatt gagaattcca cacatacaaa agtatcaact catgaccagt tatatttcat    58800
ttataatcct acttctccct tttttatta tttgaaagca aaccccaatt atcctcttat    58860
ttcatctata agtatttcag tatctctata gatgaggact cttctttatt tttaaaactt   58920
tatttttaaa atgatggtca gatgcagtgt tcatgcctgt aatcccagaa ctttgggagg   58980
```

```
ccaagctggg cggatcactt gaacctggga gtttgagacc agcccgggaa acatggcgaa    59040
accccatgtc ttaaagaaaa aaatcagcca agtgtggtga tgcatgcctg tagtcccagc    59100
tacttgggag gctgagatgg gagggtcaca tgagcctgga agatcaaggc tgcagtgatc    59160
catgattgta ccactgcact ccatcctggg tgatggagca agattctgtc tcaaaaaaac    59220
aaaactgcaa aacaacgtca caaaacagtg ccattgttag acctgaaaat attaaacatt    59280
tcctacatca aatacccacc aactcattat caattttttct ctctactctt ttggaatcag    59340
catctaaata aaattggtcg ataaggattg taaatctctt tgatgaactg gttcccctcc    59400
atcccagttt ttttcccctta gagttcattt attgagaaac cagattgttt gtcttctaag    59460
ttttcctgtg gtctgatata ctgcttccat ctccactgtg taaattaaca ccttttttctc    59520 ttctctgtat ttcctgtaaa tcaataattg gaggaaaagc cttgtcagat ttagtgtata    59580
ttttatatct gagtccagta tttcttatat aatattttaa gataagtgta ctcttttaaa    59640
aagtattgaa actatatgct caatttttttt taactgatgc ttttaagaag gctgcttgat    59700
cataaaagtt tagagatcat tggtctgatg ggaaaagcaa ataattacta aaccgtttag    59760
caaggttgag gtgcacatgg tgggggcctgg agaagttcag tcatgagccg tcacttatgg    59820
gcacgtggaa tctgacccgg cacagagttg ggagaagaca ggagctttat agacagaaaa    59880
tgtggtcttt gctaagtccc aggagtgaaa gggtgagaca gtgctcacag cacacgagtg    59940
tgggtgcgta gacagagcaa gggtgggtcc tgaaaaggcc tgcaggcttt ctcatagatt    60000
agcaagagtg ctggttacgg aggtttctaa catttgtgaa cagatcgaaa ctgtgttaaa    60060
ttgggattgc agtaatcctg gaaggacagg gatagagggt gaaggggaaa aaagggtatg    60120
gatgtgagac ttaattgctg attttcttaa gacctttctc caaagtaaat aaatgatgtg    60180
gcacattttt gaactggcaa attctaaact ctagatatga ttatctctat aacatatctt    60240
actccatctt cttttgacta aaaactgttc ttaattaaat taccatgaga cgttcaattc    60300
agcaaatgta gtttggctaa ccatatttaa ttagaattta atataatcct aggcctggcc    60360
aaactattaa gcaagtgtgg gcaaaatatt gataatttta gatatgcagg aacttagttt    60420
gctttccatg tgtgcttttc gaaaaaggaa taaattgaaa aatagaggaa gccctgaaat    60480
ccaagaagca aactctctca cctaggcatg cagtaaaagc aattctagga tgattgctgt    60540
ttggcgcgta gttcgtatta gaaaccattc ttccttgaata aatagtatgt ttaagaagct    60600
gggcagaggg aaggcatatg catatattat caacaaggag ggagaaaaag gcaattagta    60660
accatccata ggagggtcag caagatttat aaaggaaatt tgtgatccaa gtatgaagca    60720
aaataaggtg cagaataaat tttaagcaag taatagatta gagtaagaga acccatttga    60780
ccattaacct tgggacattc tctttcaaat gacatggagt agtactgaaa tctttctttc    60840
tttctgagtc taggttattg tgactggact cagaaagaaa tatttcatta ttgcagtgaa    60900
taacatttgt gaacattatt gttcataaat tatgcagtga ataacattta tgaacacgtg    60960
atgtgtaaga tacatactgt ttattttttag ttaagttttt tggctcaact tctaggcaga    61020
gaacattaaa tgtaaatagt gttacctagg agcatgtaaa tggaaatctc catagtatga    61080
aagcagtgct gttgctaaca gaatttagga gggggcagat gaggtgaagg aaatgtgggt    61140
gctgatttcc ttattacatt gagaggagcc aggagattct tgttcaaaa tggatggctt    61200 aagaagtcaa agtataagct gattacgtag agcaggtacc caaaaatgtt ttgtgtaagg    61260
ggccagatag taaatatttt cagtcttgca ggccatccca agtctgtggc agctactcaa    61320
```

```
cactacctttt gtagcatgaa agcagccaca ggcagcccat aaatgtggct ctgttccggt   61380
gaaactttag gtacaaaagc aggtgcaggc cagacctgac ctgtgcactg tggtttgctg   61440
acctgggatt cagggdgtata gaagttacca tcagaagagc taaaagtgag acttttact    61500 ttatactctt ctacactgtc tgattttgaa aaaagaaac atgtatttta taatattaaa    61560 gataggggttg gcaaatagca aataaaaata cagaatacca gtgaaatttg aacttcagat   61620
acattatgag taattttatg gtgtaagtat attccaaatc atgtgggaca tacttacact    61680
acaaaattat tgttgtttg tttacagttt aaatttgagt gccttgtatt ttatctggca     61740
actgtaatta aagggaaaaa gaataaaattc attatgttca tataatgtga tatagcaggg   61800
gtccccaacc cccaggctgc agagtggtac tggtccatgg gtccccaacc cccaggctgc   61860
agagcggtat tggtccatgg cctgttagga accaggctgc ccagcaggaa gtgagcagca   61920
ggtgagctgg cattcccacc tgagcaccgc ctcctgtcag atcagtggca gcattagatt   61980
cccataggag tgcaaaccct attgtgaact gcacatgtga ggggtctagg ttgtgcgctc   62040
cttatgagaa tctaatgcct gatgatctga ggtggaacag tctcgtcttg aaaccatccc   62100
ctggccctgt ggaaaaattg tctcccatga aaccagtctc tggtgccaga aaggttgggt   62160
agcactgtga tatagtatta aaagtgctaa taaatatggc atactgcctt taaaatgtct   62220
ggtagctctt tctcagtggc actcataata gtgttttttg attttttaaat gtgtgtcaag   62280 ctgactctcc cctccgtgta tgctgggctt tattttccct ttcctagtca ccagttttgg   62340
gaaatagaga tcttcattct catgctgctc ctctagtgca agtgctccat ttatttttaa   62400
ggaattaata taacaaaaaa tcatgggaat ttagaaaaca acatggaagc taatgatcac   62460
attggtggaa gtgatagggga aatatttagg gggagaagtt aaggtataaa ctttgtcaat   62520
gaagtcctat taaaaacaac aaaaaagtga agcttaggat gcattttata aactctgacc   62580
agaacacctg tgtttctctg tttctaggtt tatgaactga cgttacatca tacacagcac   62640
caagaccaca atgttgtgac cggagccctg gagctgttgc agcagctctt cagaacgcct   62700
ccacccgagc ttctgcaaac cctgaccgca gtcgggggca ttgggcagct caccgctgct   62760
aaggaggagt ctggtggccg aagccgtagt gggagtattg tggaacttat aggcaagtta   62820
ttagcaaggt ctactcttac aattaacttt gcagtaatac tagttacact ctattgatta   62880
tgggcctgcc ctgtgctaag cagtctgcat tccatcttcc ttgccaaaac ttataataca   62940
aatttcatct ttattttata aatagggggag ttgggctggg tgtggtggct cacgcctgta   63000
atttcagcac tttggaagga tcgcttcagc ccaggagttt gagacaacct ggccaagtga   63060
gaccctgtct ctacaaaaaa aaaaaaaaaa aaaaaattag ctgggcatgg tggcacatgc   63120
ctgtagtccc agctgctttg gaggctgagg tggtaggatt gcttaagccc aagaggttga   63180
ggctgcagtg aatcttgatg gcagctgcac tgagcctggt gacagagcaa gatgctgtct   63240
caaaataaat ttaaaataa aataagagaa ttaaagttta gcaggttggg tggcaaaatg   63300
aggccacaca tttaaagccc ctcctcctga ttctttttctc tgccttggct gcctcctgtg   63360 gcatttttagg tgctgagaaa tgaaaacagt agggaaaata gttccaggat cctcatgtta   63420
atttgccaga aatggcatct tcaagtcgtc agagggatct gagagttcct tcctggcctg   63480
acttgagaaa atccgtctgt ccccagctct gcgtctgcct ccactgccca gtcacctcct   63540
ctccatgctc ttggggctgg gccctacccc accatgcagt gctgcctgg agcagtgagc     63600 ttggtgggtc ctgtctggca tgagagctgc ctttgggagc tggatcccag cctctaccac   63660
tgggtctggt gcctagcagg ctatggataa acttctgctg actccggcct ctcctaagcc   63720
```

```
actgcaacgt ggtcggtgta gtgcacagtg tgtgtgcagc gtggccttac tcacagcctc  63780
cacattagag agaatctgac tgaagtctta ctgctgcctc gtgtgaacat aaatgtttgc  63840
cagaaccatg agcaggaaat gttaatctgc cttgtttcct gtcctttaca cggaagaatt  63900
tttttctgta tggaatgcgt gccttacaaa taatgagtgg aaatacccat cgctaatgaa  63960
aagttatact tgactgttag tcagctaaat aatctgagat ttctaatact tttaatttgg  64020
cttttacaat gcaatttatc ttagcttttt tgatttctta ggtcatatct ttagaactat  64080
atatttgaat gttaatgtaa ttttcatatt gaaattaaaa tgttgaactg cgatgttaag  64140
tgtttcctgt ggaaaaacgt tcacattttc tctagtttta aagttgaatc aagctgtttg  64200
aagattttca catttcttct agattttatc agcttgttac tttatctgtc actttctgtg  64260
atttgcagct ggagggggtt cctcatgcag ccctgtcctt tcaagaaaac aaaaaggtga  64320
ttatttcaga aatcagagtc ttgtgttgaa tcttactgat tttcttgtat ttctgtaatg  64380
taatgtatct tgtatttctt gtaatactgt attggactct gtgtatatct cttctcagat  64440
gagtgattat atgtgtgaat gttgctggaa tctgataacc aggcctgaat agttttgtag  64500
ggtggctttt aaaaattact ttcatatcag aattgctttg tcataaattt tgaacgcatc  64560
ataaatttct aatgttcggg gtcagcagac ttttttttgta aagggacaga gtgtaaacat  64620
cttagcttta tgggccatat ggtctctttt gcaacattca gctctgccct gtgacaggaa  64680
tgcagttgta aagacatgag ctactggcca gctatgttcc agtagaactt tacttacaga  64740
aacagacagg ctgtagtttg ccaatacctg ccttagggaa tgtgttgtta tattttgtga  64800
gttaccttct cagtaaattt tatttagtat tagtcaggaa tattattaag tagcttcttt  64860
tccagcctgg tcaacatagt gagacccggt ctctaccaaa acaaaacaaa acaaaaaaac  64920
agccacgcat gtggcatgtg cctgtagcct cagctgctgc tcaggggct gaggcaagag  64980 gattgtttga gcccaggagt ttgaggtcac agtgagctgt agtcatgcca ctgcactcca  65040
gcctaggcaa cagaatgaga ccttgtgtct taaaaaaaaa aagtttcctt tgttgggtta  65100
ttttaatttg gacctggtta tcattttca gccatattta actttgtaca tatcagaatg  65160
ttctgataaa acttaacttt tattaaagtg tttgtgtatat aatctgctag ttttggtaca  65220
cattatcttt tgcaatgcca gttatttct tttccagtgt gggtttgcat aggaaaagaa  65280
ttgctgtcac tttctatttt gaaatcttaa aagactgatc cttttttgtg tcatgatttg  65340
agtatttaat tgagagccta atgcctaata ttatttgcag tattaaatgg gatcttaaca  65400
ggaatagcat tctagccttc attgaattaa gtaaacattt cttaagagaa cttggaatct  65460 ataaatttg cgtcatcata gtatgagata cttaatcaag tttgagattt tagtgaaaca  65520
ttgtttagaa gccaaaagga ttctaggaaa aattaatgtc tatattcttg aattaggaga  65580
gattttggga cgtgtgacta agttacgctg acacttgttt gtttcttagt cgcttttttcc  65640 agtggcggtg agaacgaaga tgactgattc acattgctca gatgagttta tcctcttctg  65700
gctgggacat gggatatatc ctgtctcttt taagccttt tggtattttt cccccattga  65760
gagctgtgtc ttcaaactct tctgttatag ctggaaaatc cttttttaagt gaaatctgcc  65820 caaattataa gacagatgaa ggtagagttg tgttggatat aggattaggg tgaaagtagt  65880
gggggtgtcc tggagcctct cttctggtgg cagcctagct cttgtgcctt tgaggaaatt  65940
accctgggga cggctctgtg gaacatattt gcaaaccact gatttggaag atagagatgg  66000
cttttgttaa gatctgaatt cacctttttg gcattttatt tgatttctca aggtaaagaa  66060
```

```
cttatttttgt aataaagttt cctattattt agtagatagg ccaagttgct gtgttaattc    66120
catgtagatt tgggttttcc tttgctcatt ttttcactct taatctcaca tcattgtaag    66180
tttatggaag ttatcatact tctgactttt tctttgaaga gcagaaatta gaaattccca    66240
ataattattt tgatagtgtc atttaatgac actcacatgt gatgtagcca caaagattta    66300
atgagttcag ttttaaatca tattaagact gttggtttca tttgttctca ttaatgtaat    66360
tctgaagatg aacaataaaa tgtatttta gaactttcaa atgaaatatt atttcatcct    66420
tccagatcat ataatgctta agttctgatt gttaatcata aagtctagaa aattaaaaga    66480
taataaaatg aaagtgactt ttaggtatta gagttttatt ataaattctg gtgtgtcatt    66540
ggagctatga catgaatatt tcaaaggcca atagcattgg atctttacag ttataactta    66600
ccatttttaa gtttaagtag taatatagat tatttaataa tcaaaatcaa taaatattaa    66660
ttattaaaat gttttgtggt atagtttgag aatcattgct tttaactttt tccatatagg    66720
tttattgact ttaatagcat tctaaacata acatctctac attctttgtg tttaatactg    66780
tggaggtata aaaatactta tatatgatga taaactatat tagagtaaat taaatattct    66840
tatgagtttc attttagagt gcatttactt aattttgaag tccttatttt tagcaaaacta   66900 aaaggaatgt tggtacatta tttactaggc aaagtgctct taggagaaga agaagccttg    66960
gaggatgact ctgaatcgag atcggatgtc agcagctctg ccttaacagg tagttctcac    67020
tagttagccg ctggtgtgga ccttcactgt ctgccttcca ccccttgccc ttcctgctcg    67080 tcccctgca cctggtggac agcacgactg ggggcagcag tggagccagg ttgcttaaat     67140
ggggcatatt cgggcttctt ttataatact tactctgaag cttgtgtgtc tgtggtgttt    67200
gcatcatata tttgttgttt tccatggttt aggctgtttt aaaattaggt ttatggcttg    67260
agcatagggc tttgtgagta ggggatggca ggtcgaaaca tctcatgagt tggatgggtt    67320
atgctggggg ttgggaaatg ggatgaaaaa ttatgggatg aaaaattgcc tatggatagt    67380
ttaacttgaa agaatctgcc tttgtttaca gatagttatc ttttttcttt tttgagatag    67440
agtctcacac tgtcacccag tgcagatacc cagtgtcact ggagtgcagt ggtgtgctct    67500
tggtgcactg cagcctccgc cttctgggtt ccagcgattc tcctgcctca gcctcccaag    67560
tagctgggac tacaggtgcc cgccaccacg cttggctaat ttttgtattt ttttgtggag    67620
acggtttttt gccatgttgg tcaggctggt cttgaactcc tgacctcaag tgatctgcct    67680
gcctcagcct cccacagtgc cgggattaca ggagtgagcc actgtgcccg gccagttaca    67740
gatacttatc taatgaaatt ctctgtgtac tttataaaag atgaggatta actgaaggta    67800
ctaataactg gattatatga gggtggtttt ggttgtataa tcctatctaa aagaatattt    67860
tagctataac tgaaagtaag acttaaatat ttagagagga aaatctgaat aattctagta    67920
gtaattattt atttacaaaa taaaaataga ttttttttg attacacaaa ttaaacaaca    67980
ataaaacatc acagcaatcc ggatactata aagctcacat gcttaccgac ccaactgccc    68040
caggagtgac cactgccaac agcttcatgt cgaccttttt gccataattt ttatatagcc    68100
ttttttgttt ttaaatggta atttagaaag tcaactagga aaatgtgtta caggtttatc    68160
ttccaggaga ataggactgg agtcgagatc ttgaatgtgg cttggaagaa ggcaagccca    68220
ccccagagag atgagttgac agttgtttct gaccactgct tgcttagagg gcctgcgtgt    68280
ctgtgaccgc ctagctttgc gcccctgact aggctgcccc ttaattacaa atgtctttat    68340
atattgctcc agctaaggct tggagtagtc ggttaagaac ttgaacttcg gttttgcag    68400 tgaaacagca tttgagaata tcaccttctg ataagcctta ttttataagg tgggtactgt    68460
```

```
agtgggaggc agtgtgagag atgcttgaag gatgcactgc tgtcctgcat ttcagcatct  68520
tcaggatgct gtgcagctga acatttgat aacggtggaa ctgttcgtta ttttgcaagc  68580
ctgtgattcc ctattgaatg ttttctctcg ccatttgaca aatgagtgtt tctctgtctt  68640
cagcctcagt gaaggatgag atcagtggag agctggctgc ttcttcaggg gtttccactc  68700
cagggtcagc aggtcatgac atcatcacag aacagccacg gtcacagcac acactgcagg  68760
cggactcagt ggatctggcc agctgtgact tgacaagctc tgccactgat ggggatgagg  68820
aggatatctt gagccacagc tccagccagg tcagcgccgt cccatctgac cctgccatgg  68880
acctgaatga tgggacccag gcctcgtcgc ccatcagcga cagctcccag accaccaccg  68940
aagggcctga ttcagctgtt acccctttcag acagttctga aattgtaagt gggcagaggg  69000
gcctgacatc tttttttta tttttatt gagacagagt ctcactccat agtgcagtgg  69060
aggccgggca caggggctca tgcctgtaat cccagcactt tgggagactg aggcaggcgg  69120
atcacttgag gtcaggagtt cgagaccagc ctggccaaca tggtgaaacc ctgtctctac  69180
taaaaataca aaaattagtt gggcgtggtg gcacatgtct gtagtcccag ctgttaggga  69240
ggctgaggca ggagaattgc ttgagcctgg gaggcagagg ttgcaatgag ccgagatcgt  69300
gacactgcac tccagcccgg gcaacagagc aagactccat ttcaaaaaaa ataaaaaaat  69360
aaagtgcagt ggctcgttct cagcccactg caacttctgc ctcccaggct cgagcgattc  69420
tcccgcctca gcctcctgag taggtgggat tacaggtggg caccaccaca ctcagctaat  69480
gtttgtattt tcagtagaga cagggtttca ccatgttggc caggctggtc tcaaactcct  69540
gaccttagat gatccaccca ccttggcctc ctaaagtatt gggattatag ttgtgagcca  69600
ccatgcccgg ccctgccacc tgccatcttt tgagttcttc cctggagacc tagacctgaa  69660
ccctcctgct tgttctcttg ttatctaata cccctattga cagcgcagct tagatcatta  69720
atggagagct tgacctcatc tgataccttc actgaaggaa acaacttagt gtcttttgtg  69780
ttgaacactg aggtaaaaaa ttggaatagt tgattatatg aactctgcta aaattgagtg  69840
cattttacat ttttttaagc cttgttgggc cctggttaaa taattatttt taaaaatcct  69900
taaggagcct attataaaca gatctgtggt cttaatgaaa tgtgattaat actgtgcatt  69960
attttaagaa cttttgactt ttcaaaaaac ttttacaaca tttcccattt gatagcggca  70020
taggtttaag cacttctcat ctctaagtta gtggacaaaa aaccctcatg gatagtctaa  70080
taatgtttgc tacaagtcca tgttgagttt tatactccat tttattttca gttttaaaaa  70140
ctgtggttaa atatgtgtaa cataaaattt atgttcttaa ccatttttg cgtatacagt  70200
tcgctggtat taaatacatt taaataatgt catggaatca ttgctaccac ccatctctgt  70260
aaccttttga tcatgtaaca ctgaagctct gttcccattg aactctattc ctcctttccc  70320
gccaagtccc tggcaaccac gattcttctt tctgtcttct gaatttgact actttgggtt  70380
ctcatatact ttaggagtca cacagtattt gttttactta gcataatgtc cccaaagctc  70440
atgcatgttg tagcctatgt tagaacttcc taatgtttca ggccaaatac tattccattg  70500
tatggatagg ccacattttg cttttccatt cctctgtcca tggacacttg tattgcttca  70560
tgttttagcc attgtgaatc atgctgttat gaacgtgggt gtacagatag ctcctggaga  70620
ctctgctttc cattttttg gctaaatacc cagaaatgga gttgctttta cattccaatt  70680
ttaatttaaa acattcatat cattgagtgt tttacttaat agtatagtag ttaacaaact  70740
taataaaata gtattttggt aataaatttgc tggtagtcca ttgttcagtt ttttaggta   70800
```

```
aattacacag gacatttcaa gtggacatga aacatcttgt gatgtggaat catgccccaa    70860
gctgatggct aaacatatga aataccatac cctaaattta gtagatttag tctttgcaat    70920
ttaggagata acctgttata ttgttaggtt tttgtcgaaa agctttgtcc tcatatttcc    70980
aacttgctgt aaaatttgtt tgtgaagaca aatattttg tatgggtttt ttcttttttca    71040 tattaaaaag aaatgtccac attggaattt ttttggagtt tttagagcta atagagcttt    71100
tcataatgta gtgggaatga gtgatcagta agctcttagc agtttccatg cgtgcatttc    71160
tgtgccttga aataaatgac agatgagtac atttgtgttc tgtgtgtaaa atgtgctctt    71220
tcctcattgc acttccatgt tggagggctt gtctcttggt gatcacactt caaaattctc    71280
acagcccccc ttgaaccgtt taggtgttag acggtaccga caaccagtat ttgggcctgc    71340
agattggaca gccccaggat gaagatgagg aagccacagg tattcttcct gatgaagcct    71400
cggaggcctt caggaactct tccatgggta tgtggactac aggtgatgcg ctacaaagtg    71460
gtttgtattc agacctggac atcttaatta tatctttgct tccaagaaga agtcctttga    71520
tactgttttc tgagttctga atagctgatg aaaatgacca attgaggaat aatcatactt    71580
tttcttgatc taaatcttat acttttgagt tatcttagca taaatgtata attgtatttt    71640
aagtggaaat ttgtcactta atcttgattt ctctgttttt aaagcccttc aacaggcaca    71700
tttattgaaa aacatgagtc actgcaggca gccttctgac agcagtgttg ataaatttgt    71760
gttgagagat gaagctactg aaccgggtga tcaagaaaac aaggtgaggg acataggctt    71820
gagacgactt ggtgtttctg agcttgtgtg aggatttaaa atcgccctgg ctactgtcta    71880
ctttattgct ttcccatccc tgggccttta aatttcccct ttaaatacca gctcttccca    71940
ggcctgttgt tttctgcctt tccaggtact acccacagcc ttgagaattg cctgagttct    72000
gcctcctttg agagtgtgcc ccagacaaat ctattctgta ctgaatgttt ccttgtctga    72060
tttcttggat cattcatttg atggttgcgt atggcctgca acgtttcttg ttttggttct    72120
actgaactgt tctaaaagtc tctcttcata ttatcttttt acatgtaaat gtaactgtct    72180 tcactttaa ttcctcaagg acaaggaata gcgtttcaca gttcgtccca tcaatcagaa    72240
ttatagcctt tggcatctcc ctatctacca ggcccacttc ctcttagatt tgggcttccc    72300
caggctgttg cctttcccca gtagcttct gcttgtcctg tagaagacct ttcatgcttt    72360
gcttctgcag cagccgttcc tgaatgccta gtgtcaactg ccttcttacc acgcccaccc    72420
tccctgcatg ctgcatttat cccctgccac agccctgtga ccctgtgtcc tgctgcctct    72480
gacttgtctg tttctgcttg gccatggtct ctgtgaggtc aggtgtgcat atgggcacaa    72540
accagggcat ctctttatcc ccagcacctg gcttaagtgc tgctctggaa ctatctgttg    72600
aatgaactaa tgcatgaatg tattgttgag tatgagacaa acaagtgtca ttgtctcctt    72660
tctagccttg ccgcatcaaa ggtgacattg gacagtccac tgatgatgac tctgcacctc    72720
ttgtccattg tgtccgcctt ttatctgctt cgttttgct aacagggga aaaaatggtg    72780 agtacaaaag gggatgtgca cagttgaagg aaataactag gtttcagagg tcagcttggt    72840
ggcctgtttt tgccttgcgt gcagcagagg aagtagaatc tgaggatgag tttggttttc    72900
actagccgag gggagggagg aaatgatggg agcaggtagg ttattgggtc tggttttgtt    72960
catttgaaaa caatctgttg tttgaggctg aaggtggctt gggtgatttc ttggcagtgc    73020
tggttccgga cagggatgtg agggtcagcg tgaaggccct ggcctcagc tgtgtgggag    73080 cagctgtggc cctccacccg gaatctttct tcagcaaact ctataaagtt cctcttgaca    73140
ccacggaata ccctggtatg ttaaaagttc acatcttatt ttctcagatt taatcattat    73200
```

```
tgtaaaaact atttcagtat tgactatttt agttttagag cagtaagtgt tttgagttca   73260
tttgggatat ttgacctgcg ttgtagctct tcagaaaaca catgaatagt gaagttcttt   73320
gtttcatggg ttccctttag atgaaaccca tagaggagaa aagtagaaac ctcagcacgt   73380
aagagccaac atatatacac atcggattta aacctaaagc acaaattgtg cctggtcgca   73440
gtggcgctga gtcgcactca gccaggccag gcattcacac tcagggtgag tgggaaccag   73500
gactggctga ggcagcagtg gacccaagtc tccatcgcgc ccatgcttac tatggagcct   73560
tctcgttctc tcttttttct tgggtgagag ggtacacttg tgttttttgaa tttatatgag   73620 gtaagtgtgt aatagggttt tttctaatct tttttaagtg gaatctggaa ttttaatcag   73680
atttattatc tgcaaccta gaattataat ccagaaagtc tgtggtattg aggacatatt   73740
ggcaatatga tgaatctcta attcttaaat cctgaaactt tttttttttt aatcacttag   73800
ggttattata gtgaagtcat ttctgaattt ggatcttctc ttcacacctc tttttctctt   73860
tcctgagaat taagctttg tttcgagtta gaaagttgat agtagggaat tgttccatgg   73920
ctgagcaatt tatctccaca gaggaacagt atgtctcaga catcttgaac tacatcgatc   73980
atggagaccc acaggttcga ggagccactg ccattctctg tgggaccctc atctgctcca   74040
tcctcagcag gtcccgcttc cacgtgggag attggatggg caccattaga accctcacag   74100
gtaacggcca gttttcagc tgtgtttttt ctagttatgc ttactaaggt ttaagtttag   74160
atgatgatgt ttgttgcttg ttcttctggt taggaaatac atttcttg gcggattgca   74220 ttcctttgct gcggaaaaca ctgaaggatg agtcttctgt tacttgcaag ttagcttgta   74280
cagctgtgag ggtgagcata atcttctgtg gaaccatttc ttcacttagt ggacatttta   74340
tcattgctac aattaaaatt ggagcttaat aggaaatatt tccatgcact ctaaagctgt   74400
aaccagtaat acccaccatg tatccatctc tcagctttag aaagaaaacg ttgccagtaa   74460
agttaatgct tcataaactt cagtttaagt tctaattctc agaatatttg tttgaaatag   74520
acctcttcct aaaggatata tttagaaata acctatcatt aagtgtaaag tctgttgaat   74580
atgctgggca cggtgactca cacctgtaat ctgaccactt tgggaggcca aggtggaagg   74640
attgcttgag cccaggagtt caagactatg ggcaacatag ttgaccctgt ccctacagaa   74700
aattaaaaaa aaaaaaaaaa aaagtagctg ggtatggtgg tgcatacctg tagtctcagc   74760
tactcgggaa gctgaggtgg aggggggatt gcttgagccc cagagatcaa ggctgcagta   74820
aggcgtggtt acaccactgc cctctagcct gggcaacaga gtgagactgt ctcaaaaata   74880
atagtaataa taatcagttg aattaaaaaa aaaaaaaaa aaaccactgt gctaggccca   74940
tagtatggta agagttaaag tgagccttag ggattattta ctcaacctct gtttctgtat   75000
aaagtggaat aggctcaatt ctttaagtga tagcatgttg aaccttttcca taccaactgg   75060 ctcataagtc acaactggcc agtcaacaag agtaaaaatt aactggtaaa aatcaaagca   75120
aaaaacctac aattgtcaaa tttgtgggat aactcccct tttaaaatgt catgcctgac   75180
agtaatttct ctctagtttc caggttttca gtcagttgtg tctttttttga gcagaaggaa   75240 gcatgctaag agctcaatct tgtggctagc tgggggtctt tgtgtcagcc atgcatgtga   75300
tggtgcccct gggtgcttgg ggctgcaggg gaggggtaca gcagtagggg cctgttctgt   75360
tctctcgtgc tgtggagtac atagtgacat agtggggtgg tccttggtgt aggtcccttg   75420
ttcctacccc tgggtctgag atttatttag aagtggtgtt ggggctgtgc ggcaggcccc   75480
tctgtaactg atcaatgttt gtgaagttgc tgtttgagag ttgaaaccat gacataagca   75540
```

```
gaaatggaag gaagaaagaa ccagttatgt gaaagggaca catttacttt taagcttgta    75600
tttactgaga taaagtattc ttaatcaatg ttcttgagag gtgtgggaaa aatgcaacat    75660
cctggttgca gttaaaccca gaacattgtg tgttgaagag tgacggttct caaaccgtca    75720
agacgcgggt actgagtggg actaacctgc tgtcctcttg ccttggacct tgtgttccag    75780
aactgtgtca tgagtctctg cagcagcagc tacagtgagt taggactgca gctgatcatc    75840
gatgtgctga ctctgaggaa cagttcctat tggctggtga ggacagagct tctgaaaacc    75900
cttgcagaga ttgacttcag gtaagtgagt cacatccatt agatttcatg aactaagctc    75960
aattgaaagt tctgggatca cttgatgcaa ggaatgatgt tatcaagtac cctgtccatc    76020
agaaatccga gtggtttagg tagatgacag tgattttctc ctcccagtgg cttttttgctg   76080 aactttgccc tatgcttgga attttatttt atttattat ttatttagag acaagatctt     76140
gctctgtcgc ccaggcttga atgcagtagc acaatcatag ctcactgaag ctttgaactc    76200
taggactcaa gtggtcctcc tgcctcagcc tcccgattag ctaggagaat aggtgtgtgc    76260
cgtcacactg gctaatattt tttgtagaaa tggggtcttg ctatgttgcc caggctggtc    76320
tcaaactcct gggcttgatt gatcctccat cttggcctcc caaagtgctg ggattacagg    76380
catgagccac tgtgcctggc ctagaatttt aaaatataag tagaagagta gattttttt    76440 tttggtagtc ctcgtcattt aagtattctg gatagtggga ataaaagagc ttagaatttt    76500
tcatctttgt cttaaacttt taaaaaaatg tagcttatat taattctgct tgtttaaaaa    76560
gaatatactc ttcattatac tgaacctagg taagacagct ggtttatatt ttgttgcaat    76620
taaaaaacgt gagctgtggt tgcagtgagc caagattgtg gccattgcac ttcagcctgg    76680
caacagagtg agacttggcc tcaaaaaaaa aaaataaca tgagctgtgt tggcactttc     76740
attttctaag agtagttttg gctggagaag ttttctttca gtactttctt ttagaaggga    76800 aatttttcctt tataatttag ggtttgtttt tttttttttcc aagccacctt ttatagagcc   76860
cttgtgggtt atttcattta atccttagaa tgttataaaa tctgggcttg ttctcggctc    76920
cacccacaga tagggacgct gagcgtgcat gagtgggcag caagatagca ggttatggag    76980
ggcccagctc acccttctg tggcttgagc caatttttata gggcacttac agagtctttt     77040
gaaatagtat ttattttgaa gaaaaagaaa aacagtttac tgagtactgt cttattgagt    77100
ctggaattgt gagaggaatg ccacctctat ttatttaaag ccattggcct ttttttgttgt    77160 tttgagtaag tgctgcccaa ggtccttcca gggcacctgg atgagcctgc tctggagcaa    77220
gctggcggta agtgtttact gagtaactaa atgatttcat tgttaaatgt gctcttttgt     77280
taggctggtg agcttttttgg aggcaaaagc agaaaactta cacagagggg ctcatcatta   77340 tacagggta agcggtttat ttttgtgaga tgctgtttta ccttcaagaa ggtgaaagtg     77400
aggctttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580
atttttatta tccttctctc taaagctttt aaaactgcaa gaacgagtgc tcaataatgt    77640
tgtcatccat ttgcttggag atgaagaccc cagggtgcga catgttgccg cagcatcact    77700
aattaggtat ttaccaatat tttatctctt ttcctttttt ggttgaagta ctaaaagata    77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaaacaacaa aatactaact gtccattgta aaaagtaatg cactttcatt    77940
```

```
gtaaaaattt tggactatag agaatagtac taagaagaaa aaaaaaatca ccttcaattc   78000
tgctgccacc tggaggtaat cactgttaat attttgctat atactctatg agtttcttgt   78060
tcaaaatcag gtcaaaatta catgcaattt tgtaatctga caatttccac ttaatatttt   78120
attagcattt tcctgttatg aaacagtaat tttagttatg ggtcgttgtt ttgctatgcg   78180
gttgggataa aattttatat acttttttg gcaattactt attatacata aatgtttgtg    78240
tatagttttc tttttctgag aattcctgga agttgagtta ccaggcccgg ctttgaattt   78300
ttttttttat tttttttttg agacagagtc ctgctctatt gtccaggtgc tatctcggct   78360
cactgcaacc tctgtctccc tggttcaagc gattctcctg cctcagcctc ccgagtagct   78420
gggattacag gggcacacca ccacgcccaa ttaattttg tattttagt agagacaggg     78480 tttcacgata ttggccaggc tggtctcgaa cttctgaccc cgtgatccac ctgcattggc   78540
ctcccaaagt gctgggatta caggcgtgag ccatggcgcc tggccaggct ttaaatttaa   78600
aacaaatctt ctaatagctt tatggaggtt ataatttaca tttcttgaaa tgtactcact   78660
ttgagtgtat agtaaactcc aattttatca catttctgtc accccaaatg tatccttgtg   78720
cccatttgct gtaacctccg gttcctgccc caactcctag gcagccactc atctattttc   78780
tgtcccttaa gatttgtgtt ttcgccaggc gctcatgcct gtaatcccag cactttggga   78840
ggccgaggtt ggtggatcac ttgaggtcag gagttcgaga ccagcctggc caacatggtg   78900
aaaccttgtc tctactaaaa atacaaaaat tagtcggatg tggtggcaca cgcctgtaat   78960
cccagctact cgggaggctg aggcaggaga atcacttgaa cctgggaggc ggaggttgca   79020
gtgagcagag atcgcgccac tgccttccaa cctgggcaac agagagagac tgtctcaaaa   79080
caaacaaaga tttgtatttt ctggacattt tatagtactg gggtcatagt atagatggac   79140
ttttgcattt ggcttctttt acttaattgt gagattggtt cttgttgtag catgtatcag   79200
tagtttgttc attttattg gcgaaagtat tctattatat gaataatacc atattttatc    79260
tatccatcag atggatatta tagagttcat gttttggcta atttatgaat tatggtactg   79320
tgaacatttg cctgcaagat tttgtgtaga catgtcttca tttctcttga gtagatcacc   79380
tagaagtgga tttttaaata attttggtac ttactgtgaa actgctcttc aaaaacatac   79440
cattgttcct tccttccttc cttccttcct tccttcttc tttccttcct ccctttcctcc    79500 ctcccttccc tacttccctc tcccttccc tttccttcc ccttttccct tccccttccc      79560
gcctgcctgc ctgcctgcct tccttccttc cttccttcgt ttctttctac atatacacat   79620 tttttttaaat ttcaatggtt tttggggtac aagtggtttt tggttacatg gctgaatttt   79680
ggttacatgg tgaagtctga gattttagta cacctgtcac ccgagtagtg taccttgtac   79740
ccaatatgta gttttttgtc cctccacctt cagccttccg ccttgtgagt ctccaatgtc   79800
cattatacca cactgtatgc ccttgcgtac ccacagctca gctcccactt ctgagaacat   79860
atagcagaaa catgccaaag tatactccca ctaccagaat gtgattgtgc ctgattcttc   79920
tcaccagtac aaatatttca aaaaagtta aatatgtatc agttttttgg gcagaagttg    79980
atacttctct ttattatttt attttttttg agatagggtc tcattctatg atgcccaggc   80040
tggagtgtgg tggtgcgatc tcggctcact gcagtctctg cctcccaggt tcaagtgatt   80100
cccacgtcag cctcccagga agctggaatt acaggcgagg gccaccactg ccagctaatt   80160
tttgtatttt ttggtagaga tggggtttca ccatgttggc cagactggtc tcaagctcct   80220
gacctcaagt gatccacctg ccttggcctt ccaaagtgct gggattacag gcgtgagcta   80280
```

-continued

```
ccacacccgg ctgatatttc tttttaaaat aacttacctt cttttgaaag taatacatgt    80340
ttaatgaaca gaatttaagg aaaatataaa aaaacgaaat aatctttgta atcaaactac    80400
tgaaaagaaa accaaagtta cattttggtg catattcttt ttcattttca tcattgtaat    80460
ttgcatttct ttgattactt gtgagacact cctttcattt acttaatagg tttatatgac    80520
ttgcctattc agagattttg cagctttacc attttctgca aatgatagca acttcttttt    80580
gtttgtttgt ttgtggagac agagtctcgc tctgtcactc aggcaggaat gcagtggtgg    80640
aatcttggct cattgcaact attgcctcct gggttcaagc gattttcctg cctcagcctc    80700
ccaagtagct gggattacag gagtgtgcca ccatgcccgg ctaatttttg tatctttagt    80760
agagatgggg ttttgccatg ttggccgggc tgatcttgaa ctcctggcct caagcggtcc    80820
ccctgtctcg gcctcccaaa gtgctgggat tacaggcgtg agccaccgta cccagccagt    80880
agttacttct tatattctag aaaaaattct actcatgatc aagtctccat gaggaaagag    80940
actttaattg aagatcatgg ggcttgcaga ccaatatgat aaaatagttc attgtttcta    81000
aaagtattac tgagtgttga tggcagatat gaaccctttt gttttgtag aaaatgtta    81060 cccgtattct ccatttgaat tcagtttaga tttgttagga atcgcagctt aagctttgcc    81120
atctgggagt gtttgggaca gttttgcaga caaaattgca aaagtgccta aggaatgcag    81180
ctggcattca gacctgctct gtgctcagta ctctgtggac agacactgtt cagcacttgt    81240
tgatcagaag gtttagaaag agaactttca aagttggttt ttaattaaag catttaatag    81300
tgtaaataga aagggattaa attttatgac agacaaaaga aagtacagca cccagctggg    81360
cgtgggggct cacgcctgta atccagcact atgggggggct gaggtgggtg gatcacgagg    81420
tcaggagttc aagagttcaa gaacagcctg gccaaggtga tgaaccctg tctctactaa    81480 aactacaaaa attagccggg cgcggtggca ggcgcctgta atcccagcta ctcaggaggc    81540
tgaggcagga gaatcacttg aacctggacg gcagaggttg cagtgagcca agattgcacc    81600
attgtactcc ggcctgggcc acagagtgac attctgtctc aaaaaaaaaa aaaaaagaaa    81660 aaagaaagt acagcaccca gttatgtccg agtgggtgca tgagagtgac cctgagattg    81720
gagacaacgc tgtcacgtgc ttgaagaacg ccacctgaga aaggggggcga gaagtggtgt    81780 ccgctggtaa ccagaggtgt tggcttagcc atctgcaggg aggagggtgg tctatcacag    81840
gtgagtttca tctactttct taagcaaatt aaccttactt ttgtgttagg cttgtcccaa    81900
agctgtttta taaatgtgac caaggacaag ctgatccagt agtggccgtg gcaagagatc    81960
aaagcagtgt ttacctgaaa cttctcatgc atgagacgca gcctccatct catttctccg    82020
tcagcacaat aaccaggtat gctgacccag tggcatcttc acattgtcgg gaaaatgccc    82080
tttcctgatg cctttcttta ggctttaatt gaaaacattt tattttctag aaaaaagctt    82140
cagctcagga tgtttgagtg taggtcagtc ctttgatagg atattatcat tttgaggatt    82200
gaccacacca cctctgtatt taagctctgc cacaatcact cagctgtgac actgtaaatc    82260
tcttaatagt ttattacatt ccatgtgctg acagttgtat ttttgtttgt gacacttacg    82320
tattatctgt taaaacattt tcactttagt tgtgttacct ttaaagagga ttgtattcta    82380
tcatgcctgt tgatttttg gtgagcgggc tattaaagtc agtgttattt agggttatcc    82440
actagttcag tgatttgcga gattatcatt cacatttatt gtggagcttt tgaatatcgt    82500
gtcaaatggc cacatatatc ccattcttat ctgcttctta ggtgagtggg acacagtgct    82560
ttaatgaagc tataatcttc agaattctag cttgcagaga agattgcaga agtgataaga    82620 cttgtgctt ttaatttgt cttttaaatg ttattttaaa aattggcttt atatgatact    82680
```

```
cttttttttct gctgagtaac agtgttttac aaaacttgga ctaaatgact tctaagctta    82740
aatgatcact tgatgctttt tttctgaatt aggaactcag cttatcaaat atcaaagtca    82800
taattcctga ataaataacg tctttttttca tgtaaagact gctttaaaaa acacatggaa   82860
ggctgggtgc ggtggctcac gcctgtaatc ctaacacttt gggaggccca ggtgggcagg    82920
tcgcttgagc tcaggggttc aagaccaccc agggcaacat ggcaaaaccc acctctactc   82980
aaatacaaaa aattagccag gcgtggtggc gggcccctgt aatcccagct actcggagg    83040 ctgagggatg agaatcactt gagccccgga ggcagaggtt gcagtgagcc aagattgtgc    83100
cattgcactc ccagcttggg ctacagagtg agactctgtc tcaaaaaaag acacacacac    83160
aaacaaaaaa aacatggaga cattttttttg gccaccttaa tatttcccct cagataattt   83220
cctttgttta aactcagaac tggcattttc tctcttggag aagattcagg acaaatactc    83280
ctttaagata agtagaagca gtgaaagagg atttgattat caggaatttg ataagcttag    83340
aataaattgt tgcttcttaa tgtcatttca gaagatgaat atttattaat agatgccaac    83400
tgagatatca ttaaaattga ttactaacta ctacttggaa aagtctccca gttccaaact    83460
tcagcaggcc tcttgacaat tcagctgtgg tcaattgggg cttgcgtgat agatacaatg    83520
accaattgtg cagcagagtg tgctgcttag ctgcctattc tgttagcatt catgtgttaa    83580
cttaaaatca taatctcctt agttttgttg agtgtctccg tggacaagac actgtgaggg    83640
atacaaaatc agattggctt tattcaaacc actgggtat tataattcat ttataattta     83700 ttttatttttt tgccttttttt ccatgtgttc taaaggaatt agagtttgta tataactata  83760
atgggggata gaaattgaca tgtgccatga agggaatgca aaaaagtgcc gtgggagatg    83820
agaagtggag aaaggaattt cttttttctt ggaagcagga ataacttcat gaagcatgta    83880
tttcaactta aacagatagt aggcaacgct gtaagggag tatggctgca gcaaaagtgt     83940
tcggggcaga ctgggaggaa gggagggaat aaattcagcc attgttatgg aataatgatc    84000
aaaatttatt ttcagcccgt ttcacttaaa agttgagact gcttaactttt ttttaatctt   84060 taatcttaaa ctttttaaatg ccattttgatc tttaaaaata tatgtttttaa tagtgtatttt 84120 taagtctcta tattttttgtt attagaatat atagaggcta taacctacta ccaagcataa   84180
cagacgtcac tatggaaaat aacctttcaa gagttattgc agcagtttct catgaactaa    84240
tcacatcaac caccagagca ctcacagtaa gtctctttct tgatcggtct tactgacatt    84300
gtaatagttt ttggtagctt gtatggccag ttagttgtat ggtcatctta cggtgaggtg    84360
cttgtcttac agctcttact tatccatgag gcttgctaag aaattgtgct tctgtgaaaa    84420
gaatctcagc ttactccagg aatgtaaatg actatgtttt ttctgattat taaagtaata   84480
cacgcccaaa ataaaaaat tcagccaatt taggaagaca caacaattaa aataagccag    84540
gcatggtggc tcatgcctgt aatcccagca ctttgggagg ccaaggttgg gggctcactt   84600
gaggtcagga gtcggatacc agcctggcca acgtggtgaa acccatctc tactaaaaat    84660 acaaaaatta gctgggcgtg gtggcgggcg cctgtaatcc cagctactca ggaggctgag    84720
gcaggagaat cgcttgaacc tgggaggtag aggttgcagt gagctgaggt caagccactg    84780
cactccagcc tgtgcaatag agcgagactc tgtctcaaaa aaaaaaaaaa aaaagaaaa    84840 gaaaaaagta aactactgtc acctgcattg gtaatgtatc agaagtttaa aatgtctaga    84900
ttataattaa ctcagtgacc tggtaatata tactaaggga aaaatattta aatttacat    84960 ttttacattt ttattttttt aatttttatta ttttttttttt gagacagagt tttgctcttg    85020
```

```
ttgcccaggc tggagtgcaa tggcatgatc tcagctcacc acaacctcca cctcccgggt   85080
tcaagcaatt ctcctgcctc agcctcctga gtagctggga ttacaggcat gcaccaccat   85140
gcccggctaa ttttgtattt ttagtagaga cagggtttct ccatgttggt caggctggtc   85200
tcaaactccc aacctcaggt gatccgcccc cctcgacccc ccaaagtgct gggattacag   85260
gtgtgagcca ccatgcctgg ccttacattt ttataataag aatttatgtt gctgacatta   85320
gaaaagaacc ataatatcca agaatccaag aataattaaa ttatgtacat atgctagtat   85380
atagtgtgat gctttggaga attttttaaca atatggagat gtataatctg gattgtaata   85440
ttgagtgaaa aaaggcagaa tacaaacctg gtgggggtat agtcggattt cagttaagaa   85500
aaataatatt tacatatata catttctcac actggcagat aatcaccaag ataaattttg   85560
ggattgtgga tgattttttt cttctttata ttttcagat attctcaaat tttctaaaat   85620
gagcaagtat aacttttgtt atcagaaaaa aataatatac aaaagtaatg ttaatttgct   85680
ggtgaccagg ttaaaccttt ttatttttat ttttgagat ggaatctcac tctgttgccc   85740
aggctagagc acagtggcat gatcttggct cactgcagcc tccgcttcct gggttcaaat   85800
gattctctgg ccccagcctc ctgagtggct ggaattacag gcgtgtggca ccacacctgg   85860 ctaattttg tattttagt agaggtaggg tttcaccagg ttggtcaggc tggtctcgaa   85920
ctcctgacct cgtgatccac ccacctcggc ctcccaaagt gctgggatta caggcgtgag   85980
ctactgcgcc cagccagacc tttttatttt atttgacaaa agaaatactt ccatgttata   86040
gaagactaaa tattgtttgg gctgtctgca gtatggtctt cccttgattt gttcaaaata   86100
tcgtaaactt tgcttattta tttttattgt ggccgactgt gtcgggcact gttgtaggct   86160
tgggatggaa aaacaggatt cctgcccctta gggtttctgc aggctggtca gggagacgat   86220
gtggtaagct ggagctcagc tcctaaggat gtgcaggggc agttgagagg cggaagggtg   86280
ggagatcatt ccagggtgtg ggcagcacag gaacctctct tcattgggat ataattgcca   86340
ttctgataac acgtgtttga ggtgtctaaa gtaggaagtt gtaccatggt gggacagata   86400
tcctgtggtt atcatacaca gatctcagtt ttcttctcat tgtttgtact ttttataaag   86460
ggtaacagga gatataattc aataaacctt tgtggtgttt gggtgtgatt ttattgtttc   86520
tttcttctca gtttggatgc tgtgaagctt tgtgtcttct ttccactgcc ttcccagttt   86580
gcatttggag tttaggttgg cactgtgggt atgtattttc ctcagtatat attaatagtt   86640
gtctacaaca gtatgacata aacatagtta ttaggatgcc ctttttcttt cttttttaagt   86700 ctttatcaa tttggctttt tggaaaaata tctgatggaa tacttgtttc tgctatatta   86760
gctgtgtgag actagtgaca ggagctgtgg gaaatgaatg ccaaatgttc ttaggcattg   86820
atgggaattt cagggtgtgg tcttcaagtt catttaaggg aattttcata tgctggcaaa   86880
aggcttttct cattagcttg actctttcca aaattatttg ctgtgaatta aagtttagg   86940 aaccttttt cacttaattg tgacctagca tacgaaatgg tgatgattta ggaactactg   87000
ttcttgtatt aacagctttt atttaaaaat gattttcctc cagtagatgg ccctactagc   87060
atctgggaaa taatttcaag tcttctccag cattcaggaa taggctttca ttttgtgtat   87120
caattactga gaatgatttt ggtgactcac atcacatttg agaagtaaac ctgcagattt   87180
cttgtgtgtg tcagcaaatg accaactgat atttgcttga agtggattac attatctgct   87240
ctagaatgat tgcttttccca ccttcctcac atacagactg agcagctacg gtttctaatc   87300
ataggtctgg cactagactt cacttctggg caacttggc attggagtaa aatgtattaa   87360
tttaaagaaa gttaaaaatc cgttcaagta aacatacagt tctaatactt tttacaattt   87420
```

-continued

```
aaaatataga tttaaatgat aaaataaaaa agaaaatatg ggtagacacc ataatcctcg    87480
tttctgcatc tgttcacaag gggttgatat ttatgagttc tattctccat atccattcta    87540
tgttctctta atgctcagtc agcacctcag gtggttggag ttcaatgctt ggtagtttga    87600
cttacactgt cttttctagg ggattgagcc ctgggtagtc ctgcttattt gaggttgcaa    87660
tttgtctttc aataactttt actacaagat atggcgtgtt aaaggatacc attggggaac    87720
caacataata atatcaggaa aactaaccac gtcagacctg ccccattgtg tatcaagtac    87780 actattttc catagtaata aagagttcac cccagccaat tctcttttat tttgtgcctg     87840
tttactcaat ggcattaaca tgcccaaatg tctgggtagc tgtctcatct ccagttcagc    87900
agaaccattg tcatatgccc tagtaaaagc attccttcat tggacactta ggccccaata    87960 cttttcattca gatctactac ctgatttcat ttctcaaatg attttatgg agctctgatt    88020 tataggaaag atgttagttg attaaaaata aaacaatttc tgagctggta taaaatgtat    88080
tgtgacatgc cttcctcttg gaattgcaag agaaaggaag actgttgttt gcttaaaaat    88140
tgtctataat ttgactttgc aaatgtctgc ttccagagtg cctccactga gtgcctcaga    88200
tgagtctagg aagagctgta ccgttgggat ggccacaatg attctgaccc tgctctcgtc    88260
agcttggttc ccattggatc tctcagccca tcaagatgct ttgattttgg ccggaaactt    88320
gcttgcaggt actggtactg agttgaaaca gggactccag gacttggatt ttgatttcct    88380 taggggaat gggggtggtg agcatatgag gggaaaatac tataaggtca ttgccagtga    88440
tggcttgtcc ctttagtcaa atttcagatg ttacctatat gcataaacac atgcagttgg    88500
cagctgttct gtgctgagta ttttaaagta gcctcttccc aatatagccc ctcagttaac    88560
tacaagtaaa ctcattttga atttcatttt aatgggcacc atatgccagt actccctcgg    88620
gcactgggat gttaagaaag tataatgtat ggacttcatt ctcaagttag ttttagatta    88680
gagggggata cacgtaaaca aaagtgcagt ggtcacacag agtggcccta atcactctcc    88740
ttgggcagat ttatgggctg gtaggaaaga gcacaacacg gagagggtgt agcaccttgg    88800
cgatgataat ggaggatgtg gccagcaagg aagacggagt ccattgaaat tgattttggg    88860
agaagttgcc aatctccatg aaagaattgg ggcctgtgct atttgcttca gggggctata    88920
ggagagtttc gtgaaaggga ctaaaagatg agtattttaa taagatcatt catccaactt    88980
gaacatgggc tggaggagaa ggtagggaga ctcaggagat taatgttgat gctaaggcaa    89040
gataatggct ttgggactgt agggaagaca ctgattgtaa gagaatgaag gaggcagaat    89100
tgccaggcct ggttcaccaa ctgaacttcg gttgtgaaga caaagaaacc tgggatgact    89160
tcacatcctg ggcaggtgtg tggtggtgac agtcatggaa attgggaaca cagatttgtg    89220
cgggaaacat cagtttcagt ttgagtttgg cttatcagtt gaatatcagg cacagatgtc    89280
tggccaactc tcaacatagg gtcttaaatg acttcagttc cccaagcaat ttgtccttcc    89340
catgctattg gggtggagag gtaatgtctg tgcccatatc acagccagtg ctcccaaatc    89400
tctgagaagt tcatgggcct ctgaagaaga agccaaccca gcagccacca agcaagagga    89460
ggtctggcca gccctggggg accgggccct ggtgccatg gtggagcagc tcttctctca    89520
cctgctgaag gtgattaaca tttgtgccca cgtcctggat gacgtggctc ctggaccgc    89580 aataaaggta atgtcccact tgggtgctgg attcatacag ccttaatgac tatgggtttc    89640
cagactacct ttgtttagta atctgtccct tctttattct cttttgctt taaatgaaca    89700 aaattgctca gattgtgaca ctaaatttaa catcaaaatg tgaccatgtg gatgggtgca    89760
```

```
gtggctcgtg cctgttattc cagcactttg ggagactgag gcaagtggat cacttgaggc   89820
caagagttcg agaccagcct gggcaacatc acgaaacccc ctctctacta aaatacaaa    89880 aaattagatg ggttgggccg ggcgtggtgg ctcaagcctg taatcccagc actttgggag   89940
gccgaggtgg gcggatcacg aggtcaagag atcaagacca tcctggctaa cacagtgaaa   90000
ccccgtctct actaaaaata caaaaaaatt atctgagcat ggtggcgggc gcctgtagtc   90060
ccagctgctc gggaggctga ggcaggagaa tggcgtgaat ccgggaggcg gagcttgcag   90120
tgagccgaga tcgtgccact gcactccagc ctgggtgaca gagcgagact ccgtctcaaa   90180
aaaaaaatta gatgggcatg gtggtgcgtg cctgtaatcc cagctacttg ggaggctgag   90240
gcaagagagt tgcttgaacc tgggaggcgg agtttgcagt aagccttgat tgtgccgctg   90300
cactccagcc tgggtgacag agtcagactc tttccaaaag aagaaaaaaa tgtgaccatg   90360
tgttttatag ctctttttagt atcatcagtc actgttatcc ctaagaggga aatacctagc   90420
tttagtttta ggtttccagc attagccaag aaagctcaga attgatgttc ctggccaagt   90480
acctcattgc tgtctcctta aatcttggtt aatggctact gtcctggcta gcatagttat   90540
ggagcatttc catggttgta gaatgttctg ccaatctcag ggacagtttt gcttttctgt   90600
gaagcaataa aatcaacttc aaaacaaatg ttaactattt gtacaatgga tttaagatag   90660
accagttcac atactttttt ttttttttt ttttgagatg gagtttcatt cttgttgcct   90720
gggctggagt gcaatggtgt gatctcagct cactgcaact tctgcctcct gggttcaaac   90780
gattcttctg cctcagcctc tcgaggcaga ttacagctgg gattacaggc atgcaccacc   90840
acacccagct aatttttttg tagttttagt agagacgggg tttcaccatg ttggtcaggt   90900
tggtctcaaa ctcctgacct gaagtgatct atccgcttcg gcctcccaaa gtgttgggat   90960
tacgggcatg agccaccacg cccagcctaa gatagaccag ttcacttact gtttatatct   91020
gattactctc tctttgcctt gtcttctacc tttaaaaatc tccctactaa cttcccattc   91080
tcctttagct gccatcagtc ttctcccttc tctgcaaaca tctctggaga gtcccagcct   91140
cagcccacag agcttcccac tgctctgagg tggaccttgt ttgcaaggct tctttggctc   91200
tcttggcctg gaccctgtct actacttcag ccatccttcc ttaaccctg ctggtggttt    91260 ctgttgccac actccatagc agcgtttccc gcccagatca tgtctttaca tctctgggca   91320
ctgctctggt cctgcctgcc tttcctctct tgtatcctgc aggctgctac ccccatcttg   91380
agtgtcctct tcagttggct ttcagagggc ctcctgggtg ttcccttacc cacttgccac   91440
tccccagtca ctgggttcag tccttcctgc ccaccagcac atgctttcta ggctctgtcc   91500
taggccgtct tctctctttg tagtctctgg gccagtgctg ttctagagag tggcagaatt   91560
ttctataacc atggcagtgc tccatagcta tgccaggcaa gacagtagcc actaaacaca   91620
tatagctgtt gagcccttga aatgcagcta gtgtgactga agaactgaac cccgattcgg   91680
tttaattttc attaaattta aatttaaata accttatgtg ggtagtggct ccagtattgg   91740
gcagggcagc ctgagagtcg gggctgttct cctgtcttca gtgtctagat gagggacctc   91800
agaggacctg tctctggagc tgcagttcaa tgtagccagc tgccccgtga cacttacata   91860
tagctgattt gtggatatgt cagacacggt gtgatgagct cagctttctg tcctcctccc   91920
cacatctgcc cctgccccat ttaccccact tgtgtctta tcaagctaga aacaggtcac    91980
cacaagtctt catttccact caccaagtct tttgtttccc ctactaaata ttttgcgaga   92040
agaaagtgtg taccctttgta ttcacataca tgtacatgca catatacatg cacatatgca   92100
ggggtcccca acctctgtta aaaaccggac tgcaggccgt gcgtggtggc tcacgcctgt   92160
```

```
aattccagaa ctttgggagg ccgagaccag tgcatcacaa ggtcaggaga tcgagaccat   92220
tccggctcac acggtgaaac cccgtctcta ctaaaaatac aaaaaaaaat tagccgggtg   92280
tggtggcggg cgcccatagt cccagctacc tgggaggctg atgcaggaga acggcgtgaa   92340
cctgggaggc ggagcttgca gtgagccgag attgtgccat tgcactccag cctgggcgac   92400
agagcgagac tctgtctcaa aaacaaaaca aaacaaaaaa aaaaaaaacc aggctgcaca   92460
ggaagaagtg agcaagcatt accatctgag ctctatctcc tctcaggcca gtggtggcat   92520
tagattctca taggagcgtg tatgagttcg ttctcacact tctgtaaaga catacctgag   92580
acatataaag aaaagaggtt taattggctc acagttctgc aggctgtaca ggcttctgtt   92640
tctgggaagg cctcaggaaa cttgcagtca tggcagaagg tgaaggggaa gtaggcacat   92700
cttcacatgg cccacaggaa aaagagagaa ggagagagag agagagacag agagagagag   92760
agaaaaagaa agattgagag ggagagagga gggagaaagg agagtgcctg taggggagt    92820 tgctacacaa aggagcacca gggggatggt gctcaaccat tagaaactac ccccatgatc   92880
caatcacctc ccaccaggcc ccacctccga cactggagat tacaattcag catgagattt   92940
gggtggggac acagagccaa accatatcag agcatgaacc ctattgtgaa ctgcacattt   93000
gagggatcta ggttgcatgc tccttatgag aatctaatgc ctgatgatga tttgaggtgg   93060
aacagtttca tcccgaaacc atcccccgcc aaccctggtt tgtggaaaaa ttgtcttcca   93120
cagaaccggt ccctggtgcc aaaaagtttg gggacctctg cacatatgca tgcacctgta   93180
catggacaca taatacatgt acatatgcat actttatatt ctctgccact tctggtccag   93240
actgatatac tatctcattt ggattactgc actagccttt tgttttggaa acagcatttt   93300
ttaaaaaatt taatttaatt tttttgagat agggtgtcat tctgttgccc agcttggagt   93360
gcagtgtcat gatcatagct cactgcggcc tcgatctccc aggctcaagt gatccttctg   93420
cctcagcctt ctcagtagtt gggactacag gcatacccac catgcccagc taatttttg    93480 attttttttt tttttttgaga cagagtctca gcctgtcgcc caggctggag tgggttggcg   93540
cgatctcagc tcactgcaac ttctgcctcc caggttcaag tgattctcct gcctcagcct   93600
cccgagtagt tgggattaca ggcgcctgcc accacaccca gctaactttt tgtattttta   93660
gtagagacgg ggtttcacca tgttggccag gctggtctcg aacttgtgac ctcgtgatta   93720
gcccgcctcg gcctcccaaa gtgctgggat tacaggcgtg agctaccgct cccagccagg   93780
aaacagcatt cttgagataa ttcatataat tcacccattt aaagtatata attcattctc   93840
tttagtatgc ccacagagtt gtacagccat caccagaatc agttttagaa cccataaagg   93900
aactctgtac tctttaccca aaacctccat gcctccagct gcaggcagcc actaacctgc   93960
cttctgtctc tgtgactcta cgtcttctgg acattactgt ggatgggctc atacagtcag   94020
tgagcttgtg actggtgcct tctaccaagc agggttttca gtgtagcagc ctctctgttt   94080 ttctttttt tttaaattgt gacggaactt ctgcctccg ggttcaagcg attctcctgc     94140
ctcagcctcc cgagtggctg ggactacagg cccatgtcac catgcctggc taatttttt    94200 tttttttttt tttagtagag atgggttca acatgttagc cagggtggtc tcgatctcct   94260
gacttcatga tccgcctgcc tcggcctccc aaagtgctgg gattacaggc gtgagccacc   94320
atgcccggct aacctttcat ttactgtctg catttcttcc ctgatgcctt ccagtccatg   94380
cacccgattg tagccattca tcctattatg gtttaaggtg actgtcttag tcagcatggg   94440
ttgccataac aaaataccat agcctgggtg gcttcaacaa cagaatttac ttctcacact   94500
```

```
tctggaggtt gggaagtcca agatccagga ctttcgcctt gccctcatgt ggtgaggggg    94560
tgaggaagct ctgtggggcc tcttatatat ggatgctaat ctcattcatg agggttctgc    94620
cctcatgacc cagtcacctc ccaaaggccc cacctcctaa taccatcacc ctggtaatta    94680
agtttcagtg tataaatttg ggggactata gacattgaaa ccataacaag cacttttcta    94740
agatcaggga gtgagtaagt agcagagcta ggacctcaat tccacatgtc agtcatcttg    94800
ccttcactct gctccatgat ggctgcctcc tagagcattg ggagtctcga tgttctatat    94860
gctctcatgt gttgtgtatt ggagatagtt gaggctttat gaatacatct ggatttgttg    94920
acttctagct ttgctggtaa ccagctgtga ccttgaataa gttacttcat ctctgagcct    94980
gtttcctctt ttagaaacag gagtttaaaa tgctgctttg ggttgggcac ggtggctcat    95040
gcctgtaatt ccagcacttt gggaggctga gatgggagga tcactggagc ttggagttcg    95100
agaccagcct gggcatcata gtgtgagatc ctgtctcctc aagaaattaa aaaattagct    95160
gggtgatgtg gcgtgtgcct gtggtcccat ctactctgga ggctgaggtg ggaggattgc    95220
ttgagcccag gaggttgagg ctacaatgaa atatgattgc accccatcct gggtgacgag    95280
tgagaccctg tctcaaaaaa gaaaaaaaaa atgctgcttt gtaccccttt catgtcatgg    95340
cgtcatggcc aacatagaat gccctggttg tttgctgttg gagggcatgg gcctgggggc    95400
tccctgaggg ctccttccat cttcaactca ttctctgtgc acctgttagg aagttgtggg    95460
ccagtcccta ccatgtatca ttgtgtgggt aaaagtaaat aaaatgtgta cagtgtctga    95520
actgtacata tcagggtcca agaacaaaat gagtgacatg ggttagctct ttttaataaa    95580
tggtaaaacc aaatattcta attttcagtt ttgttatact tccatcacat gttttgtttt    95640
ttttgttttt tgttttttgtt tttctatttt aggcagcctt gccttctcta acaaacccc    95700 cttctctaag tcccatccga cgaaagggga aggagaaaga accaggagaa caagcatctg    95760
taccgttgag tcccaagaaa ggcagtgagg ccagtgcagg taggaaacag cgtggggaag    95820
ggagggacat gagtgcagca tctgtcatgt agaaacatag gatttaagta acttggtgtt    95880
ttagagaaat aaatataata cacatcagta aagtgagaga agtttctcc aggtgcggtt    95940 caagatatta gaaactaatg actgatgtac acagaccacc ttttggtctg aagcatttct    96000
aagtgccact ggctgacatg cagcccctac agcctccagg cttccagccc tagcatggag    96060
catcactctc ctatgcttcc ctggttgcag gtgatggctg gagaggcctc ctgattttca    96120
gtaagggaag tggtgtagat gcttaggaat agatgtagtg agtgaaaaaa ctgattctga    96180
tatgtcaaaa attctgattg gaaatggaat atttacattt ggaagagcta aaggcgagag    96240
aaagtgggga taaagtcatc tgagttggag gagcttaaac cattcacaag tttggaggac    96300 cttttttac ccatgaaaag gtcagaacag aaggggctag gatttaggtg tgactgcagt    96360
ttattgaatt cccatccata ctgctctcgg tgggcagtgg caggggcagg agaggagcct    96420
ggcaaagcat gaagtgactg ctgctgcctc tgctatctgg gacgcctggc cacctgtctg    96480
tacagtctcc ctccagaccc attctcacgc tgtctcttgg cacccagggg ccagtgatgg    96540
ttctcccatt tgttttgtgt atatagcatt tatatcaagg ctatttattt atttatttat    96600
tttatttatt tattttttttg agacagagtc tcactctgtc acccaggctg gagtgcagtg    96660
gtgcaatctc ggctcagtgc aagctctgcc tcctgggttc aagcaattct cctgcctcag    96720
cctcctgagt agctgggact acaggtgtgc accaccacac ctggctaatt ttttgtattt    96780 tttatttagtg gagacggggt ttcaccttgt tggccaggat ggtcttgatc tcctgacctc    96840
gtgatccgtc cacctcagcc tctcaaagtg ctgggattac aggcatgagt cactgtaccc    96900
```

```
ggcctattta tttattttta attgacaaaa ttgtatatat ctgtaatata caacatgatg   96960
tttgaaatat gtgtacattg gccaggcgtg gtggctcaca cctgtaatcc cagcactttg   97020
ggaggctgag gtgggcggat cacgaggtcg ggagttcaag accaaactgg ccagcatggt   97080
gaaatcctgt ctctactaaa aataccacaa aaaaaaaaaa aaaaaaaaaa agccgggcat   97140
ggtggctcgc gccagtcgtc ccagctactt gggaggctga ggcaggagaa ttgcttgaat   97200
ctggcaggtg gaggttgcag tgagctgagt tcatgccact gcactctagc ctgggcgata   97260
gagcgagact ccgtctcaaa aaaaaaaaaa aaagaagaaa tacatatgca ttgtggaatg   97320
gctaattaac ctgtgcatca cctcacgtat cattgttttg tggtgagaac acttaaaatc   97380
tactctttca gtgattttct tgcatatggt acattgctat taactgcagt caccatgcta   97440
tacagtagat ctcttgaact cattcctcct gtctataaat gaaattttgt atccttgacc   97500
aacacattca aggttttttt tgagatggag tcttcttcac ccaggctgga gtaccatggc   97560
acgatctcat ctcactgcaa cctccgcctc ccaggttcaa gcaattctcc tgcctcagcc   97620
tcctgagtag ctgggattac aggcacatgc tactgcacct ggctaatttt tgtatttta   97680 gtagaagtgg agtttcacca tgttggccag gctggtctcg aactcctgac ctcaagtgat   97740
ccgcctgcct tggcctgcca aagtgctggg attacaggtg tgagccactg cacccggcct   97800
caagcgtttt aaaagatgct cttttctaag gattgactgt agtacaggag gaagattgac   97860
ctgttgaaaa gcctcagcct ttacaagtgt aaaattatca gtatattact atcatctttc   97920
tgatgaatta aataaactaa ggactccaag tcaaaagtct tcaaactgaa gtagaatagt   97980
tgtatatagt gcttggcact ttaatattta gtatcggttt aatgataatg tttgtgcctt   98040
tgccgtcttt aaaacatttt tacatcatcc ctgtttgatt acttggtgtg ctcatgaagt   98100
tgttggccac taaggaatct taggctcaga gaggttctgg aattggccag tggtccttga   98160
atcagctgct cctatgattc tctaactgat ttctcacaaa gcaaacaagc aatcataaca   98220
aaacaactgt gcacactgct cttcttattt tgttatttaa aaagtactta ggctctactt   98280
atgtttgtta gtcaatttct cattacttct agttaatcaa aaggtcagag gaaatacttg   98340
aatattttca tactagaata ctttaaaaaa tcatgatttc cagtaatctc tttaaaactt   98400
ggcaagttat tttgatctaa aagtttatct tttgtgtgca tattttaaa gcttctagac   98460 aatctgatac ctcaggtcct gttacaacaa gtaaatcctc atcactgggg agtttctatc   98520
atcttccttc atacctcaaa ctgcatgatg tcctgaaagc tacacacgct aactacaagg   98580
tatgggcctc tgcatctttt aaaaatatat atgcacacat acttacgtct aatggatagt   98640
tgatgttttt cttatgattt gtaggatgta taagcccttt gagatatgag ttacatttag   98700 tttttcaag tttgtttgtc tttcagcttt gtttatgata gcttctatca tacaggtgtt   98760
ttggattttc atattgtttg tactcacagc taagattgat tacagtgaca gagctaggat   98820
gtgcagccag gttatagggg gaagtggccc tggtggagtc tggagggatc cgtgtacagg   98880
cttccttccc tcccgtgagg ctcacacaaa aatacagcaa catgctggtc ctgcaggtac   98940
cctctgccta acatgagcca caattccaga ctcacagaag aaaagcaggt gttcggcata   99000
aaccatgtgt ttcaaatagt ctgggcatgg tgagccactt gttatcagct agggaaagtt   99060
tatgtcagcg taagaaactg ttcaccagat accccccaaga gccagccttt ctgtctaggg   99120
atgttttagt ttttagttc attttttttt ttaactttaa aattttctgt tcatctgcaa   99180
tttgttagat atgaagtatg tgtctaattt aattttttgtt tttggttgtc cccaataatg   99240
```

```
tttacagaag aattttcctg cactaattgg cttgagttac ttacattctc atagttctct   99300
agtttcagta gtttcatttta ttattttgtt atatcaatct atctgtctgc tcatctatta   99360
gaagcatcct tgttttttt ttttctttt tagacagagt cttgctctgt ccccaggttg   99420
gagtgcagtg gtgcaaccat gcctccctgc agtctcaggg ctcaagtgat cctcccacct   99480
cagctcctga gtacctggga ctaccggcat gtgccaccac acccagctaa ttttacatt   99540
ttttgtagag acagggtctc cctaagttgc ctgggctggt ctcaagctcc tggcttaagt   99600
aatcctccct ccttggcctc ccaaagtgct gggattacag gtgtgagcaa ctgcacccgg   99660
ctacaagtat acttcttaat tattgtagct taatggtatt tatgagggga tcagttcccc   99720
tgttgttctt tagaattttc tggatattct tctttattga ttttgggatg tgaacaatag   99780
aatcaacttc tacttgtaga ttgatttagg gagaacttat acctcagatg ttaagtcacc   99840
ctgtccagaa tgtgggatgc tttcctattt gttcagaact ttttaaatta cctcagaagc   99900
acatgaaatt taaaggattt taaaaaaaac ttaaagatta tttcacatag ctcttgcaca   99960
tttcttgata aatgaatcct caggtattcc tctgttttg ttactaatag ttacttctta  100020
tgggttttt ttcccctgaa aatcatttat caaacgtatg tggcttattt tctgaaggat  100080
gtttgataat tttggaagat atgaaagtct tcatatttta caaggtttga ggtctcttta  100140
agctgcatgg ttctcatgtc agctcccaaa gcagaagacg gcatgttgaa aaatgccgta  100200
gagaagatac ttcttttcca cctgttttca actcatatca tcttgaattt cagggcacct  100260
ttccatgctc ctagtgcttg ctatctgttt attatttcc ttcctgaata ccctgaactc  100320
cagcatgttc tgctgtaatt ctggcctccc tggcatcttg gactcctgtt tcctttgctc  100380
tgtcatcccc gcggtcagct cctgctgcgc agcttctcag ctgaagtgcg tttggagtgc  100440
ctggcgtgtc ttgctggatc tttgagtatt gcctctggtt tccttggttc cttctgctga  100500
gttgctcagc gtctccactc cccatttctt gtgtggccct tcctgcactc ctctgattcc  100560
ttttgtcttc cctggtttct tgcttggtt tcgagtctcc acagaacttt tgcagctctt  100620
ctgaagacct ggaagctttt tcatcttaat tctcatctca tgacctcttt tcccttcttt  100680
gagagctaga acttcccatg gtgaacttct cttttccagaa ttccatgcct tcttttccct  100740
cccacttacc tgttgtccag gagaggtcag attgctgtgc atattggagg agaaccctt  100800
cttccctggg ctcttcatct cacatgacat caccacatca cctcgttcct tggaccctca  100860
gtggtgtcac tgctggattt ttcttcctt tggctggcct tagggcacac ccaggttgac  100920
tagcgtagtc atggtattta gatccactca cattttcagt ttctgtgtct gtctcttgcc  100980
tgcttctgac ttcgcccaga gaaagcttct cttttcacaag ggttcttaga tttatgttca  101040
ctgagcacct tcttttctga ggcagtgttt taccaatatt tattttccta gtcagtctcg  101100
ccttaccttt cttgttatgc atgtctttgg tcctgaccca ttctctgagt ctgtaaaata  101160
gaattgctgt ataatttaat tacatgaaat cctttagaat cttaacacat cttacacctg  101220
atttaatatt ttattgtatc caaattgaac caaccctatg tgaatttgac agtgattct  101280
cccagggatc ctagtgtata aggaatagga cttagtattt tctatttttt gatataccac  101340
ataccagata ctgattatga tggacattta accctttttt ctcattatga aagaaagtta  101400
ggaattattt cttccagtag cgccagtgta acctgaaagc ctttgaaaga gtagttttg   101460
tatagctatc tgaaaggaat ttcttttccaa aatatttttc cagtgctgac aacaaacacg  101520
cagacacacc ctgcaaggtg agtgtacggc gccgcacagt ggaggcatct gctgcagccg  101580
tcgatgtttg tgtctttggt tgtacattat gagatcgtga cagggccagt aaccgtgtgt  101640
```

```
tctctccttc accttcccaa ggtcacgctg gatcttcaga acagcacgga aaagtttgga  101700
gggtttctcc gctcagcctt ggatgttctt tctcagatac tagagctggc cacactgcag  101760
gacattggga aggtttgtgt cttgttttt ctccttgggt tgtggctggc acacttgatg  101820
tgcgtcttct gggctgagtt catctaggat ggagcctggt tctccagggt gcctccggga  101880
gactcctccc tgccccacgt gcttgcgtca caggacccaa gtctgactct gccttagcca  101940
tgaagtttag ggggaagttt ctatttgtat tctatttttg tctgttatca tgtattagct  102000
tagacccagt ttagtttgga aaatcagtgg gtttcaaaat gtgtttgtag agtccttat  102060 ttcttaactt gaccttttca agtggaaagg ggcaaaacag acgggtaagg gggcggggcg  102120
ggaggtgtga cttgctcttt tgtgcctgag gaagtaacag agctggggtt gacagtcata  102180
ttctctgaca cagatagtct ctgacttatc tcacagaaag tcagcggcag agcctgagtt  102240
aaaagtctcg tagattttct ttttcttttt tttggtggct aatttcagtt ttatttatat  102300
ttgtttattt atttattata ctttaagttc tgggttacat gtgcagaatg tgcagttttg  102360
ttacataggt atacacgtgc catgatggtt tgctgcaccc atcaacccat cacctacatt  102420
aggtatttct cctaatgtta tccctccccc agtcccctca ctcccatgg gccccggtgt  102480 gtgatgttct cctccctgtg cccatgtgtt ctcattgttc aatttccact tgtgagtgag  102540
aacatgcggt gtttggtttt ctgatcttgt gatagtttgc tgagaatgat ggtttccagc  102600
atcatccatg tgcctgcaaa ggacatgaac tcatccttt ttatggctgt atagtattcc  102660
atggtgtata tgtgccacat tttcttaatc cagtctatca ttgatggaca ttcgggttgg  102720
ttccaagtct ttgctattgt gactagtgcc acaataaaca tacatgtgca tgtgtcttta  102780
tcgtagaatg atttataatc ctttgggtat atgcccagta atgggattgc tgggtcaaat  102840
ggtatttcta gttctagacc tttgaggaat cgccagactg tcttccacaa tagttgaact  102900
aatttacact cccaccaaca gtgtaaaagt gttcctattt ttccacaacc tctccagcat  102960
ctgttgtttc gtgactttt aacgatcgcc atcctaactg gcgtgagatg gtatctcatt  103020
gtgattttga tctgcatttc tctaatgacc agtggtgatg agcatttttt cgtatgtctg  103080
ttggctgcat aaatgtcttc ttttgcgaag tgtctgttca tatcctttgt ccatttttg  103140 atggggttgt ttgcttttt ttcgtaaatt tgtttaagtt cttttgtagat tctggatgtt  103200 aatcttttgt cagatgggta gattgcaaaa atttatccc attctgtagg ttgcctgttc  103260
actctgatga tagtttcttt tgctatgcag aagctcttta gtttaattag atcccgtttg  103320
tcaatttggg cttttgttgc cattgctttt ggtgttttag acatgaagtc tttgcctatg  103380
cctatgtcct gaatgttatg gcccaggttt tcttctagga ttttatggt cctaggtctt  103440 atgtttaagt ctttgatcca tcttgagttg atttttgtgt aaggtataag gaaggggtcc  103500
agtttcagtt ttctgcatgt ggctagccag ttttcccaac accatttat aaatagggaa  103560 tcttttcccc attgcttatg tgtgtcaggt tgtcaaaga tcagatgatt gtagatgtgt  103620
ggtggtattt ctgaggcctc tgttctgttc cattggtcta tatatctgtt ttggtaccag  103680
taccatgcag ttttggttac tgtagtgttg tagtatagtt tgaagtcagg tagtgtgatg  103740
cctccagctt tgttcttcta gcccaggatt gtcttggcta tgcaggctct tttttggttc  103800
catatgaagt ttaaaatagt ttttccaat tctgtgaaga aagtcagtga tagcttgatg  103860
gggggatagc attgaatcta taaattactt tgggcagcaa ggccattttc acgatattga  103920
ttcgtcctat ccatgaacat ggaatgtttt tctatttgtt tgtgtcctct cttatttcct  103980
```

```
tgagcagtgg tttgtagttc tccttgaaga ggtccttcac atcccttgta agttgtcttc    104040
ctaggtgttt cattcccttg gtagcatttg tgaatgggag ttcactcatg atttggctct    104100
ctgtttgtct gttattggtg tataggaatg cttgtgattt ttgcacattg attttgtatc    104160
ctgagacttt gctgaagttg ctaatcagct taaggagatt ttgagctgaa ccaatagggt    104220
tttctaaata tacaatcatg tcatctgcaa acagggacag ttttacttcc tctcttccta    104280
tttgaatacc ctttattgct ttctcttgcc tgattgcgct ggccagaact tccaatacta    104340
tgttgaatag gagtggtgag agagggcatc cttgtcttgt gccggttttc gaagggaatg    104400
cttccagttt ttgcccattc agtatgatat tagctgtggg tttgtcataa atagctctta    104460
ctatgttgag atacgttcca tcgataccta gtttattgag agttttttagc atgaaaggct    104520 gttgaatttt gtcaaaggcc ttttctgcat ctgttgagat aatcatatgg tttttgttgt    104580
tggttctgtt tatgtgatgg attacgttta ttgatttgcg tatgttgaac cagccttgca    104640
ttccagggat gaagctgact tgattgtggg ggataagctt tttgatgtgc tgctggattc    104700
agtttgccag tattttattg aggattttca catcgatgtt catcagggat attggcctaa    104760
aattctcttt ttttgttgtg tctctgccag gctttggtat caggatgatg ctggcctcat    104820
aaaatgagtt agggaggatt ctctcttttt ctattgattg gaatagtttc agaaggaatg    104880
gtaccatctc ctctttgtac ctctggtaga attcggctgt gaatccatcc tggacttttt    104940
ttggttagta ggctattaac tattgcctca agtttagaac ctgttatcag tctattcaga    105000
gattcagctt ttttctggtt tagtcttggg agggtgtatg tgtccaggaa tttatccatt    105060
tcttctagat tttctagttt atttgggtag agatgtttat agtattctct gatggtagtt    105120
tgtatttctg tgggatcggt ggtgatatcc cctttatcgt ttttattgag tctatttgat    105180
tcttctctct tttcttcttt attagtcttg ctagcggtct acctatttta ttgatctttt    105240
caaaaaacca gcacctggat tcattgattt tttttggagg gttttttttc gtgtctctat    105300
ctccttcagt tctgctctga tcttagttat ttttttgtctt ctgctagctt ttgaatttgt    105360
ttgctcttgc ttttctagtt ctttttaattg tgatgttagg gtgttaattt tagatcttttt    105420 ctgctttctc ttgtgggcat ttagtgctat aaatttccct ctacacactg ctttaaatgt    105480
gtcccagaga ttctggtatg ttgtgtcttc gttctcattg gtttccaaga aaatttttat    105540
ttctgccttc atttcgttat ttacccagta gtcattcaag agcaggttgt tcagtttcca    105600
tgtagttgtg tggttttgag tgagattctc aatcctgagt tctaatttga ttgcactgtg    105660
gtctgacaga cagtttgttg tgatttctgt tcttttacat ttgctgagga gtgttttact    105720
tccaactatg tggtcagttt tagaataagt gcaatgtggt gctgagaaga atgtatgttc    105780
tgttgatttg gggtgcagag ttctgtagat gtctattagg tccgcttggt ccagtgctga    105840
gttcaagtcc tggatatcct tgttaatttt ctggctcatt gatctgccta atattgacag    105900
tggggtgtta aagtctccca ctattaccgg gtgggagtct ctttgtaggt ctctaagaac    105960
ttgcttcatg aatctgggtg ctcctgtatt ggggcgtgt atatttagga tagttagctc    106020
ttcttgttga attgatccct ttaccattat gtaatggcct tctttgtctc ctttgaactt    106080
tgttgattta aagtctgttt tatcagagac taggattgca atccctgctt ttttttttgct    106140 ttccatttgc ttgttagatc ttcctccatc cctttatttt gagccaatga gtgtctttgc    106200
atgtgagatg ggtctcctga atacagcaca ccaatgggtc ttgactcttt atccaatttg    106260
ccagtctgtg tcttttaatt ggggcattta gcccatttac atttaaggtt aatattgcta    106320
tgtgtgaatt tgatcctgtc attatgatcc tagttggtta ttttgcccgt taactgatgc    106380
```

```
agtttcttca tagcgtcagt agtctttaca atttggcatg tttttgcagt ggctggtact 106440
ggttgttcct ttccatgttt agtgcttcct tcaggagctc ttgtaaggca ggcctggtgg 106500
tgacaaaatc tctgcatttg cttgtctgta aaggatttta tttctcgttc acttatgaag 106560
cttagtttgg ctggatatga aattctgggt tgaaaatact tttttttaaag aatgttgaat 106620
attggctccc actctttttct ggcttgtagg atttctgcag agagatctgc tgttagtctg 106680
atgggcttcc ctttgtgggt aacccgacct ttctctctgg ctgccctttc cttcatttca 106740
atcttggtgg atctgatgat tatgtgtctt ggggttgctc ttctcgagga gtatctttgt 106800
ggtgttctct gtatttcctg aatttgaatg ttggtctgcc ttgctaggtt ggggaagttc 106860
tcctggataa tatcctgaag agtgttttct aacttggttc tattctcccc atcactttca 106920
ggtacaccaa tcaaacgtag atttggtctt ttcacatagt cccatatttc ttggaggctt 106980
ggttcatttc ttttcactct tttttctcta atcttgtctt ctcgctttat ttcattaatt 107040
tgatcttcaa tcactgatat ccttctcttct gcttgattga atcggctgtc gaagcttgtg 107100
tatacttcac aaaattctcg ttctgtggtt tttagctcca tcaggtcatt taagctcttc 107160
tctacactgg ttattctagc cattagtcta acatttttttt caaggttttt agcttccttg 107220
tgatgggtta gaacatgctc ctttagctcg agaagtttg ttattaccga ccttctgaag 107280
cctacttctg tcaattcatc aaactcattc tccatccagt tttgttccct tgctggtgag 107340
gagttgtgat cctttggagg agaagaggtg ttctggtttt tggaattttc agcctttctg 107400
ctatggtttc tccccatcat tgtggtttta tctacctttg gtctttgatg ttggtgacct 107460
acggatgggg ttttggtgtg ggtgtccttt ttgttgatgt tgatgctatt cctttctgtt 107520
tgttagtttt ccttctaaca gacaggcccc tcagctgcag gtctgttgga gtttgctgga 107580
ggtccactcc aggccctgtt tgcctgggca tcaccagcag aggctgcaga acagcaaata 107640
ttgctgcctg atccttcctc tggaaacatc gtcccagagc acgaaggtgt ctgcctgtat 107700
gaggtgtttg ttggcccta ctgggaggtg tctcccagtc aggctacatg ggggtcaggg 107760
acccacttga ggcagtctgt tcattatcgg agcttgaatg ccgtaccggg agaaccactg 107820
ctctcttcag agctgtcagg cacgtatgtt taaatctgga gaagctgtct gctgcctttt 107880
gttcagatgt gcccttcccc cagaggtgga atctagagag gcagtaggcc ttgctgagct 107940
gcagtgggct ctgcccagtt cgagcttccc tgctgctttg tttacactgt gagcatagaa 108000
ccacctactc tagcctcagc agtggtggac acccctcccc cagccaagct cctgcatccc 108060
aggtcgattt cagagtgctg cgctagcagt gagcaaggcc ccatgggcgt gggacccgct 108120
gagccaggca caggagagaa tctcctggtc tgctggttgt gaagactgtg ggaaaagtgc 108180
agtatttggg caggagtgta ctgctccttc aggtacagtc actcatggct ccttttggct 108240
tggaaaggga agtcccccga cccccttgtgc ttcccaggtg aggcaacacc ccgccctgct 108300
tcggcttgcc ctccgtgggc tgcacccact gtccagcaag tcccagtgag atgaactagg 108360
tacctcagtt ggaaatgcag aaatcacctg tcttctgtgt cgatctcact gggagctgta 108420
gactggagct gttcctattc ggccattttg gaagcatccc ttgttttttg aggtggagtc 108480
ttgctctgtc gcccaggctg acgtgcatcg gcacaatctc ggcccactgc aacctttgcc 108540
tcctggtttc aagcgattct cctacctcag cctccggagt agctgggatt acaggcacct 108600
gccaccatgc ctggctaatt ttttgtattt ttagtggaga tggggtttca ccacattggc 108660
caggctagtc tcgaactcct gaccttgtga tccacccacc tcagcctcct agagtgctgg 108720
```

```
gatcacaggt gtcagccacc acgcccagcc atattttcag atctccctct ctttgcccta 108780
aaccactgtg cttaataagt agttttagt ggccagcagt ctccatgtat aacacatttt 108840
agcaaaatgg aaaatactat atgttttaaa tttgaacgtg agattatact gaaataaaaa 108900
tcatctaact gggattcttt aaatagtaag attttctttt ttgtatgtgg gtttttttt 108960 aaccttatta ttatgactgt catatataga aatggctgtt tttcagttac agtcagtgaa 109020
tgtatcaaat gctgccttat ccaaataata aaagtaaatt attaataagt cacaatttaa 109080
tgaagattga tgttagttga tctttatatt cttgaaatca gccatatggt tgtgtgtgta 109140
tgtatatatt tttaaaggta cataaagata ataagctcat ctctgaaaat ttttacattt 109200
ggcataagaa taactggata attaagcatc ttattctctg gcctgtgtct ttacagttaa 109260
aggtagattt actcacctct cctttttgt ttttctaagt tcatctttt tgctgtttca 109320 agacagaggc ccattttagc tttctcgcat atccttttgt ttgtactttg aagcctcac 109380 ctgcttaatt gttgagtttt tatccgtggt cttttagagg gggatatgta gggtagaagc 109440
tttcacaggt tcttgtttgc acttggcccc tgactgtttt gaggaatctc cctcactgac 109500
tcacagcatg gcaaggtttc agatctcttt ctgccacaca gcagttctga ggcagctgga 109560
aagatatcca gatgcttaga ttgtcaggcc aggcttgaga tatacaaact attgagcctt 109620
atctgtgacc ttgcttaggt gaaggcatca gagcccctgc accaacatgc ataggcctct 109680
gcatgtgtgc ggggctgggt gttgaggtct gagcacaagt gtagctggag aggtgagctt 109740
gatgtggcga cgggtatgag caggttttct tcagacttct gtgagtttac ctagttccag 109800
gatttaaagg cacagagact ttagaattaa aatagaatca tttctttt ctaaatagca 109860 acactaggaa taaaaataa taattccaca ttcttgacag gtaatgtttt ttcttgtctt 109920
ctaatcctta tttattccat actcattttt atacataatt gaaatgtatt atgcattgga 109980
tttttctttt gcattatatt atagacgatt tttcatgtaa ctccttactg ttccattta 110040 tatgttttgt ctggtttaag actttatctg caaaccggga aactgtctct acaaaaagaa 110100
aaacaaaaat agttggccgc agtggcatgc gtctgtggtc ccagctactc ggggctgagg 110160
tgggaggatt gcttgagcct tgggaggttg aggctgcaaa gagccatgat catgccattg 110220
cactccagca tgggtgacag actttatact gtctgttttg ggtgatttga taatgatatg 110280
ccctgatgta gttttttat atctgtgtt tcttgtgcct gggtttattg aggttgggtc 110340
tgtggcttca tagtatttt aaagtttgga aaattttagg ccattctttc tttctttctt 110400
tctttttttt tttttgaga cagtgtctcg ctctgtcgcc tgcgttggag tgcagtgaca 110460
ctatcttggc tcactgcaag ctctgcctcc tgggttcacg ccattctcct gcctcagcct 110520
cctgagtagc tgggactaca ggcgcctgcc accacgcctg gctaattttt tgtattttta 110580
gtagagacga ggtttcactg tgttagccag gatggtctca atctcctgac ctcgtgatct 110640
gcccgcctgg gcctcccaaa gtgctgggat tacaggcgtg agccactgca cccagctagg 110700
ccattatttc ttcaaagatt ttttttctgc cctgcctccc tcctttttc cctctcttaa 110760 agggggctgtg atttcctgaa tgattgctta gtgttgtccc atagcttact gatgctcttt 110820
tcagtgtttg attgttttat gtgttttctg ttttgtatag tttctattat tgtgttttca 110880
agttctctga tcttttcttc tacagtgtct actctgttgt taatctgtta atctgttgtt 110940
aatcctgtcc agcgtatttt ttttttgtt tttgaaacag tctcactctg ttgcccaggc 111000
tggagtttag tggtgcgata tcagctcact gcaacctcca cctcccaggc tcaagcaatt 111060
cttctgcctc agcctcccga gtagctggga ctataggcac gtgccaccac acctggctaa 111120
```

```
tttgtgtatt tttattagag atggggtttc accatgttgg ccaaactggc cttgaactcc  111180
tgacctcagg tgattcatcc gcctcggtct cccaaagtgt tgggattata ggcatgagcc  111240
accgtgtctg gccccctgttc agtgtatatc actaattttg ttttttatctc tagaagtttg  111300
```

```
atttaggtct tttaaaaatg tctccctgtg tttctgttta gctttgtgaa cacaattgta  111360
ataactgttt taatatcctt ctctgctagt tctaagatct tctaataact tcccagttct  111420
tggtgtttct cattggttga ttgatactcc tcgttttggg ttgtattttc ctgcctcttt  111480
gtatggctgc caattttta ttggatgccc aaccttgtga attttacttt gttggatgct  111540 atatatttt gtgttcccat agatcttctt gagctttgtt ctgaggttag ttgagttaca  111600
tatagatggt ttactctttt gggtcttgct ttataatttg tcagatgggt tggagcagtg  111660
cttagtttag gactaatttt tttttttggac taattattcc tctttaggaa taattaggta  111720
ccatgcttag gaggcaagac catcctgagt actctaccta atgaaccaga aagtttgggt  111780
tttccagtcc gcctgctgag aacagtgact ttctagccct gtgtgagcgc tgagctctgc  111840
tccttctaat cctttccaat gcttctttcc ctggcctcag ggagttttct cacacacata  111900
tctctgctga gtactcgaga gggaccttcc ccagatctcc agagctctct ctgtcttgtt  111960
ttctcttctc tggtgctctg tcttatgaac tgtggctgtc ttggtctcct tagattctca  112020
gcacctcttc aattcagagg gttgcctgtc cctcctcctt gtgccacagc ctaggaactc  112080
tctcaaagca gcgagttggg gcagccatag ggctgactta gtctctcgtc tcccagggat  112140
cactgtcctt cattgctcat gtccagtgtc ttgaggactc tgggttttgt ctgttttgtt  112200
ttttggtttg ctttggttgt ctcaggcagg agggtaaacc cagtccctca ccctcattgt  112260
gctcagtagt ggaagtctca ctctattaca ttagatatta gtatttgtag cagagccctg  112320
gttccctggt acttggggag ctcttgaaag gccagaaaca gcatgctttc tcacctttc  112380 cagggcttca gtttctggtg cacatcaagc attccataca catttgttaa agtccttgt  112440 tagacaagta gtgattcaca ggttctattt gtaattttt cagttaacat gtattgggta  112500
tctgctggga gctagtaaaa acaaaaagtg gtgtgtgaca aattcaattc tgacaagaac  112560
aaccttaaac acttagaata tactttgagc atatcagaat tttaaaaatg tgtggccctt  112620
gagtatttga aaccaacaag aatctattgc ttattagtag aggatatttt gttaaacaag  112680
tggagagaga ggcattttca gtctaattgg tgttggcttt tagcagctga tggaaaccag  112740
ttcgtgatta gccaggcagt ggtgaaacag gctgtgcatt ctgaatgcct aggtatctag  112800
gcattcagaa tggtggcgct ctttgagtta gcatcttctt cttttcttgat tctttttttt  112860 ttttttttga gatggacttt cgctcttgtt gcccaggtaa caactccagt gcaatggcgc  112920
catctcggct cactgtaacc tctgcctccc tggttcaagc gattctcctg cctcagcctc  112980
tcaagtagct gggattacag gtgtgcgcca ccacgcctgg ctaattttgt attttttggta  113040 gagatggggt ttcactatat tggtcaggct ggtcttgaac tcctgacctc aagtgatgca  113100
cctgcctcga tctcccaaaa tgctgggatt acaggcgtga gccaccactc ccagcccctt  113160
cttgattctt gaaaaggaca ttgggtgctg tacatctcgt tatagatgtt gataaaaatg  113220
cttgtgagaa gagtaacatt aaggtagtta tttggtcatt tttgcagatt attttaagac  113280
aattctagga ctgatttgtg gtaaatcaca cattgctgta tcatagttgt gttcactgaa  113340
catattcagg ggctctacag atgcagggct cttagctgct ttgcacactt ctgaattcct  113400
gccctgcgaa caggactgga tacctaatag acaacaggta cttgataaca gtttattgaa  113460
```

```
ttaatgagtg aatgaacaga tacataaatg catgaaagaa tggttgtaat gtatataact   113520
tggatttcaa gacttttac tgactgttca aaataagaaa ttgaaaactt tcctctgatt    113580
ttcctctact atttacacaa tttaaatgga agttatcttg taccttcaat ttctgtctag   113640
gattcgtaca ataacgggtc atctctgagt cgcttaatgt ctcacttgtc tttctacagt   113700
gtgttgaaga gatcctagga tacctgaaat cctgctttag tcgagaacca atgatggcaa   113760
ctgtttgtgt tcaacaagta agagcttcat tcttttcctc ttctgttaag acgttcgggt   113820
atgacagcaa aacgctgcta ctccttaaga ggcaggcgct gttggcataa tcagctggga   113880
ggattgtggg gtccagcgca gcacttttg gctcagtcca tgattgagcc aagaggccat    113940
ccttcccttc actccccagg aggacgaggt ctgtcactgt ggagggcaga ggacaccaga   114000
agctcctctg caacctcgct agttaacttc cagtccctcg gagtttctgt ttagaatgct   114060
caatctcatt tagaattgca aggaaaccca aaacgcctat ttaaggtaca aacagcactt   114120
catacaatat ctcatgaggt attaatagtg attcacagga agaatttcac gctgtgagtc   114180
tttgctaaca tatccagtta tttacagatg gatttgatat ttgtgtggga gattcttaaa   114240
agtgttgttc acgccacatt gttgatgcct cattttttc actgtagttg ttgaagactc   114300
tctttggcac aaacttggcc tcccagtttg atggcttatc ttccaacccc agcaagtcac   114360
aaggccgagc acagcgcctt ggctcctcca gtgtgaggcc aggcttgtac cactactgct   114420
tcatggcccc gtacacccac ttcacccagg ccctcgctga cgccagcctg aggaacatgg   114480
tgcaggcgga gcaggagaac gacacctcgg ggtaacagtt gtggcaagaa tgctgtcgtt   114540
ggtggaagca cgaaagagca agcaggaaat actttgtaaa agaataaaaa cgaaaaatgt   114600
tagcgaacat cttctaatag tctgctgtat tcagagaact ctaggagata tatatggttg   114660
atgcaaagat gatttaaggc atagcccggc cttccaagaa gtgtgtggcc agtgagtgag   114720
atgggcttgg gacttacaca tctcagaggt gggggtagag gaggaggaac actgagtggg   114780
ctgagaagca gccagctctc attgccaaag tgtgtcagca aaccagaatg cagttcataa   114840
tgtccccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctcttt cacttaaatt tgttttttt tttttgaga cggagtcttg    115080
ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttcc ttttataaat ttagcgatta   115500
aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat ctttaaatg accttcacct ttctctcaaa    115800
tctcacttaa gactgggctg agtagtcagt ttcctgtagc agaaaaaagc tcagacttga   115860
```

```
gtagccttct gcgagtgagg agacttgatg gctgtcaggc agctgtaaac tctaaataga 115920
gtgtcattat ctgaagaggg cgatgctgcc acactgagtg gcctttcaag ttgtttctca 115980
atctgacacg ttctgatcgt gtgaatgtga aattggtttg agcaggagta tatctgagtg 116040
cagaggagat tatttaaaga tattctcatt ctctgcttcc cttttattcc catttggcag 116100
atggtttgat gtcctccaga aagtgtctac ccagttgaag acaaacctca cgagtgtcac 116160
aaagaaccgt gcagataagg taaatggtgc cgtttgtggc atgtgaactc aggcgtgtca 116220
gtgctagaga ggaaactgga gctgagactt ccaggtatt ttgcttgaag cttttagttg 116280
aaggcttact tatggattct ttcttctt ttttctttt tatagaatgc tattcataat 116340
cacattcgtt tgtttgaacc tcttgttata aaagctttaa aacagtacac gactacaaca 116400
tgtgtgcagt tacagaagca ggttttagat ttgctggcgc agctggttca gttacggggtt 116460 aattactgtc ttctggattc agatcaggtt tgtcacttt atctttcatc catcatacct 116520
gttcctaatt tagtacaaat taccctaaaa gacactgaaa tctactttaa agaaatgtgg 116580
tctgcatgtt tccctcatca gttgctgctg cttatctttt tcatgcacct agctggtgca 116640
gaaggcctgg ggcatagcca gcctcagcaa gtcagcatcc ttgccccagc tccctggact 116700
caaggctaac ctggggttgg ctgttaggga tttccaaagg tttgtcccat ccacttgcct 116760
cccctccaaa ataagtttga atttaaattg tgagatacaa ttaagattta ttgtttgggg 116820 aacattttg caaaatctag agttagtttaa aacagattat caattattac cataattgat 116880
catctgcagt ttcaagctat ctaacaggtt cacttacctc tttaaaaagg aatggaattt 116940
agcaggacag taactgagac ccgtgctcct ggagtccatg tgggagctgt gtggctctgc 117000
acaagcattt gcacgcttcc cctcttgact gcattacctt cctcctatag ttgctgtggg 117060
caccagattc tggctagtcc tgtcccttca tgatgcacat tttcctcaag attcgtccca 117120
gttaaatcac tgcagatgaa actgcctttt catcgtcaaa atttaactgt cattttgag 117180 ccgtgatctt gggctacttt cttatgtggg gtaggaatat ttgtgagtta gaaatattac 117240
acttctctat ttccttctag acgtaaatct gttaatcctg tcagcactgt tactcacctg 117300
aaagggtctg tttccctagg agaactgagg gcactcggtc aacactgatt ttccacagtg 117360
ggtattgggg tggtatctgc ttgttttttt tgttgttgtt gtttgttttt ttttgttttt 117420 ttttgagat ggagtctcgc tctgtcaccc aggctggagt gcaggggtgc gatctcggct 117480
cactgccagc tccgcctcag aggttcacgc cattctcctg cctcagcctc ccgagtagct 117540
gggactacag gcacccacca ctacgccagg ctaattttt gtattttag tagagacgag 117600 gtttcactgt gttagccagg atggtctcca tctcctgacc tcgtgatctg cccgcctcgg 117660
cctcccaaag tgctgggatg acaggcgtga gccaccgcgc ccggcctggg gtctgctttt 117720
aatgaaggag gcatcaaggg gtgggctttg cgttggcctg atgctttcat ctttctttca 117780
caaaacctgt ccgaagaaaa tccgtctaaa tgggccattg ctctcctcag gaaatagtca 117840
ttgggaactt cttttccttt cctttgacac taggaggctg actggggaga gccctggtc 117900 tatggctgtg ggcagcaggg gctgagagga gcaggctctc aggggggcac gggtaccccca 117960 agggaagcca gagccctgat ttgttccatt ctagtaagaa caaagactgc tctggtttca 118020
tgtttgttct gattgccttt catcaaccgg tccccttct cccagttctt aagattcagt 118080
acagtgacag ttttatgaac aagaatagaa cactagaaca gacaaaccat tgaactctat 118140
gctgataaag atttattgag ctcctgctgt atgtttgcat tctgcccaga ggctctgaga 118200
```

```
aaaccaggcc atatgctcca tgctttatcc atggaagctc cccgtcaggt tgggaaagct    118260
gacagctgca gggaatacag tgtgacacaa aactggctcc catgcagccc ttacgtgtcg    118320
cctctcagat ggttggggga cgaaggtcga ctcctttggg tatcttatta ctaaaccagt    118380
ttcagggaat ctgtgccacc ctatctgcca ttaacgtgaa cagatgagtc cccaaggtgt    118440
aattttgggt attgtctgat gtctcttgga atttattatt tgttttcca atgagatttc     118500 acctcagggt atagtaaagt tgttgagggg attcctggat gtgttctgca attatctagg    118560
ctgatttcag aatagagtta tgcttatagt caaatttatc agctgtcaag aattttattt    118620
aaaatttatg cagataagca ggaggaaaag aagcctggtt tttacatttt aatcctatta    118680
ttgatgtgaa attttatttt ccttcctgta ggtgtttatt ggctttgtat tgaaacagtt    118740
tgaatacatt gaagtgggcc agttcaggta atagcatttt attatttag attttttct      118800 tcttcttgtg tacttacatg taatttaggt tattaagtga atgtttaaac tactgttagg    118860 cattttgct gttttcttta aatggaaatc tgactaacat actgtgcatt tttgcttctc      118920
ttaaaaatta atgtatatct caagactgt ttggaagtag ttatgtatct gaaaattcca     118980
tatgttgtca gtattcattg cacatttcaa agcatttaat tgtgttgaca gatggtggaa    119040
tgaaatcttg tggtggagca ctagttttta aatcttctta gagaaagcag ttttatataa    119100
tgttgtcttt agtaattatt atgcatttgt attctctgca gctttttctt gctagatgtt    119160
gaggttttaa tacttcttgc tagtccatta caggtttata attattaaaa gttaaaattc    119220
ttttagtacc taaatgctt aataaacatt gtaattagga aaatttagtg cagaaggaaa     119280
gtgttcccag attccctggg gtctggaaac atagtgttta ttctaattac atgcacactc    119340
cactgtgttt tggggcaagt tactgtttct cttttgagtt tcaatttctt caagagcaaa    119400
gaggcagagg agagctagga agatcgtagc tgctgtgccc ctgtgccgtc gggtgccttc    119460
tacctgctgc ctccgaacct ttacacatgt ccctgctctg cgcgagggca cagatgggat    119520
gcactgtggc aggggtgggg ttagagtaga tcacggacac ctgttagctt gatgtgtgct    119580
tgctgtcaag gttgaatcat gaattatttt atgttgctta tattgatatg tatcttaatt    119640
ttaaaagaaa ggtctaaatg gatgttttg tttttaggga atcagaggca atcattccaa     119700 acatctttt cttcttggta ttactatctt atgaacgcta tcattcaaaa cagatcattg     119760
gaattcctaa aatcattcag ctctgtgatg gcatcatggc cagtggaagg aaggctgtga    119820
cacatggtaa cgggacacac cttttcactgt cgtcttcggt gtcgtgatgt gcttggcagt   119880
gttcgttttc atatacccac tttgaacgtt gtcagtggca gccatgtgct tctcaggctc    119940
tgcatgtgtg tctgtgtatg tgaaggtact ggttagagac gtttcaaaag agaagagagc    120000
atattcttta ctctcagcaa tttgtaatct tctcagggaa aaaaattcaa gaaacagtaa    120060
gataacctaa ggtacagata gattctgaat ataaagttcc tgttcattca catgaaacgc    120120
taaaagttct tcacttgatc ttagccaaaa ggccaagaag cgatgcaaca ctaaaaattc    120180
ttaaatcgaa cttgccgtga attaaatttt gatctctcat ccagtggtat tggagatata    120240
gtttgacttg ggttcagggc tttctgtttt gcctgatgat tttgctggag cttaaataag    120300
gaacccagga gatggccagc tgtgcaagcc cccagcctgt ggaaggagct agtgtggttt    120360
tatgaatgag ttgcaaatct ttctttgagc tttttgaact gatcttccag cattgcccta    120420
ttgacccctc cctgactcct ttgctggaat ctgtaggctt ttgaactttg acagggacac    120480
atcctaagac ccttgcaaac tcccagatgt gagaatggca ctactactta gagtcttttc    120540
gactcagcgt gtgtgcagaa gagcatcaac cgggctgtgt tgcgaggcag ggccttggct    120600
```

```
gacctctcag tgtttacata gctaagccag ttagtgtttg ccacggcctc acaagggctt   120660
cagattcaca cagccaaagt atagattatt aaaggcatag gtgtttggtt tcctggactt   120720
ggagggtctt tggacagaaa atcagtaggc aaccacaccc agtactttgt gctgggaagc   120780
ttggtcatct gtgagagggt cagagagtat acccatgcgt gcatgccacc gaagggtcag   120840
tgagtattcc tgtgtgtgca tgtctcaggg ccggagagag tatgtgtcac tgagaggtca   120900 gagtgttttgt gtgtgtgtca aagagggttg cattgtgccc ttcactgagg ggtcagaggg   120960
tgcctcgcgt gtgtgtgtgt gtacgtgtgt gtgtgtcact gagggggtcag agtgtgcctg   121020 tgtgtgtgct tgtgtgtgcg tacatgtcac tgaggggtca gagtgtgcct ctgtgtgtgt   121080
gctcatgtgt gtgcatacgt gtcactgagg ggtcagagtg tgcctctgtg tgtgctcatt   121140
tgtgagcgta tgtgtcactg aggggggtcag agtgtgcctc tgtgtgtgtg ctcatgtgtg   121200
agcgtatgtg tcactgaggg ggtcagagtg tgcctctgtg tgtgtgctca tgtgtgagcg   121260
tatgtgtcac tgaggggtca gtgttcctat gtgctcatga cattgagggt cagagtgtgc   121320
ctgtgtgcca atgaaaggca tttcttatat ttttttatat gtggtcatag tagaccagtt   121380
aatttatttt gactcctgtg ttagaccaaa ataagacttg ggggaaagtc ccttatctat   121440
ctaatgacag agtgagttta cttaaaaaag cataataatc cagtggcttt gactaaatgt   121500
attatgtgga agtctttatt gtcttttcag atgaatcaag tagattattc ttgagaccag   121560
gaatgttgct gttttggtta tttggaaagt tttatcattt tcaaattgac ttttgaattt   121620
gagtcacctt ttttcagaag tggtgttaaa ttataggagc cctaggtttt ttttcttttt   121680
ttagaagtca tcacaaaatg atcagtgttc agaggaagag ctttgacctt ccacatggta   121740
taatgattga taaccttaat tcatctctta ccataaacca agtatgtgta agggttttct   121800
ttatttcttg aaagcatttt gtagatgttg agagcagttt tccaaatgta atttccatga   121860
aatgcctgat aagggtaccc ttttgtcccc acagccatac cggctctgca gcccatagtc   121920
cacgacctct ttgtattaag aggaacaaat aaagctgatg caggaaaaga gcttgaaacc   121980
caaaaagagg tggtggtgtc aatgttactg agactcatcc agtaccatca ggtaagagga   122040
atgtatgttg gaactgtcgt ggatacttta ttgacccgtg cagatggaag gaagtgccat   122100
gtggtaacgc tcactgttaa ctgtgttact ttgaaccagg tttgggcttt ctggggcctg   122160
ggtagatgcc ggtgcagggg gatggggagg gaggcggggg gtgggggggt gtggtggagt   122220
tggggaggtg cagtggcagg aggtgttgtt ggtgtgtatc cttttttttt ttttgagatg   122280
gagtctctct ccgtcgccca ggctggagtg tggtggcacg atcttggctc attgcaagct   122340
ccacctcccg ggtttaagca attctcctgc ctccacctcc cgagtagctg ggattacagg   122400
catgcaccac catgcccagc aaattttttt tttgtattt ttagtagaga tggggtttca   122460
ccatgatggc caagctgttt cgaactcctg acctcaagtg atcctcctgc cttggcctcc   122520
caaagtgcta ggattacagg cgtgagccac catgcccagc ctggtgttta tctttaaagt   122580
gggcacagcc acaggagttc acctgactcc tggtctgaga gtcacgagat cgttcaagat   122640
agtgaggccc tcttttccaa aacgaggacc aaaaatcaat tgacagtgtt ggtcaagatg   122700
gtagaaacct taaaatgata gaaatctcaa ctctgaaata aaaactttat ttgtatattt   122760
atttaccact attttgacat agggctaagg tctttttctt tgagctgatt tctggttttg   122820
ttttcttaaa gtggcataag aattcaaaga cattttgagg aaggctgagt gcagaaatct   122880 ctcttttttaa atgacttctc ctttctttta acttgcactg ttgtctagcc ctcacttatt   122940
```

```
ttgtcaattc ttttttagctg tttgtctttg aatcttcata aagccatagc tttttctcata  123000 agaagcagca ctttctttgt tcattcatat tttaatgaac ccctgtagta tttaattaaa   123060
tacttaatgc ctaattaaat cacataattg caatgcaaaa gtacatgtat cataaagagg   123120
tctgaaaatg agcaactggc aagcaggtgg tggcaggcag agctgcttgg gtgggtgggt   123180
gtcatggaga ggagttcatc agccacatgt tcagtgagct ctggatatgt ctgtttagaa   123240
atgatcacta ataaacttgt gctcaaccat gtatacctct gggaagcagg tgctcttcag   123300
tagattgcct ctgcagagaa cacagaattg aagtgaatgt ccacaaaggc aatgagccac   123360
ctgcagaata gtttagtcaa ggctgtgttt gaagtttgcc aaagattaat atacatttga   123420
ttttcatgtt gtgcctttc tctgattgtg aaatattaca aattctatac aaataacaat    123480
gatggcaaat cctcctgagc aaagtgtgca ccttgtatgt gccctagagg aacttgtgtt   123540
tcgttctgat tcccctacat ttctcatgtc atagagtggg ggttgcatta gtgtccccct   123600
gtcctcgctg ggatcacatc tgtttggatc ctagagtctt ccagctgaac tgggacaagt   123660
ataacagacg gacacgtagg ggtggaaagg cgtctcttgg cagcagactt tctaattgtg   123720
cacgctctta taggtgttgg agatgttcat tcttgtcctg cagcagtgcc acaaggagaa   123780
tgaagacaag tggaagcgac tgtctcgaca gatagctgac atcatcctcc caatgttagc   123840
caaacagcag gtttgtcccc gcagccttgg cttgttgttg catagtgatg gtagcttaag   123900
gtccttgtga aaggtgggtg gctggaatca gctcttcctt cagtcctaat ctgtgccttg   123960
atagcagttc tccgtgctag tcatgggaca gctgacttca tttcttctca caatgccatc   124020
tcaggttggt attgcccacc tactttacag ggggatccc acagctccga gaggttatgg    124080
aggtgatcag gcagcacaca gctttagagt gctggggtga gggcgggcca aggctaactc   124140
taaagcccga accccttacct cctacactgc ctcctgcatt ctggtcaacc cagtgtttta   124200
tttggtggtt agatttttgt ttttgttacc ttactgcttg taatttagca gttttccttt   124260
cctttccctt cctttccttt ccgacagggt ctcactctgt cacccaggct agagtgcagt   124320
cgtgtaatct cactgcaaca acctctgcct cccaggttca accaattctc ccacctcagc   124380
ctcctgagta gcaaggacca caggtgtgca ccactacgcc tggctagttt tttgtatttt   124440
tagtagagat gaggtctcgc tgtgttgccc aggctggttt taaactcctg ggcgcaagtg   124500
atccaccaac cttggcctgc caaagtgctg gcattacagg tgtgagccac ctcgcctggc   124560
ctattcatca ctaatcagaa tttctatgat caaatgacat gaatcattgt ttccacaact   124620
gcagtggaag gaaatggcct ggcagtgcca gtttcagaag cagcctgccc ccagtcaggc   124680
acaggccact gtgcccccag tgtagcagca cctctgtagc tcacagagaa gggtggtggg   124740
gacctccttg aggcagctct gccagaaaat tcatgagct gcctggcaca gcttgaggtt    124800
gccttttaag tggactcagc aaatacatgt ttgttcatct tgattataca caataaacaa   124860
ctactctgta tagtacgagt agtccgtggt ttttggcatt tgatttaaac ttagaggcat   124920
gtgatattga tgttactgcc ttcatgactg caccccatt ctgatttcat aatgaatgt     124980 tatcttgaga ccagttagac aacaggacag ggatcttggc ttctggtgag attgacagca   125040
gttttagtgt ggtcagggtc tccctgccta cagatggttt tagaatggtg ccctggaagc   125100
tttatcccat tcttttctgt gcgtaatctg agtgagtgg agatcgaagg cctgaataca    125160
tagtaaatac ctgacttaat atctgccgca atggaaattg tgtgatacaa catttatgaa   125220
acgcttagtg cagcacctgc caggtagctc accacaggtg catgttgcat tcagaagtag   125280
tgctagatac tatcctgtta ctggcagtgc atacatcagt gatcaaagca gattaaagaa   125340
```

```
agaccccctg ccttcttgga gtgaagattt tgttgggatg cgggtaaggg gacagacaat   125400
agaaaagcaa gtgagtgaag tctataccat ggcggctgat caggaacacc gtacagaaga   125460
atccaggagg gaagagagtt aggtggtgtc tgcggtggga gtggcattgt tcagctggtg   125520
atgagaagaa gctttggtga tctggtgaca tttgagtgaa tttgcagaaa ggaaagatac   125580
aagcctagga gatacctggg gaaggaacat tccaggcaga gcaaatagca gtgcaaaggc   125640
cctggcgggg ggcggacatg ctgttagggt acaagcaatg agggtggagg agtggggcag   125700
ccatggggag ggaagggagt gaggcctggt ggggtgaggc cagtgtggag gagccttgag   125760
agggtttgcg ctgatgtggt gtaggtttta gcaggatcat tcttattcct gagttgagaa   125820
tagccttgag ggggaggtga gggcagagca gggccaccca tgtgagaccc ggcactggag   125880
tggaatggcc caagtcagca tcccttggca gcatgaaagc aaaaccagca aggtttgctg   125940
gtggcttaga tgtggcatgt gagagagagc agggctttgg gggtgatttc agggtgagga   126000
cagggtggct gtgacaagg tagggcagac attgggggca gcaggaggtc agagcctgtc   126060
tggatgtagc agttgagacc ccataggtgc ctaatgaggt gaggccagca tcaggtgtat   126120
gagcctggag ttgtcgagag actgtgggc aggggggtcag catctgagat gtccactcac   126180
agtggaccca gactggctgg agaggaggag gagcttgaat accgagcctg ctgagtccca   126240
gctccaaggt caggtaggtg aggggagcca gtgctgggc agggggagta ggcaggtgtg   126300
gggttcctaa agccaagatt tttttaagg cattttgtgc aggagggcga catctgctgt   126360
cagcaccttg ggaacttggc ccaggtttgg cagcaccgag ggcactgatg agtgcttttg   126420
gaggagcaaa gggagccaaa ccctaatggg aatgtgttcc tgaaaggaca ggagagagac   126480
ttgggaaaag gttttacttg aagagggaac ggagaaatag ggcagtagcc agaggaggag   126540
aggagtcggc aatgggttaa gttggcagaa atgaaggcct gtttacgcac tgagggcaga   126600
agcaacaggg aggatcagtt catgacacag gagacacaaa tcgccgttgt ggtgttcaca   126660
gacatgggtt aggattggct gcatggatga cagagcactg tgggttctcc cagagttgct   126720
ggggaggagg cagagttggt gagcacaggc gagggtccag gatgcaggaa tcctggagct   126780
caagtcagtt gttcccttgt tgtaagatgt ggccagtgtt gtgagcttca catctgtgcc   126840
ttgaaaaaca ccacatctgt ttgcagagtt gtttactatg tatacacact cagtagaaac   126900
aaaaattgga aacagtcagt gcccaccatc aataagtaat ggttgaacac actgtggtat   126960
aagcttagac tattttagct tgggctattt tgcatgatta aaaatgttct ggccaggtgt   127020
ggtggctcat gcctgtaatc ccagcacttt gggaggccaa ggcaggcaga ttgcttgagc   127080
tcaggagttt gagaccagcc tgggcaacat ggtgaaaccc tgtctctact agaaatacaa   127140
aaagtagctg ggtgtggtgg tgtgcgcctg tagtcctggc taactcagga ggctgaggtg   127200
ggaggatcac ttgagcccat tcgtgcgcca ctgcactcct ggggcacaga gtgagactct   127260
gttagaaaga gagagagaga aagaagagag agggagggag gaaggaagga aggaaataaa   127320
tggaagaaat ggaagggagg aaggggaggg aggaaggaag aaaggaagtt cagccagttg   127380
ccttgggagt tctccattgc actgggttaa gtgagaagag cagagacgtt tatgattttt   127440
caaaacaact aaaacaaaac ctctgtgggt gaggggggcaa ggatatggct ataggaacat   127500
ggggcagatt aagaaaggga tatacacaca ccacttagca tttgttacaa ctgttgtggg   127560
agggatggag tgcagaaaaa gaaaaaaaaa agtgcacacc atcccatgta tgtgtataca   127620
aagggacgct tggaagactg gtccccaaaa tgttggtaat gattgtgtca gggtgctgca   127680
```

```
gtgctagttg attttttttc acactttgt atatttgagt cttttacaga aagcatttat  127740
tatttatgta ataaaaatct aaatgacaag atttctgtta tgggaaaaat gtagctatac  127800
agtgttgttg taaaaatgtt tgcttggttc accactgaac ttaaaatgct tttaaatgag  127860
ggaaggtgac gatgagatga ttatgatgat ttgcccttga gttacatagc tggtgtacag  127920
gaagctgtcg tttcttttgg cttacgtaga aatgtttgtg gtgtctaatt ccacagatgc  127980
acattgactc tcatgaagcc cttggagtgt taaatacatt atttgagatt ttggccccctt  128040
cctccctccg tccggtagac atgcttttac ggagtatgtt cgtcactcca aacacaatgg  128100
tgagtctctc gcctggctca gcagatgaat ctggacggct tgttcaggct ctgattactg  128160
ggaccacccc cagaatgtct gagtcagtca gtttgggtag ggcttcttga gagtttgctt  128220
tttttttttt tttttttttt ggtgtggggg tggtgcggaa cagagtctca ctctgtcgcc  128280
caggctggag tacagtgtca tgatctcggc tcactgcaag ctctgccttc cagcttcaca  128340
ccattctcct gcctcagcct cccgagttgc tgggactaca gcgcccacc accacgcccg  128400
gctaattttt ttgtattttt agtagagatg gggtttcacc gtgttagcca ggatggtctt  128460
gatctcctga cctcgtgacc cgcccatctc agcctcccaa agtgctggga ttacaggcgt  128520
gagccaccgc acccggcctt tttatttttt ttggagatgg agccttgctc tgtcacccag  128580
gctggagtac agtggcgcta cctcgactca ctgcaacctc cgcctccgg gttcaagcaa  128640
ttttcctgcc tcagcctccc gagtagctgg gactacaggt gcgtgccact gtgcccggct  128700
aattttttgt attttttagta gagacggggt ttcactgtgt tagccaggat ggtcgcgatc  128760
tcctgacctt gtgatccgcc cgcctcggcc tcccaaagtg ttgggattac aggtggctct  128820
cgcaccaagc caagagtttg cattttttagc aaattcccag gtgaaactaa tgcctgcttt  128880
tctgggagca cactttggga ctcagtgata gagaggttta ttggtaggat agtaaaatag  128940
gagttatttt ctttcacaaa attggcaatt gggggaaatt taatcttcct tttttcttca  129000
gctgtgactt atgtattatg tttattttag gcgtccgtga gcactgttca actgtggata  129060
tcgggaattc tggccatttt gagggttctg atttcccagt caactgaaga tattgttctt  129120
tctcgtattc aggagctctc cttctctccg tatttaatct cctgtacagt aattaatagg  129180
ttaagagatg gggacagtac ttcaacgcta gaagaacaca gtgaagggaa acaaataaag  129240
aatttgccag aagaaacatt ttcaaggtat gctttctatc tgagcctata actaacccat  129300
gccttttggg aagtcacgtg atgtttcaca gtcagtaagt ctggaataat acctggtctt  129360
gcttcacttc tgagttgggt aaagaagtct gtatcagtgt aatttttctaa tccgtcctgc  129420
attatctatg gctcttggtt catacctgtc ttgaagttct gtcatgttct gtctcttgtc  129480
ctcagtagag atgctacagc agtggctcgc ctcaggcagg gcagggcagt ggggtggctg  129540
tcctgggggc aggcagtagg ggcacgctga cgtcaggaa gttgaaaccc aagagaagcc  129600
agtaaaagtg agtctcagat tgtcaccatg tgctggcagt tttacacgct gtcagtaata  129660
aaagtcttct ccctgcaggg cagcctgcct ccaataaata cgtgtagtat caaatcctgt  129720
cttccctcat aaattgtttg gaagctcccc aaggacagtg atgaggcact cgtaagtgct  129780
tgctgcctag atgggtccct ctccacccttt gctagattct gagcattcac tgagttagag  129840
ctgcttctgc aaatgtgctg cttctgctaa gtggctgtga cttcatgcag ccttcacttg  129900
gtttgtcatc agtgggagatg ccctgtgttg tcgaaggaga taagcccagt aagcctgctg  129960
ggcacctttt ggtttgcagg ttcagcaggc agccatggc tttccctgtg tcgcattgaa  130020
gcagctggct aaaattgatg atacattaaa ttcctgtgac agatgatcag cttgtatttg  130080
```

```
tgtaatggtg tacagttcac aaagcttaaa aaaatgctac ctgccatttc atcctcagtg   130140
aggaaggtga tacacagaga gaccaagtga ctgtgtccac ggcgacggcg ctctgcattt   130200
cactttagcg gttaatgtac tctacctata tttttacttt atatttacca tatatctttt   130260
catgtatact tggcgtaagt gctttatagt agtcacctaa ttcactgtca tcttttttgt   130320
ttcttggaag gtttctatta caactggttg gtattctttt agaagacatt gttacaaaac   130380
agctgaaggt ggaaatgagt gagcagcaac atactttcta ttgccaggaa ctaggcacac   130440
tgctaatgtg tctgatccac atcttcaagt ctggtaggtg aatcacatta gtcttcctgg   130500
agtgtctcgt tccccattct gcactataca ctctcagagt gtaggagctg tgctgcccgg   130560
tagaaactct gccttgccca gtgtgccagt tgaaaatatt tgttgctgta agagtacacc   130620
tgataccatg tgacccagca gttccactct tgggtatata cccaaaagaa tggaaagcag   130680
ggtggtgaaa agatatttgc atgccagcat tcatagcagc attattcacg atagctaaaa   130740
tgtggaacca actgaagtgt ccctcgatgg atgaatggaa aagcaaaatc tggtgtatat   130800
ttacagtgga atattattca gccttaaaaa aaggacattc tgacacatgc acaacatgg    130860 gtgacccctta aggacattat gctaaatgaa ataagccagt cacaaaagga caaatactat   130920
gtgattccac ttacatgagg gacctggagt agttaattca tagatataga aagtagaatg   130980
gtggttgcca ggggctgcag gggaggggag ttattttttac aagatgaaga gagttattct   131040
agaaatgaat ggtggtgatg gttgtataac attatgaatg tacttaatgc tactgaactg   131100
tacagttaaa aatagttaag aggaccaggt gtcatggctc atgcctgaaa tccaagcact   131160
ttgagaggcc aaggcaggag gattgcttga gccaaggagt ttgagaccag cctcagcaac   131220
atggtaggac cccatctgta caaacaaact agccggggat agtggtgtgc atgtggtccc   131280
agctactcag gagactgagg ctggaggatc gcttgagccc aggaggttaa gtctctagtg   131340
agatgtgttc atgccactgc actccagcct cggctataga gtaagaccct gcctcaaaaa   131400
aacaaaacaa aacaagacaa gagccaaaaa tggttaagat gggccaatca cagtggctta   131460
tgcctgtaat cccaacactt tgggaggtca aggtaaaagg atcacttgaa gccaggagct   131520
tgggaccagc ctgagcaaca tatcgagacc cctatctcta caaagaaaat caaaaactag   131580
ctagatatgg tgggcacatg cctgtagtcc cagctacttg ggaggctgag gtgggaggat   131640
ctcttgagct caggagttcg aggctgcagg gagctattat tgcactccag cctgggctac   131700
agaatgatac cctgcctctt attaaaaaaa aatccaaaaa aaaaaaaaag taaacctgag   131760
agcttcctcc tcctgtgtta aatttggagg ccaagatgtt tttgttactt ttacaaatga   131820
tcaaggacgg tgaaggttgg gcatggtagc tcacacctga atcccagca ctttgggagg    131880 ctgaggcggg gtgatcgctt gagcttgaga ccagcctgga caacatagca agagacccca   131940
tctccacaaa aataaaaaaa taaaaaaaaa tagccaggag tagtggcatg agcctgagcc   132000
caggaggtca agctgtagtg agccatgatc atgccactgc actccagcct gggcgagatc   132060
gagaccatgt ctctagagaa agaaaatgac aaggacagtg aacccaagaa agtcataaga   132120
tgccagctgt gcagcaagca tggaaagcag ccagtccaaa ttaggacagt gtgttttcca   132180
agaagaacga tcgtttgtaa tgagaatgct ttgctttaaa taaatgacta aatagctaga   132240
agcctagttc taggggatag gcacgtcttt cttctctcaa gaaaatagaa aggcaattct   132300
aatttctagt aacagcaaac agcattaagt catggtccaa atatgaggca aaccaaaatg   132360
tggcttgatt gttcagcagt tgatctgttg gaagcccttg atattaaaaa ggttctcctt   132420
```

```
taagcggctt aggagtcacg atcaaagacc tatagaaaga gatgccatcc ttctaggatc 132480
cttggctctc ttgggaacta gattcagata gtcataatgt aaatactgct tgagctttct 132540
ttctttcttt cttcttttct tttttttttt gagacagagt ttcactcttg ttgcccatcc 132600
tggagtgcaa tggtgccatc tcggctcacc gcaacctctg cctcccaggt tcaagcaatt 132660
ctcctgcctc agcctcccga gtagctggga ttacgggcat gcaccaccac gcctggctaa 132720
ttttttgtat ttttagtaga cagggtttt ctccatgttg aggctggtct cgaactcctg 132780
acctcaggtg atccacccgc ctcggcctcc caaagtgctg ggattacagg tgtgagccac 132840
cgcacccggc ccgagctttc attttttgaaa tcaatgtatg actgaaacac tgaagactta 132900
ctgacttaat tatggtttca gaacagaatg aaaatgtctt cggttctgat gaatataaaa 132960
ggaaaactaa ccaagttaat ttggcaagta gatggtagag atagaggtgg ggagtggaag 133020
gggaactaaa atcttcacct agcattgttg ggattatatg gttacatcat ctgaagttga 133080
cagaccaaaa tatagaggct tcagaggtct ccaaatagaa ctaaacatgt aattcagatt 133140
gttaggaggt agtataaatg agctaaatct catctttatt acggtagagt taatgggtga 133200
tgtctaaagt tgtctgaagt ctataaatca tgacaaatta tgatgtggtg attgtattca 133260
acagtctttc agttgcaggg ataaaacccc agtttaaact agagtaagag aaagaatgtg 133320
ttggtttaag ctcctggaaa gtgcaggcaa gggtagttgg taggactgca tctagtgttg 133380
taattctgtg gtctgcattg tatatttatg catctcagct ctgctttctt cttttcattt 133440
atataatttt taaattttat tttaaagata gggtctcact tgtcgcccta ggctgaagtg 133500
cagtggcatg aagtgcagtg cgaggctcac tctagcctcg aactcctggg ctctagagtt 133560
cttcctgcct cagccttcta agtagctgag acaataggca tgtaccaaca tgcctggata 133620
ggttttaaaa tttttttgta gaaatggaag tcttgctgtg ttgcccaggc gggtctttaa 133680
ctcttagctt caggcgatcc tcctgcctct gcctcccaaa atgctgaggt tataggtgtc 133740
acccaccacg cccagtctca tctctgcttc ctgtgttagt tttgttctct ggtgggctgt 133800
tttcacatga ccgaagatga cctctagcag gctgtgttct cagcccctca gtaggccta 133860 tgtgattggc cttgcatgag taatatgggt gaccataaac ccctgaatgc tctggtccac 133920
atgggccaaa tgggagactg gacagcattc cattgatgag gaggtggggc tggtctccgg 133980
gagtaaggga gaggagcaca tgcagtaact gatggtctgc tgcaagggat agcagcacag 134040
cagttagaat tttggaggta actaccagaa ctgaaaacag aaatgataac aagtagttgc 134100
cttaaaaagg gatgggagca gggtgctttt gtgatcaaag ctcctttctc ttactggatt 134160
tttgtacaca ttttgcatac atatcttaga gtaaaagata gcattttcag ccttggtcca 134220
tttgaggata ctcttggcgt ggcccgcctc catgctagca ggctctggtt gtgccaagtt 134280
cagttgagca tcctggctct tgcctgcacg gaacttccag tcagtgcgtc agtatcacaa 134340
gtcttgatat ttcctatgaa gaagaacagt agtgcagtga cagacgaaat gggtgggcag 134400
gcagaggcag gatttctgag ggagagaagt agctagcttt ttgcagagaa gagttccggc 134460
acccaagaga gcagctgaga gtacaggcag gcaggcagga tgccggtagg gcccggccgc 134520
acggcgccac agaatcctgg agaaaggggc ctcttcatgg cctctgcatt cagctgctgt 134580 cacccctccgc acaggccatg gccaaaattt aattttcata gtggactcta gttttgagc 134640 cttacttgct attattgaaa taattttctt gtttctttt aaagatcttc ggattatgct 134700
tcactgacca ctgtaataag tttaaagttg agaaaatatg gcttgttaat gaatgatagg 134760 tcaatttag tatgttggtc attttaatat tttgccacca gttggtttgg atttgatgcc 134820
```

```
aggaggagac agcctcattt ctaaggacta gtcttgcctt tgtgggataa gggtggtgtg  134880
ttctgtgtcc ttctacatgt ccgagcgatc tctgtgcagc tcaaatgtgg tcactgtctt  134940
attgcgctga tttcctctcc ttccatctca caattgaggc aaaatattgt tactgttgaa  135000
gtgttgtcca ataggacttc cagcagagac aggatgtctg cactgtctaa tttagttgcc  135060
tttagccaca tgtggtgttc tgtacctgaa atgtggctgg tctgattgga tagcttaatt  135120
tataatttta tttaattta attaacttaa atttaaacag ctctgtgtgg atagtggctc  135180
ctgtatgaga cagtgcaggt ctgttgagaa gcagctttac tggtgggagt ggagggcttg  135240
gagagggcac gtgggtttcc tgctggtatc ttttgacctt atttaatctg cccaacattt  135300
gcaagtaagt tgtgtgtgtg tgtatatata aatgtgtgtt tctgtcttct tgtttccttt  135360
gactgcattt atttgaaaga cactaggtgg cagaattact gtatttgatt ggtttcaaga  135420
taagagttga aataattcat ctcgtgtttt tatataagta aggtgtgttt agcatgtaaa  135480
attggtaata tgtattcacg tactgcttaa acaaaggcta tgaattccac ccataaaccg  135540
aaaatgaaga cctttaaatt tgtccatttc aggcgtgggt acttcttaaa taatacctgg  135600
ttcaggaact agtcagaatg gcacccttga cttttttgttt cctgcttttc ctcttgttgg  135660
gagaggaggg tattcatccc aaagtggttt gcctatttca cattccatct aggataagca  135720
gaatagccaa gaaagatagc tgtcctcctg tttacaacat tgggtaac cagcatccct  135780 ctcttttggt ccaagataga ctggtttaga aacagatgat ggcaccagag gcccaggagg  135840
tggaaacatc agctttgttt gttgtccatg tggctgaatt agagctgtct ggccttgtag  135900
cctcaacacg gccttccagc tttgctcacc gtgattttca aggacacatc ttgtgctctt  135960
ccctgcctgc catccagact atcccagtc agggtggcag gagctgctgc cccttcctcc  136020
ctgagtcctg gtcgtgggtg gtggagatgt gccatgacgc tcacggaggc atgctcaccc  136080
cttcctctgt ggcagagggg atggctgcac gacagctctt ccctgtcctt tccaaagcgt  136140
ctgtggttcc acttttggg gcaaagcagg aatactggaa gagagagaaa gtggtccttt  136200
ctatagtaat aaagttgaca ttgattcaag ttcatgcttg gggaaggac agggctacta  136260 acaattataa tgctgggagc aatggaattt tctcatgggt atgtggtagg tttaatttta  136320
attatcccag ttaattctta gaactgctct gtgaagtatt tcccgctttg tgcttaagtt  136380 ctaaagatc ctgtgccaaa accaagaatg aaaacccaag cattctttct tgcccatcga  136440
tctttctctc atcaggccac ttcttgggtt gatagtggtg agtgtagccg ctgccacttt  136500 cagaatacccc accatgggcc ccagtcactg tgtggcgtgg agaagagatg gttctctctg  136560
tgtcatagct gaacaagccc agcccagaga ggtttctgcc ctaggagctc tcgatggtgg  136620
aattgggatg cgatcccaca tcctgcctgt tttgaaaaca gcattcttta tttccaattc  136680
ctgcttccat tgttcctttt aatatttctt tgtttagctc acaaaaacac ggcttgcgga  136740
gctgctgcgt gcagctgtag ctgtttctct gggtgcagcc tgcatccgcc ttcctgcccg  136800
cctcctttcc tgcactgcca tcgtggtctc cgggcacttg gtccctttct cttcccctga  136860
gtcccttggg ctcccctgtg ccaccttgt gatccacagg ctctgccttc tttctgtctc  136920
agactgctgc tcatcactac tcgggaccct aggaagggag gttccaccga gaagcatctt  136980
ctcatctcag ccacgttctc agtgccactg ttgtctttgt taggtaatgg tagctactgt  137040
aacaaataaa ccaacatttc catggcttca caccagagaa ggttgttct tggtttatg  137100 acaatgtatt gagggtgttc ttggttcacg gatggttttc ctccatgtgg gaattcgggg  137160
```

```
acccaggctc ctttccttct tttggttctg ttctccaggc cttcacatcc tctgtgtctg   137220
gttggggaca aggagaggga aggtaaagaa ggctttgtgg ccttggataa gtgacaggca   137280
tgcctttgct ggtgttctct cgtggtgaca ggtcacagcc ccaccctgta aaggggact    137340 gagagacgtc gtcctgctgc ttcccagcag cagcactgtg gtctctgatg tgttttctgt   137400
gaggataaaa acaggtgatt ccaggatgag gaaagtcagg gaaacccttg gaaggagggg   137460
accaggcggg tgtcaccatg ggattagtgg tggcttcaga atgagctgca gcgagtgcca   137520
tgccttctaa agcttttgct attctgatat gcccacacca tgcccagcag gtgtctgcct   137580
tgctctccgc agagagagtg atgaatcctt ctcatgagcc tctgtccagt tgttcctccc   137640
tccacctgga agggaccctg ggttcctcat aacatcccag cggaacaggg gaccttctat   137700
cctgtcccca agttcatcct catcctcctg ccggcttcct ggcccctctt atgtctgctt   137760
cctgacgcca catccttctg gattctctgg aattgaattt tgcctttgat gcttatttaa   137820
aaatatccat tgcaggccag gtgtggtggc tcacacctgt aatcctgtgc actttgggaa   137880
gccaaggtgg gcagattgct tgagcccagg agtttgagat tagcctgagc aacatgttga   137940
aatcctgttt ctatagaaaa tacaaaaatt agctgggcat ggtggcgcac acctatactc   138000
ccagctactc aggaacctga gacaggagga tcaattgagc cccggaggcc aaagctacag   138060
tgggctgtga tcgtgccact gtactccagt ctggtcaaac agagtgagac cctgtctgaa   138120
aaaaaaaaaa aaatccattg catacttcac cgtagcgaaa catgtatgtc ttaccttcc    138180 tttcctgcct gtagctgctc ttttacactt aacagccaca ctaagccagc cttaaatgaa   138240
aaacaaacca gcacttcctg tgccctcctg cttccttcat gagggtccc tccctctgtg    138300 tacactccat tctcattgcc catggtggtt tgtttccctc ttgtttctca agccatggca   138360
gcctgcctct tgccctcttt actaaaaagg cctttgcaga ggctgcctgt gttctttctt   138420
tctaggtctc tctcatccta ggccctccag cttgattctg tggagctgcc ctcttgtcac   138480
tcagtagctt gtggggtctt ctctgtctag ccacttaatt gattgtgttc ctcgagttgc   138540
tgtccatggt ctctcgttac tgttttctct gtgtttctgc ctctctcctt ggccttggta   138600
ggtccatccc ctttgtgacc ttggctgttg ctctcatgga caactttctc ttgctggtcc   138660
ttgtagtcct ggcatccagc ttctcgacac gggacttgtc ctgccagtac ctcagacttg   138720
cacttaaaat tgaactagca ccactgtcac tctccagggc ctcttcttgt taattagatc   138780
attagggatg ttcagaatcc cagcatcata gtatgttcct cctcccgcta ccccaggaac   138840
cctaacctta cctcctcctc tctatctact aggaggtggc cctcagagtc cgtctcatct   138900
tccacctgaa cttccctaat aggctccagc agctgccacc ccggggctg agtacttcct     138960 ccatgccttg tgcagtgctg agcccttac ctgggttctc ctgtttgctc cttattacag     139020
ccctgcgaac agatactgct cttaattcca tcttacacct aaggaagctg aggccccagg   139080
taaggtgcat ccaaggtcac ccaggtagta gacagtagag ccacgatctg aaccaggcag   139140
tctgattcag agcctgtgtt gacactcagc cacctagaac acagcttgga ttgtgggttt   139200
ctattacctg ttcaaaaccc ctacatcccg ggtctgtccc tgcacgtgct ctgtggcctg   139260
gctgcatctt ccttgaaggc agtgcatgcc tcttcactca gggggcccat gcaggaacag   139320
agggccccac agaaggatga ggccagtgca gaatgggctg gaggggacaa tgctgaccag   139380
gaagcaagtg tagagaaatc ccaggaaacc tggaggagcc agagacaagg cattagaact   139440
cctcgtcgtg acctggtctg cattctctga gtgtgctgct tctgttagct cgcttccttg   139500
gtctcaggtt atagtttaag gcattgtgga gccctaaaaa gcctgtactc tgtttttacc   139560
```

```
tgtttagga ccctttcact ttggggatgt gttgattttt ttttttttt tttttttttt 139620 tttgagatag agtctcgctc cattgcccag gctagagtgc agtggcacga tcttggccac 139680
tgctgcccct gcctcctggg ttcaagcaat tcttgtgctc ccgcctccca aatacctggg 139740
attacaggca cccgccacca cactcggcca attttgtat ttttagtgga gacagggttt 139800
taccatgttg gtcaggctgg tctcgaactc ctgacctcaa gtgatctgcc caccttggcc 139860
tcccaaagtg ctgtgattat aggcgtgagc caccacaccc ggcctgaaat ttaaatcaga 139920
aataaaattt tgatcccaac agtgatgcca ggcagcccag atctggggga gagggtggcc 139980
ttggccagct gggcctttct ctgtttccca agtcttgctg cctctccctg ctgggctttg 140040
cagcctgtgc atgtctctgt gcctttgacc ttgtttatcc aaaggagagg atagaatgaa 140100
gtcatgattc ctggagccct gagaaggatg ctgtggagaa atttgccggt agaatctagc 140160
tgagtgtgtt gctgaggtgc cagcattgtg tgtggggagg ctgaccgctt ggcctgccta 140220
ggcccaggat gctccatggc cgggcacaga ggccacttgg ctgtcaggtg tcaggagcct 140280
gcagagggca cacagagcct ggaccgcagg ggggtcctgc tttctcacct ggcctccttc 140340
agcatttctg tccctcagtc cttagcaagc ccaggagctg ttgagtttgg caggtgccga 140400
gtgctgttcc tgcctgtgta gctgtggctc agtcctgtgg gggcccgct gtggcccgag 140460 tgcagtgatt cgaggcgctg agtgttccct gactccttct ccaggagctg tgttcagact 140520
ttcgcagctc ttggcttgga gctcctggag gcttggcat tgccgaccaa tgtggaggtc 140580
gacagtgaga gaggaggaat gctagctttc ttgaccagtc cattaaataa gtgggatatt 140640
ggccaggcac ggcggctcac gccttaatcc cagcactttg ggaggctgag gcgggtggat 140700
cacgagctca ggagttcaag accagcctgg ccaacatggt gaaaccccct ctatactaaa 140760
aatacaaata ttagctgggc gtggtggcag gcgcctgtaa tcctagctac ttgggaggct 140820
gaggcaggag aacagcttga aaccggaagg tggagtttgc agtgagccaa gattgcgcca 140880
ctgcactcca acctgggcaa caagagcaaa actctatctc aaaaaaaaaa aaaaagtag 140940 gatatctgtt tctgcttaga aaatcagaa ttttctaaat gccaggtgtt ctgaatacgt 141000
aagtatggga gacgactcag cctgtttcat ttttatgtaa aatcttcgcg tagccatgtg 141060
gcactggacc gagatgaaag caaagacatt tctccttaac tttgtttcta ggaatgttcc 141120
ggagaatcac agcagctgcc actaggctgt tccgcagtga tggctgtggc ggcagtttct 141180
acaccctgga cagcttgaac ttgcgggctc gttccatgat caccacccac ccggccctgg 141240
tgctgctctg tgtcagata ctgctgcttg tcaaccacac cgactaccgc tggtgggcag 141300
aagtgcagca gaccccgaag taggttcata atgccccaca gcccagggcg ccagcccagc 141360
accctgtcct gagactccca gtaacctgag ctttggccac cgttaaagca ttttcatttt 141420 ccatttttg tgagggcttg tgaaatttct gctgcatatt aatattcctt tcatggacag 141480
catattattg ggacaaacat gcggtccagc taaaggcatt caaaatagca gttgctttct 141540
aaatgcgatt ttctttggca ggttctttga caccattgca tcttgtggga tatgcttgtc 141600
atgctctgtg gctcctacta agttctagtc cttaaattgg ttccatagcc agacatgttg 141660
caatgtctta acctcattat aaagtaaatg tggttctggt tatccttaga taatgaagta 141720
acagtgtagc aaatttcaaa acctcttgga aatgttattt taccattcaa aaaggcttac 141780
taaggttctc gttatgggtg gccctctttt tgcaaaaggt tttcaggctt aagctccatt 141840
tctaggtgct ccaacactcc attatttgta tatgtatgga aataaaagct gtgaccaccc 141900
```

```
ccaaccctgg cccccgccca gctgaatcct cagcacagta tttctggaag gctcaagatc   141960
ccacgctggg gaaaagaagt tctggagaca aaagagggca ggtgctgccg tgcctctctg   142020
ctcagtatgg atactggacc ttgtgctgcc agggctccca gtagggccag ttcatggcac   142080
tcagctggaa agtccactgt tgggaggcat tcttaaccat ccactctgtg ccgtatgtag   142140
tggggtctgg tcattctgtt ggaggagaca gaccagtgac gacatttgaa atgcttggtg   142200
gatgtcttag gcctgttacg atgactgagc actgtggggg caggagacag aaagtcagtg   142260
tctcctagtt ctgtgctgct ttaacgtgca tagaaatcag ctgcggattc agcagatcac   142320
tccttttctg acagatgggc ctgcttactc tgatgttata tcagaaagct ctgaatctgg   142380
gaattgtgtc ccctgaattg gagtaacaga aatgcttaga tgatgagtgt ttaaaagaaa   142440
taaaccaaag gtaaatttag tttggaattc agcaagcgtc ttcattcagc cctctgaggg   142500
caaactacag cttttgtaa atgtaggtaa attctgtgac tgtttcgtga cccctctga   142560 tccagttttc ctttataacc ttctgtattg ttccttctat tatcctgaaa taacattaat   142620
agattaggct gggcgtggtg gctcatgcct ataatcccag caccttggga gccaaggcg   142680 ggcagatcac ctgaggccag gacttcgaga ccagcctggc caacatgatg aaatgctgtc   142740
tctactgaaa ataacaaaaa ttagccgagc atggtgacag gtgcctgtag tccctgctac   142800
tcagaaggct gaggcgggag aatcgcttga acctaggagg aaaaggttgc agtgagctga   142860
gatcgcgcca ctgcactcta gcctgggtga cagagtgaga ctccatctca aaaaaaaaa   142920 aaaaaaaaa aaattaatgg atcaatggat ttttaaccta ataattaaat ttcaaaaaat   142980
atcgttcttt aatggtaatg taaaggtaaa attaagataa tatgtaacaa gcatgtgagt   143040
gtctaaggtg tccccgtggt ggaaggaaaa aataaatccc cataagtgtc caagatgccc   143100
atagagagca gagctgttct ggtttaaacc cctgctctta gcactgtgtt tttccagctg   143160
tgggtggtgg gggatgagta tctttttatt tccatgagat gagaaaaatg aattactaga   143220
agtgtgaaat acaaaacaca gctgctcttt ttttagccat agactcagca gccataaaat   143280
tgctgtatcc agttgcagaa attcctgctg cttactcttg accctctctc ggtttgtgtg   143340
catctcctct caggctggct cccagatggg agctggctcc aggcgacact gggtgctctg   143400
ctccaggagg tccttatgtg ggtcctgccc tagcctagcc cctctcttat ggactctgtc   143460
actgtgggtt tatgattcac tctcaatctg tcttacctct tggtgaactg ttagagtcct   143520
gcctatactt tggcgcttgt gggtgtgttg tggtacacat gatgtgttgg tcacttccca   143580
gctcatcttg ttctgagtca ccctagattt gggacattca ttcgccacca gtaccgggcg   143640
gtgtatggcc tgagatttgg gggggcttgt gctgctacaa attggggctg aatttgagtt   143700
gacagtggac cttctttatg tctactgctc atatttgaat tgcaaatact gcctcttctc   143760
tttcagaggc tcattaccct atagctgtat tattgcaaag tgcacaatta cagcttgagt   143820
gtaagtcaca ctgcgctggc aggacggccc actgagaaag gcacgtttc ctgttcgtta   143880 gttttcacat tgacacataa tttacaatac agtaaaatgt acttttctat caactgtagt   143940
cagtaacagc ccccctcccc caaccacatc aagatataga ggagtgctgt cacttcaaac   144000
agttccctct tcctctgcca catcctgccc ctccccaggt ctaaccacca atccgtgctc   144060
tgtccctctg ttcagcccat tgcagaaggc catagaaata gaatctatag gctaggtgtg   144120
gtggctcatg cctgtaatcc cagtattttg agaggctgaa gtgggaggat gacttgaggc   144180
tgggagttca agactagcct gggctgccta gcaagacccc atctccagaa aaaaaaaatt   144240
taaaaattac aatcacgtcc ctgtagttca gctgcttggg aggctgaggc aggaggatca   144300
```

```
cttgagctca ggagttagag gttacagtga gctatgatcg tgccactgtg ctccagccta 144360
ggtgacacag caagacgttg tctctgggga aaaagaaag aaacggaacc acgcggtgtg 144420
cagccttctg agtctggccc ctttcggtga gcagtgtcta aagttctgtc gcgtgttgcc 144480
cacgcgtcgg tggctcgctc cttgcaactg ctgagcattg tatggctagg ctgtagtttg 144540
ttttcacttc accagttggg aaacagagaa aaggcacttt ttaaaaagtt taaatctgta 144600
gaattttggt ttttaccagt tctcttctaa atcctgaggg attacaggaa aagttgttgt 144660
atttcagaat attcttagct tgatgtgacc tctgtccccg ttaaggccct ttgccgcaat 144720
gggaaggacg tcgctcggtc agaccctgaa ggtcagaggg gcagtttggg agtgtgtcaa 144780
cattttaact gtatggacta gagccaagag tctcaaggtt tataattccc acgtattcaa 144840
aaagaaaaaa acaataaagt gagaagtcag tgtagagtga aataacctgt gttagtgggg 144900
aagaagtgtt tttaaacagg atttccataa cgtataacat caacatgttt agagtggtga 144960
tgtttcattg ggaaacgaac agtaaaacat gaaagcaggg aggttttcat tctggcagtt 145020
ggcaactttc acggcagatg gagaatttca aaagcaattg ctcaattatc aaacatagcc 145080
agtgtgagtt ctgaaataaa ggtgctgatt gaatgtgcag ctttatggtg gattttgcta 145140
ttcaggcaag cattttaatt ttctgcctgt taaattctgt tttctttagt ttttcatatg 145200
tggtttattg tagcttagga atagataact gagagtatat attacacata caacattctg 145260
atatggcaat atttaaaaca acttgtctgt tttagaacta gaattaaaca taatcatctt 145320
cagtattttg caaataagct cactgccatc cagaaacatt gtcaatgcat ctgttgctcc 145380
ttctagaaga cacagtctgt ccagcacaaa gttacttagt ccccagatgt ctggagaaga 145440
ggaggattct gacttggcag ccaaacttgg aatgtgcaat agagaaatag tacgaagagg 145500
ggctctcatt ctcttctgtg attatgtcgt aagtttgaaa tgcctgtaaa cggggttgag 145560
ggaggtgggg accaggagaa catcctgtgt agatgacact tgcatggacc ctctggaacc 145620
cagaccgccc ggtgtcctgc caagctccat cgaaactaaa tctagaatga atgtttactt 145680
ctgctgtgac atataattgg agaccaggcc tggccttcca gtcactggat tctaagttgg 145740
actgtgagag tttttgcagc tgactcattt atcaaatgcc cggctattgg ctcacgccta 145800
catgatgctg ggtatgtttg ttaatttgag ggaagcaatg gaataataat aactaatgat 145860
ttaaaaaaca aagtaagtgc attgactgta gtggggttct gattttaaat tttttttaaaa 145920
attaatacca ggagcagtgg cttatgccta aattccagca actcgagagg ctgaggtagg 145980
aagatcactt gagcccagga gtttgagaca agcctgggct atggtgtgag acacccatct 146040
ctaaaaaaat aaaaaataaa aaattatcca agtgtggtgg ctcgtgcctg taatcacagc 146100
tctttgagaa gctgagggcg gaggatggct tgagcctggg agttcgagac cagcctggca 146160
acacagagaa accctgcctc taccaaaaaa agaaagagag gaagaaagaa aaattagcct 146220
ggcgtggtgg tgcatgcctg tggtcccagc cacctgagag actgagaagg gaggattgct 146280
tgagcccaga agtttgaggc tgcagtgagc tgtgactgtg tcactgcact ccggcctggg 146340
tgacaaggcg agaccctgc tctaaaataa tttttttaag ttaatttgta gaaaggtgt 146400
tagatgttct ttgtcacatt ttatgatgga ttcctgttta aatgccgttc tctttaaaga 146460
aaaaaaata acttgtggga gttttttaacc ataaaactag catcacatat ttaccatgga 146520
gaatttacaa aaaaacaaat aaacggagga aaataaaacc tcctgtaatc atactactca 146580
gagataactt gctgttagat tttggtctag atttaatact ttttctatat ttatattaaa 146640
```

```
aatatttaaa acatatgcat ttctttgtca caaacatggt atcttataga tactactgtc 146700
acatagcaaa acagtgttaa atattctgaa tcagaaaagg aagccgactc tccaactgaa 146760
agaggtgtta tcctagagac ttttttctggt gatgacaatt tattaatagt cacttttttgc 146820 tttactttct ctattgaagt agttttctta tttttgttcta cttttaagga taatataatt 146880
tataatgctg ttttttcacag aaatataaga aaaagatac taattttata agttaataaa 146940
gtttgatcat cccaaatcca aaaatctgaa atccaaaatg ctccaaattc tgaagctttt 147000
tgagtgctga cattatgttc aaaggaaatg ttcattggaa ggtttcagat tttcggattt 147060
agggagctca acaaataagt ataatgcaca tatttcaaaa cctgaaaaaa atcctaaatt 147120
cagaatactt ctgatcccaa acatttcaga taagggttat tcaacctgta ctgtcagatg 147180
atcccaaatg aaaatatta atcgttaacc aaatatcaag gaattgatca cattttacag 147240
tttctgccta ggattatgaa tcaagatgaa aaggctctgc atgtttaaaa atatatattt 147300 ttatttctt ataaatctta aatatctaca cttaagattt atttgatatg tgggatccat 147360
tcatattttg gattcaacag ttctgtcaaa actgtggcag tgatagggga ttctttttt 147420 cccactgaac tatcacaaaa ttggaaaaag agtaattgga gaacccccact ggcttagccg 147480 gcccgaagcc cgggagaggg caggcagtgc tgtggatggg gtcatcccag cgcaacgctg 147540
cccctgctac ctgcggatct cgctgaggcc tgcctttgtc ctttgacccct tggccatttg 147600 ttagtgtctc tgagagctgg actgctgtac cctacttccc caggggggcct aacttcacac 147660 agcctctgcc gcagtgcgtg gttggaggtg acggccttgg taaatcgagt ttcctacctc 147720
ctcaattatt tgtgctcata cactgtatat ttttagtgag gttatatttt gggatgtgtt 147780
ttctccttct taccctttct ggcctttcta tggcattaat acctggtctc ttcttgtgta 147840
cttgaaaatg aatctctcat catatttttc cttagtgtca gaacctccat gactccgagc 147900
acttaacgtg gctcattgta aatcacattc aagatctgat cagccttttcc cacgagcctc 147960 cagtacagga cttcatcagt gccgttcatc ggaactctgc tgccagcggc ctgttcatcc 148020
aggcaattca gtctcgttgt gaaaaccttt caactgtacg tcttcatcct gccgactatt 148080
gccagttgca gttttccctg ccttaaaaat ggagtattga aattttttaac tttaatttct 148140 gatttgcaaa atagtcatct tttgttctttt tccttcttgc tgttagccaa ccatgctgaa 148200
gaaaactctt cagtgcttgg aggggatcca tctcagccag tcgggagctg tgctcacgct 148260
gtatgtggac aggcttctgt gcaccccttt ccgtgtgctg gctcgcatgg tcgacatcct 148320
tgcttgtcgc cgggtagaaa tgcttctggc tgcaaattta caggtattgg gaagagaaac 148380
cctgatattg atttatattg aaaatttagc aggccaagca aaacaggtgg ctggctttt 148440 cctccgtaag tatggtcttg acatggtcac cgatagaaac atggaaacat ctgcaaactt 148500
gccgttactc gtgtgtccga tctgactgtt tcttgtattt ttttctagtc tgcccttact 148560
aggatgaact gtacacatca gttcatcctt tttaaatgag catgaggtta ttttgggttg 148620
ttaggtgtta caaacacact aatgtgtttt tgtctattag agcagcatgg cccagttgcc 148680
aatggaagaa ctcaacagaa tccaggaata ccttcagagc agcgggctcg ctcagaggta 148740
atgctgaaaa cacaggtcgt ccttgtgtta ggacaaccca ggatataaag gatatagatt 148800
tgtacgggaa taaattcaca ggacaagaaa tcgatgtgcc ttataggtgg gtttactgca 148860
gaagtgccat aatagaacct tcctactttt aaaacaacca gatctcactt tctaaagagt 148920
aaaggatgac cggcaggatc acgtctgtga cgtgagtgga ggcagtttgc actcctggtg 148980
gctgtttgag aggtagcatt tagaatgcct gtattcactg tcctgtgatg agtgggaaaa 149040
```

```
taggttatca ggtttatctt agcaaaatca aagcatgtca tctaattgct aaacaagagt 149100
tggcaaatct gagagacatt actcaatcct tggcatgcag gacttacatc tgcatcctgt 149160
tgccatttta tgtcttcaaa gcatttaatc atttagttgt gtttgcaaag tctttgagaa 149220
gcctttgtca gaaatcccta catctcctat gtgagtgtat ttccatgact gcagaataag 149280
ttaaactttt accttttcc ttcccttgcg gggcggggtg gggggcaggg attgtgtgtg 149340
tgagagggag agagagacag cagagaagga gaatataatt atcatgctgt gtactttgag 149400
ctgaaactgc aaaaaaggaa aaacacacaa aaattattat gcttttcagt ctttagagta 149460
ccttgtctat tatgcttttc agtctttaga gtaccttgtt gatggtgttt ttaaatggga 149520
ttgggcacaa ttaggtggac agtttgggat gattttcag tctgtagggc caagctcttt 149580
tgtaatttgc attatgaagt tgtcactctc atagcagatg gcgggagata aactattatt 149640
acttttgac cctagactta gtcttcagtc cagatgaggg agattaaaag attataaata 149700
tcttgtgcca gatgaggtga ttttattttg aaatgaccat gaattcctat cagttgtctt 149760
actgggatat ttgatagtgg aatttgtgca tttgagtctt agatgatctg ttttacattt 149820
attaagaaag cctttattag ctttttatact gtgtattgcc tgttgcagtg tttgagtata 149880
aatgaaattt ctggaaaata ttaatggagt acaaactgtg atacttaaaa gtaaactagg 149940
gcctgcattt gtatcatgac ctgttttgagt attgatgaga agtagctgt gaagaaaaag 150000
gtttaaacaa gtgtattttc cttaagaag ccactaatag tgcatctcct tagagtgtat 150060
atttctagaa tcctagtgtg cagagtttag actaagacta aaaaaaaaaa aaaacaaatt 150120
atactgtaat ttcattttta tttgtatttt agacaccaaa ggctctattc cctgctggac 150180
aggtttcgtc tctccaccat gcaagactca cttagtccct ctcctccagt ctcttcccac 150240
ccgctggacg gggatgggca cgtgtcactg gaaacagtga gtccggacaa agtaagtgtc 150300
cagcgtgtct gcatgggagg cacagggcgc tgagtgcctc tgtcacctgt ggcagataca 150360
gagagtgcag aggaggtgcc gtggacccaa ggagttctgg cgctcggctc ggctcagtga 150420
agctgtggtt agagacgtgg ggggccatca aggtctgagg gagccaagca gtgctgatgt 150480
gggaccctt tggtaggagt gtggggtgag tagttagtgg gtgaatcaag gaatagtcgg 150540
ccgtggcctg caggcccctg actgcacagg ccttcaagca catgtcaatg ccgttagcct 150600
ccctccatct cctcatacct tctggccacc tgtgagttgc actgccactg ccagccattc 150660
tggtatgttg tcagcacctc cactgctcat acctcatggt tagggaccac ctggagcctt 150720
ggtagagcct tggtagagcc ttggtactct actttcctgg acaaagttca gcttatgaat 150780
atgaattag atttcaaaaa ccagcagccc aagtataaga agcgaaggt tcagtcctgc 150840
cttcttaggc tctattcgct aagcacctgc cctgccctgg ttgctgggga gatgagta 150900
aagcagacaa cccaggagag gatggcaaag gggccgctaa cccttagtgg tttagctata 150960
tttgaaggc ctattggaag ttcaccaggt gaaggggag gctgtgaggg tgcccaggca 151020
ggtaacagaa gtccaaaggg gaaaacctgt ggtgtggtga gccgtatagc cacagcctgc 151080
cggccggcag ccctctcagc ctagtgcggt gttcccaagc actggcctag gcctgtagct 151140
ccagggatgt gaagtcccct tgaacgccgc ccatcatgtt ccccttatcc atttttttct 151200
tcccaggact ggtacgttca tcttgtcaaa tcccagtgtt ggaccaggtc agattctgca 151260
ctgctggaag gtgcagagct ggtgaatcgg attcctgctg aagatatgaa tgccttcatg 151320
atgaactcgg tacggggga gcagtggagg caaggaatcc tcagcttttc ttgtgacttc 151380
```

```
caagtgggat tgtctcatc atcatgtgac ccacttgttg acaacacatg ttggggactc    151440
cagtctgggc agggacggga tgtcggagag actccactct gaatgggcc gggaagtggg    151500 gaggactcca tttcagatgg ggtcgggaca tggggggttat gctgatcgag acagaaaagc   151560
acattgtttc agccacatta gaatccacgg aggtgttgtt ttgaaatcca gctggcccca   151620
aggctgggtg tatggtttgg gatgagaact atctggcctc cactggagga acaaacacag   151680
gatgttatca tctaagctcc atggccaaga cagaatggaa gtcaaggttg cgtatttgcc   151740
gtagacttca acacagtgtc gtaatgcgtg acgtcaataa cttgtttcta gtgtcttgga   151800
agttgatctt tagtcgtaaa agagacccttt ggatgcagcg agatttcctc tactcacacc   151860
tctgttagat gtagtgaggt tcttcacccc ccaaccccag atgtcagagg gcaccctgcg   151920
cagagctagg aggccatgca aagccttggt gtccctgtcc ctcacccgtg ggcaggtcct   151980
gtgagcagtg ggggggccac ctcttgggta tggtgcagcc atggcccaag cagggcttct   152040
tctcagacct actaggacgg gagaaacctc ctggtgcttt agccctgcgt tgatatgcag   152100
caaatgggag ggaagtgggc acctggggagg acaaatgcct gtagaggccg ggagtgacgg   152160
caggtgttca tgaaaagaga ccttgtgggg agggcaacac aacagtgtgt tctgatgtac   152220
tgaagagctc aactgaaaac aacaggagaa ttagcccaaa atccatttac taaaattgtt   152280 tatcttttt ttttttttg agacaaagtc tcgctgttgt ccccaggct ggagtgcaat   152340 ggcgctatct tggctcactg caacctccgc ctcctgggtt catacgattc tcctgcctca   152400
gcctcccaaa tagctggtat taacaggcat gcaccaccac gcccggctaa ttttttgtatt   152460 tttagtagag acgggattttc accatgttgg ccaggctggt ctcaaactcc tgacctcagg   152520
tgatccgccc acctcggcct cccaaagtgc tgggattata ggcctgagcc accacgcccg   152580
gcctaaaatt gtttatctta agattcatgc agtgaaagct aacttactga gtgataaatt   152640
tgcttagtga tctgtttatt aggttttcca aatttgctaa ttgggctttg aacagctgta   152700
aaagttctga ctgtaaaaga aagcttcaac ttttggcatt catgatgctt ttctgagtat   152760
taaactaaga tagatgtttt acctgaagga tcggccacca atctttaaat ggctaaacaa   152820
aagggttgct aaaacataat ccaaattgac ataagaaata ccattttttcc aaccaaaatt   152880 ttggcattca tatggctact tttacgtatt tcagctgcat ttgaacatct ttttcaaact   152940
ttagggtggt tggtgtatca ctgaggtctt ggatgacact ttagctttga ttttgtttt   153000 atgaattaaa attgtcatac caaaatttt atttcaagca aatccaagag cataaaaaat   153060
taaaatatta cttaaaatac taagagagaa cagatatata ttttactaag catatgttga   153120
atgaaattgt tcaaatattt ataacaggca tagagtagaa ttttcttaaa aatatttttg   153180
atggtatacc aatttgtatt ttctcagaaa catttgcctt attcttttt ctgttgtgtt   153240 tttcttacct gattgaaagc tcataatctg ttgttattgt ttgttaacct ttaatgctct   153300
gatttcagga gttcaaccta agcctgctag ctccatgctt aagcctaggg atgagtgaaa   153360
tttctggtgg ccagaagagt gccctttttg aagcagcccg tgaggtgact ctggcccgtg   153420
tgagcggcac cgtgcagcag ctccctgctg tccatcatgt cttccagccc gagctgcctg   153480
cagagccggc ggcctactgg agcaagttga atgatctgtt tggtaattaa aattaaaatt   153540
tatcttattt ttaaaagca ttccagggcc agtatagtac tttgcaccaa gtaaatgtac   153600
aataaaggca gtggatctaa tacattgaaa gcgtttacag aggtagctaa agagcagcac   153660
gggtgtcctc ggctcagaat ttcttcctgt gtgtttgcca ctttgccatt cattgacatg   153720
gtcatggaca tagggctcta agcccttgag gaaggctggg ccagacctca ggggagatgc   153780
```

```
agccccaaac cacgtgcagt cctgtggacg gatgtgtaga gtgccactg aggaacaatg   153840 tcttgagctt tcatcagatt ctcagagaat tgcttgactg cctttcgaag ttgatgcatc   153900
tgtgctcacg tttgcaccca cccacgaggt ccttctgttt caggggatgc tgcactgtat   153960
cagtccctgc ccactctggc ccgggccctg gcacagtacc tggtggtggt ctccaaactg   154020
cccagtcatt tgcaccttcc tcctgagaaa gagaaggaca ttgtgaaatt cgtggtggca   154080
acccttgagg taagaggcag ctcgggagct cagtgttgct gtggggaggg ggcatggggc   154140
tgacactgaa gagggtaaag cagttttatt tgaaaagcaa gatctctgac cagtccagtc   154200
acttttccat ctcagcctgg cagtaagtct tgtcaccgtc aagttattgt agccatcctt   154260
caccctcacc tcgccactcc tcatggtggc ctgtgaggtc agccaggtcc ccttctcatc   154320
tgcacctacc atgttaggtg gatcctaatt ttagagacat gaaaaataat catctggaag   154380
tactttatgt cttaagttgg cctggacatg tcagccaagg aatacttact tggtttgtgt   154440
tagtgcttgt aattcgcccc cagaatgtgt acacgttctg gatgcattaa agtctggcct   154500
gtatccttaa agggccatcg ctgtgctgcc tgccctcagc aaggacacac tttgcagacc   154560
cacagaggct ccgcctccac ctcacaccaa agaaagggag gagtccaaag ggcatcagtg   154620
ccattactca caaaatgata aatacaccct tattctgaac cacgtggagt catatggttt   154680
gtgatccctg tccttcaggt ttcagcttag tggggaagtg ggaaagtcag cgtgtgatca   154740
cagcacaggg tgattgctgc tgattatatt atgtgcctgc tgtatgcagg atgaaatact   154800
ttatatgcgt catcttattt gactctcaca accccctgtg agataggctc tgttactccc   154860
atttgacagg tgaggaaagc aaggcttaga gaatttcagt gacttgccca ggtcctctga   154920
gctaggaagt agccattctg gcatttgaac ccaaggcctg ctatccctag aacccacgct   154980
ctcaaattca acctatgaca gaggcaagcc ctggtgctgt gggagcccca aggaagagcc   155040
tctggcctgg tggccacgta gcccaggaga gatttctaca ggagcccaca gcgctgaagg   155100
agagagaggc agcagagtaa gggggctttg tggcagagag gggactggca ctttggggaa   155160
taggtgggtc aggactgaat gtaatggagc catgtcagag ctgtccttct ggaagggcaa   155220
gggcacctgg acgcgctgcc cctcagtgct ttggacggtt ccacaactgt gattcacacg   155280
gcttccccaa acgaaggtac acgagtgggc attctgtgac tcggtacttc cctttaggcc   155340
ctgtcctggc atttgatcca tgagcagatc ccgctgagtc tggatctcca ggcagggctg   155400
gactgctgct gcctggccct gcagctgcct ggcctctgga gcgtggtctc ctccacagag   155460
tttgtgaccc acgcctgctc cctcatctac tgtgtgcact tcatcctgga ggccggtgag   155520
tccccgtcca tgaacggtgg gttcctatca tagttcctgt ctgcttcacc atgttttat   155580 tttgtgctgc ctgtttgcca ggtactaagc taggaattgg ggatggagag gtagataaaa   155640
tatgcatcag gaagggctgg gccccatctc ttactctcca atatattgga gtctacactg   155700
gaatttaact ggaatttgct ttttagtca ttttatttag attttgaagt ttcagctttc   155760
atcaaaaata cctctaaact ttatgtctct gtgatctttg gtcttagctg ttttatgtat   155820
ttagtcttat atgatcataa gattaataac attacattca gaagattatt tgttttctgt   155880
cagagttaaa atgtttgttt ttatactgca ttgtaatatt aacgtactgt aaaataaaag   155940
tggcttgttc ttttcaagga acagtatcct caacaagggt cattagccac aattttaaa   156000 aaattggacg tcatagttta catgttagag ggcgttttga agctttgtat ttttaaatta   156060
aatgttatag agtgatgttt tcatgtttca taattgtttt catctgtgca tttgtagcca   156120
```

```
acttgaaaac aaagatccag ggattactac ttaaaagcca gacttcttgg aggttatagt   156180
gatgattttg atagtatctt gagccgtctc ataataacct cagggtgaga gatggccaac   156240
aggagacagt cgagggactt agaaatctga atgaaatctg aagttcaaat cttcagacat   156300
ataccactaa ccaagagatt ggtacctcag tctagtattg tctgtttgtc taaaattggt   156360
tctaaggaat ctaggctagt ctgtctatcc ctttcaactt ttgtgaggct gcacaaatgt   156420
aaaatgttga ataaaaagca ctgatggaag tgtgtagaaa ttcttctctt tgttctgttg   156480
taattttagt tgcagtgcag cctggagagc agcttcttag tccagaaaga aggacaaata   156540
ccccaaaagc catcagcgag gaggaggagg aagtagatcc aaacacacag agtaagtctc   156600
aggacccatt tttttcttac atgttgttcc tccaggactt aaaaatcatt cacagagacg   156660
tgcaccgcgg tgagtgtgga ctcctggaag cgcaccgtag ctccgctgtg tcctgctgct   156720
cctccctagc tgtcagggag gctgtagtcc attgctttgc cagctctttt gtttccgagt   156780
gaacacctta tccgtacaca tgcggctgtc tctgacccta cagaccagct gggatgccac   156840
tgggggagcg ctcccttccc cccgcacttc ccacactctg cagttattct gagatccttg   156900
agggcaggga acaggtttgt cttctttgtg ttctcagaaa ttaatgctcg gcctctggtc   156960
agcaagcaac aaccttttgt tgagtgataa tgaataaata aatgtttccc acatgagtat   157020
tcagtaacct cagtgtcagg ttcagccatc tgttttggtg atatttaaa agaaaattcc   157080 gcttttccta cagaaaaaaa aaaaaatcca atcccagtg atttaagcca gttatagact   157140
tagacatata ctacggcttt tcatgcactt tcctcccaat tctagagtag gtattttact   157200
aggaaaatgg tggcagtgcc tgttgggagg aagattcttt ggccaagtgt cttttgttct   157260
tgccagggcc cctaggctgc tggggtgctt cagcttcttt agcccagtgt ctggtgggga   157320
atggcccctg ttgcctgtcc cacagaggtg ggggtgcctc acctggagcc tgtccacaca   157380
ttttacacag cacgcttacc tggagcatca ggcatctttt ccatgctctg tggctcagga   157440
aacacgcctt ttcaatcatg agtgcaccag tgctttggg cttttttctcc ccgcttttgt   157500 gcaatcctgg ttgtggatgg agttttcctg tctttagtct tctgcatagt acttttctct   157560
tctggttccc ggttcaaggt tttgtaatta gagaatgacc cagaagcaat ggcattttaa   157620
tgcacagcca aggacttctc tgaatttgta tctcaaacct ctgtgggtcc ttcaggcttc   157680
agtttgtgat ttcatgattt cttgttgcta cctaaggaat atgaaaacac ccacctcccct   157740 actctgcatc ttccagccga gtggcacctc aggctgtgga tcctgtgctt ctgtggtgag   157800
gataagaata gtgccaaccg tgtggattga aatcaatcag ttaatccctc catgtaaagc   157860
acctggaacg gatgacagtc ttgttatgaa tactcaacaa atgctatcat gattttagt   157920 tagatttcca ttgctttaaa acagttgaga catcttggcg gtttgagtta gagcaacggg   157980
ccctgaagtg ggttctgttt gggtgaagat gattatgctt attccccatg gccctcttta   158040
ggcaagagtg ggaagctttc tttgttttt taatcacctc gataggacgt tacttcttaa   158100
aggtcatcca ataaatatta ataggccggg cgcggtggct cacgcctgta atcccagcac   158160
tttgggaggc cgaggcgggc ggatcacgag gtcaggagat cgagaccatc ccagctaaaa   158220
cggtgaaacc ccgtctctac taaaaataca aaaaattagc cgggcgtagt ggcgggcgcc   158280
tgtagtccca gctacttggg aggctgaggc aggagaatgg cgtgaacccg ggaggcggag   158340
cttgcagtga gccgagatcc cgccactgca ctccagcctg ggcgacagag caagactccg   158400
tctcaaaaaa aaaaaaaaat attaataaag ccaactcgtt agcgtggggc ttaattgctt   158460
aagtccaatg agaagtcctt ctctatccta ggaagttgcc caaactgtag aatctcgtgg   158520
```

```
cctgtgggta atagccacgt aatacacact cactgcctca acaaatcata ttttagtagg 158580
tatgatattc tagactcaag acaccattct gtggatcttc ccaagggtgt gaagtgtcca 158640
cagcgtctgc cttgggagtt tccatgccca ccagaaccat gccccaagcc cctcaagcac 158700
tctgacctag gaaagccagt gaagcaagga tgacaacatg gcccttgat actagctgag 158760
ggacagacac aggtcctggg agaccagaga aagacgaggg cagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgccccac tggtgagtct gctcgttcct tgcagaagac 159360
caagtacggt gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg gttttctaa 159540
aatgaactga ggcccacat ccctaagaga ttagtgttag acctgattct agagcaacta 159600
gaccactttg cttaatagca gaccagaaac cacacccct cgagtgagtg agatttcct 159660
ttggagataa ttcatgtttt tctacacagt tttgcagttg tcttcagaat tggtttaaag 159720
taggtgttat tgccaggcgc agtagctcat gcctgtaatc ccagcacttt gggaagccaa 159780
ggtgggcgga tcacttgagg tcaggatttc gagaccagcc tggccaacat ggtgaaaccc 159840
catctctact aaaaatataa aaattagcca ggtgtggtgg tgtacgcctg taatcccagc 159900
tactcaggag actgagacag gagaatcgct tgaacccagg aggcgaaggt tgcagtaagc 159960
cgagatcgcg ccactgcact ctagcctggg caacagagca agactccgtc tcaaaaaaaa 160020
aaaaggtagg tgttattgat cagaacccct gtttcagata acatgaggag cttagcttga 160080
ggagagtgag ggttgatgga gggggactga cttctgccca gtgaaatggc atcatctccc 160140
accagcccgc tgaaataaga tgatggggcc tgttccttag ggcctgcagc atcctcaggc 160200
aggaaagaaa ggccgacctg gcagggtgtg agccagcagg tgtaggtcag ggagaatgga 160260
gccaggtccc agggaagagg cttgtggctg cctgagaagg gtgcgtgcct gcctgtgtgt 160320
gtgtgtgcac gtgtgtgtat gtatgctgga gagtctaggg aggcttgctc caaggacgca 160380
gtattgtttg atcctgagag ataaggattc tgccgcaggg aatgaaggta ttccagatgg 160440
cgggcttatt ccgaagaaga ggccagtgcc tggcggtgct ggaagcagtt gcagaacagg 160500
gagttgtagg cttttcctggg aagagagcag cagggggtgct ggagaagcag gccacacttg 160560
ctgcatgggg ttgctctcgg ccccactctt ggtgcacagc gagtcactgt gggttcatta 160620
gcatctggtt atgagacagt aactgctcct ttggagggggc tcgtgagac catgcaggag 160680
ggcacggtct tgaggtcatg ccgtccagag cacacctgag gataggccag gacgggctgc 160740
acgctgtagg taaaattcct ccagcaagct cttcactggc attgaggagt tccctgagtg 160800
cggtcatctg gaaggcagct gtaacaggca ctgcagtctc tccctgggtg ggtaccagag 160860
```

```
aggagcatag gggagcataa ccgatttaaa gagagggctt tcctgtggtg aggtaagaga 160920
ttagctggtc attatcatag agccccctct gcctttgtgc agatgggctg tgggaatcct 160980
ggggttccgt tgggtccttt gtcacctcac tgaaggcatg taagctgagc tggccagacc 161040
gtgagctgat cctgccactt gaacagcatc aagcctgcct ctggattctt ctgtgcatgg 161100
cacttgtctg agcacctcac gcacagagaa ctggacttca gagtttacag aaataagctg 161160
tatggttcat tttcatgcct gcttgccaat aaacatatct gagctgaacc tcattgaacg 161220
cctgccttta ttctagcaca gcacctgctg tttgtgggcg aggggtgctg tctctaactc 161280
ctgcctgctt ctcccagcac tccctgagtg gggtgtgcca gcagcctcag gatgaggaca 161340
ggaagtggga gggcagagca gatttgggag ggccacttga tggggaagga agtcccagga 161400
agcagttgga gctgttttct gggggagaag gtgccagctc tgggacagtg ttggggtagt 161460
gaggagggag cccagtggag agaagtcggg cttcctgctt cctcacagta tgtctgtcct 161520
gactcaactc ggatgatgtc acttcctttt catcttctca ggtgtggaag cttggatggt 161580
cacccaaacc ggggaggggat tttggcacag cattccctga gatcccgtg gagttcctcc 161640
aggaaaagga agtctttaag gagttcatct accgcatcaa cacactaggt actcttgggg 161700
cctctccttc aggtcaccat tgtcggacat ctaccgggag gaaatccaga gcccccagta 161760
ctgggatctt ctcatttgac tccagaaaag atttaagcat gataataata caaacctatg 161820
tgaatacatt ttgcagtgtt ggcaaaactc cttttatact gagaaaatag atcccagttc 161880
ctgtgttttg tggcttgaat cccagctttg tgtattccgg gcttgtttga agtcaggaaa 161940
ggttcatgtg tagtggacaa cgtgagacca aattctgcct tagattttgc atttaggcta 162000
aacagtggca gcacttgtct cagaatgttt tcttgtgttc accagtctga tcctgttgtg 162060
tctcagtggt ccattttctc atatgggaac aagcagacgg gagcagatgg agtcaggttt 162120
cttggcactc gccttcccca gagcctagag gcagcatggg gagaaagcag gcttggggct 162180
cagacagtcc tggtctgctt ccagcccctcc tacctgagca gcgcagggca agtccgtcta 162240
acctctagag accctcagtt ttgtcatatg taaaatgggg gtcgtgtcta tttcatagaa 162300
ttgttgcaga tttagaaatt acatttctaa acaaatgtta ccccttattt ctaaataagt 162360
gtctaaatga ataagtcacc acttttgccc ctatttgatg gcaagaggtg tgatcttgtg 162420
gtgggactgt aatcagtcag ttctcagtga ctgtgccctg ctgtggtgtt tcctggaatg 162480
ttcctgtctt gtcctagaaa gtctggcagg ggcaccctga ctccactgtc cagtcctctc 162540
cccagtccct cgggcttctg cagatttgag gcttgtttgg atcccagaag gttgtggcag 162600
gagacacctt gcctctactt tcccctttat aattcaatgt ccaaagagag ccctgagcag 162660
gtacctcacg ccagctgcct cacggagctc ctcctcttcc tggctgtgag gatcggtatc 162720
agtggcctcc tgctctctcc cccttgccta acacgagcac ctttgcttac ttgggtgccc 162780
ttgctcttga actgcccatc ggacgtgcgt gacccaagac tgtgccgcag tccttgcctt 162840
gtctgtgctc attttctttg ttcattttt tccctgtaac gtaaattgtt atatttgtct 162900
gtatctgtgt ctgaatcagt cctgcacgct ctccttctct ctgtctcttg ttctttcttt 162960
accccgttta tcacggggac cccgatgtcc attgctctag ttctcctgtc ctaagcaccc 163020
catcccgtct ctctggcctt accacaagtg gcgtggctgc ctcagacatc atgatgggga 163080
catgaagcac agctgtcaga aacaactgtt cgttagatac actcgaatgc agctcatcaa 163140
tagggatgga gggtctgtcg gatgtatttt cactgaatcc ccgttcctac cttgatacac 163200
tcttttttaat ctattcttct agacaggtca gaggaaccat tactttgact tttaaatttt 163260
```

```
tagcagcttt attgaggtag aattcacata ctacagattt cacccactct aagcggacag 163320
cttggtggcc attagttta tccacagagt tgtgcagcca gctgcacagt ctcagggctg 163380
gactccaggg aagattttag cccatttagt gagtggggca gaagtggccc tggccctgca 163440
cgaggttgcc tgcatgggcg tccctgccct gtccctgtgt ctgctccact gggggttgac 163500
caggctgcca gggccgactt gggcctgtgc cacctgcctc tcatgtgtct cggacagtgc 163560
agccgatgtc tatacttcgg tttcctcaat gatgaaatgg aggggatagt gttccccgca 163620
tcatagaact gtgtgaggtt taagggactc actgcccttg gcgtggagcc ttctccaggg 163680
gccgtgctgt gtcggcgtag ctgtcagctc tccgttacag gcttgagaag ggttgacact 163740
ctctcatgta acatttatat ttctaggctg gaccagtcgt actcagtttg aagaaacttg 163800
ggccaccctc cttggtgtcc tggtgacgca gcccctcgtg atggagcagg aggagagccc 163860
accagaagta aggccacacc ctgtgctggt tggcacatgg gcagttatgg ccgcttgcag 163920
gcctttggtg gggaataaaa taaggcagca agctggtgtt cttttttct cttaccttat 163980 ttttgaaaga gtagctgaat ggtgtcttga ctgatattcc agagcaggga caaagcctgc 164040
tgaggtctgg gggctgcgat taccaatggc tggaatgcat tttattacgg tgcattccat 164100
gttaaggatc aatacgattg tgccctttct ggaaaatatc ttttagttta tcaatattca 164160
gaggagtgta ggttgaatta aaatgaaaag gcactttata aaggccatga gtagtacctg 164220
gtttcatttt tctaatgtct tgcagagatt ttatcaggct tcttgaagtg ttcacgtaca 164280
ttacgctaac acgatattaa taataactgt gctctggtac agcggagcca gcagaatggg 164340
aagttgtgga atgcaggccc ttgattctga tagaaggtgt ggtttgaact cacagaaatg 164400
acagtttgga gggtagacat atgtcacaag tcatcaagat tgtctttaaa ttcatgcata 164460
gaagctaaca gggtgtcata agcaaggcct gtaaaatgta tgagggaatt caaagataat 164520
ttattaaaaa gtaattcatg tttggagttt tgtgcccaaa ggagtccttg atttgaaaaa 164580
tgggcttttg cccatcagat tgtttcaggg cccgtgtgtg cggaggccct gccttgtgcc 164640
ccgtgagctc agcctgacag aaatcctttg gtagcactta aggctcctct tcctcccatt 164700
gaggcaggga agactctggg ttctgcaggc agaggtggtt gtgggtgtct tgctgctctt 164760
gttgacatgt gggctctcct tccaggaaga cacagagagg acccagatca acgtcctggc 164820
cgtgcaggcc atcacctcac tggtgctcag tgcaatgact gtgcctgtgg ccggcaaccc 164880
agctgtaagc tgcttggagc agcagccccg gaacaagcct ctgaaagctc tcgacaccag 164940
gtttgcttga gttcccacgt gtctctggga catagcaggt gctggggaca gtgggttccc 165000
cgctgaagcg tccagcagct tcaaccaggc cgttttcctt cattgctaga attgaaaaca 165060
ccgtccgtgt ggcctgtgca ggagatgcag acccaaaggt ggcctcctgg tcagtgagaa 165120
gctggaaacg tgacaggaac tgacgtgggg ttattgagca tttagggaa gacgttagca 165180 gagcaggaat gagcaggcaa ctagtagaac acccacttaa gggctcacgg acaggtgctc 165240
acttaggaag tgagtttcat ttggtattac accaggttcc tttaggcaaa gcggagggaa 165300
agttctggtg ttttttcactt gtaagatttt gaaggaaaca aaacactctt tacctttttt 165360
ctaaaatgta ggtttgggag gaagctgagc attatcagag ggattgtgga gcaagagatt 165420
caagcaatgg tttcaaagag agagaatatt gccacccatc atttatatca ggcatgggat 165480
cctgtccctt ctctgtctcc ggctactaca ggtacctgag ggaaagggtg cggggagcg 165540 gttgtacttg ggctagaatg agagaagact ggcatgctca ccacaccagt gatgcgggaa 165600
```

```
gacctgagtg tggtctgagt tggaggctgt ggtgctaaat acgctgcccc tttcataagc   165660
aggagtctta gtcaggccca gggaggaagt aaaatctgga aatgaatgag aagcattctc   165720
tcctgccagt caagaaatga gaagcgaaag aattctcacg ggctgtaaga ccagcaggat   165780
ttaaaagttg aattagttgc ttatgttaag aactcaacca agttcatcta cacaagctga   165840
atctccagct tttcctaaga aaccatgtgt ggcagtggct gcagggcagg gcacagctgg   165900
gcctgagcac cccgctccct gcacctctcc cctccctggg ccctgcctgt cactgcccac   165960
tctcccacca agccttccgg ttgtgtgcct gccctatcac aggcatcgga gcttgtcacc   166020
tggtttaaaa gaagagagtt gtgtgggdat ttgggatgca cgttttcac tcaaaagtat   166080
tttagcgtag agctctgtga ttccgtagct atttaggagt ttaagcacct tgaaggcttt   166140
aattgcagaa agttctatgt ggacgtgcaa tgtgttatac gcagtgtcta tgagactcaa   166200
atgtttatta gggcgttgaa gtaaactgag cacttggagg gccatggatc cagccttcaa   166260
ggagctcata agtcaggagg acccaggagc aatgacctgt catagaaggc agaaaagagg   166320
ggcacagagg tgggtgggag gcatacacag gcagctcctg gagctccaag gggagcaagt   166380
gcttccaggg aagggggcgt ggaggcccct ttggaggagg caagttgatc tggggtctgg   166440
cagagggtta gctggggaca tttagcggga ggctggtgcc cgggaattgg ggggatgccc   166500
agcagaaaga catgaggagg ctggcctggg gcgtgggggg gtgtgaaagg ttaagtgggg   166560
gcattatcct gctcccgctc ctgccggctg tatctggtca gctgggcac cgaggtgggg   166620
ttctggaagg cactgttcac caaaatgctt atctgggtcc cccagagagc ttgcctgcct   166680
ggactgtcgg ctcgcctgca actgctgact cctaagcttt tgcagctcag cccacaacca   166740
gttcctattc acagaggtgg gagctgaggg gtgacaagtg actgctgcag tcttatttgt   166800
catagagaaa aagtgacaga gtccagcttg cccactggcc ctgccagctt aactggttat   166860
aaagtgacaa atccccaaga cccacagggc tctgcacaac ctgggccctc ctgccagtgg   166920
cggcgagggc aggtggctca cggctgggtg cctgtctggg caggagctgg gctggtatgg   166980
ggtgggcctg cggccctgcc cccctgtgca gatcaagact cagggtgctg tgttcacag   167040
gtgccctcat cagccacgag aagctgctgc tacagatcaa ccccgagcgg gagctgggga   167100
gcatgagcta caaactcggc caggtcagtc tcgcgccccc gccgcctggc ctctgtccgt   167160
ttctgtcctc agactttggc gcttgacaca cccaggagaa aagctcagtg cacttttaa   167220
atgaaaggaa gttttccttt tttttaaaaa aaaatttaat gttcattgtt tttatctgtt   167280
ttattcctag gtcccgcaag cagaggaagc attagttttg tttttattta tgttctgtat   167340
tccagaaagt agttaagaga cctcacatgt agcgatagag atgtgtgtaa gagacagtga   167400
gagggcgtga cttggactta agcaaggacc gtgagacaca aaagggggg tgaggacaga   167460
gtggagtcag ctgaaatgct caggaggaag tagacgccat gaagggccat ggtatggggg   167520
gccgcaggcg tggccgtgag tgtccctggg gccagctctt gggggctcc ctgagtgtcc   167580
ctgtccctgt ggccagttct gggtgggagc ccgtgtgca ggcagacagc tcggccactt   167640
cctagcaggt cacattggtc tgtgcttctg tttcctcctc agataagtga agggattcaa   167700
gggtctgggt gtggtggcta acacctgtaa tctataacat tttaggagc tgaggcagga   167760
ggcttacctg agctcaggag gttgaggctg cagtgagcca tgattgcacc actgcactcc   167820
agcctgggca acagaccagt actctgtccc ttaaaaaaaa atgtaaacag aaacgtaggg   167880
ccatttgcat atgatggcac atggcgtgga gccctacagg tgtatgctgg gcggggcccg   167940
gctgtgctgg ccgacttgca cctttcctc caccccggtg ctgtgtcttt cgctcaccgg   168000
```

```
gttcctgatt tagtgaaagc agttgtgcag gacagttctc tttgtagctt ttgtttctgt 168060
ggaaatgggt cagaatatgg tgtttagaaa cacttatgag ctctgagagt ttcctcttct 168120
gagttcctgg cctgcagcct tcacagcaga aaccctgtga tgtcacaagc ctgtttctgt 168180
tccctgctct ctgcctgtac tgtcctgttt tgtgcctgcc ggtttcagtg acaggaagca 168240
gggagctact ggaccagcct gtattttct agacatagtt ggaaaaagaa gtcccactct 168300
tctgtccttt cacctttgac agatgtttcc accccaagat aagtgaaaat gaccaatagg 168360
atgcactgta tttttcatga aagtgtttct gaagggcagg ctgagagtga gaggcctggg 168420
gctcactggg tgcctctggc cttgtcctgg gcccagggac actggtctgt gcccgaggta 168480
ttccctatcc ccccaacccc gctgcatttg ccacatcct tcaatgtttg cgttgtgtcc 168540
agcgtccgca aaccaactgt catgggatca tactggggct gaagtacggt cccacccctg 168600
ccctgtctgg ggctgaagta cagtgccacc cctgccctgt ctgggctga aggacagtgc 168660
cacccctgcc ctgtctgggg ctgaagtaca gtgccacccc tgccctgtct ggggctgaag 168720
gacagtgcca ccccttccct gtctggggct gaaggacagt gccacccctg ccctgtctgg 168780
ggctgaagga cagtgccacc cctgccctgt ctggggctga aggacagtgc cacccctgcc 168840
ctgtctgggg ctgaaggaca gtgccacccc tgccctgtct ggggctgaag acagtgcca 168900
ccctgccct gtctggggct gaaggacagt gccacccctg ccctgtctgg ggctgaagga 168960
cagtgccacc cctgccctgt ctggggctga aggacagtgc cacccctgcc ctgtctgggg 169020
ctgaaggaca gtgccacccc tgccctgtct ggggctgaag acagtgcca ccctgccct 169080
gtctggggct gaaggacagt gccacccctg ccctgtctgg ggctgaagga cagtgccacc 169140
cctgccctgt ctggggctga aggacagtgc cacccctgcc ctgtctgggg ctgaaggaca 169200
gtgccacccc tgccctgtct gggatgttta gcccctagat gccactggac tgagccgcta 169260
cttgcttttg ggaaagaggg gtggggtta ggggtctggg cgaggggagt gcaggggctc 169320
ctccttggcc tgagagctgt tcatacagac tcctcgccca ctccctgcag ggtgctgggt 169380
cccaggggg aaatggccct tggtgccaag aacgtgagtt ggggctagtg ccagtgatga 169440
tggagaacag ctttttatgg gcacacagcc cacagcactg tgccaagtgc tcgaggcttc 169500
ccgagaacca ggcagaaagg aggacagtcg aggtgtgctg actgcgtggt ggctgcgtga 169560
tctagagcgc gggtcacaaa ggcgcgaggg agctctggcc ttgggtttac cgcaatgact 169620
gccagtgcgg gagactggaa aaggaatctc acgtattggt tccgtgtttt ggggactcca 169680
ttcagatgtc acttaggagt gaaagcatcc cttcgtagag cctctttctg tgtcaccctc 169740
ctcagctgct cctggggttg actggcccct gattcatgcc tttagcatgt gctggagctt 169800
cccagcagct gtccagcccc tgccccaccc tctctgtggg ctcccttgcc cgtaacctgg 169860
ggtgtctgaa cgaccccttgc taagggcag actgttagac ggtaggcatg tgctgagtcc 169920
cagtggccac acccacccac caggagcctg gcactgtggc cgcagcactg agcagtgccc 169980
cgtttctgtg gcaggtgtcc atacactccg tgtggctggg aacagcatc acacccctga 170040
gggaggagga atgggacgag gaagaggagg aggaggccga cgcccctgca ccttcgtcac 170100
cacccacgtc tccagtcaac tccaggtttt ccaatggcct ttttcttttt aacagaaatt 170160
tgaaatttct tatcagtcat ttgatttgtt tgaggtgctt cttgaaatga gcctctcatc 170220
tcatgtactg gaaaatacc catctcgcat attccacagg aaacaccggg ctggagttga 170280
catccactcc tgttcgcagt ttttgcttga gttgtacagc cgctggatcc tgccgtccag 170340
```

```
ctcagccagg aggaccccgg ccatcctgat cagtgaggtg gtcagatccg taagtgagcc   170400
ttcccattcc cctcacacct gcacgtgcca cacgcaccac acacgccaca caccccacac   170460
acacacaccg cccacacaca tgccacttgc acacacaccc ctcatgcatg caacacacac   170520
acaggccaca cgcaccatag acaccacaca cacatgccac atgcacacac atacacggca   170580
tgcaccatac acacaacaca cacagcacac atgccacaca cacacgccac accacatgca   170640
ccacacacat gccacatgca cacacactcc acatgcatgc accacacaca cacacacaca   170700
ccacacacac cacatgcacc acaccacaca ggttacatgc acacaacaca cacatgccac   170760
gtgcacacac cccacacacc acatgtatgt gccacacaca gcacacaacc acacacatgc   170820
accacacaca tgccacatgt gcatgcacca gacacatggc acacactaca cacacgccac   170880
gtgcacacac cccacacaca tgtacgcacc acacacatgc cacacacaca tgcaccacac   170940
acatgccaca tgtacacaca tgtatataca caccccacac cacacacaca ccacttgcac   171000
accacgcaca cacaccacat gcgcacacac acccacata cgccacatgt acacaccata   171060
cacacaccat acatgcacca cgtgtaccac gcacccacac agacacagca cacgcataca   171120
ccacacacac acgcacacat gcgtcccgca cagtaatgtc tcttgggtgt aagaacacga   171180
cttgccagta gtagcgttct ggatgcgttg cctggattct aacagcgcga ttctcccctt   171240
gccctcctgg ttttccacat ctccagcttc tagtggtctc agacttgttc accgagcgca   171300
accagtttga gctgatgtat gtgacgctga cagaactgcg aagggtgcac ccttcagaag   171360
acgagatcct cgctcagtac ctggtgcctg ccacctgcaa ggcagctgcc gtccttggga   171420
tggtaagtga caggtggcac agaggtttct gtgctgaagc cacggggggcc catctgcctt   171480 gggacctggt gttggccaga ggtgccgggt gcggctgcct ccttccaaga gttgacccga   171540
accggactcc acgcccacg tgagctgcag tgcttctcag atggaggggg ttcagcgacg   171600
gtcagtgcca ttcacaggtc actgtgatgt gggttgtggc ggccaagcca tggtttgggg   171660
tcccgtatcc ctgggcttat gacatcattg tagtagccca tccccacaga accacggtgt   171720
gtggtggcgc tgaggcatcg tagatggtgg aaatgctact ggcttcccca tgctctgccc   171780
tgaggcctga ctgcctcact cccccttctca gttatgttcc aggcccccgg agcttcctgg   171840
ctggacagct tctctcctgg gggccgtttt gtcacagtga ccctgtgttt ctagtcccaa   171900
atctgggtgc tatagtctct ttttagcgtg gtggttgtct tagtctttt tggctgctac   171960 cacaagttac cttagactgg gtaatttata aacagtggaa atttacttct caccgttctg   172020
ggggctggaa gttttcatgg tcaaggtgcc agcagatttg gtgtgtgatg agggctgctc   172080
tctgcttcat agatggcatc ttctggctgg gtcctcacgg tggaaggagt gaacaagctc   172140
cctcaggcct tttagaaggg ccccaatcca caagggctct cccatcatga cctcatcacc   172200
tcccaaggcc ccaccttctt gtactgtggc actgcaaatt aggtgtcagt gtaggagttt   172260
caggagggat agaaacattc agaccatccc agcggtcaag tgttcatcct cttgagttcc   172320
tccttattct gcttctggtt tatcaggatt cagccagtgc agcatggtac ctgtattctg   172380
tggcacatca ccacatggta tttgccaagt atccatcacc tgcacacgtg aaatcattgc   172440
ccgtgggtcc cgacatctgg cgaagcatat tcaaggatgg cagaactgtc agagctggca   172500
cctctggttc cttgtcatgt ggcattacct agtaatccat tttatgatag caatggaaac   172560
tcatttcttc aacaaacacc tgagtggctg ccgtgtgcca gccgtctggg gcccttggtg   172620
agaatggcat ggtggtgccc atcagggcct gcctagcccg tgctctggac gggctcctgt   172680
gtgtcaggaa cgacaatgct gtcatgacgg tgaatgattt tttttttgc catcactcca   172740
```

```
gccgctaaca tttgcggagc tcttcctccc gcaccccac ctgacaaggc caagggtgac 172800
cttggcccca ccctaggcgg ccaaggtcag aggttagctg gcttgtctgg gtcacacaaa 172860
atgcagcaga ggttgaggtg agcacatgtc cgtgacctgg agcctgactc cctctctgcg 172920
agtcttgact gctcttgcct agactctgtc ctccccgagc ccaaacgcca gtcatcttcc 172980
cttgtgggtg tccttcagcc tggtgccatg ctggtgactc agcagccgtc cagggagtgg 173040
aaacaattga gtgtgtgggt tccctgtgtg ggcatctctc ttcacggcga cacccctctg 173100
ggtgttgccc acacgatgtc aaagcggctc ttggaagggg tccttctcct tgtgggaag 173160 tttcagctgc tgggctaact tgaattgtaa ctgtggtttt gtgctcaggc ccagatcccc 173220
ctaggcaagt gttgtgccat cagtaatcaa atgagaaata atcattttga aaagcagatc 173280
ctaaggcagg atggtcatgg acactcactc ccagctcttt gtgcactcat gcttctgga 173340 agatggccat cctctgtgaa ggttttcagc gcgtcatgct tggtacccac gtatccagag 173400
catgtcgttt tgaggtattt gcccaccgtt gtgaaatccg tgccacccga gagcaggtcc 173460
tgatgtgggg ctttcagaag tgggacctgg ggccgtacgc agtccttagg gaggggccgt 173520
gtggcgttgt gcgtgtgagg ggatagcaca gggtgaggtg ggggcccaag aaggaagtga 173580
cccacaaaga acagcctcct cttttggtcc ttgttcctgg gatggctggg agtggcttct 173640
gtgtcgtccg gccatttccc ctgcggagag gctcctacca ctgccgagaa cctcatcatt 173700
ccacaaaaac aagaggccgc ctggccatcc agcgctccat gggaattctg tgtccccata 173760
gtcttgggct gaaggagggt gacattcctt gctgacttct gcaggggtct cctcactgtt 173820
aaagagcaga ttgaaagtga agaacgtggg ctaagtgttt aggtcgatat ttaaccctgc 173880
taggttttgg atactaagtg aaattgaggc cattttggtt gaagttgaca gaaaccacta 173940
tcagggatcc ccaagactac cccaggcttt tctagaaaga ctctcagcta agatgtgtta 174000
tggtaaaagc acacaaaaca aaatcagcaa agaaaattag caagggcaga ggcccatggg 174060
gcgatgtccc gaggacacca ggcttgagct tccagaatcc tctcccagcg gggtcgtgca 174120
ggacgcactt aactccccgc acagtgagcc gtgacagcgc gtgtgcagtg tcgtcgccag 174180
gaaagcacac tagagactcg gtgccagggt ttttactggg ggctgggcac atgggcaccc 174240
tctgcctgcc tcgtgcccag actctggact cccggaggga aggcaagttc tcagcaccaa 174300
ccctggtgcc cacacaagca gctgagcaca gggagcccct cctcagtgag gatggtgggc 174360
accgtcccaa caccagccag gggccagcct tgcacacagg cctctcagga tggtctccgg 174420
cctgctgtgt agtctcttct gcacacaagc gtgagggcag cgcccccgcc tcggctgtgg 174480
ggaggagcca ctgggacgtg agctctggtg gcatgcagca gcttttgtct gtgtgtgcct 174540
aggacaaggc cgtggcggag cctgtcagcc gcctgctgga gagcacgctc aggagcagcc 174600
acctgcccag cagggttgga gccctgcacg gcgtcctcta tgtgctggag tgcgacctgc 174660
tggacgacac tgccaagcag ctcatcccgg tcatcagcga ctatcctctc tccaacctga 174720
aagggatcgc ccagtgagtg ggagcctggc tggggctggg gcggggggtct cagaatgagc 174780 tgtgaaggaa gcagcatcac cctctccaag tgcccaggct cctggccaga tgcaggcca 174840 ggtatcagtg ggaacccagg tgggtgccat ggctgaggtc agtgagacgc aagagcacag 174900
gtgcgtccta gaggcttcct cgggcacctc cagcgagctg gagctctcgc ctctgctgct 174960
gtctcatgtg gcgcttagca cactctccca cgtgcccatt cctgactctg ctctcgaggc 175020
catcggctct cattctctgc tcccagaacc ctgttattac ccaggctagc ctcctctctg 175080
```

```
caccttcccc gccctggccc agtacctccc tcttgtttcc actgtgattc cgacctcacc    175140
ttatcttaaa gctgctggac ggcaggttct gtacacacgt gtccttgaca aagcacggct    175200
ggtgccgcaa cccctcagcg agcaagtcaa gctcttcaca gcgatgtctt acaagcgcag    175260
agggctctgt gacaccctgg tctcaccgcc actcttccaa agtcgcagag gctttagcag    175320
agatgggccc agcctctctg agtcataggc ttctgcacac gggagctgtc tttagaggga    175380
gggtggaatt tcatcagcca cccacatggg ggagttgagg gcaagaatta ggagcaaaga    175440
tgggaagggg tctgggagga atggccagtg atcccctttg acaagtgggc aggaaacggg    175500
ggctaggtca aagttgagtg gaagacctgg agggagacgg gaaggtctct gtaggcacag    175560
ttcagacagg agggaggtgt gagccagggc acatgccggt ggccgtctgg caggatttgg    175620
gacatgctgg agcagggaca gcggctcatc aggggccatt gccctcatcc aggccagagt    175680
gtcacaagcc cgtggggagg cccttctcgc ctgtcatcct tgctgggcag tgggtgctgt    175740
gctagcagga caggcggacg gctggcaact gtctctgcat ccctggagcc tggcataggg    175800
ccaagtcaca cggggcacag gcctgcaaat caggcacata tgttggtgca gtgacgtgat    175860
tttgggggc agccccagaa caggcccag acacaggcca aagccctgcc tgtgctggtg    175920
tgtttgggctg ttctatggct cttgctgtgg gcatggagga ctcagggaag gagagttgag    175980
gtggtccagg agttgcgttt gggatgcaga gagcttgtgg catccaggta gaaatggtgc    176040
gtggggctga cctcagcacc atgggcagag gggccgtgtc acgtgcctcc gaggtggagg    176100
tgggaccacg tggtgacaga tatacgcatc actgggcacg ttttttgtggg tgttgggggg    176160
catcgtattg gctcctctgt tcacagtggc cactcattca gtccctggct accaggtcct    176220
cactgtgcca tggggaaggc cggcgctgtc ggggatcac agaaggcagc acgtcatgat    176280
ggcatgtgcc atgaaggaaa agcacagggc actcaggaag tagaggggac tggcctgggg    176340
tgtgggaatc tagggcctcg ttgagggaca gagagaggaa gtgtgtggtg gccagcatgg    176400
aggtggccac aggggaggct gagttaggcc gagagggcag ggcgttgggg aggtagacgg    176460
gctcagccac tcagggagtg gtcaagcaga ggctgaaggg tcaggccagg ttgcaggggc    176520
ctgggggagc cactcagggt aggcgctccc gggagcccgc ctggcccata gctctacact    176580
cccgcgtggg gccggacatg ctgtgaagcc ctctccacgt tggatggggg tggctgagcc    176640
tggatgctgt ctcccgtttt cagctgcgtg aacattcaca gccagcagca cgtactggtc    176700
atgtgtgcca ctgcgtttta cctcattgag aactatcctc tggacgtagg gccggaattt    176760
tcagcatcaa taatacaggt gagtgggccc tggctgtctt cctctgcaca cggggagtgg    176820
gcttccctt tctttttcctt gcaggatcat accagtgggc cagttttgac ttggtcggga    176880
ggaggcatga acacctgaga ctgtgcagcg attctttgac acagaggcct ttctccctgt    176940
gcagatgtgt ggggtgatgc tgtctggaag tgaggagtcc accccctcca tcatttacca    177000
ctgtgccctc agaggcctgg agcgcctcct gctctctgag cagctctccc gcctggatgc    177060
agaatcgctg gtcaagctga gtgtggacag agtgaacgtg cacagcccgc accgggccat    177120
ggcggctctg ggcctgatgc tcacctgcat gtacacaggt gagcatgtac acggtgccca    177180
taaggccagc ccaagtcctg ttcaaggag gcaggagcat gctcactcaa gggacctcga    177240
ctaggtgccc tctgatttca cacttctggt gttgccccaa gccggcccca tcaccttgca    177300
agaaaggctc tggagccccc agggctggag tacctggtca gggttgaccg tccctgtggt    177360
cactcatccc atgtgctga gctggctgg gtcctgggca agcaaggggc tgatatcacc    177420
tgctttcaga tctccaggga ctcactggac ccctgtgtac aaagcactgt ctacagagcc    177480
```

```
tattgggttg tatagaggta accttcgtac tgaacacttt tgttacagga aaggagaaag  177540
tcagtccggg tagaacttca gaccctaatc ctgcagcccc cgacagcgag tcagtgattg  177600
ttgctatgga gcgggtatct gttcttttttg ataggtaaga agcgaagccc catccctcag  177660
ccgttagctt ccctagaact ttggcctgaa gctgtgcttt tgtgtgtgtc tgctgatccc  177720
ctggcgctgt tgctggagtc ctgccagtga ttccccacca cagcctgacc atgggctgcc  177780
ttggctcagg gttccactgg cgagctggtg gtccttggac cccagcactc aggtgtagcg  177840
ttgaccagtt ccaaggttgt cccagtgcct gcccatctct cctgagggct cagggacagt  177900
acctggcagt tgggggtgtg gcaggggggca ggaatgacca gcctctggga gggtggggca  177960
gaagcctgta cagtgaggag gagctggctc agcctggctg cctatcgtga gagggagcc   178020 cacggggctg tgggagggggg gccgtggtgc ctgtgagcag ggtgaggagc agcggcagga  178080
ggatgaaggt ggaacccaca catgcatctt tgagacccgt gtggtcagtg gcttctgccc  178140
cccaccaccc cccactgctg tgcgtgcata gaattggctt ccctcacctg ctctggaagt  178200
gggttaggag cttggtaggg cttttttctca aggacaaggg cccctgatttt gctctcaggc  178260 ctcagtcctg gcgacatggt ggatctggag ccttgttgca ctgccttgcc tgtgctctcc  178320
aatcagggtg gccagtgggg agccatttgg ctttttctcaa gagcatactc aggtggacct  178380
tgctccactg tttgaccaga tgaggcattc tgaacagcca agcctgtgct ggtctgtttt  178440
catgttgatt ttttttttttc ttttcttttt gagatggagt ttttcccttg tcacccaggc  178500
tggagtgcaa tggtgtgatc tcggctcact gcaacctccg cctccgggt tcaagtgatt  178560 ctcctgcctc agcctcccta gtagctggga ttacaggcac accaccat gcccagctaa    178620 ttttttgtgtt tttagtagag acggggtttc accgtgttgg ctgggctggt ctcgaactcc  178680
tgaactcaag tgatccaccc tccttggcct cccaaagtgc tgggattgca ggcgtgagcc  178740
actgcgcccg gccccccatgt cgatttttaa atgcacctct gcatcgttct tcagtcccca  178800
tatgctcact gagcaccact gcgactggca gacgggcaca gggaggcgcc acgaccagtc  178860
ctggccttca aggggcttgt ggtctagtgg gcccaatgct aggtggcgag tgctccaaag  178920
agtgtggtgc acgccttccg cttgaccgct tccagacgc cacagggagg cacctcgcag  178980
ctgaccacag atttctctct gtggagcagt gtcttcagag cggctgccat gccactgctg  179040
ggcgagggtc tgcgggcggg tagagccagg agcacctgtg aggaagtgca ctgccatttt  179100
cgtagctgct tcccgtgtgt ctcagttaca cacggctggc atgtgtgcac tgatgagacg  179160
ggaacgtgat ggttgctttt cagcactgaa agggatactg ctcaggggc gtgtttcagg   179220 atctggttag ggaagaagca gcgagagcac agatggggcc ctgtgtggta acaagaaaaa  179280
agtcctggtt gacaacagtg ccacgaagcg ttagaacaca tagggatgtt tgtggagcat  179340
ttgcatgtgg aaagcagcaa aaacataatg ggaacgggtt cttttgttat gatttttaaa  179400
aatctctttt gtaacatcct tcccgctgcg ccgtttctgc atattccttt atgtagcttt  179460
caaactcctc ttaggagttc tggtccctac agggcgtggg agcccaggct ttacgtagct  179520
ttcaaactcc tcttaggagt tctggtccct acagggtgtg ggagcccagg gcctgtgccg  179580
agcagcctgc ctccacgagc tagacagagg aagggctggg gttttgcctt tttagtctca  179640
aaattcgtac tccagttgct taggctctga ctttccccac ttggaaagtc cctcacggcc  179700
gagggtccct cccagccctg atttcacatc ggcattttcc ccagtattag agccaaggcc  179760
ctccgcgggc aggtggggca gctgtgggag ctggtgccag tctctgacct gcgtccctcc  179820
```

```
tcccaggatc aggaaaggct ttccttgtga agccagagtg gtggccagga tcctgcccca   179880
gtttctagac gacttcttcc caccccagga catcatgaac aaagtcatcg gagagtttct   179940
gtccaaccag cagccatacc cccagttcat ggccaccgtg gtgtataagg tgaggttgca   180000
tgtgggatgg ggatggagtg ggaaagcctg gaggtggagt tgcctccgac ttcccagcag   180060
attcgccagc agagcccagc tcctccgctt taaagcagca atgcctctgg cccccacccc   180120 accccgcca cccaggcgca gcaggtgctt cccgtcccc cagccctgac actcaggcac   180180
ctgcttgctc cttgcaggtg tttcagactc tgcacagcac cgggcagtcg tccatggtcc   180240
gggactgggt catgctgtcc ctctccaact tcacgcagag gccccggtc gccatggcca   180300 cgtggagcct ctcctgcttc tttgtcagcg cgtccaccag cccgtgggtc gcggcgatgt   180360
atcctctctg ggtccctggt gctggccccg tttcccttgt caacaccgag gctcatgttt   180420
catgataagg ttttgaaacc taacctttgc aaaaacccca cagatgccag ggtgacaggc   180480
cctcagcccc agggaagtaa aatgctgaca ggggtacaga aaggagcacg tccagacatt   180540
tgctgaccag ggcctctcag aggggccggt gtatggcagg agggtcgcag ctgaggggcc   180600
tttctgtgga gggcctgggt gaggggagcg agggtgggcg gtggtctctg cagacgtccc   180660
gcccactcgc gggctctgtg tggctgggct tctcctgaca ctgcttctca ttagctttgg   180720
tcattgtgcc tcgatcgccc tctcggggaa aggcttaagt aaagatccag ttcccacccc   180780
cagatgctgg ctgccaggag tttcccttc cacagccctt ccccaagaca gaccacaaga   180840
gcctccaagc agcacagttg tcctggtgct gacagcacag ccttgcccgg cgtgcctggc   180900
acggctctgc cctcactgca ttggagcagg gctagtggag gccagcggaa gcaccggcca   180960
ccagcgctgc acaggagcca ggccaggtga gtgctgccga gtgggtgccc tgcctgcagg   181020
gcatccagcc agccaagggt tgcaggaatg gaggtggagg cgctgatgca gctggaggca   181080
tccaggtggc ccttccgggg ctctgctcgc tctccaggct ccctggaccc ctttgtagac   181140
tgtttcagga gaggaactcc caggtgagga cagggaggca gcattcccct catttgccgg   181200 ccttttttcct taactcctgc accagcctcc cacatgtcat cagcaggatg ggcaagctgg   181260
agcaggtgga cgtgaacctt ttctgcctgg tcgccacaga cttctacaga caccagatag   181320
aggaggagct cgaccgcagg gccttccagt ctgtgcttga ggtggttgca gccccaggaa   181380
gcccatatca ccggctgctg acttgtttac gaaatgtcca caaggtcacc acctgctgag   181440
cgccatggtg ggagagactg tgaggcggca gctggggccg gagcctttgg aagtctgcgc   181500
ccttgtgccc tgcctccacc gagccagctt ggtccctatg ggcttccgca catgccgcgg   181560
gcggccaggc aacgtgcgtg tctctgccat gtggcagaag tgctctttgt ggcagtggcc   181620 aggcaggag tgtctgcagt cctggtgggg ctgagcctga ggccttccag aaagcaggag   181680
cagctgtgct gcacccccatg tgggtgacca ggtccttct cctgatagtc acctgctggt   181740
tgttgccagg ttgcagctgc tcttgcatct gggccagaag tcctccctcc tgcaggctgg   181800
ctgttggccc ctctgctgtc ctgcagtaga aggtgccgtg agcaggcttt gggaacactg   181860
gcctgggtct ccctggtggg gtgtgcatgc cacgccccgt gtctggatgc acagatgcca   181920
tggcctgtgc tgggccagtg gctggggggtg ctagacaccc ggcaccattc tcccttctct   181980
cttttcttct caggatttaa aatttaatta tatcagtaaa gagattaatt ttaacgtaac   182040
tctttctatg cccgtgtaaa gtatgtgaat cgcaaggcct gtgctgcatg cgacagcgtc   182100
cggggtggtg gacagggccc ccggccacgc tccctctcct gtagccactg gcatagccct   182160
cctgagcacc cgctgacatt tccgttgtac atgttcctgt ttatgcattc acaaggtgac   182220
```

```
tgggatgtag agaggcgtta gtgggcaggt ggccacagca ggactgagga caggccccca    182280
ttatcctagg ggtgcgctca cctgcagccc ctcctcctcg ggcacagacg actgtcgttc    182340
tccacccacc agtcagggac agcagcctcc ctgtcactca gctgagaagg ccagccctcc    182400
ctggctgtga gcagcctcca ctgtgtccag agacatgggc ctcccactcc tgttccttgc    182460
tagccctggg gtggcgtctg cctaggagct ggctggcagg tgttgggacc tgctgctcca    182520
tggatgcatg ccctaagagt gtcactgagc tgtgttttgt ctgagcctct ctcggtcaac    182580
agcaaagctt ggtgtcttgg cactgttagt gacagagccc agcatcccct ctgccccgt     182640
tccagctgac atcttgcacg gtgacccctt ttagtcagga gagtgcagat ctgtgctcat    182700
cggagactgc cccacggccc tgtcagagcc gccactccta tccccaggcc aggtccctgg    182760
accagcctcc tgtttgcagg cccagaggag ccaagtcatt aaaatggaag tggattctgg    182820
atggccgggc tgctgctgat gtaggagctg gatttgggag ctctgcttgc cgactggctg    182880
tgagacgagg caggggctct gcttcctcag ccctagaggc gagccaggca aggttggcga    182940
ctgtcatgtg gcttggtttg gtcatgcccg tcgatgtttt gggtattgaa tgtggtaagt    183000
ggaggaaatg ttggaactct gtgcaggtgc tgccttgaga ccccccaagct tccacctgtc    183060
cctctcctat gtggcagctg gggagcagct gagatgtgga cttgtatgct gcccacatac    183120
gtgaggggga gctgaaaggg agcccctcct ctgagcagcc tctgccaggc ctgtatgagg    183180
cttttcccac cagctcccaa cagaggcctc ccccagccag gaccacctcg tcctcgtggc    183240
ggggcagcag gagcggtaga aaggggtccg atgtttgagg aggcccttaa gggaagctac    183300
tgaattataa cacgtaagaa aatcaccatt ccgtattggt tgggggctcc tgtttctcat    183360
cctagctttt tcctggaaag cccgctagaa ggtttgggaa cgaggggaaa gttctcagaa    183420
ctgttggctg ctccccaccc gcctcccgcc tcccccgcag gttatgtcag cagctctgag    183480
acagcagtat cacaggccag atgttgttcc tggctagatg tttacatttg taagaaataa    183540
cactgtgaat gtaaaacaga gccattccct tggaatgcat atcgctgggc tcaacataga    183600
gtttgtcttc ctcttgttta cgacgtgatc taaaccagtc cttagcaagg ggctcagaac    183660
accccgctct ggcagtaggt gtcccccacc cccaaagacc tgcctgtgtg ctccggagat    183720
gaatatgagc tcattagtaa aaatgacttc acccacgcat atacataaag tatccatgca    183780
tgtgcatata gacacatcta taattttaca cacacacctc tcaagacgga gatgcatggc    183840
ctctaagagt gcccgtgtcg gttcttcctg gaagttgact ttccttagac ccgccaggtc    183900
aagttagccg cgtgacggac atccaggcgt gggacgtggt cagggcaggg ctcattcatt    183960
gcccactagg atcccactgg cgaagatggt ctccatatca gctctctgca gaagggagga    184020
agactttatc atgttcctaa aaatctgtgg caagcaccca tcgtattatc caaatttgt     184080
tgcaaatgtg attaatttgg ttgtcaagtt ttgggggtgg gctgtgggga gattgctttt    184140
gtttttcctgc tggtaatatc gggaaagatt ttaatgaaac cagggtagaa ttgtttggca    184200
atgcactgaa gcgtgtttct ttcccaaaat gtgcctccct tccgctgcgg gcccagctga    184260
gtctatgtag gtgatgtttc cagctgccaa gtgctctttg ttactgtcca ccctcatttc    184320
tgccagcgca tgtgtccttt caaggggaaa atgtgaagct gaaccccctc cagacaccca    184380
gaatgtagca tctgagaagg ccctgtgccc taaaggacac ccctcgcccc catcttcatg    184440
gaggggggtca tttcagagcc ctcggagcca atgaacagct cctcctcttg gagctgagat    184500
gagccccacg tggagctcgg gacggatagt agacagcaat aactcggtgt gtggccgcct    184560
```

```
ggcaggtgga acttcctccc gttgcggggt ggagtgaggt tagttctgtg tgtctggtgg   184620
gtggagtcag gcttctcttg ctacctgtga gcatccttcc cagcagacat cctcatcggg   184680
ctttgtccct cccccgcttc ctccctctgc ggggaggacc cgggaccaca gctgctggcc   184740
agggtagact tggagctgtc ctccagaggg gtcacgtgta ggagtgagaa gaaggaagat   184800
cttgagagct gctgagggac cttggagagc tcaggatggc tcagacgagg acactcgctt   184860
gccgggcctg ggcctcctgg gaaggaggga gctgctcaga atgccgcatg acaactgaag   184920
gcaacctgga aggttcaggg gccgctcttc ccccatgtgc ctgtcacgct ctggtgcagt   184980
caaaggaacg ccttcccctc agttgtttct aagagcagag tctcccgctg caatctgggt   185040
ggtaactgcc agccttggag gatcgtggcc aacgtggacc tgcctacgga gggtgggctc   185100
tgacccaagt ggggcctcct tgtccaggtc tcactgcttt gcaccgtggt cagagggact   185160
gtcagctgag cttgagctcc cctggagcca gcagggctgt gatgggcgag tcccggagcc   185220
ccacccagac ctgaatgctt ctgagagcaa agggaaggac tgacgagaga tgtatattta   185280
attttttaac tgctgcaaac attgtacatc caaattaaag gaaaaaaatg gaaaccatca   185340
gttgttgctg tgtgaggctt gctttgcttc atgagaacct agaccttgct gagctggagt   185400
cttaggaagc agtctcctaa gtgcttctcc agcaggggca gaaactgtcc caccagctaa   185460
catctggcat tatggagggt cccccaggca gctgccagca gggacaggcc ccgtgttttc   185520
tgtagccagg gatgaggaag tggccccagg gcatgggcct ggctgggtgc ttctgcaagg   185580
gccttcccaa accacagtac aggtggtctt cctgccctgc agatgggagc tgtgggagct   185640
gctggagctg ctggagcctt catggtcaag tgacatcata agcttatatg acatacacaa   185700
gcctcaggac ttggcccatg gcactgaagc aggtcatcag gcccagcaca gagactagag   185760
ctgtgttctc acagggccca ccaccttcc acctccttgg ccattgacac ctgcgtccct   185820
ggcccagctg ctcccaggta accccaaag cagctggcac atcccacctc tggtgtggcc   185880
ggggctgctg tgtgtccgca gggcctgccc cgtctattct agcttgtttg tcctgtctga   185940
accagcgcct actccaagaa gcctctgctc agcccagcgg ggatgcttct aagctccgga   186000
cgagcctctc ggaagccttg tgattggtg gtgtagtcat cttgggatgc agatgtctta   186060
ccaacctgca agaacaaaaa ccctgtggct tcctctggtg cagggtattt agtcaatgtt   186120
tgctgaggtc ccgtctggtt ctggctaatt ggcaggggtc gtccacccat tctttccctg   186180
ctctgctgtc tgtgccagga gagacggggg ccagtcggcc aaggggccag ctcctgctgc   186240
ctgctcctct tgggcacgtg cggggcccc ctttctctga gcaggatag ggatcagtct   186300 gccggaggga tgtggtggac aggcctaaag catttggggc ggggcatgcc acttgagctc   186360
cctaaatctg tctcctcata ggtgacaccg ctccagggcc ccccagtggc ctctcctttc   186420
agagctacct aaattctggt cacttcagag aaatggagca ccccttctc cctggtccag   186480 gtgtggacag cctggcacac tgagcacacc tggcatggct ggtaatttca gaaagaagag   186540
gggccggggt ccagtgggaa gcagcggtga acccctcgtg agtgggcttt gcagtccctc   186600
cccatgccac ggcagagctg ccctcaacac agccttcctc ttcctcatcg gagagcacac   186660 cctgtccct tgccgagctg tgccctgtgc cttcggtggt atttgatttt ggctgctact   186720
ggctttgttg ggatctggaa gtcgcttccc ctgcgtggtg cgtggagcac tgtaagtcag   186780
atgagggaag tagccagggt gaggtgagta ccgggtggag ccgccactga agggactggg   186840 tagggggggcc ttgcctctac atgatgtgac acagccaacc gaggacagag gaagcccgt   186900 tcctgggggt gtggggtgca cccctcaggg aagcctgcag tggggcctga ggaaaggcat   186960
```

```
cctccgcgag cccacgagtc tggtccatga gcaccgtgac agtgtctgtg ggtagaggtg    187020
gacccggcct tgtgtcatca ccaggacctc ttttgggaaa ccatgtggac atcgcttgcg    187080
ggtcccccag gctctgcagc cccagcagcc tggctgcctt ttgggcaagt ggcttgagcc    187140
acagaggacc cagtcctgtt gcagccacat cctctggggg ggcccgccag tgtggccggc    187200
tttctccacc ctacaccagg cctccaggtg tcctggtcgg gggtgtctgg gccctgggtg    187260
ggccctgtgg acctgtgagg tcagggtcag ggcatcactg gaggcagagg ctgaagttgt    187320
tgggtctggg ttcccttgt gtgcacaggc ccctgccctc catgcttggt caggcagcta    187380
cccccaaaac tgctaggaca ggctggtcct gaggtggatc ctggcccctg taccctctgg    187440
acagcccacc cgcccaacct tctaccctgc cccagcggcg gcagtgttgg ccacatcctt    187500
ccctcctgg ccccaattgc tctggggaag tccaggctcc ggagcctgcc caggggcccc    187560
ccgtgatttg ggcccaggac tccacgtggt tctctgcctt cacccaagcc ctgaactcct    187620
cagctgccaa atccccaccc atctgcacag gctgtgctca ccactgctgc tcctggaagg    187680
tgcccctcag tgggacgccc acctcctctc tgggcttctg tgtttgggag ccctgctgcc    187740
cccacccttg gtcagtcccc atgtcctgct ggcctgtcag gcagggcaga aaatccaccc    187800
agaaatgctg agcaggatga gagtctagtt gggcccagcc tcattattta gaagggatgg    187860
aggcctaggg agcatgcttc tagcctgagc ccagcagggc cccgcccatg tcccaggtct    187920
gcaccaggga cagctcctgc cgaggcctga cctgccccctt ctccctcagg tgctgctggt    187980
tgaccagcct ctggccctag gagacccgt agcgactgag ggtccagca ggccatgcag    188040
ctttgccaag gtacgagccc ctccccagca ggggacagat gtggggaccc tcccaggcag    188100
gagcagctgg gtgcctggtg ctgccatctg ctgcctgcct ggttcttgtc ctcacattgg    188160
aggtcagtgt gagggctctg cctcgggaaa ggccatggag cttgccctgt ccagggcctc    188220
ccatgtgcac tgagcctggg aagagagggt tggagttgag ccttttaccc tgggaatgct    188280
gcctggagga tggtgcgggt gtggggtggc accctgccag gcagggccct gcctccctgc    188340
gcccactgga actcgggcag gcaggggtgt aggtgcctcc tctagagccg tccggtgggg    188400
gccccggca gtggtggtgg tgtccactgg ccagcagctg ccccttcagc caggacagta    188460
ggcctgacgc tgtccccagc agctccaagg tggatttgtg gaagggggta gagggcacgt    188520
agaggcccca tgacctcccc agggttctgg gagggctgtg ccccccttagc cagcaccatg    188580
ctgggtgata tagtcagatc ctgttacccc tgttgtggag gtgaggaaac aggttagtgg    188640
ggaggacatg actaaggtcc atgctgagtc gctagagctg cacccagaac cactgctggg    188700
accccatgcc tttctgctta ccccttgtgc cgggagatgc caagagatgc tgggagccag    188760
ccccacctct gcccttggag tcatggctac ggaaagggca ttcggaccgg tcctgacct    188820
caccggggag ggccgaaccc tgttcctgag gagccagggc ttcctagagg aggtaggcct    188880
tctagtcact ccttcatctg caggcactcc acagagctct ctgtgccagc ccccagcacg    188940
gagggctgac cttagtcgag tggagatgcc ccagtgccag gcagtaggga tgatgtctcc    189000
tgaggcccag atggaaggga ctggactagt ctcatgggc tgatggtggg gccaggcctt    189060
gaccaggggac ccagtgtagg gggtgcagag accctctga gttcctcaca catccctggg    189120
gccctcccca tacacttcct atcctgactg cgggcaagag ggagcccag ttcgccttcc    189180
ctatgctggg cacccacagt ggggctgggc accccgccca tgcccctgcc ctgtccttcc    189240
cctgagagcc tcggtcccac ctccaaggtg cctcagagga cagcaggggc agcgggcaga    189300
```

```
ggccgagatg cctcctcatt ccaggctcag ctgcccttct tggggcagcc cacacctgag 189360
agtctcctgc agttggtcag gcctgaggag ggcaggggggg tgcctgctgt ccctctgctg 189420
accacagtgg catttagcct gggcaccgcg cccagcacag tccatgctgc acaggtgccg 189480
tgggctccac agagccctgc ctgacatgca tgtgttacgt ttcgggtgcc gatgcccttg 189540
ggcggcactt ctccgggcag aaccccccagg ccaccgctcc ggttccggtt ccgctgcatc 189600
tggggctctc ggcaggctgt ggtcctccgg ccagcctggg ggcatctcag tcccttcagcc 189660 ccacagggggc ctgccccgca gcctgggcct cgagcccgt ctccgcacgc tgtgccgaat 189720
ctggctgccc atcagctccc tgcgtaccca gactgtgccc tgccatgccc gtggctcttc 189780
ccaggagtgc cctgtggcct cccctggct tgctgggctg attccctcct gtgtctcaaa 189840
cagagctcac ctttgccatc actgctgtcc tcaccggccg gtgccagagg cccgtgtctg 189900
tgtaccctgt gtctgcacct ctgggcaggg cctggctctg accaacccgg gcttccagtg 189960
tccacagacc taaggcccag ggcgcctggg ggctggagca agagaagcaa aaggagccaa 190020
gggtgggggt ttggggttct tgtgagggcc cagccccagg accccaggac caggacaccc 190080
aggagcccca gggcccagcc ccagttcaga aggcaggggc cttctgaggg agcttaaggg 190140
tcccacagcc caggaccccc accagggcca gtggccagcg ttgggggact cagcctcctc 190200
gtcgctcgtc ctctctgttt ctcccaccctt ttgccccctt tctccttgcc tgttcccacc 190260
cgaggccccc tcttggcctg cgtgagccgg ggcggcactg aactggggggc cgatccgcct 190320 gggcggcggt gagaggcagg gccgggagcc gggccgctgg gtttgggcct ggcccgctcg 190380
ccgcaatatt gatgggcccgt cagtgcagcc ctgattcctg tgctttcagt taaaaggttt 190440
ctgttgttgt agcttatgca gttgctctgt tgctatggaa acgtgacatc aaaatgacgt 190500
ttcccgttta aaagctttta actaaaattcc tgcctgtcag atgtaggccc cattttgagc 190560
gtggagctgc cttcgagcga gcgtgagcgg cgcctcccgc ccatggtgcg tggggccggg 190620 ccgggggccct cgctgagcgc gctctctcac cccacaggcg cctccggcat ggcggcggcc 190680
gaggggcccg gctacctcgt gtctccccag gcggagaagc accggcgggc ccgcaactgg 190740
acggacgccg agatgcgcgg cctcatgctg gtctgggagg agttcttcga cgagctcaag 190800
cagaccaagc gcaacgccaa ggtgtacgag aagatggcca gcaagctctt cgagatgacc 190860
ggcgagcgca ggctgggcga ggagatcaag atcaagatca ccaacatgac cttccagtac 190920
aggtgggcga gcgggcagtg tgggccccac caggacgggc gggcccgggc gtggcgggcc 190980
gctcctgact tcttggagc tctgagtcgg gacgatgtgt gggtcgtggc ctgcctgtcg 191040
gtctcctctg gccgggtatg ggcagaaccc cacggggtga cacggggccc acggaaaccg 191100
tgtgtgcagc cttccattgg ggaagtgggg aaactgaggc ccagcaaggg caggaaacca 191160
gtctaagagc tgaggggtag caggggtggg gctggtgctg ggcagaggcc aggatggctc 191220
ccaggacgta tgggcggtct gggcactgtc cctcggaggc agcaacactc atggtggtgc 191280
ccactgacct cacaccctgc tcccccatag ggaggcggcg gctgccagtg ccctccccac 191340
caccaagctc ccaagctcag caggggtttc aggggcctac tgcgtcattg gggaaattga 191400
gactgcaagt gagaaggagg ctcagtgctc tgcgacttgg agcatccact gagcctctgc 191460
catgagccgg tgagcccccac tggggctggc cctagggtca cggtggggta tttccagaaa 191520
tcaccaggtg aggtgcagga ccagccagcg catgggtggg gcttacggtg cgaagaagaa 191580
agaggtggag gcctgccctg gcccaggact cccagcgtgg gggctcccgg cctgccccca 191640
cctctgctcc tgctacatgg caggtgggcc cttcctgccc tggcaacctg cagggaaggc 191700
```

```
cggaggggac cacccagcca gggagatgtt ggcgtctagg aggggacagg tgtggtccca  191760
cacacccagc atcttaaagt gcgtgggtcc ccagcccatt aggacagggt cccgggtggg  191820
caggggtcat ggtggggtga aggtctcagg cacaggcaag gtcacaggtg cggtgagggt  191880
cttgcagggt gtgaaggtca taggtgtgcg gtgaaggtca caggtgtggg gtgatggttt  191940
tgggtgtggg gagggtcttg cacggagcga gggtggcagc aagagctgga agctgcaggg  192000
ggagaatggc agcagagagc acccggccct gtgggcggcc tggacagggc tgggcctggg  192060
gctgccggag agcctgtcag cttccaggat gggagtggcc tcactcagct gctccacctc  192120
cgggtcaggc aggtgagcct ggggcagaga ggctgagagc acctgagcca cttgtgggag  192180
aggccacccc cactgccccc ctcaggcgag gagccggcct ccagcacagc agaagggaac  192240
ccccagtccc cagccctagt gggagtgggg aagaggccca gcaaggcccc ggacagaccg  192300
ccagcctgtg aggtctccgc tttcagttgc gttgatttga ttttttctga gccttgaagg  192360
aggggtccgg ggcctggccc tgcccaaagg cccctaggca ggcccaaagg ccgggaccta  192420
gggtgctgag catgacggat gttgggtttg agcggctggc ttgcgacgtg agggctgagg  192480
tgtgagcctg ggtatcttca gaggttcggt ggacacaggc agctgcccgc ggccccactg  192540
ttcccgtggc ctcctagtcc tgctcaggca cctggtgagg aagggacgca gagggcagtg  192600
ggaggtggcc acgactgttc cagcaggctc ccctctgact caggaattca cgggcaccac  192660
ctccctggct ggctctggtt ggtgtctggc caggttattc attatttatg ctgaaagcct  192720
cttcagagtc ccaggggagg gtttctgtct ccattcctgg aggctgagag atgagggtgc  192780
agcagagtgg gggcctccac tccagaccct gcagtctggg ctggccaagg gctgcaccgg  192840
tgcactgcac gtcatggctg atgaagcact tccacaccgc agccctcag agctgccaca  192900 gtcagcctta gttcaccgag ggggaagctg aggcccagag catgagaggg acttgcccag  192960
ggccacatag tccttagcag aggaagctgt ggctgggtga ctcgatcttt gtccttttc  193020 tttatacccg cagtctcccc atagcagagg cttttctttt tttttctttt tctttttttt  193080 ttttttttaca agaactcttt atatattaag gctgttgggc tgaagaagcc tgagagggtg  193140
gctggttctg tggagcatgg tttgttgaag tacagtttgg gggcctccta cactgagaat  193200
aggccttttc tcgtttctcc aaagagtggg ctggctcaag tagggcagag agagaagcct  193260
ggggcagagg ttagggatgg gcacccagcg cctgccctca cacgctctgt gctggtgtct  193320
tcacagccac gtgccaccct gggcagcatc ccctgctcac catctggctg tgcctgtttg  193380
ctgggggcac ctcattcaga atccagctta ttgtttccaa cggccaatgg ccacaccctg  193440
gcaggtagca agagtaggag agaggagaca cccactccga gcacaggttg ggtttggagc  193500
ccggccttgg ggcactctgt cactcaaagg cagagtgggg agtgggcact gggccttagg  193560
aggtactggg tccagtgagg cagagatgcc cctgccccac cccaccttg tggcttcttc  193620 cctggcctgg ccagagctgt ctggccgcca tgggccctg tgtctcctgc cttgacctcc  193680
cagagggcag ccgaggccca ggggaggcct ggggacttag cctctcaggg caggacctgt  193740
ctgcaggagt aggtgggtgc tgggggtccc agtggtaatg aggcatcagg cagtgtggga  193800
aggggcccat ccggcccacc ccagggcctc tgggcaggtt gcaggttgta gcgctggatc  193860
taggctcctg cccagactgt aggttcaacc aagaatggca tgggagccca gcctgctgtt  193920
tgctttatta aatctgccct gtagctgggg gaggggctta ctttgatcat cactatgtca  193980
ttgatataaa aatagaggct cagagaggtg aatgaacctg cccaaagtca cacagcaaag  194040
```

```
tgtggagatg agatactgac tcagggctgt ggacactgaa gcctgtgctc taacgccagt   194100
ggctgtcgct ccctgaggca ttctctcccg aacaacacag ttattatatt acaaaatatt   194160
atcactatat ttatatatct tataatacct tattattaca ataaaacctt attactctac   194220
ctttcaaaat gaattattta aaaagcagta tttgctcatt gcagagagtc tagaaactat   194280
agaaaagcaa gggaaaagca ataggaccag ccccaaggtc ccagcatgca cagataacct   194340
tagtaatact gggacgtgtg cttccttttt aacatctgag cccgtgtagg tcctgaagcc   194400
cagcttcttt ctaagtccat tgtcatcttg accctggagc ctggccgatt ttgctgggga   194460
ggcccttgcc agccgagagc ggctcctgcc tgtgccggcg tggcgcgccc ctctgctgag   194520
gctgggcagg acagggggctg gccagctct gtttctcacc cttggctctt gtgtctctcg    194580
tttcaggaaa ttaaaatgca tgacagatag cgagtccgcc ccgcccgact ggccctatta   194640
cctagccatt gatgggattc tggccaaggt ccccgagtcc tgtgatggca aactgccgga   194700
cagccagccg ccggggccct ccacgtccca gaccgaggcg tccctgtcgc cgcccgctaa   194760
gtccacccct ctgtacttcc cgtataacca gtgctcctac gaaggccgct tcgaggatga   194820
tcgctccgac agctcctcca gcttactgtc ccttaagttc aggtagtgtg tctgcttgtc   194880 cttccctgc cctggggtat ctcagccccc accatttaga gaaagggact gggagtggca    194940
aggccggcgg cggcggccac agtggttgca gaggccgtgg ctgcgggcag cgcctccagg   195000
gacaggcggc ctcagaccag ggagggcttt agtgtccaca ggcagaccga gtttgtctcc   195060
cagctccatc acttttgagc tgcacggaaa gttccttgac ttctctggcc tcagtctccc   195120
tcctataaaa tgggggtaaa tcagtaccTt tctcagaggg tggctgggag catcacagga   195180
gagaagacgc agcatggggc ccggcacacg gagggagacc aagccccaga ccccagaatg   195240 cgcccctgg cctcccttag cccacacaga ccccaccctc acaggctagc tgccctctca    195300
gcactgggga gggtgtcggg ctgcacctca tcacgtgttg ccgtgggcat gacccgtccc   195360
ctctgccatc catcccacac ctcagacccg tcccgtgctg ccacgtgac tgtgcctgca    195420 agatgctcac agggcagccg ggagccaggc agcatgcagg acagacacct gcggggtggg   195480
cctggggagc ccagagaagg tgcttttgag gaggggacat ttggggtggg ctttcaaggt   195540
aaaatagaag ttggccattt ggaggcaaga acaggaagat tgtggatttg agtcacagct   195600
tctcccctgc cctggtcttc aagtctttct gacaggaggt gtcagaaaag tatctttagt   195660
agagaaggcg tctccgagga gggtccctct catgccgggg gccgctgctt gactcaggat   195720
ttctcattga agacctgaga caaaaacgct tttgctggca gctagaagga accagcagga   195780
ggcctgagat ttgtggctgt tgttcccgtg gactgagccc agttctcaga ctcagctgcc   195840
tggggccttg cacaggactg gggcgtgggg gctgccctcc ctgatcaggc ccaaagcgcg   195900
gatctcacgc ccctgaggtt ggctgtaccc tctcagctca gagcagagtg tgggccaggg   195960
atgagcaggc actggagcag ggccctgggt tctgtgggtt ttggcagctc cctgcccttc   196020
agggaggtct gctgagacca cggtggccc ctacccagc agcagagctc tcaggaggcg     196080
cccacagggc tggactgcct ttactcacca cctctaccag agctctgagg tcctggggag   196140
agagcccagg cctcttgtgg gccccacacc tctaggtgc ctgtccttct gcctctctac    196200
caaggtgtgc cggccccatt tctaggccgc cgggagataa gggggctcac atctcaggcc   196260
cttccttctg ggacctcagt ttccccatct gcctaaggcc gggtgggggct ggtggtcttg   196320 gcttccctac aggggtcctg agtactctgc actacccagc accccccacc cctgccttca   196380
tctctccctg ggggtggtct ctccaccccT ggccccCaac tggggctgag ccccCacctg   196440
```

```
cccagtttgg tgggtgaagg gtgctccctg gcaggatatg cccctctgca gcccagaaca  196500
tcccacccct tccagaccga aggggtgtgg attgtcctgg gaccctggtc attggggtca  196560
tccgctagtc gcaaaggacg gcaatgcctg tggcctctct ttctttcttt ttcttttttt  196620
tttttttga gacggagtct cgctcttgtg cagagagcag tggcgcgatc ttggctcact  196680
gcaacctccg cctcgtgggt tcaagcgatt ctcctgcctc agcctcccga gtagctggga  196740
ttacaggcac cgccacaac gcctggctaa tttttgtatt tttagtagag atggggtttc  196800
accatgttgg ccaggctggt cttgaactcc tgacctcagg tgatccacct gcctctgcct  196860
cccaaagtgc tgggattaca ggcataagcc tccacacccg gccacccctg ttactttctg  196920
tcaaaggcgg tgggttctgg cccctccttt gcacatggaa tatgagaccc tgagtaagtg  196980
acctgactcc ctggggcctc agtttcccca tttgcccagt aggattgtcg ggagggtccg  197040
gtgaggcccc tggtgtgccc aggctctgtg gccagcacgt ccacagccgg cactgtcctt  197100
ccaggtcgga ggagcggccg gtgaagaagc gcaaggtgca gagctgccac ctgcagaaga  197160
agcagctgcg gctgctggag gccatggtgg aggagcagcg ccggctgagc cgcgccgtgg  197220
aggagacctg ccgcgaggtg cgccgcgtgc tggaccagca gcacatcctg caggtgcaga  197280
gcctgcagct gcaggagcgc atgatgagtc tgctggagag gatcatcacc aagtccagcg  197340
tctaggccag caggcggcgg cggcggcggg gccgggcggc tggtggtact gctcaggcca  197400
cccagggcag gccactcagg ccaggcgggc aaggggggccg ccccgcgagc ggagaccgcc  197460
ttccacctgg cctctggcag gatgtcccctt ctgaggggta ttttgaggaa ccccaggcc  197520
ctggggaccg tgaggctcca gtctccagca tgaatgccct tcctcggaca caggccaggg  197580
cctctggggt tcactccgag taagaacgtc ctagagccac tctccagtgt cgttactatc  197640
aatgatactt gacgtggctt tgatattaaa cgtatacttt ttcattcttg cctggaacgc  197700
acagtttgct gttgctggct tggtgaggat gccctgattg atggatcccg aaaatgaaag  197760
cagatggaaa cgggttgggg caggctggag ctggggagc tctctcctga agggaaccct   197820
gtgtcctccc tcaccaggac ctctgcgtct ctccttaaat ggcctctgac gcctgatgaa  197880
aaccccagcg accttccagg aggcttttat tcagctctgt ttggagcatc aggtgtttcc  197940
actgcctcct tagcaatgac actaataaaa gtcgtaacac ctgttcacat gcacagccct  198000
gttgagtgtt ctgggtgctg gagatatcat ggtggatgac acaaaggccc tggcctcttg  198060
gagcttatgc tcccatgcgg ggaagacaca tgggtcagta gagaaatggt tgcaggttgt  198120
gataagtgct ggaagggagg ggttggcctg aggacacgga ggcagacata cgtggagctg  198180
ggaacagtgg ccacacaggg aacggccagt gcgaaggccc agaggcagag gacactggag  198240
caagcccagg agcagctagg aggctggtgg ccagcagcca ggcacggaa gcccgtgcag  198300
cccgtgggga ggagtgttca tgcttttcaa gcttagtggg agtcttttgg ccagtgcagc  198360
tctgggtctg acatcggtgg gggacagagg ggtggtggag cggccacagc tgcaagctca  198420
cctcactgcc ggcccttcca ccagtttcaa actctttcta gaagctccag ctttcccaaa  198480
gctgaattct ctatgagcct ccttggccgg gactcgggcg tctggttgcc ctggctgcaa  198540
aggaggctgg ggccaggtgt gtttgagtca cctcctggaa ttaggcaagt tgctgcccaa  198600
atagaaggtt gttggcaggt gggtcagcag gtgaacagca tggtttgact cagggttcag  198660
aaaaatctcc ctctgctgc caagcgagca ggccgtggag acaggtgcag aggcaggtgt  198720
ggcagcaggc atcctgccag gcagtgctgc agtcatcctg cgacaagcag cagcagctca  198780
```

```
tcctaccctc tagggggtct tgaggtcagc caggcaagag agcagcttgg actccactgg   198840
gtgtgggacc agcctgtgga ccatggtggt gtggagggtg ccctcggcct gcctgtgtga   198900
aggagaggcc ggcgtgttct gtggagccca aaggggagct gggcaagcag gattcacttc   198960
actctgaggg tcctggagct cccaccctcc tcagccatct ccccagagcc tgtgtgccga   199020
ggactcggcc catgttgctg tgggatgaga ggcagagtgt cgtgagggtg taaggagcgg   199080
cggcagtggt gggaggaggg agcagcagcc agcgctacgg tgccagtttc agctgccag   199140
atgacgccgc tgaccctgtg gttgagaaga gatgcacaga gccagctctt gcaagccagt   199200
gtggctgcca tagcacctgc cgagaagcag aaggaagggt ggcccagga ggacagagga    199260
tgcgggcaca tctgatgcgg gcctgagttt tgggagcttt tgctctagcc agtttccagc   199320
tccgggaccc acccgcctcg taggcaagac accacccaag aaatcatttg cttaacaaac   199380
acactgggct ccaactggac acctgtgcca ccctagatgc tgggaaccca gccatgacac   199440
aggcacctgc ccccagctgc tgaccactga ggctggctag cagctcccat ggggccagtg   199500
tggggttccc cagcctccta acaggagcc agtcacaagc cctcgagagg gaagggtgcc    199560
cgcggccctg gcaggaaggt taggctggac gctcccacaa gacataacag atggaggttc   199620
taaatgatgt agcaacttct tcaccctgaa actgctgtag agtcagccat gacgcaccgg   199680
tacttcagta actgccaggc atccgggaca gcacaccgcg agtcgctgct gtgcttgggt   199740
tagaagtggt ttggtctgtt ttcttctcgc cctctctaat cagagtcagt gattcatgcc   199800
cttccatcac cttagagaag gggcaggcgc tgcccgacct tctccaggct ggagcagcat   199860
cgcctcatgt cagcagaact cagctgtaga atatcgtggg gttggtgcct ttcatcagca   199920
gcatgtcctt aacaactttc tgatttcttc cttagttgtt ggtccattaa ggagaaaaaa   199980
aatgatctca gccattgcta aaatatttga taagattcag caaagcagca tgttaacatt   200040
gaaaactaga atcaggagcc aggcagatgt gcttgctttt cacctgtagt atttcatgtt   200100
gttttgacgt ttttagctaa tgcattaaga taaataaaca aaagccgggc acggtggttc   200160
acgcctgtaa tcccagcact ttgggaggct gaggcgggag gatcctctga ggtcaggagt   200220
tcaagaccag cctgaccaac atggagaaac ctcgtcatta ctaaaaatac aaaattagct   200280
gggcgtggtg gtgcatgcct gtaatcccag ctacttggga ggctgaggca ggagaatcgc   200340
ttgaacccgg gaggcggagg ttgcagtgag ctgagattgc accactgcac tccagcctgg   200400
gtgacagtga aactcggtct caaaaaaaaa aaaaaattaa aaaagataa ataaaataag    200460
caggataaga aatgaagaaa gtagagttac ctttgttttc agatttcatt tttgtatacc   200520
cagaaagcca aatgtacaaa agactgggag ctctttaaac cagcttaaac ttgttgaaaa   200580
tgaggatgaa gaaatatccc attcagagtt ggaatgaatt taacccagaa ggaacaggac   200640
ctctactgaa gagaactatg cagtcttact gaaaaatcta ataataccct gagcgctgga   200700
gaaacttcgc acactcctga aagctccaaa gtcaatgtca tcattttatt aatgtcattc   200760
caaacatagt ctcaataata tcacttcttg gttttgacat ggacgcgatg atgtttaaat   200820
tcatatgaaa aaagaacggg gccaaaagtc caaggccagt cagcgtgaga agaccgctcg   200880
gcctccctcg gagtcgggga gttggaaccg cagactgaga tcatgtggct gctgaggcc    200940
aggacgaacg tcgggaaatg gagactcctg cgttgctggt gggatgtggt gcagccgctt   201000
ccaggagcaa tttggtgtcc cgtcctaaag ctgaagaaac gcattcctc tggtcagtgc    201060
cactcctaga caggccaccc tgcggcagcc gtcctcaaac tggtctgagg acccctcaac   201120
gctcttaaaa atcattaaaa gtgggccagg tgcggtggct cacacctgta atcccagcac   201180
```

```
tttgggaggc caagacaggc ggatcacgag gtcaggacat tgagatcatc ctggctaaca  201240
cggtgaaacc ccgtctctac taaaaataca aaaaattagc cgggcgtggt ggcgggcgcc  201300
tgtagtccca gctacttggg aggctgagcc aggagaatgg cgtgaaccca ggaggtggag  201360
cttgcagtga gctgagatca ctccactgca ctccagcctg ggcagcagag cgagactctg  201420
tctcaaaaaa aaataataaa taaataaata aaaataaaat aaaataaaat tcattaaaag  201480
tgccaaagaa cttttgctta tgtgagttct aatgaccaat attaatacac attagaatat  201540
cttattagaa attaaacctg agacctttag aaaacatgta ttcatttcaa aatagcaata  201600
aacccatgac atattaacat aaataacaat tgtatgaaaa atatattttc caaaacaaaa  201660
agttttcggg agaagtgtgg catagtttta catggtcgta aatctctggc ttaagagaag  201720
cccactggcc tctcagcagg ctctgggtcc gtccactttg gggtgtttt ggttgtgaag  201780
tataggagtg aatggagaag ctcattctta cccagatgtg tatttgaaaa gaaaaggaac  201840
attttaataa ccttttgcaaa taatcggtat attcttccgt gatcctattc caacactgga  201900
caggtggtgg tttgttttt tttttggag acggagtccc gctctgtcac tcaggctgga  201960
gtgcagtggc gcgatttcag ctcactgcaa gctccgcctc c                      202001
```

```
<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
tcacagctat cttctcatc                                               19

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3
taaattgtca tcacc                                                   15

<210> SEQ ID NO 4
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 4
ataaattgtc atcacca                                                 17

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 5
cacagctatc ttctcat                                                 17

<210> SEQ ID NO 6
```

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6
cacagctatc ttctcat                                                  17

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 7
aattgtcatc accag                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 8
ttgtcatcac cagaa                                                    15

<210> SEQ ID NO 9
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 9
attgtcatca ccaga                                                    15

<210> SEQ ID NO 10
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 10
aattgtcatc accag                                                    15

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 11
ataaattgtc atcacca                                                  17

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
```
aataaattgt catcacctt                                    19

<210> SEQ ID NO 13
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 13
taaattgtca tcacc                                        15

<210> SEQ ID NO 14
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 14
taaattgtca tcacc                                        15

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 15
taaattgtca tcacc                                        15

<210> SEQ ID NO 16
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 16
taaattgtca tcacc                                        15

<210> SEQ ID NO 17
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 17
ataaattgtc atcacca                                      17

<210> SEQ ID NO 18
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 18
ataaattgtc atcacca                                      17

<210> SEQ ID NO 19
<211> LENGTH: 17
<212> TYPE: DNA

```
<213> ORGANISM: Artificial Sequence
<220> FEATURE:
<223> OTHER INFORMATION: Synthetic oligonucleotide

<400> SEQUENCE: 19
ataaattgtc atcacca                                                    17

<210> SEQ ID NO 20
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 20
ataaattgtc atcacca                                                    17

<210> SEQ ID NO 21
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 21
ataaattgtc atcacca                                                    17

<210> SEQ ID NO 22
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 22
ataaattgtc atcacca                                                    17

<210> SEQ ID NO 23
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 23
taaattgtca tcacca                                                     16

<210> SEQ ID NO 24
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 24
ataaattgtc atcacc                                                     16

<210> SEQ ID NO 25
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 25
taaattgtca tcacc                                                      15
```

```
<210> SEQ ID NO 26
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 26
taaattgtca tcacc                                                      15

<210> SEQ ID NO 27
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 27
acagctatct tctca                                                      15

<210> SEQ ID NO 28
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 28
acagctatct tctca                                                      15

<210> SEQ ID NO 29
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 29
cacagctatc ttctcat                                                    17

<210> SEQ ID NO 30
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 30
cacagctatc ttctcat                                                    17

<210> SEQ ID NO 31
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 31
taaattgtca tcaccag                                                    17

<210> SEQ ID NO 32
<211> LENGTH: 17
<212> TYPE: DNA
<213> ORGANISM: Artificial Sequence
<220> FEATURE:
```

<223> OTHER INFORMATION: Synthetic oligonucleotide

<400> SEQUENCE: 32
taattttcta gacttta                                                17

<210> SEQ ID NO 33
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 33
gaatacgggt aacattt                                                17

<210> SEQ ID NO 34
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 34
aaattgtcat caccaga                                                17

<210> SEQ ID NO 35
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 35
taattttcta gacttta                                                17

<210> SEQ ID NO 36
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 36
aattttctag actttat                                                17

<210> SEQ ID NO 37
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 37
tcaagctagt aacgatg                                                17

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 38
cacagctatc ttctcat                                                17

```
<210> SEQ ID NO 39
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 39
acagctatct tctcatc                                                   17

<210> SEQ ID NO 40
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 40
ttgatctgta gcagcag                                                   17

<210> SEQ ID NO 41
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 41
tgatctgtag cagcagc                                                   17

<210> SEQ ID NO 42
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 42
gaatacgggt aacattt                                                   17

<210> SEQ ID NO 43
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 43
aatacgggta acatttt                                                   17

<210> SEQ ID NO 44
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 44
taattttcta gacttta                                                   17

<210> SEQ ID NO 45
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 45
ttgatctgta gcagcag                                                    17

<210> SEQ ID NO 46
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 46
cacagctatc ttctcat                                                    17

<210> SEQ ID NO 47
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 47
taaattgtca tcacc                                                      15

<210> SEQ ID NO 48
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 48
attgtcatca ccaga                                                      15

<210> SEQ ID NO 49
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 49
ataaattgtc atcacca                                                    17

<210> SEQ ID NO 50
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 50
ataaattgtc atcacca                                                    17

<210> SEQ ID NO 51
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 51
taaattgtca tcaccag                                                    17

<210> SEQ ID NO 52
<211> LENGTH: 17
```

```
<212> TYPE: DNA
<213> ORGANISM: Artificial Sequence
<220> FEATURE:
<223> OTHER INFORMATION: Synthetic oligonucleotide

<400> SEQUENCE: 52
ataaattgtc atcacca                                                          17

<210> SEQ ID NO 53
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 53
ataaattgtc atcacca                                                          17

<210> SEQ ID NO 54
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 54
taaattgtca tcacca                                                           16

<210> SEQ ID NO 55
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 55
taaattgtca tcacca                                                           16

<210> SEQ ID NO 56
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 56
taaattgtca tcacca                                                           16

<210> SEQ ID NO 57
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 57
taaattgtca tcacca                                                           16

<210> SEQ ID NO 58
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 58
```
taaattgtca tcacca                                                    16

<210> SEQ ID NO 59
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 59
taaattgtca tcacca                                                    16

<210> SEQ ID NO 60
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 60
ataaattgtc atcacca                                                   17

<210> SEQ ID NO 61
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 61
ataaattgtc atcacca                                                   17

<210> SEQ ID NO 62
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 62
ataaattgtc atcacca                                                   17

<210> SEQ ID NO 63
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 63
taaattgtca tcaccag                                                   17

<210> SEQ ID NO 64
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 64
aaattgtcat caccaga                                                   17

<210> SEQ ID NO 65
<211> LENGTH: 17
<212> TYPE: DNA
<213> ORGANISM: Artificial Sequence

```
<220> FEATURE:
<223> OTHER INFORMATION: Synthetic oligonucleotide

<400> SEQUENCE: 65
aattgtcatc accagaa                                                    17

<210> SEQ ID NO 66
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 66
ataaattgtc atcacca                                                    17

<210> SEQ ID NO 67
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 67
ataaattgtc atcacca                                                    17

<210> SEQ ID NO 68
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 68
ataaattgtc atcacca                                                    17

<210> SEQ ID NO 69
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 69
ataaattgtc atcacca                                                    17

<210> SEQ ID NO 70
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 70
ataaattgtc atcacc                                                     16

<210> SEQ ID NO 71
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 71
ataaattgtc atcacc                                                     16
```

```
<210> SEQ ID NO 72
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 72
ataaattgtc atcacc                                                      16

<210> SEQ ID NO 73
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 73
ataaattgtc atcacc                                                      16

<210> SEQ ID NO 74
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 74
ataaattgtc atcacc                                                      16

<210> SEQ ID NO 75
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 75
ataaattgtc atcacc                                                      16

<210> SEQ ID NO 76
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 76
aataaattgt catcaccag                                                   19

<210> SEQ ID NO 77
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 77
ataaattgtc atcaccaga                                                   19

<210> SEQ ID NO 78
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 78
taaattgtca tcaccagaa                                                19

<210> SEQ ID NO 79
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 79
aaattgtcat caccagaaa                                                19

<210> SEQ ID NO 80
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 80
aattgtcatc accagaaaa                                                19

<210> SEQ ID NO 81
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 81
attgtcatca ccagaaaaa                                                19

<210> SEQ ID NO 82
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 82
taataaattg tcatcacca                                                19

<210> SEQ ID NO 83
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 83
ttaataaatt gtcatcacc                                                19

<210> SEQ ID NO 84
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 84
taattttcta gacttta                                                  17

<210> SEQ ID NO 85
```

```
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 85
taatttctct agacttta                                                 18

<210> SEQ ID NO 86
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 86
taatttctct agacttta                                                 18

<210> SEQ ID NO 87
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 87
aattttctct agatttat                                                 18

<210> SEQ ID NO 88
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 88
aatacgggta acatttt                                                  17

<210> SEQ ID NO 89
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 89
gaatacgggt aactttt                                                  17

<210> SEQ ID NO 90
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 90
aaattgtcat caccaga                                                  17

<210> SEQ ID NO 91
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 91
```
ataaattgtc atcacca 17

<210> SEQ ID NO 92
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 92
aattttctag acttta 16

<210> SEQ ID NO 93
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 93
taattttcta gacttt 16

<210> SEQ ID NO 94
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 94
attttctaga cttta 15

<210> SEQ ID NO 95
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 95
aattttctag acttt 15

<210> SEQ ID NO 96
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 96
taattttcta gactt 15

<210> SEQ ID NO 97
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 97
attttctaga ctttat 16

<210> SEQ ID NO 98
<211> LENGTH: 16
<212> TYPE: DNA

```
<213> ORGANISM: Artificial Sequence
<220> FEATURE:
<223> OTHER INFORMATION: Synthetic oligonucleotide

<400> SEQUENCE: 98
aattttctag acttta                                                        16

<210> SEQ ID NO 99
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 99
ttttctagac tttat                                                         15

<210> SEQ ID NO 100
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 100
attttctaga cttta                                                         15

<210> SEQ ID NO 101
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 101
aattttctag acttt                                                         15

<210> SEQ ID NO 102
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 102
caagctagta acgatg                                                        16

<210> SEQ ID NO 103
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 103
tcaagctagt aacgat                                                        16

<210> SEQ ID NO 104
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 104
aagctagtaa cgatg                                                         15
```

<210> SEQ ID NO 105
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 105
caagctagta acgat                                                    15

<210> SEQ ID NO 106
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 106
tcaagctagt aacga                                                    15

<210> SEQ ID NO 107
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 107
atacgggtaa catttt                                                   16

<210> SEQ ID NO 108
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 108
aatacgggta acattt                                                   16

<210> SEQ ID NO 109
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 109
tacgggtaac atttt                                                    15

<210> SEQ ID NO 110
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 110
atacgggtaa cattt                                                    15

<210> SEQ ID NO 111
<211> LENGTH: 15
<212> TYPE: DNA
<213> ORGANISM: Artificial Sequence
<220> FEATURE:

<223> OTHER INFORMATION: Synthetic oligonucleotide

<400> SEQUENCE: 111
aatacgggta acatt                                                        15

<210> SEQ ID NO 112
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 112
aatacgggta acattt                                                       16

<210> SEQ ID NO 113
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 113
gaatacgggt aacatt                                                       16

<210> SEQ ID NO 114
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 114
atacgggtaa cattt                                                        15

<210> SEQ ID NO 115
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 115
aatacgggta acatt                                                        15

<210> SEQ ID NO 116
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 116
gaatacgggt aacat                                                        15

<210> SEQ ID NO 117
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 117
gatctgtagc agcagc                                                       16

```
<210> SEQ ID NO 118
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 118
tgatctgtag cagcag                                                    16

<210> SEQ ID NO 119
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 119
atctgtagca gcagc                                                     15

<210> SEQ ID NO 120
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 120
gatctgtagc agcag                                                     15

<210> SEQ ID NO 121
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 121
tgatctgtag cagca                                                     15

<210> SEQ ID NO 122
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 122
tgatctgtag cagcag                                                    16

<210> SEQ ID NO 123
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 123
ttgatctgta gcagca                                                    16

<210> SEQ ID NO 124
<211> LENGTH: 15
<212> TYPE: DNA
<213> ORGANISM: Artificial Sequence
<220> FEATURE:
<223> OTHER INFORMATION: Synthetic oligonucleotide
```

<400> SEQUENCE: 124
gatctgtagc agcag                                                    15

<210> SEQ ID NO 125
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 125
tgatctgtag cagca                                                    15

<210> SEQ ID NO 126
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 126
ttgatctgta gcagc                                                    15

<210> SEQ ID NO 127
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 127
aattttctag acttta                                                   16

<210> SEQ ID NO 128
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 128
taattttcta gacttt                                                   16

<210> SEQ ID NO 129
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 129
attttctaga cttta                                                    15

<210> SEQ ID NO 130
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 130
aattttctag acttt                                                    15

<210> SEQ ID NO 131
<211> LENGTH: 15

```
<212> TYPE: DNA
<213> ORGANISM: Artificial Sequence
<220> FEATURE:
<223> OTHER INFORMATION: Synthetic oligonucleotide

<400> SEQUENCE: 131
taattttcta gactt                                                        15

<210> SEQ ID NO 132
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 132
taaattgcca tcacc                                                        15

<210> SEQ ID NO 133
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 133
aaattgccat cacca                                                        15

<210> SEQ ID NO 134
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 134
aattgccatc accag                                                        15

<210> SEQ ID NO 135
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 135
attgccatca ccaga                                                        15

<210> SEQ ID NO 136
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 136
taaattgcca tcacc                                                        15

<210> SEQ ID NO 137
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 137
```

```
aaattgccat cacca                                                    15

<210> SEQ ID NO 138
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 138
aattgccatc accag                                                    15

<210> SEQ ID NO 139
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 139
attgccatca ccaga                                                    15

<210> SEQ ID NO 140
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 140
taaattgcca tcaccag                                                  17

<210> SEQ ID NO 141
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 141
aaattgccat caccaga                                                  17

<210> SEQ ID NO 142
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 142
aattgccatc accagaa                                                  17

<210> SEQ ID NO 143
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 143
attgccatca ccagaaa                                                  17

<210> SEQ ID NO 144
<211> LENGTH: 17
<212> TYPE: DNA
<213> ORGANISM: Artificial Sequence
```

```
<220> FEATURE:
<223> OTHER INFORMATION: Synthetic oligonucleotide

<400> SEQUENCE: 144
taaattgcca tcaccag                                                   17

<210> SEQ ID NO 145
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 145
aaattgccat caccaga                                                   17

<210> SEQ ID NO 146
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 146
aattgccatc accagaa                                                   17

<210> SEQ ID NO 147
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 147
attgccatca ccagaaa                                                   17

<210> SEQ ID NO 148
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 148
gggcacagac ttcca                                                     15

<210> SEQ ID NO 149
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 149
agggcacaga cttcc                                                     15

<210> SEQ ID NO 150
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 150
aagggcacag acttc                                                     15
```

```
<210> SEQ ID NO 151
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 151
caagggcaca gactt                                                      15

<210> SEQ ID NO 152
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 152
gggcacagac ttccaa                                                     16

<210> SEQ ID NO 153
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 153
agggcacaga cttcca                                                     16

<210> SEQ ID NO 154
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 154
aagggcacag acttcc                                                     16

<210> SEQ ID NO 155
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 155
caagggcaca gacttc                                                     16

<210> SEQ ID NO 156
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 156
agagaacaag aaggc                                                      15

<210> SEQ ID NO 157
<211> LENGTH: 15
<212> TYPE: DNA
<213> ORGANISM: Artificial Sequence
<220> FEATURE:
<223> OTHER INFORMATION: Synthetic oligonucleotide
```

<400> SEQUENCE: 157
gagaacaaga aggct    15

<210> SEQ ID NO 158
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 158
agaacaagaa ggctc    15

<210> SEQ ID NO 159
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 159
gaacaagaag gctcc    15

<210> SEQ ID NO 160
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 160
agagaacaag aaggct    16

<210> SEQ ID NO 161
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 161
gagaacaaga aggctc    16

<210> SEQ ID NO 162
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 162
agaacaagaa ggctcc    16

<210> SEQ ID NO 163
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 163
gaacaagaag gctcca    16

<210> SEQ ID NO 164

```
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 164
taaattgcca tcacc                                                    15

<210> SEQ ID NO 165
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 165
ataaattgcc atcacca                                                  17

<210> SEQ ID NO 166
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 166
ataaattgcc atcacca                                                  17

<210> SEQ ID NO 167
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 167
ataaattgcc atcacc                                                   16

<210> SEQ ID NO 168
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 168
taaattgcca tcacc                                                    15

<210> SEQ ID NO 169
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 169
taaattgcca tcacc                                                    15

<210> SEQ ID NO 170
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 170
```

-continued

```
attgccatca ccaga                                                    15

<210> SEQ ID NO 171
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 171
taaattgcca tcacca                                                   16

<210> SEQ ID NO 172
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 172
ataaattgcc atcacca                                                  17

<210> SEQ ID NO 173
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 173
taaattgcca tcaccag                                                  17

<210> SEQ ID NO 174
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 174
acacagtaga tgagg                                                    15

<210> SEQ ID NO 175
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 175
gcacacagta gatgaggga                                                19

<210> SEQ ID NO 176
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 176
aagggatgct gacttgggc                                                19

<210> SEQ ID NO 177
<211> LENGTH: 15
<212> TYPE: DNA
```

```
<213> ORGANISM: Artificial Sequence
<220> FEATURE:
<223> OTHER INFORMATION: Synthetic oligonucleotide

<400> SEQUENCE: 177
cagtgctacc caacc                                                    15

<210> SEQ ID NO 178
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 178
acagtgctac ccaacct                                                  17

<210> SEQ ID NO 179
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 179
ttcaagctag taacgatgc                                                19

<210> SEQ ID NO 180
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 180
cttcaagcta gtaacga                                                  17

<210> SEQ ID NO 181
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 181
acagctatct tctca                                                    15

<210> SEQ ID NO 182
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 182
ataaattgtc atcaccag                                                 18

<210> SEQ ID NO 183
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 183
aataaattgt catcaccag                                                19
```

<210> SEQ ID NO 184
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 184
ataaattgtc atcacca                                                  17

<210> SEQ ID NO 185
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 185
gcacacagta gatgaggga                                                19

<210> SEQ ID NO 186
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 186
gcacacagta gatgaggga                                                19

<210> SEQ ID NO 187
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 187
gcacacagta gatgaggga                                                19

<210> SEQ ID NO 188
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 188
acagtagatg agggagcag                                                19

<210> SEQ ID NO 189
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 189
cacacagtag atgaggg                                                  17

<210> SEQ ID NO 190
<211> LENGTH: 19
<212> TYPE: DNA
<213> ORGANISM: Artificial Sequence
<220> FEATURE:

<223> OTHER INFORMATION: Synthetic oligonucleotide

<400> SEQUENCE: 190
aagggatgct gacttgggc                                          19

<210> SEQ ID NO 191
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 191
gggatgctga cttgg                                              15

<210> SEQ ID NO 192
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 192
ataaattgtc atcacca                                            17

<210> SEQ ID NO 193
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 193
ataaattgtc atcacca                                            17

<210> SEQ ID NO 194
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 194
aataaattgt catcaccag                                          19

<210> SEQ ID NO 195
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 195
aataaattgt catcaccag                                          19

<210> SEQ ID NO 196
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 196
aataaattgt catcaccag                                          19

```
<210> SEQ ID NO 197
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 197
acagtgctac ccaacct                                                    17

<210> SEQ ID NO 198
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 198
ttcaagctag taacg                                                      15

<210> SEQ ID NO 199
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 199
gagcagctgc aacctggca                                                  19

<210> SEQ ID NO 200
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 200
gagcagctgc aacctggca                                                  19

<210> SEQ ID NO 201
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 201
gcagctgcaa cctgg                                                      15

<210> SEQ ID NO 202
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 202
ttgatctgta gcagcagct                                                  19

<210> SEQ ID NO 203
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 203
ccttcctcac tgaggatga                                                19

<210> SEQ ID NO 204
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 204
taacactcga ttaaccctg                                                19

<210> SEQ ID NO 205
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 205
aagaagcctg ataaaatct                                                19

<210> SEQ ID NO 206
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 206
tgcttcagag ctgagcagaa                                               20

<210> SEQ ID NO 207
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 207
accacaacgg cgatt                                                    15

<210> SEQ ID NO 208
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 208
tacctaagag cacat                                                    15

<210> SEQ ID NO 209
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 209
tagttcatcc cagtg                                                    15

<210> SEQ ID NO 210
<211> LENGTH: 15
```

```
<212> TYPE: DNA
<213> ORGANISM: Artificial Sequence
<220> FEATURE:
<223> OTHER INFORMATION: Synthetic oligonucleotide

<400> SEQUENCE: 210
gaggaggtat actgt                                                      15

<210> SEQ ID NO 211
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 211
tggtgccggg tgtct                                                      15

<210> SEQ ID NO 212
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 212
aaacggcgca gcggg                                                      15

<210> SEQ ID NO 213
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 213
cgcctatacc ataca                                                      15

<210> SEQ ID NO 214
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 214
gataatatcc tatca                                                      15

<210> SEQ ID NO 215
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 215
agagaacaag aaggc                                                      15

<210> SEQ ID NO 216
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 216
```
aaccactgtg ggatg                                              15

<210> SEQ ID NO 217
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 217
ctaaaactaa cttga                                              15

<210> SEQ ID NO 218
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 218
cgttgaagta ctgtc                                              15

<210> SEQ ID NO 219
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 219
taacactcga ttaac                                              15

<210> SEQ ID NO 220
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 220
cctaaatcaa tctac                                              15

<210> SEQ ID NO 221
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 221
attttctaga cttta                                              15

<210> SEQ ID NO 222
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 222
cttcctcact gagga                                              15

<210> SEQ ID NO 223
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 223
gaaatgggtt tttcc                                                    15

<210> SEQ ID NO 224
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 224
taagaaacac aatca                                                    15

<210> SEQ ID NO 225
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 225
gaacaaacag aagaa                                                    15

<210> SEQ ID NO 226
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 226
tggtgccagg tgtct                                                    15

<210> SEQ ID NO 227
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 227
aaacggcaca gcggg                                                    15

<210> SEQ ID NO 228
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 228
acttcaagct agtaacgat                                                19

<210> SEQ ID NO 229
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 229
acaccacaac ggcgatttg                                                19

<210> SEQ ID NO 230
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 230
cttacctaag agcacattt                                                  19

<210> SEQ ID NO 231
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 231
gctagttcat cccagtgag                                                  19

<210> SEQ ID NO 232
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 232
cagaggaggt atactgtat                                                  19

<210> SEQ ID NO 233
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 233
aatggtgccg ggtgtctag                                                  19

<210> SEQ ID NO 234
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 234
agaaacggcg cagcgggaa                                                  19

<210> SEQ ID NO 235
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 235
tccgcctata ccatacaat                                                  19

<210> SEQ ID NO 236
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 236
atgataatat cctatcaaa                                              19

<210> SEQ ID NO 237
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 237
agagagaaca agaaggctc                                              19

<210> SEQ ID NO 238
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 238
caaaccactg tgggatgaa                                              19

<210> SEQ ID NO 239
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 239
atctaaaact aacttgaga                                              19

<210> SEQ ID NO 240
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 240
agcgttgaag tactgtccc                                              19

<210> SEQ ID NO 241
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 241
gttaacactc gattaaccc                                              19

<210> SEQ ID NO 242
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 242
tccctaaatc aatctacaa                                              19

<210> SEQ ID NO 243

```
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 243
taattttcta gactttatg                                                19

<210> SEQ ID NO 244
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 244
accttcctca ctgaggatg                                                19

<210> SEQ ID NO 245
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 245
tggaaatggg tttttccac                                                19

<210> SEQ ID NO 246
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 246
aataagaaac acaatcaaa                                                19

<210> SEQ ID NO 247
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 247
cagaacaaac agaagaatt                                                19

<210> SEQ ID NO 248
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 248
aatggtgcca ggtgtctag                                                19

<210> SEQ ID NO 249
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 249
```
agaaacggca cagcgggaa                                            19

<210> SEQ ID NO 250
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 250
agaatacggg taaca                                                15

<210> SEQ ID NO 251
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 251
ctgagcggag aaacc                                                15

<210> SEQ ID NO 252
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 252
ttccctaaaa acaaa                                                15

<210> SEQ ID NO 253
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 253
cttttctatt gtctg                                                15

<210> SEQ ID NO 254
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 254
tagaggacgc cgtgc                                                15

<210> SEQ ID NO 255
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 255
ttccctagaa acaaa                                                15

<210> SEQ ID NO 256
<211> LENGTH: 15
<212> TYPE: DNA

<213> ORGANISM: Artificial Sequence
<220> FEATURE:
<223> OTHER INFORMATION: Synthetic oligonucleotide

<400> SEQUENCE: 256
caagggcaca gactt                                        15

<210> SEQ ID NO 257
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 257
taaccgtggc atggg                                        15

<210> SEQ ID NO 258
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 258
gactatagca cccag                                        15

<210> SEQ ID NO 259
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 259
gtgtgtacag aacct                                        15

<210> SEQ ID NO 260
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 260
gaagcctgat aaaat                                        15

<210> SEQ ID NO 261
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 261
ttcagaatgc ctcat                                        15

<210> SEQ ID NO 262
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 262
ggacagggtg tgctc                                        15

<210> SEQ ID NO 263
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 263
agctaggcta aagag                                                    15

<210> SEQ ID NO 264
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 264
tgggcagaaa ggact                                                    15

<210> SEQ ID NO 265
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 265
tgatctgtag cagca                                                    15

<210> SEQ ID NO 266
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 266
cttttccgtg ctgtt                                                    15

<210> SEQ ID NO 267
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 267
ggagaatacg ggtaacatt                                                19

<210> SEQ ID NO 268
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 268
ggctgagcgg agaaaccct                                                19

<210> SEQ ID NO 269
<211> LENGTH: 19
<212> TYPE: DNA
<213> ORGANISM: Artificial Sequence
<220> FEATURE:

<223> OTHER INFORMATION: Synthetic oligonucleotide

<400> SEQUENCE: 269
gattccctaa aacaaaaa                                                    19

<210> SEQ ID NO 270
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 270
tgcttttcta ttgtctgtc                                                   19

<210> SEQ ID NO 271
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 271
catagaggac gccgtgcag                                                   19

<210> SEQ ID NO 272
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 272
gattccctag aaacaaaaa                                                   19

<210> SEQ ID NO 273
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 273
cacaagggca cagacttcc                                                   19

<210> SEQ ID NO 274
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 274
tttaaccgtg gcatgggca                                                   19

<210> SEQ ID NO 275
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 275
gagactatag cacccagat                                                   19

```
<210> SEQ ID NO 276
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 276
acgtgtgtac agaacctgc                                               19

<210> SEQ ID NO 277
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 277
tgttcagaat gcctcatct                                               19

<210> SEQ ID NO 278
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 278
ggggacaggg tgtgctctc                                               19

<210> SEQ ID NO 279
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 279
gcagctaggc taaagagtc                                               19

<210> SEQ ID NO 280
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 280
ggtgggcaga aaggactga                                               19

<210> SEQ ID NO 281
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 281
gttgatctgt agcagcagc                                               19

<210> SEQ ID NO 282
<211> LENGTH: 19
<212> TYPE: DNA
<213> ORGANISM: Artificial Sequence
<220> FEATURE:
<223> OTHER INFORMATION: Synthetic oligonucleotide
```

<400> SEQUENCE: 282
aacttttccg tgctgttct                          19

<210> SEQ ID NO 283
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 283
aacactcgat taaccct                            17

<210> SEQ ID NO 284
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 284
taacactcga ttaaccc                            17

<210> SEQ ID NO 285
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 285
ttaacactcg attaacc                            17

<210> SEQ ID NO 286
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 286
gttaacactc gattaac                            17

<210> SEQ ID NO 287
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 287
agttaacact cgattaa                            17

<210> SEQ ID NO 288
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 288
aacactcgat taccct                             17

<210> SEQ ID NO 289
<211> LENGTH: 17

```
<212> TYPE: DNA
<213> ORGANISM: Artificial Sequence
<220> FEATURE:
<223> OTHER INFORMATION: Synthetic oligonucleotide

<400> SEQUENCE: 289
taacactcga ttaaccc                                                 17

<210> SEQ ID NO 290
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 290
ttaacactcg attaacc                                                 17

<210> SEQ ID NO 291
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 291
gttaacactc gattaac                                                 17

<210> SEQ ID NO 292
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 292
agttaacact cgattaa                                                 17

<210> SEQ ID NO 293
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 293
acactcgatt aaccctg                                                 17

<210> SEQ ID NO 294
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 294
aacactcgat taaccct                                                 17

<210> SEQ ID NO 295
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 295
```
taacactcga ttaaccc                                                    17

<210> SEQ ID NO 296
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 296
ttaacactcg attaacc                                                    17

<210> SEQ ID NO 297
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 297
gttaacactc gattaac                                                    17

<210> SEQ ID NO 298
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 298
agttaacact cgattaa                                                    17

<210> SEQ ID NO 299
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 299
acactcgatt aaccctg                                                    17

<210> SEQ ID NO 300
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 300
aacactcgat taaccct                                                    17

<210> SEQ ID NO 301
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 301
taacactcga ttaaccc                                                    17

<210> SEQ ID NO 302
<211> LENGTH: 17
<212> TYPE: DNA
<213> ORGANISM: Artificial Sequence

```
<220> FEATURE:
<223> OTHER INFORMATION: Synthetic oligonucleotide

<400> SEQUENCE: 302
ttaacactcg attaacc                                                    17

<210> SEQ ID NO 303
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 303
gttaacactc gattaac                                                    17

<210> SEQ ID NO 304
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 304
agttaacact cgattaa                                                    17

<210> SEQ ID NO 305
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 305
aaattgtcat caccaga                                                    17

<210> SEQ ID NO 306
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 306
aataaattgt catcacc                                                    17

<210> SEQ ID NO 307
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 307
taataaattg tcatcac                                                    17

<210> SEQ ID NO 308
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 308
aaattgtcat caccaga                                                    17
```

```
<210> SEQ ID NO 309
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 309
taaattgtca tcaccag                                                    17

<210> SEQ ID NO 310
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 310
ataaattgtc atcacca                                                    17

<210> SEQ ID NO 311
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 311
aataaattgt catcacc                                                    17

<210> SEQ ID NO 312
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 312
taataaattg tcatcac                                                    17

<210> SEQ ID NO 313
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 313
aattgtcatc accagaa                                                    17

<210> SEQ ID NO 314
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 314
taaattgtca tcaccag                                                    17

<210> SEQ ID NO 315
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 315
ataaattgtc atcacca                                                  17

<210> SEQ ID NO 316
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 316
aataaattgt catcacc                                                  17

<210> SEQ ID NO 317
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 317
taataaattg tcatcac                                                  17

<210> SEQ ID NO 318
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 318
aattgtcatc accagaa                                                  17

<210> SEQ ID NO 319
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 319
aaattgtcat caccaga                                                  17

<210> SEQ ID NO 320
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 320
taaattgtca tcaccag                                                  17

<210> SEQ ID NO 321
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 321
ataaattgtc atcacca                                                  17

<210> SEQ ID NO 322
```

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 322
aataaattgt catcacc                                                  17

<210> SEQ ID NO 323
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 323
taataaattg tcatcac                                                  17

<210> SEQ ID NO 324
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 324
tcaagctagt aacgatg                                                  17

<210> SEQ ID NO 325
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 325
ttcaagctag taacgat                                                  17

<210> SEQ ID NO 326
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 326
cttcaagcta gtaacga                                                  17

<210> SEQ ID NO 327
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 327
acttcaagct agtaacg                                                  17

<210> SEQ ID NO 328
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 328
```
aacttcaagc tagtaac                                                17

<210> SEQ ID NO 329
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 329
caagctagta acgatgc                                                17

<210> SEQ ID NO 330
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 330
ttcaagctag taacgat                                                17

<210> SEQ ID NO 331
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 331
cttcaagcta gtaacga                                                17

<210> SEQ ID NO 332
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 332
acttcaagct agtaacg                                                17

<210> SEQ ID NO 333
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 333
aacttcaagc tagtaac                                                17

<210> SEQ ID NO 334
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 334
ttttctagac tttatga                                                17

<210> SEQ ID NO 335
<211> LENGTH: 17
<212> TYPE: DNA

```
<213> ORGANISM: Artificial Sequence
<220> FEATURE:
<223> OTHER INFORMATION: Synthetic oligonucleotide

<400> SEQUENCE: 335
attttctaga ctttatg                                                    17

<210> SEQ ID NO 336
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 336
aattttctag actttat                                                    17

<210> SEQ ID NO 337
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 337
ttaattttct agacttt                                                    17

<210> SEQ ID NO 338
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 338
ttttctagac tttatga                                                    17

<210> SEQ ID NO 339
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 339
attttctaga ctttatg                                                    17

<210> SEQ ID NO 340
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 340
aattttctag actttat                                                    17

<210> SEQ ID NO 341
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 341
taattttcta gacttta                                                    17
```

<210> SEQ ID NO 342
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 342
ttaattttct agacttt                                                      17

<210> SEQ ID NO 343
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 343
tttctagact ttatgat                                                      17

<210> SEQ ID NO 344
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 344
ttttctagac tttatga                                                      17

<210> SEQ ID NO 345
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 345
attttctaga ctttatg                                                      17

<210> SEQ ID NO 346
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 346
ttaattttct agacttt                                                      17

<210> SEQ ID NO 347
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 347
tttctagact ttatgat                                                      17

<210> SEQ ID NO 348
<211> LENGTH: 17
<212> TYPE: DNA
<213> ORGANISM: Artificial Sequence
<220> FEATURE:

<223> OTHER INFORMATION: Synthetic oligonucleotide

<400> SEQUENCE: 348
ttttctagac tttatga                                                   17

<210> SEQ ID NO 349
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 349
attttctaga ctttatg                                                   17

<210> SEQ ID NO 350
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 350
aattttctag actttat                                                   17

<210> SEQ ID NO 351
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 351
ttaattttct agacttt                                                   17

<210> SEQ ID NO 352
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 352
ttcctcactg aggatga                                                   17

<210> SEQ ID NO 353
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 353
cttcctcact gaggatg                                                   17

<210> SEQ ID NO 354
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 354
ccttcctcac tgaggat                                                   17

```
<210> SEQ ID NO 355
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 355
accttcctca ctgagga                                                  17

<210> SEQ ID NO 356
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 356
caccttcctc actgagg                                                  17

<210> SEQ ID NO 357
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 357
ttcctcactg aggatga                                                  17

<210> SEQ ID NO 358
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 358
cttcctcact gaggatg                                                  17

<210> SEQ ID NO 359
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 359
ccttcctcac tgaggat                                                  17

<210> SEQ ID NO 360
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 360
accttcctca ctgagga                                                  17

<210> SEQ ID NO 361
<211> LENGTH: 17
<212> TYPE: DNA
<213> ORGANISM: Artificial Sequence
<220> FEATURE:
<223> OTHER INFORMATION: Synthetic oligonucleotide
```

<400> SEQUENCE: 361
caccttcctc actgagg    17

<210> SEQ ID NO 362
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 362
tcctcactga ggatgaa    17

<210> SEQ ID NO 363
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 363
ttcctcactg aggatga    17

<210> SEQ ID NO 364
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 364
cttcctcact gaggatg    17

<210> SEQ ID NO 365
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 365
ccttcctcac tgaggat    17

<210> SEQ ID NO 366
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 366
accttcctca ctgagga    17

<210> SEQ ID NO 367
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 367
caccttcctc actgagg    17

<210> SEQ ID NO 368
<211> LENGTH: 17

```
<212> TYPE: DNA
<213> ORGANISM: Artificial Sequence
<220> FEATURE:
<223> OTHER INFORMATION: Synthetic oligonucleotide

<400> SEQUENCE: 368
tcctcactga ggatgaa                                              17

<210> SEQ ID NO 369
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 369
ttcctcactg aggatga                                              17

<210> SEQ ID NO 370
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 370
cttcctcact gaggatg                                              17

<210> SEQ ID NO 371
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 371
ccttcctcac tgaggat                                              17

<210> SEQ ID NO 372
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 372
accttcctca ctgagga                                              17

<210> SEQ ID NO 373
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 373
caccttcctc actgagg                                              17

<210> SEQ ID NO 374
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 374
```

```
accactttgg gatgaat                                                    17

<210> SEQ ID NO 375
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 375
aaccactttg ggatgaa                                                    17

<210> SEQ ID NO 376
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 376
aaaccacttt gggatga                                                    17

<210> SEQ ID NO 377
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 377
caaaccactt tgggatg                                                    17

<210> SEQ ID NO 378
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 378
gcaaaccact ttgggat                                                    17

<210> SEQ ID NO 379
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 379
ccactttggg atgaata                                                    17

<210> SEQ ID NO 380
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 380
accactttgg gatgaat                                                    17

<210> SEQ ID NO 381
<211> LENGTH: 17
<212> TYPE: DNA
<213> ORGANISM: Artificial Sequence
```

```
<220> FEATURE:
<223> OTHER INFORMATION: Synthetic oligonucleotide

<400> SEQUENCE: 381
aaccactttg ggatgaa                                                    17

<210> SEQ ID NO 382
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 382
aaaccacttt gggatga                                                    17

<210> SEQ ID NO 383
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 383
caaaccactt tgggatg                                                    17

<210> SEQ ID NO 384
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 384
gcaaaccact ttgggat                                                    17

<210> SEQ ID NO 385
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 385
agttcatccc agtgaga                                                    17

<210> SEQ ID NO 386
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 386
tagttcatcc cagtgag                                                    17

<210> SEQ ID NO 387
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 387
ctagttcatc ccagtga                                                    17
```

<210> SEQ ID NO 388
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 388
gctagttcat cccagtg                                                    17

<210> SEQ ID NO 389
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 389
tgctagttca tcccagt                                                    17

<210> SEQ ID NO 390
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 390
agttcatccc agtgaga                                                    17

<210> SEQ ID NO 391
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 391
tagttcatcc cagtgag                                                    17

<210> SEQ ID NO 392
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 392
ctagttcatc ccagtga                                                    17

<210> SEQ ID NO 393
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 393
gctagttcat cccagtg                                                    17

<210> SEQ ID NO 394
<211> LENGTH: 17
<212> TYPE: DNA
<213> ORGANISM: Artificial Sequence
<220> FEATURE:
<223> OTHER INFORMATION: Synthetic oligonucleotide

```
<400> SEQUENCE: 394
tgctagttca tcccagt                                                      17

<210> SEQ ID NO 395
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 395
gttcatccca gtgagaa                                                      17

<210> SEQ ID NO 396
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 396
agttcatccc agtgaga                                                      17

<210> SEQ ID NO 397
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 397
tagttcatcc cagtgag                                                      17

<210> SEQ ID NO 398
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 398
ctagttcatc ccagtga                                                      17

<210> SEQ ID NO 399
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 399
gctagttcat cccagtg                                                      17

<210> SEQ ID NO 400
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 400
tgctagttca tcccagt                                                      17

<210> SEQ ID NO 401
```

<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 401
gttcatccca gtgagaa                                                       17

<210> SEQ ID NO 402
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 402
agttcatccc agtgaga                                                       17

<210> SEQ ID NO 403
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 403
tagttcatcc cagtgag                                                       17

<210> SEQ ID NO 404
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 404
ctagttcatc ccagtga                                                       17

<210> SEQ ID NO 405
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 405
gctagttcat cccagtg                                                       17

<210> SEQ ID NO 406
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 406
tgctagttca tcccagt                                                       17

<210> SEQ ID NO 407
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 407
aggaggcata ctgtatt                                                  17

<210> SEQ ID NO 408
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 408
gaggaggcat actgtat                                                  17

<210> SEQ ID NO 409
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 409
agaggaggca tactgta                                                  17

<210> SEQ ID NO 410
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 410
cagaggaggc atactgt                                                  17

<210> SEQ ID NO 411
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 411
acagaggagg catactg                                                  17

<210> SEQ ID NO 412
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 412
ggaggcatac tgtattt                                                  17

<210> SEQ ID NO 413
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 413
aggaggcata ctgtatt                                                  17

<210> SEQ ID NO 414
<211> LENGTH: 17
<212> TYPE: DNA

```
<213> ORGANISM: Artificial Sequence
<220> FEATURE:
<223> OTHER INFORMATION: Synthetic oligonucleotide

<400> SEQUENCE: 414
gaggaggcat actgtat                                                    17

<210> SEQ ID NO 415
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 415
agaggaggca tactgta                                                    17

<210> SEQ ID NO 416
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 416
cagaggaggc atactgt                                                    17

<210> SEQ ID NO 417
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 417
acagaggagg catactg                                                    17

<210> SEQ ID NO 418
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 418
gagaacgaga aggctcc                                                    17

<210> SEQ ID NO 419
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 419
agagaacgag aaggctc                                                    17

<210> SEQ ID NO 420
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 420
gagagaacga gaaggct                                                    17
```

<210> SEQ ID NO 421
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 421
agagagaacg agaaggc                                                17

<210> SEQ ID NO 422
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 422
aagagagaac gagaagg                                                17

<210> SEQ ID NO 423
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 423
agaacgagaa ggctcca                                                17

<210> SEQ ID NO 424
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 424
gagaacgaga aggctcc                                                17

<210> SEQ ID NO 425
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 425
agagaacgag aaggctc                                                17

<210> SEQ ID NO 426
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 426
gagagaacga gaaggct                                                17

<210> SEQ ID NO 427
<211> LENGTH: 17
<212> TYPE: DNA
<213> ORGANISM: Artificial Sequence
<220> FEATURE:

<223> OTHER INFORMATION: Synthetic oligonucleotide

<400> SEQUENCE: 427
agagagaacg agaaggc                                                17

<210> SEQ ID NO 428
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 428
aagagagaac gagaagg                                                17

<210> SEQ ID NO 429
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 429
gatctgtagc agcagct                                                17

<210> SEQ ID NO 430
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 430
tgatctgtag cagcagc                                                17

<210> SEQ ID NO 431
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 431
ttgatctgta gcagcag                                                17

<210> SEQ ID NO 432
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 432
gttgatctgt agcagca                                                17

<210> SEQ ID NO 433
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 433
ggttgatctg tagcagc                                                17

<210> SEQ ID NO 434
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 434
gatctgtagc agcagct                                                 17

<210> SEQ ID NO 435
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 435
tgatctgtag cagcagc                                                 17

<210> SEQ ID NO 436
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 436
ttgatctgta gcagcag                                                 17

<210> SEQ ID NO 437
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 437
gttgatctgt agcagca                                                 17

<210> SEQ ID NO 438
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 438
ggttgatctg tagcagc                                                 17

<210> SEQ ID NO 439
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 439
atctgtagca gcagctt                                                 17

<210> SEQ ID NO 440
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 440
gatctgtagc agcagct					17

<210> SEQ ID NO 441
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 441
gttgatctgt agcagca					17

<210> SEQ ID NO 442
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 442
ggttgatctg tagcagc					17

<210> SEQ ID NO 443
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 443
atctgtagca gcagctt					17

<210> SEQ ID NO 444
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 444
gatctgtagc agcagct					17

<210> SEQ ID NO 445
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 445
tgatctgtag cagcagc					17

<210> SEQ ID NO 446
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 446
gttgatctgt agcagca					17

<210> SEQ ID NO 447
<211> LENGTH: 17

```
<212> TYPE: DNA
<213> ORGANISM: Artificial Sequence
<220> FEATURE:
<223> OTHER INFORMATION: Synthetic oligonucleotide

<400> SEQUENCE: 447
ggttgatctg tagcagc                                              17

<210> SEQ ID NO 448
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 448
cagctatctt ctcatca                                              17

<210> SEQ ID NO 449
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 449
acagctatct tctcatc                                              17

<210> SEQ ID NO 450
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 450
cacagctatc ttctcat                                              17

<210> SEQ ID NO 451
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 451
tcacagctat cttctca                                              17

<210> SEQ ID NO 452
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 452
ttcacagcta tcttctc                                              17

<210> SEQ ID NO 453
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 453
```

```
cagctatctt ctcatca                                                    17

<210> SEQ ID NO 454
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 454
acagctatct tctcatc                                                    17

<210> SEQ ID NO 455
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 455
cacagctatc ttctcat                                                    17

<210> SEQ ID NO 456
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 456
tcacagctat cttctca                                                    17

<210> SEQ ID NO 457
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 457
ttcacagcta tcttctc                                                    17

<210> SEQ ID NO 458
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 458
agctatcttc tcatcaa                                                    17

<210> SEQ ID NO 459
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 459
cagctatctt ctcatca                                                    17

<210> SEQ ID NO 460
<211> LENGTH: 17
<212> TYPE: DNA
<213> ORGANISM: Artificial Sequence
```

```
<220> FEATURE:
<223> OTHER INFORMATION: Synthetic oligonucleotide

<400> SEQUENCE: 460
tcacagctat cttctca                                                    17

<210> SEQ ID NO 461
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 461
ttcacagcta tcttctc                                                    17

<210> SEQ ID NO 462
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 462
agctatcttc tcatcaa                                                    17

<210> SEQ ID NO 463
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 463
cagctatctt ctcatca                                                    17

<210> SEQ ID NO 464
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 464
acagctatct tctcatc                                                    17

<210> SEQ ID NO 465
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 465
cacagctatc ttctcat                                                    17

<210> SEQ ID NO 466
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 466
tcacagctat cttctca                                                    17
```

```
<210> SEQ ID NO 467
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 467
ttcacagcta tcttctc                                                  17

<210> SEQ ID NO 468
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 468
tgtgtacaga acctgcc                                                  17

<210> SEQ ID NO 469
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 469
gtgtgtacag aacctgc                                                  17

<210> SEQ ID NO 470
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 470
cgtgtgtaca gaacctg                                                  17

<210> SEQ ID NO 471
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 471
acgtgtgtac agaacct                                                  17

<210> SEQ ID NO 472
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 472
cacgtgtgta cagaacc                                                  17

<210> SEQ ID NO 473
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 473
tgtgtacaga acctgcc                                                    17

<210> SEQ ID NO 474
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 474
gtgtgtacag aacctgc                                                    17

<210> SEQ ID NO 475
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 475
cgtgtgtaca gaacctg                                                    17

<210> SEQ ID NO 476
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 476
acgtgtgtac agaacct                                                    17

<210> SEQ ID NO 477
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 477
cacgtgtgta cagaacc                                                    17

<210> SEQ ID NO 478
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 478
gtgtacagaa cctgccg                                                    17

<210> SEQ ID NO 479
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 479
tgtgtacaga acctgcc                                                    17

<210> SEQ ID NO 480
```

<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 480
gtgtgtacag aacctgc         17

<210> SEQ ID NO 481
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 481
cgtgtgtaca gaacctg         17

<210> SEQ ID NO 482
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 482
acgtgtgtac agaacct         17

<210> SEQ ID NO 483
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 483
cacgtgtgta cagaacc         17

<210> SEQ ID NO 484
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 484
gtgtacagaa cctgccg         17

<210> SEQ ID NO 485
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 485
tgtgtacaga acctgcc         17

<210> SEQ ID NO 486
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 486

```
gtgtgtacag aacctgc                                                    17

<210> SEQ ID NO 487
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 487
cgtgtgtaca gaacctg                                                    17

<210> SEQ ID NO 488
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 488
acgtgtgtac agaacct                                                    17

<210> SEQ ID NO 489
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 489
cacgtgtgta cagaacc                                                    17

<210> SEQ ID NO 490
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 490
tgagcggaga aaccctc                                                    17

<210> SEQ ID NO 491
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 491
ctgagcggag aaaccct                                                    17

<210> SEQ ID NO 492
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 492
gctgagcgga gaaaccc                                                    17

<210> SEQ ID NO 493
<211> LENGTH: 17
<212> TYPE: DNA
```

```
<213> ORGANISM: Artificial Sequence
<220> FEATURE:
<223> OTHER INFORMATION: Synthetic oligonucleotide

<400> SEQUENCE: 493
ggctgagcgg agaaacc                                                17

<210> SEQ ID NO 494
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 494
aggctgagcg gagaaac                                                17

<210> SEQ ID NO 495
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 495
gagcggagaa accctcc                                                17

<210> SEQ ID NO 496
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 496
tgagcggaga aaccctc                                                17

<210> SEQ ID NO 497
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 497
ctgagcggag aaaccct                                                17

<210> SEQ ID NO 498
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 498
gctgagcgga gaaaccc                                                17

<210> SEQ ID NO 499
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 499
ggctgagcgg agaaacc                                                17
```

```
<210> SEQ ID NO 500
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 500
aggctgagcg gagaaac                                                    17

<210> SEQ ID NO 501
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 501
agaatacggg taacatt                                                    17

<210> SEQ ID NO 502
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 502
gagaatacgg gtaacat                                                    17

<210> SEQ ID NO 503
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 503
ggagaatacg ggtaaca                                                    17

<210> SEQ ID NO 504
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 504
tggagaatac gggtaac                                                    17

<210> SEQ ID NO 505
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 505
agaatacggg taacatt                                                    17

<210> SEQ ID NO 506
<211> LENGTH: 17
<212> TYPE: DNA
<213> ORGANISM: Artificial Sequence
<220> FEATURE:
```

<223> OTHER INFORMATION: Synthetic oligonucleotide

<400> SEQUENCE: 506
gagaatacgg gtaacat                                                        17

<210> SEQ ID NO 507
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 507
ggagaatacg ggtaaca                                                        17

<210> SEQ ID NO 508
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 508
aaccgtggca tgggcag                                                        17

<210> SEQ ID NO 509
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 509
taaccgtggc atgggca                                                        17

<210> SEQ ID NO 510
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 510
ttaaccgtgg catgggc                                                        17

<210> SEQ ID NO 511
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 511
tttaaccgtg gcatggg                                                        17

<210> SEQ ID NO 512
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 512
ctttaaccgt ggcatgg                                                        17

```
<210> SEQ ID NO 513
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 513
accgtggcat gggcagt                                                    17

<210> SEQ ID NO 514
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 514
aaccgtggca tgggcag                                                    17

<210> SEQ ID NO 515
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 515
taaccgtggc atgggca                                                    17

<210> SEQ ID NO 516
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 516
ttaaccgtgg catgggc                                                    17

<210> SEQ ID NO 517
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 517
tttaaccgtg gcatggg                                                    17

<210> SEQ ID NO 518
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 518
ctttaaccgt ggcatgg                                                    17

<210> SEQ ID NO 519
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 519
actatagcac ccagatt                                                    17

<210> SEQ ID NO 520
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 520
gactatagca cccagat                                                    17

<210> SEQ ID NO 521
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 521
agactatagc acccaga                                                    17

<210> SEQ ID NO 522
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 522
gagactatag cacccag                                                    17

<210> SEQ ID NO 523
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 523
agagactata gcaccca                                                    17

<210> SEQ ID NO 524
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 524
actatagcac ccagatt                                                    17

<210> SEQ ID NO 525
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 525
gactatagca cccagat                                                    17

<210> SEQ ID NO 526
<211> LENGTH: 17
```

```
<212> TYPE: DNA
<213> ORGANISM: Artificial Sequence
<220> FEATURE:
<223> OTHER INFORMATION: Synthetic oligonucleotide

<400> SEQUENCE: 526
agactatagc acccaga                                                 17

<210> SEQ ID NO 527
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 527
gagactatag cacccag                                                 17

<210> SEQ ID NO 528
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 528
agagactata gcaccca                                                 17

<210> SEQ ID NO 529
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 529
ctatagcacc cagattt                                                 17

<210> SEQ ID NO 530
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 530
actatagcac ccagatt                                                 17

<210> SEQ ID NO 531
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 531
gactatagca cccagat                                                 17

<210> SEQ ID NO 532
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 532
```
agactatagc acccaga                                                    17

<210> SEQ ID NO 533
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 533
gagactatag cacccag                                                    17

<210> SEQ ID NO 534
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 534
agagactata gcaccca                                                    17

<210> SEQ ID NO 535
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 535
ctatagcacc cagattt                                                    17

<210> SEQ ID NO 536
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 536
actatagcac ccagatt                                                    17

<210> SEQ ID NO 537
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 537
gactatagca cccagat                                                    17

<210> SEQ ID NO 538
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 538
agactatagc acccaga                                                    17

<210> SEQ ID NO 539
<211> LENGTH: 17
<212> TYPE: DNA
<213> ORGANISM: Artificial Sequence

```
<220> FEATURE:
<223> OTHER INFORMATION: Synthetic oligonucleotide

<400> SEQUENCE: 539
gagactatag cacccag                                                    17

<210> SEQ ID NO 540
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 540
agagactata gcaccca                                                    17

<210> SEQ ID NO 541
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 541
ttttctattg tctgtcc                                                    17

<210> SEQ ID NO 542
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 542
cttttctatt gtctgtc                                                    17

<210> SEQ ID NO 543
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 543
gcttttctat tgtctgt                                                    17

<210> SEQ ID NO 544
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 544
tgcttttcta ttgtctg                                                    17

<210> SEQ ID NO 545
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 545
ttgcttttct attgtct                                                    17
```

```
<210> SEQ ID NO 546
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 546
tttctattgt ctgtccc                                                    17

<210> SEQ ID NO 547
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 547
ttttctattg tctgtcc                                                    17

<210> SEQ ID NO 548
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 548
cttttctatt gtctgtc                                                    17

<210> SEQ ID NO 549
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 549
gcttttctat tgtctgt                                                    17

<210> SEQ ID NO 550
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 550
tgcttttcta ttgtctg                                                    17

<210> SEQ ID NO 551
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 551
ttgcttttct attgtct                                                    17

<210> SEQ ID NO 552
<211> LENGTH: 17
<212> TYPE: DNA
<213> ORGANISM: Artificial Sequence
<220> FEATURE:
<223> OTHER INFORMATION: Synthetic oligonucleotide
```

```
<400> SEQUENCE: 552
ttttccgtgc tgttctg                                                      17

<210> SEQ ID NO 553
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 553
cttttccgtg ctgttct                                                      17

<210> SEQ ID NO 554
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 554
acttttccgt gctgttc                                                      17

<210> SEQ ID NO 555
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 555
aacttttccg tgctgtt                                                      17

<210> SEQ ID NO 556
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 556
aaacttttcc gtgctgt                                                      17

<210> SEQ ID NO 557
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 557
ttttccgtgc tgttctg                                                      17

<210> SEQ ID NO 558
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 558
cttttccgtg ctgttct                                                      17

<210> SEQ ID NO 559
```

```
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 559
acttttccgt gctgttc                                                      17

<210> SEQ ID NO 560
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 560
aacttttccg tgctgtt                                                      17

<210> SEQ ID NO 561
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 561
aaacttttcc gtgctgt                                                      17

<210> SEQ ID NO 562
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 562
tttccgtgct gttctga                                                      17

<210> SEQ ID NO 563
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 563
ttttccgtgc tgttctg                                                      17

<210> SEQ ID NO 564
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 564
cttttccgtg ctgttct                                                      17

<210> SEQ ID NO 565
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 565
```
acttttccgt gctgttc                                                17

<210> SEQ ID NO 566
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 566
aacttttccg tgctgtt                                                17

<210> SEQ ID NO 567
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 567
aaacttttcc gtgctgt                                                17

<210> SEQ ID NO 568
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 568
tttccgtgct gttctga                                                17

<210> SEQ ID NO 569
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 569
ttttccgtgc tgttctg                                                17

<210> SEQ ID NO 570
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 570
cttttccgtg ctgttct                                                17

<210> SEQ ID NO 571
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 571
acttttccgt gctgttc                                                17

<210> SEQ ID NO 572
<211> LENGTH: 17
<212> TYPE: DNA

```
<213> ORGANISM: Artificial Sequence
<220> FEATURE:
<223> OTHER INFORMATION: Synthetic oligonucleotide

<400> SEQUENCE: 572 aactttccg tgctgtt                                                       17

<210> SEQ ID NO 573
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 573 aaactttcc gtgctgt                                                       17

<210> SEQ ID NO 574
<211> LENGTH: 13481
<212> TYPE: DNA
<213> ORGANISM: Homo sapien
<220> FEATURE:
<221> NAME/KEY: CDS
<222> LOCATION: (146)..(9580)

<400> SEQUENCE: 574
```

| | | |
|---|---|---|
| gctgccggga cgggtccaag atggacggcc gctcaggttc tgcttttacc tgcggcccag | 60 |
| agccccattc attgccccgg tgctgagcgg cgccgcgagt cggcccgagg cctccgggga | 120 |

| gctgccgtgcc gggcgggaga ccgcc | atg gcg acc ctg gaa aag ctg atg aag | 172 |
| | Met Ala Thr Leu Glu Lys Leu Met Lys | |
| | 1               5 | |

| gcc ttc gag tcc ctc aag tcc ttc cag cag cag cag cag cag cag cag | 220 |
| Ala Phe Glu Ser Leu Lys Ser Phe Gln Gln Gln Gln Gln Gln Gln Gln | |
| 10              15                  20                  25 | |

| cag cag cag cag cag cag cag cag cag cag cag cag cag caa cag ccg | 268 |
| Gln Gln Gln Gln Gln Gln Gln Gln Gln Gln Gln Gln Gln Gln Gln Pro | |
|         30                  35                  40 | |

| cca ccg ccg ccg ccg ccg ccg ccg cct cct cag ctt cct cag ccg ccg | 316 |
| Pro Pro Pro Pro Pro Pro Pro Pro Pro Gln Leu Pro Gln Pro Pro | |
|             45                  50                  55 | |

| ccg cag gca cag ccg ctg ctg cct cag ccg cag ccg ccc ccg ccg ccg | 364 |
| Pro Gln Ala Gln Pro Leu Leu Pro Gln Pro Gln Pro Pro Pro Pro Pro | |
|                 60                  65                  70 | |

| ccc ccg ccg cca ccc ggc ccg gct gtg gct gag gag ccg ctg cac cga | 412 |
| Pro Pro Pro Pro Pro Gly Pro Ala Val Ala Glu Glu Pro Leu His Arg | |
|     75                  80                  85 | |

| cca aag aaa gaa ctt tca gct acc aag aaa gac cgt gtg aat cat tgt | 460 |
| Pro Lys Lys Glu Leu Ser Ala Thr Lys Lys Asp Arg Val Asn His Cys | |
| 90                  95                  100                 105 | |

| ctg aca ata tgt gaa aac ata gtg gca cag tct gtc aga aat tct cca | 508 |
| Leu Thr Ile Cys Glu Asn Ile Val Ala Gln Ser Val Arg Asn Ser Pro | |
|             110                 115                 120 | |

| gaa ttt cag aaa ctt ctg ggc atc gct atg gaa ctt ttt ctg ctg tgc | 556 |
| Glu Phe Gln Lys Leu Leu Gly Ile Ala Met Glu Leu Phe Leu Leu Cys | |
|                 125                 130                 135 | |

| agt gat gac gca gag tca gat gtc agg atg gtg gct gac gaa tgc ctc | 604 |
| Ser Asp Asp Ala Glu Ser Asp Val Arg Met Val Ala Asp Glu Cys Leu | |
|         140                 145                 150 | |

| aac aaa gtt atc aaa gct ttg atg gat tct aat ctt cca agg tta cag | 652 |
| Asn Lys Val Ile Lys Ala Leu Met Asp Ser Asn Leu Pro Arg Leu Gln | |
|     155                 160                 165 | |

-continued

| | | |
|---|---|---|
| ctc gag ctc tat aag gaa att aaa aag aat ggt gcc cct cgg agt ttg<br>Leu Glu Leu Tyr Lys Glu Ile Lys Lys Asn Gly Ala Pro Arg Ser Leu<br>170                    175                  180                 185 | 700 | |
| cgt gct gcc ctg tgg agg ttt gct gag ctg gct cac ctg gtt cgg cct<br>Arg Ala Ala Leu Trp Arg Phe Ala Glu Leu Ala His Leu Val Arg Pro<br>                 190                  195                 200 | 748 | |
| cag aaa tgc agg cct tac ctg gtg aac ctt ctg ccg tgc ctg act cga<br>Gln Lys Cys Arg Pro Tyr Leu Val Asn Leu Leu Pro Cys Leu Thr Arg<br>            205                  210                 215 | 796 | |
| aca agc aag aga ccc gaa gaa tca gtc cag gag acc ttg gct gca gct<br>Thr Ser Lys Arg Pro Glu Glu Ser Val Gln Glu Thr Leu Ala Ala Ala<br>220                    225                  230 | 844 | |
| gtt ccc aaa att atg gct tct ttt ggc aat ttt gca aat gac aat gaa<br>Val Pro Lys Ile Met Ala Ser Phe Gly Asn Phe Ala Asn Asp Asn Glu<br>235                    240                  245 | 892 | |
| att aag gtt ttg tta aag gcc ttc ata gcg aac ctg aag tca agc tcc<br>Ile Lys Val Leu Leu Lys Ala Phe Ile Ala Asn Leu Lys Ser Ser Ser<br>250                    255                  260                 265 | 940 | |
| ccc acc att cgg cgg aca gcg gct gga tca gca gtg agc atc tgc cag<br>Pro Thr Ile Arg Arg Thr Ala Ala Gly Ser Ala Val Ser Ile Cys Gln<br>                 270                  275                 280 | 988 | |
| cac tca aga agg aca caa tat ttc tat agt tgg cta cta aat gtg ctc<br>His Ser Arg Arg Thr Gln Tyr Phe Tyr Ser Trp Leu Leu Asn Val Leu<br>            285                  290                 295 | 1036 | |
| tta ggc tta ctc gtt cct gtc gag gat gaa cac tcc act ctg ctg att<br>Leu Gly Leu Leu Val Pro Val Glu Asp Glu His Ser Thr Leu Leu Ile<br>300                    305                  310 | 1084 | |
| ctt ggc gtg ctc acc ctg agg tat ttg gtg ccc ttg ctg cag cag<br>Leu Gly Val Leu Leu Thr Leu Arg Tyr Leu Val Pro Leu Leu Gln Gln<br>315                    320                  325 | 1132 | |
| cag gtc aag gac aca agc ctg aaa ggc agc ttc gga gtg aca agg aaa<br>Gln Val Lys Asp Thr Ser Leu Lys Gly Ser Phe Gly Val Thr Arg Lys<br>330                    335                  340               345 | 1180 | |
| gaa atg gaa gtc tct cct tct gca gag cag ctt gtc cag gtt tat gaa<br>Glu Met Glu Val Ser Pro Ser Ala Glu Gln Leu Val Gln Val Tyr Glu<br>                 350                  355                 360 | 1228 | |
| ctg acg tta cat cat aca cag cac caa gac cac aat gtt gtg acc gga<br>Leu Thr Leu His His Thr Gln His Gln Asp His Asn Val Val Thr Gly<br>            365                  370                 375 | 1276 | |
| gcc ctg gag ctg ttg cag cag ctc ttc aga acg cct cca ccc gag ctt<br>Ala Leu Glu Leu Leu Gln Gln Leu Phe Arg Thr Pro Pro Pro Glu Leu<br>380                    385                  390 | 1324 | |
| ctg caa acc ctg acc gca gtc ggg ggc att ggg cag ctc acc gct gct<br>Leu Gln Thr Leu Thr Ala Val Gly Gly Ile Gly Gln Leu Thr Ala Ala<br>395                    400                  405 | 1372 | |
| aag gag gag tct ggt ggc cga agc cgt agt ggg agt att gtg gaa ctt<br>Lys Glu Glu Ser Gly Gly Arg Ser Arg Ser Gly Ser Ile Val Glu Leu<br>410                    415                  420               425 | 1420 | |
| ata gct gga ggg ggt tcc tca tgc agc cct gtc ctt tca aga aaa caa<br>Ile Ala Gly Gly Gly Ser Ser Cys Ser Pro Val Leu Ser Arg Lys Gln<br>                 430                  435                 440 | 1468 | |
| aaa ggc aaa gtg ctc tta gga gaa gaa gaa gcc ttg gag gat gac tct<br>Lys Gly Lys Val Leu Leu Gly Glu Glu Glu Ala Leu Glu Asp Asp Ser<br>                 445                  450                 455 | 1516 | |
| gaa tcg aga tcg gat gtc agc agc tct gcc tta aca gcc tca gtg aag<br>Glu Ser Arg Ser Asp Val Ser Ser Ser Ala Leu Thr Ala Ser Val Lys<br>            460                  465                 470 | 1564 | |
| gat gag atc agt gga gag ctg gct gct tct tca ggg gtt tcc act cca<br>Asp Glu Ile Ser Gly Glu Leu Ala Ala Ser Ser Gly Val Ser Thr Pro<br>475                    480                  485 | 1612 | |

-continued

| | | |
|---|---|---|
| ggg tca gca ggt cat gac atc atc aca gaa cag cca cgg tca cag cac<br>Gly Ser Ala Gly His Asp Ile Ile Thr Glu Gln Pro Arg Ser Gln His<br>490                       495                     500                 505 | 1660 |
| aca ctg cag gcg gac tca gtg gat ctg gcc agc tgt gac ttg aca agc<br>Thr Leu Gln Ala Asp Ser Val Asp Leu Ala Ser Cys Asp Leu Thr Ser<br>                     510                     515                     520 | 1708 |
| tct gcc act gat ggg gat gag gag gat atc ttg agc cac agc tcc agc<br>Ser Ala Thr Asp Gly Asp Glu Glu Asp Ile Leu Ser His Ser Ser Ser<br>525                     530                     535 | 1756 |
| cag gtc agc gcc gtc cca tct gac cct gcc atg gac ctg aat gat ggg<br>Gln Val Ser Ala Val Pro Ser Asp Pro Ala Met Asp Leu Asn Asp Gly<br>    540                     545                     550 | 1804 |
| acc cag gcc tcg tcg ccc atc agc gac agc tcc cag acc acc acc gaa<br>Thr Gln Ala Ser Ser Pro Ile Ser Asp Ser Ser Gln Thr Thr Thr Glu<br>555                     560                     565 | 1852 |
| ggg cct gat tca gct gtt acc cct tca gac agt tct gaa att gtg tta<br>Gly Pro Asp Ser Ala Val Thr Pro Ser Asp Ser Ser Glu Ile Val Leu<br>570                       575                     580                 585 | 1900 |
| gac ggt acc gac aac cag tat ttg ggc ctg cag att gga cag ccc cag<br>Asp Gly Thr Asp Asn Gln Tyr Leu Gly Leu Gln Ile Gly Gln Pro Gln<br>                     590                     595                     600 | 1948 |
| gat gaa gat gag gaa gcc aca ggt att ctt cct gat gaa gcc tcg gag<br>Asp Glu Asp Glu Glu Ala Thr Gly Ile Leu Pro Asp Glu Ala Ser Glu<br>605                     610                     615 | 1996 |
| gcc ttc agg aac tct tcc atg gcc ctt caa cag gca cat tta ttg aaa<br>Ala Phe Arg Asn Ser Ser Met Ala Leu Gln Gln Ala His Leu Leu Lys<br>    620                     625                     630 | 2044 |
| aac atg agt cac tgc agg cag cct tct gac agc agt gtt gat aaa ttt<br>Asn Met Ser His Cys Arg Gln Pro Ser Asp Ser Ser Val Asp Lys Phe<br>635                     640                     645 | 2092 |
| gtg ttg aga gat gaa gct act gaa ccg ggt gat caa gaa aac aag cct<br>Val Leu Arg Asp Glu Ala Thr Glu Pro Gly Asp Gln Glu Asn Lys Pro<br>650                     655                     660                 665 | 2140 |
| tgc cgc atc aaa ggt gac att gga cag tcc act gat gat gac tct gca<br>Cys Arg Ile Lys Gly Asp Ile Gly Gln Ser Thr Asp Asp Asp Ser Ala<br>                     670                     675                     680 | 2188 |
| cct ctt gtc cat tgt gtc cgc ctt tta tct gct tcg ttt ttg cta aca<br>Pro Leu Val His Cys Val Arg Leu Leu Ser Ala Ser Phe Leu Leu Thr<br>               685                     690                     695 | 2236 |
| ggg gga aaa aat gtg ctg gtt ccg gac agg gat gtg agg gtc agc gtg<br>Gly Gly Lys Asn Val Leu Val Pro Asp Arg Asp Val Arg Val Ser Val<br>    700                     705                     710 | 2284 |
| aag gcc ctg gcc ctc agc tgt gtg gga gca gct gtg gcc ctc cac ccg<br>Lys Ala Leu Ala Leu Ser Cys Val Gly Ala Ala Val Ala Leu His Pro<br>715                     720                     725 | 2332 |
| gaa tct ttc ttc agc aaa ctc tat aaa gtt cct ctt gac acc acg gaa<br>Glu Ser Phe Phe Ser Lys Leu Tyr Lys Val Pro Leu Asp Thr Thr Glu<br>730                     735                     740                 745 | 2380 |
| tac cct gag gaa cag tat gtc tca gac atc ttg aac tac atc gat cat<br>Tyr Pro Glu Glu Gln Tyr Val Ser Asp Ile Leu Asn Tyr Ile Asp His<br>                     750                     755                     760 | 2428 |
| gga gac cca cag gtt cga gga gcc act gcc att ctc tgt ggg acc ctc<br>Gly Asp Pro Gln Val Arg Gly Ala Thr Ala Ile Leu Cys Gly Thr Leu<br>765                     770                     775 | 2476 |
| atc tgc tcc atc ctc agc agg tcc cgc ttc cac gtg gga gat tgg atg<br>Ile Cys Ser Ile Leu Ser Arg Ser Arg Phe His Val Gly Asp Trp Met<br>    780                     785                     790 | 2524 |
| ggc acc att aga acc ctc aca gga aat aca ttt tct ttg gcg gat tgc<br>Gly Thr Ile Arg Thr Leu Thr Gly Asn Thr Phe Ser Leu Ala Asp Cys | 2572 |

```
          795                 800                 805
att cct ttg ctg cgg aaa aca ctg aag gat gag tct tct gtt act tgc      2620
Ile Pro Leu Leu Arg Lys Thr Leu Lys Asp Glu Ser Ser Val Thr Cys
810                 815                 820                 825 aag tta gct tgt aca gct gtg agg aac tgt gtc atg agt ctc tgc agc      2668
Lys Leu Ala Cys Thr Ala Val Arg Asn Cys Val Met Ser Leu Cys Ser
            830                 835                 840 agc agc tac agt gag tta gga ctg cag ctg atc atc gat gtg ctg act      2716
Ser Ser Tyr Ser Glu Leu Gly Leu Gln Leu Ile Ile Asp Val Leu Thr
        845                 850                 855 ctg agg aac agt tcc tat tgg ctg gtg agg aca gag ctt ctg gaa acc      2764
Leu Arg Asn Ser Ser Tyr Trp Leu Val Arg Thr Glu Leu Leu Glu Thr
    860                 865                 870 ctt gca gag att gac ttc agg ctg gtg agc ttt ttg gag gca aaa gca      2812
Leu Ala Glu Ile Asp Phe Arg Leu Val Ser Phe Leu Glu Ala Lys Ala
875                 880                 885 gaa aac tta cac aga ggg gct cat cat tat aca ggg ctt tta aaa ctg      2860
Glu Asn Leu His Arg Gly Ala His His Tyr Thr Gly Leu Leu Lys Leu
890                 895                 900                 905 caa gaa cga gtg ctc aat aat gtt gtc atc cat ttg ctt gga gat gaa      2908
Gln Glu Arg Val Leu Asn Asn Val Val Ile His Leu Leu Gly Asp Glu
            910                 915                 920 gac ccc agg gtg cga cat gtt gcc gca gca tca cta att agg ctt gtc      2956
Asp Pro Arg Val Arg His Val Ala Ala Ala Ser Leu Ile Arg Leu Val
        925                 930                 935 cca aag ctg ttt tat aaa tgt gac caa gga caa gct gat cca gta gtg      3004
Pro Lys Leu Phe Tyr Lys Cys Asp Gln Gly Gln Ala Asp Pro Val Val
    940                 945                 950 gcc gtg gca aga gat caa agc agt gtt tac ctg aaa ctt ctc atg cat      3052
Ala Val Ala Arg Asp Gln Ser Ser Val Tyr Leu Lys Leu Leu Met His
955                 960                 965 gag acg cag cct cca tct cat ttc tcc gtc agc aca ata acc aga ata      3100
Glu Thr Gln Pro Pro Ser His Phe Ser Val Ser Thr Ile Thr Arg Ile
970                 975                 980                 985 tat aga ggc tat aac cta cta cca agc ata aca gac gtc act atg  gaa     3148
Tyr Arg Gly Tyr Asn Leu Leu Pro Ser Ile Thr Asp Val Thr Met  Glu
            990                 995                 1000 aat aac ctt tca  aga gtt att gca gca  gtt tct cat gaa cta  atc       3193
Asn Asn Leu Ser  Arg Val Ile Ala Ala  Val Ser His Glu Leu  Ile
            1005                1010                1015 aca tca acc acc  aga gca ctc aca ttt  gga tgc tgt gaa gct  ttg       3238
Thr Ser Thr Thr  Arg Ala Leu Thr Phe  Gly Cys Cys Glu Ala  Leu
            1020                1025                1030 tgt ctt ctt tcc  act gcc ttc cca gtt  tgc att tgg agt tta  ggt       3283
Cys Leu Leu Ser  Thr Ala Phe Pro Val  Cys Ile Trp Ser Leu  Gly
            1035                1040                1045 tgg cac tgt gga  gtg cct cca ctg agt  gcc tca gat gag tct  agg       3328
Trp His Cys Gly  Val Pro Pro Leu Ser  Ala Ser Asp Glu Ser  Arg
            1050                1055                1060 aag agc tgt acc  gtt ggg atg gcc aca  atg att ctg acc ctg  ctc       3373
Lys Ser Cys Thr  Val Gly Met Ala Thr  Met Ile Leu Thr Leu  Leu
            1065                1070                1075 tcg tca gct tgg  ttc cca ttg gat ctc  tca gcc cat caa gat  gct       3418
Ser Ser Ala Trp  Phe Pro Leu Asp Leu  Ser Ala His Gln Asp  Ala
            1080                1085                1090 ttg att ttg gcc  gga aac ttg ctt gca  gcc agt gct ccc aaa  tct       3463
Leu Ile Leu Ala  Gly Asn Leu Leu Ala  Ala Ser Ala Pro Lys  Ser
            1095                1100                1105 ctg aga agt tca  tgg gcc tct gaa gaa  gaa gcc aac cca gca  gcc       3508
```

```
Leu Arg Ser Ser Trp Ala Ser Glu Glu Glu Ala Asn Pro Ala  Ala
        1110            1115                1120 acc aag caa gag gag gtc tgg cca gcc ctg ggg gac cgg gcc  ctg       3553
Thr Lys Gln Glu Glu Val Trp Pro Ala Leu Gly Asp Arg Ala  Leu
        1125            1130                1135 gtg ccc atg gtg gag cag ctc ttc tct cac ctg ctg aag gtg  att       3598
Val Pro Met Val Glu Gln Leu Phe Ser His Leu Leu Lys Val  Ile
        1140            1145                1150 aac att tgt gcc cac gtc ctg gat gac gtg gct cct gga ccc  gca       3643
Asn Ile Cys Ala His Val Leu Asp Asp Val Ala Pro Gly Pro  Ala
        1155            1160                1165 ata aag gca gcc ttg cct tct cta aca aac ccc cct tct cta  agt       3688
Ile Lys Ala Ala Leu Pro Ser Leu Thr Asn Pro Pro Ser Leu  Ser
        1170            1175                1180 ccc atc cga cga aag ggg aag gag aaa gaa cca gga gaa caa  gca       3733
Pro Ile Arg Arg Lys Gly Lys Glu Lys Glu Pro Gly Glu Gln  Ala
        1185            1190                1195 tct gta ccg ttg agt ccc aag aaa ggc agt gag gcc agt gca  gct       3778
Ser Val Pro Leu Ser Pro Lys Lys Gly Ser Glu Ala Ser Ala  Ala
        1200            1205                1210 tct aga caa tct gat acc tca ggt cct gtt aca aca agt aaa  tcc       3823
Ser Arg Gln Ser Asp Thr Ser Gly Pro Val Thr Thr Ser Lys  Ser
        1215            1220                1225 tca tca ctg ggg agt ttc tat cat ctt cct tca tac ctc aaa  ctg       3868
Ser Ser Leu Gly Ser Phe Tyr His Leu Pro Ser Tyr Leu Lys  Leu
        1230            1235                1240 cat gat gtc ctg aaa gct aca cac gct aac tac aag gtc acg  ctg       3913
His Asp Val Leu Lys Ala Thr His Ala Asn Tyr Lys Val Thr  Leu
        1245            1250                1255 gat ctt cag aac agc acg gaa aag ttt gga ggg ttt ctc cgc  tca       3958
Asp Leu Gln Asn Ser Thr Glu Lys Phe Gly Gly Phe Leu Arg  Ser
        1260            1265                1270 gcc ttg gat gtt ctt tct cag ata cta gag ctg gcc aca ctg  cag       4003
Ala Leu Asp Val Leu Ser Gln Ile Leu Glu Leu Ala Thr Leu  Gln
        1275            1280                1285 gac att ggg aag tgt gtt gaa gag atc cta gga tac ctg aaa  tcc       4048
Asp Ile Gly Lys Cys Val Glu Glu Ile Leu Gly Tyr Leu Lys  Ser
        1290            1295                1300 tgc ttt agt cga gaa cca atg atg gca act gtt tgt gtt caa  caa       4093
Cys Phe Ser Arg Glu Pro Met Met Ala Thr Val Cys Val Gln  Gln
        1305            1310                1315 ttg ttg aag act ctc ttt ggc aca aac ttg gcc tcc cag ttt  gat       4138
Leu Leu Lys Thr Leu Phe Gly Thr Asn Leu Ala Ser Gln Phe  Asp
        1320            1325                1330 ggc tta tct tcc aac ccc agc aag tca caa ggc cga gca cag  cgc       4183
Gly Leu Ser Ser Asn Pro Ser Lys Ser Gln Gly Arg Ala Gln  Arg
        1335            1340                1345 ctt ggc tcc tcc agt gtg agg cca ggc ttg tac cac tac tgc  ttc       4228
Leu Gly Ser Ser Ser Val Arg Pro Gly Leu Tyr His Tyr Cys  Phe
        1350            1355                1360 atg gcc ccg tac acc cac ttc acc cag gcc ctc gct gac gcc  agc       4273
Met Ala Pro Tyr Thr His Phe Thr Gln Ala Leu Ala Asp Ala  Ser
        1365            1370                1375 ctg agg aac atg gtg cag gcg gag cag gag aac gac acc tcg  gga       4318
Leu Arg Asn Met Val Gln Ala Glu Gln Glu Asn Asp Thr Ser  Gly
        1380            1385                1390 tgg ttt gat gtc ctc cag aaa gtg tct acc cag ttg aag aca  aac       4363
Trp Phe Asp Val Leu Gln Lys Val Ser Thr Gln Leu Lys Thr  Asn
        1395            1400                1405
```

```
ctc acg agt gtc aca aag aac cgt gca gat aag aat gct att cat    4408
Leu Thr Ser Val Thr Lys Asn Arg Ala Asp Lys Asn Ala Ile His
        1410                1415                1420 aat cac att cgt ttg ttt gaa cct ctt gtt ata aaa gct tta aaa    4453
Asn His Ile Arg Leu Phe Glu Pro Leu Val Ile Lys Ala Leu Lys
        1425                1430                1435 cag tac acg act aca aca tgt gtg cag tta cag aag cag gtt tta    4498
Gln Tyr Thr Thr Thr Thr Cys Val Gln Leu Gln Lys Gln Val Leu
        1440                1445                1450 gat ttg ctg gcg cag ctg gtt cag tta cgg gtt aat tac tgt ctt    4543
Asp Leu Leu Ala Gln Leu Val Gln Leu Arg Val Asn Tyr Cys Leu
        1455                1460                1465 ctg gat tca gat cag gtg ttt att ggc ttt gta ttg aaa cag ttt    4588
Leu Asp Ser Asp Gln Val Phe Ile Gly Phe Val Leu Lys Gln Phe
        1470                1475                1480 gaa tac att gaa gtg ggc cag ttc agg gaa tca gag gca atc att    4633
Glu Tyr Ile Glu Val Gly Gln Phe Arg Glu Ser Glu Ala Ile Ile
        1485                1490                1495 cca aac atc ttt ttc ttc ttg gta tta cta tct tat gaa cgc tat    4678
Pro Asn Ile Phe Phe Phe Leu Val Leu Leu Ser Tyr Glu Arg Tyr
        1500                1505                1510 cat tca aaa cag atc att gga att cct aaa atc att cag ctc tgt    4723
His Ser Lys Gln Ile Ile Gly Ile Pro Lys Ile Ile Gln Leu Cys
        1515                1520                1525 gat ggc atc atg gcc agt gga agg aag gct gtg aca cat gcc ata    4768
Asp Gly Ile Met Ala Ser Gly Arg Lys Ala Val Thr His Ala Ile
        1530                1535                1540 ccg gct ctg cag ccc ata gtc cac gac ctc ttt gta tta aga gga    4813
Pro Ala Leu Gln Pro Ile Val His Asp Leu Phe Val Leu Arg Gly
        1545                1550                1555 aca aat aaa gct gat gca gga aaa gag ctt gaa acc caa aaa gag    4858
Thr Asn Lys Ala Asp Ala Gly Lys Glu Leu Glu Thr Gln Lys Glu
        1560                1565                1570 gtg gtg gtg tca atg tta ctg aga ctc atc cag tac cat cag gtg    4903
Val Val Val Ser Met Leu Leu Arg Leu Ile Gln Tyr His Gln Val
        1575                1580                1585 ttg gag atg ttc att ctt gtc ctg cag cag tgc cac aag gag aat    4948
Leu Glu Met Phe Ile Leu Val Leu Gln Gln Cys His Lys Glu Asn
        1590                1595                1600 gaa gac aag tgg aag cga ctg tct cga cag ata gct gac atc atc    4993
Glu Asp Lys Trp Lys Arg Leu Ser Arg Gln Ile Ala Asp Ile Ile
        1605                1610                1615 ctc cca atg tta gcc aaa cag cag atg cac att gac tct cat gaa    5038
Leu Pro Met Leu Ala Lys Gln Gln Met His Ile Asp Ser His Glu
        1620                1625                1630 gcc ctt gga gtg tta aat aca tta ttt gag att ttg gcc cct tcc    5083
Ala Leu Gly Val Leu Asn Thr Leu Phe Glu Ile Leu Ala Pro Ser
        1635                1640                1645 tcc ctc cgt ccg gta gac atg ctt tta cgg agt atg ttc gtc act    5128
Ser Leu Arg Pro Val Asp Met Leu Leu Arg Ser Met Phe Val Thr
        1650                1655                1660 cca aac aca atg gcg tcc gtg agc act gtt caa ctg tgg ata tcg    5173
Pro Asn Thr Met Ala Ser Val Ser Thr Val Gln Leu Trp Ile Ser
        1665                1670                1675 gga att ctg gcc att ttg agg gtt ctg att tcc cag tca act gaa    5218
Gly Ile Leu Ala Ile Leu Arg Val Leu Ile Ser Gln Ser Thr Glu
        1680                1685                1690 gat att gtt ctt tct cgt att cag gag ctc tcc ttc tct ccg tat    5263
Asp Ile Val Leu Ser Arg Ile Gln Glu Leu Ser Phe Ser Pro Tyr
        1695                1700                1705
```

| | | | | | | | | | | | | |
|---|---|---|---|---|---|---|---|---|---|---|---|---|
| tta | atc | tcc | tgt | aca | gta | att | aat | agg | tta | aga | gat | ggg | gac | agt | 5308 |
| Leu | Ile | Ser | Cys | Thr | Val | Ile | Asn | Arg | Leu | Arg | Asp | Gly | Asp | Ser | |
| | | | 1710 | | | | 1715 | | | | | 1720 | | | |
| act | tca | acg | cta | gaa | gaa | cac | agt | gaa | ggg | aaa | caa | ata | aag | aat | 5353 |
| Thr | Ser | Thr | Leu | Glu | Glu | His | Ser | Glu | Gly | Lys | Gln | Ile | Lys | Asn | |
| | | | 1725 | | | | 1730 | | | | | 1735 | | | |
| ttg | cca | gaa | gaa | aca | ttt | tca | agg | ttt | cta | tta | caa | ctg | gtt | ggt | 5398 |
| Leu | Pro | Glu | Glu | Thr | Phe | Ser | Arg | Phe | Leu | Leu | Gln | Leu | Val | Gly | |
| | 1740 | | | | 1745 | | | | | 1750 | | | | | |
| att | ctt | tta | gaa | gac | att | gtt | aca | aaa | cag | ctg | aag | gtg | gaa | atg | 5443 |
| Ile | Leu | Leu | Glu | Asp | Ile | Val | Thr | Lys | Gln | Leu | Lys | Val | Glu | Met | |
| | 1755 | | | | 1760 | | | | | 1765 | | | | | |
| agt | gag | cag | caa | cat | act | ttc | tat | tgc | cag | gaa | cta | ggc | aca | ctg | 5488 |
| Ser | Glu | Gln | Gln | His | Thr | Phe | Tyr | Cys | Gln | Glu | Leu | Gly | Thr | Leu | |
| 1770 | | | | 1775 | | | | | 1780 | | | | | | |
| cta | atg | tgt | ctg | atc | cac | atc | ttc | aag | tct | gga | atg | ttc | cgg | aga | 5533 |
| Leu | Met | Cys | Leu | Ile | His | Ile | Phe | Lys | Ser | Gly | Met | Phe | Arg | Arg | |
| 1785 | | | | 1790 | | | | | 1795 | | | | | | |
| atc | aca | gca | gct | gcc | act | agg | ctg | ttc | cgc | agt | gat | ggc | tgt | ggc | 5578 |
| Ile | Thr | Ala | Ala | Ala | Thr | Arg | Leu | Phe | Arg | Ser | Asp | Gly | Cys | Gly | |
| 1800 | | | | 1805 | | | | | 1810 | | | | | | |
| ggc | agt | ttc | tac | acc | ctg | gac | agc | ttg | aac | ttg | cgg | gct | cgt | tcc | 5623 |
| Gly | Ser | Phe | Tyr | Thr | Leu | Asp | Ser | Leu | Asn | Leu | Arg | Ala | Arg | Ser | |
| | 1815 | | | | 1820 | | | | | 1825 | | | | | |
| atg | atc | acc | acc | cac | ccg | gcc | ctg | gtg | ctg | ctc | tgg | tgt | cag | ata | 5668 |
| Met | Ile | Thr | Thr | His | Pro | Ala | Leu | Val | Leu | Leu | Trp | Cys | Gln | Ile | |
| | 1830 | | | | 1835 | | | | | 1840 | | | | | |
| ctg | ctg | ctt | gtc | aac | cac | acc | gac | tac | cgc | tgg | tgg | gca | gaa | gtg | 5713 |
| Leu | Leu | Leu | Val | Asn | His | Thr | Asp | Tyr | Arg | Trp | Trp | Ala | Glu | Val | |
| | 1845 | | | | 1850 | | | | | 1855 | | | | | |
| cag | cag | acc | ccg | aaa | aga | cac | agt | ctg | tcc | agc | aca | aag | tta | ctt | 5758 |
| Gln | Gln | Thr | Pro | Lys | Arg | His | Ser | Leu | Ser | Ser | Thr | Lys | Leu | Leu | |
| | | 1860 | | | | 1865 | | | | | 1870 | | | | |
| agt | ccc | cag | atg | tct | gga | gaa | gag | gag | gat | tct | gac | ttg | gca | gcc | 5803 |
| Ser | Pro | Gln | Met | Ser | Gly | Glu | Glu | Glu | Asp | Ser | Asp | Leu | Ala | Ala | |
| | | 1875 | | | | 1880 | | | | | 1885 | | | | |
| aaa | ctt | gga | atg | tgc | aat | aga | gaa | ata | gta | cga | aga | ggg | gct | ctc | 5848 |
| Lys | Leu | Gly | Met | Cys | Asn | Arg | Glu | Ile | Val | Arg | Arg | Gly | Ala | Leu | |
| | | 1890 | | | | 1895 | | | | | 1900 | | | | |
| att | ctc | ttc | tgt | gat | tat | gtc | tgt | cag | aac | ctc | cat | gac | tcc | gag | 5893 |
| Ile | Leu | Phe | Cys | Asp | Tyr | Val | Cys | Gln | Asn | Leu | His | Asp | Ser | Glu | |
| | | 1905 | | | | 1910 | | | | | 1915 | | | | |
| cac | tta | acg | tgg | ctc | att | gta | aat | cac | att | caa | gat | ctg | atc | agc | 5938 |
| His | Leu | Thr | Trp | Leu | Ile | Val | Asn | His | Ile | Gln | Asp | Leu | Ile | Ser | |
| | | 1920 | | | | 1925 | | | | | 1930 | | | | |
| ctt | tcc | cac | gag | cct | cca | gta | cag | gac | ttc | atc | agt | gcc | gtt | cat | 5983 |
| Leu | Ser | His | Glu | Pro | Pro | Val | Gln | Asp | Phe | Ile | Ser | Ala | Val | His | |
| | | 1935 | | | | 1940 | | | | | 1945 | | | | |
| cgg | aac | tct | gct | gcc | agc | ggc | ctg | ttc | atc | cag | gca | att | cag | tct | 6028 |
| Arg | Asn | Ser | Ala | Ala | Ser | Gly | Leu | Phe | Ile | Gln | Ala | Ile | Gln | Ser | |
| | | 1950 | | | | 1955 | | | | | 1960 | | | | |
| cgt | tgt | gaa | aac | ctt | tca | act | cca | acc | atg | ctg | aag | aaa | act | ctt | 6073 |
| Arg | Cys | Glu | Asn | Leu | Ser | Thr | Pro | Thr | Met | Leu | Lys | Lys | Thr | Leu | |
| | | 1965 | | | | 1970 | | | | | 1975 | | | | |
| cag | tgc | ttg | gag | ggg | atc | cat | ctc | agc | cag | tcg | gga | gct | gtg | ctc | 6118 |
| Gln | Cys | Leu | Glu | Gly | Ile | His | Leu | Ser | Gln | Ser | Gly | Ala | Val | Leu | |
| | | 1980 | | | | 1985 | | | | | 1990 | | | | |
| acg | ctg | tat | gtg | gac | agg | ctt | ctg | tgc | acc | cct | ttc | cgt | gtg | ctg | 6163 |
| Thr | Leu | Tyr | Val | Asp | Arg | Leu | Leu | Cys | Thr | Pro | Phe | Arg | Val | Leu | |

-continued

```
              1995                2000                2005
gct cgc atg gtc gac atc ctt gct tgt cgc cgg gta gaa atg ctt       6208
Ala Arg Met Val Asp Ile Leu Ala Cys Arg Arg Val Glu Met Leu
        2010                2015                2020 ctg gct gca aat tta cag agc agc atg gcc cag ttg cca atg gaa       6253
Leu Ala Ala Asn Leu Gln Ser Ser Met Ala Gln Leu Pro Met Glu
        2025                2030                2035 gaa ctc aac aga atc cag gaa tac ctt cag agc agc ggg ctc gct       6298
Glu Leu Asn Arg Ile Gln Glu Tyr Leu Gln Ser Ser Gly Leu Ala
        2040                2045                2050 cag aga cac caa agg ctc tat tcc ctg ctg gac agg ttt cgt ctc       6343
Gln Arg His Gln Arg Leu Tyr Ser Leu Leu Asp Arg Phe Arg Leu
        2055                2060                2065 tcc acc atg caa gac tca ctt agt ccc tct cct cca gtc tct tcc       6388
Ser Thr Met Gln Asp Ser Leu Ser Pro Ser Pro Pro Val Ser Ser
        2070                2075                2080 cac ccg ctg gac ggg gat ggg cac gtg tca ctg gaa aca gtg agt       6433
His Pro Leu Asp Gly Asp Gly His Val Ser Leu Glu Thr Val Ser
        2085                2090                2095 ccg gac aaa gac tgg tac gtt cat ctt gtc aaa tcc cag tgt tgg       6478
Pro Asp Lys Asp Trp Tyr Val His Leu Val Lys Ser Gln Cys Trp
        2100                2105                2110 acc agg tca gat tct gca ctg ctg gaa ggt gca gag ctg gtg aat       6523
Thr Arg Ser Asp Ser Ala Leu Leu Glu Gly Ala Glu Leu Val Asn
        2115                2120                2125 cgg att cct gct gaa gat atg aat gcc ttc atg atg aac tcg gag       6568
Arg Ile Pro Ala Glu Asp Met Asn Ala Phe Met Met Asn Ser Glu
        2130                2135                2140 ttc aac cta agc ctg cta gct cca tgc tta agc cta ggg atg agt       6613
Phe Asn Leu Ser Leu Leu Ala Pro Cys Leu Ser Leu Gly Met Ser
        2145                2150                2155 gaa att tct ggt ggc cag aag agt gcc ctt ttt gaa gca gcc cgt       6658
Glu Ile Ser Gly Gly Gln Lys Ser Ala Leu Phe Glu Ala Ala Arg
        2160                2165                2170 gag gtg act ctg gcc cgt gtg agc ggc acc gtg cag cag ctc cct       6703
Glu Val Thr Leu Ala Arg Val Ser Gly Thr Val Gln Gln Leu Pro
        2175                2180                2185 gct gtc cat cat gtc ttc cag ccc gag ctg cct gca gag ccg gcg       6748
Ala Val His His Val Phe Gln Pro Glu Leu Pro Ala Glu Pro Ala
        2190                2195                2200 gcc tac tgg agc aag ttg aat gat ctg ttt ggg gat gct gca ctg       6793
Ala Tyr Trp Ser Lys Leu Asn Asp Leu Phe Gly Asp Ala Ala Leu
        2205                2210                2215 tat cag tcc ctg ccc act ctg gcc cgg gcc ctg gca cag tac ctg       6838
Tyr Gln Ser Leu Pro Thr Leu Ala Arg Ala Leu Ala Gln Tyr Leu
        2220                2225                2230 gtg gtg gtc tcc aaa ctg ccc agt cat ttg cac ctt cct cct gag       6883
Val Val Val Ser Lys Leu Pro Ser His Leu His Leu Pro Pro Glu
        2235                2240                2245 aaa gag aag gac att gtg aaa ttc gtg gtg gca acc ctt gag gcc       6928
Lys Glu Lys Asp Ile Val Lys Phe Val Val Ala Thr Leu Glu Ala
        2250                2255                2260 ctg tcc tgg cat ttg atc cat gag cag atc ccg ctg agt ctg gat       6973
Leu Ser Trp His Leu Ile His Glu Gln Ile Pro Leu Ser Leu Asp
        2265                2270                2275 ctc cag gca ggg ctg gac tgc tgc tgc ctg gcc ctg cag ctg cct       7018
Leu Gln Ala Gly Leu Asp Cys Cys Cys Leu Ala Leu Gln Leu Pro
        2280                2285                2290 ggc ctc tgg agc gtg gtc tcc tcc aca gag ttt gtg acc cac gcc       7063
```

```
Gly Leu Trp Ser   Val Val Ser Ser   Thr Glu Phe Val   Thr His Ala
        2295              2300              2305 tgc tcc ctc atc   tac tgt gtg cac   ttc atc ctg gag   gcc gtt gca       7108
Cys Ser Leu Ile   Tyr Cys Val His   Phe Ile Leu Glu   Ala Val Ala
        2310              2315              2320 gtg cag cct gga   gag cag ctt ctt   agt cca gaa aga   agg aca aat       7153
Val Gln Pro Gly   Glu Gln Leu Leu   Ser Pro Glu Arg   Arg Thr Asn
        2325              2330              2335 acc cca aaa gcc   atc agc gag gag   gag gaa gta gat   cca aac           7198
Thr Pro Lys Ala   Ile Ser Glu Glu   Glu Glu Val Asp   Pro Asn
        2340              2345              2350 aca cag aat cct   aag tat atc act   gca gcc tgt gag   atg gtg gca       7243
Thr Gln Asn Pro   Lys Tyr Ile Thr   Ala Ala Cys Glu   Met Val Ala
        2355              2360              2365 gaa atg gtg gag   tct ctg cag tcg   gtg ttg gcc ttg   ggt cat aaa       7288
Glu Met Val Glu   Ser Leu Gln Ser   Val Leu Ala Leu   Gly His Lys
        2370              2375              2380 agg aat agc ggc   gtg ccg gcg ttt   ctc acg cca ttg   cta agg aac       7333
Arg Asn Ser Gly   Val Pro Ala Phe   Leu Thr Pro Leu   Leu Arg Asn
        2385              2390              2395 atc atc atc agc   ctg gcc cgc ctg   ccc ctt gtc aac   agc tac aca       7378
Ile Ile Ile Ser   Leu Ala Arg Leu   Pro Leu Val Asn   Ser Tyr Thr
        2400              2405              2410 cgt gtg ccc cca   ctg gtg tgg aag   ctt gga tgg tca   ccc aaa ccg       7423
Arg Val Pro Pro   Leu Val Trp Lys   Leu Gly Trp Ser   Pro Lys Pro
        2415              2420              2425 gga ggg gat ttt   ggc aca gca ttc   cct gag atc ccc   gtg gag ttc       7468
Gly Gly Asp Phe   Gly Thr Ala Phe   Pro Glu Ile Pro   Val Glu Phe
        2430              2435              2440 ctc cag gaa aag   gaa gtc ttt aag   gag ttc atc tac   cgc atc aac       7513
Leu Gln Glu Lys   Glu Val Phe Lys   Glu Phe Ile Tyr   Arg Ile Asn
        2445              2450              2455 aca cta ggc tgg   acc agt cgt act   cag ttt gaa gaa   act tgg gcc       7558
Thr Leu Gly Trp   Thr Ser Arg Thr   Gln Phe Glu Glu   Thr Trp Ala
        2460              2465              2470 acc ctc ctt ggt   gtc ctg gtg acg   cag ccc ctc gtg   atg gag cag       7603
Thr Leu Leu Gly   Val Leu Val Thr   Gln Pro Leu Val   Met Glu Gln
        2475              2480              2485 gag gag agc cca   cca gaa gaa gac   aca gag agg acc   cag atc aac       7648
Glu Glu Ser Pro   Pro Glu Glu Asp   Thr Glu Arg Thr   Gln Ile Asn
        2490              2495              2500 gtc ctg gcc gtg   cag gcc atc acc   tca ctg gtg ctc   agt gca atg       7693
Val Leu Ala Val   Gln Ala Ile Thr   Ser Leu Val Leu   Ser Ala Met
        2505              2510              2515 act gtg cct gtg   gcc ggc aac cca   gct gta agc tgc   ttg gag cag       7738
Thr Val Pro Val   Ala Gly Asn Pro   Ala Val Ser Cys   Leu Glu Gln
        2520              2525              2530 cag ccc cgg aac   aag cct ctg aaa   gct ctc gac acc   agg ttt ggg       7783
Gln Pro Arg Asn   Lys Pro Leu Lys   Ala Leu Asp Thr   Arg Phe Gly
        2535              2540              2545 agg aag ctg agc   att atc aga ggg   att gtg gag caa   gag att caa       7828
Arg Lys Leu Ser   Ile Ile Arg Gly   Ile Val Glu Gln   Glu Ile Gln
        2550              2555              2560 gca atg gtt tca   aag aga gag aat   att gcc acc cat   cat tta tat       7873
Ala Met Val Ser   Lys Arg Glu Asn   Ile Ala Thr His   His Leu Tyr
        2565              2570              2575 cag gca tgg gat   cct gtc cct tct   ctg tct ccg gct   act aca ggt       7918
Gln Ala Trp Asp   Pro Val Pro Ser   Leu Ser Pro Ala   Thr Thr Gly
        2580              2585              2590
```

-continued

| | | | | | | | | | | | | |
|---|---|---|---|---|---|---|---|---|---|---|---|---|
| gcc | ctc | atc | agc | cac | gag | aag | ctg | ctg | cta | cag | atc | aac | ccc | gag | 7963 |
| Ala | Leu | Ile | Ser | His | Glu | Lys | Leu | Leu | Leu | Gln | Ile | Asn | Pro | Glu | |
| | | | 2595 | | | | 2600 | | | | | 2605 | | | | cgg gag ctg ggg agc atg agc tac aaa ctc ggc cag gtg tcc ata    8008
Arg Glu Leu Gly Ser Met Ser Tyr Lys Leu Gly Gln Val Ser Ile
            2610            2615            2620 cac tcc gtg tgg ctg ggg aac agc atc aca ccc ctg agg gag gag    8053
His Ser Val Trp Leu Gly Asn Ser Ile Thr Pro Leu Arg Glu Glu
            2625            2630            2635 gaa tgg gac gag gaa gag gag gag gcc gac gcc cct gca cct        8098
Glu Trp Asp Glu Glu Glu Glu Glu Ala Asp Ala Pro Ala Pro
            2640            2645            2650 tcg tca cca ccc acg tct cca gtc aac tcc agg aaa cac cgg gct    8143
Ser Ser Pro Pro Thr Ser Pro Val Asn Ser Arg Lys His Arg Ala
            2655            2660            2665 gga gtt gac atc cac tcc tgt tcg cag ttt ttg ctt gag ttg tac    8188
Gly Val Asp Ile His Ser Cys Ser Gln Phe Leu Leu Glu Leu Tyr
            2670            2675            2680 agc cgc tgg atc ctg ccg tcc agc tca gcc agg agg acc ccg gcc    8233
Ser Arg Trp Ile Leu Pro Ser Ser Ser Ala Arg Arg Thr Pro Ala
            2685            2690            2695 atc ctg atc agt gag gtg gtc aga tcc ctt cta gtg gtc tca gac    8278
Ile Leu Ile Ser Glu Val Val Arg Ser Leu Leu Val Val Ser Asp
            2700            2705            2710 ttg ttc acc gag cgc aac cag ttt gag ctg atg tat gtg acg ctg    8323
Leu Phe Thr Glu Arg Asn Gln Phe Glu Leu Met Tyr Val Thr Leu
            2715            2720            2725 aca gaa ctg cga agg gtg cac cct tca gaa gac gag atc ctc gct    8368
Thr Glu Leu Arg Arg Val His Pro Ser Glu Asp Glu Ile Leu Ala
            2730            2735            2740 cag tac ctg gtg cct gcc acc tgc aag gca gct gcc gtc ctt ggg    8413
Gln Tyr Leu Val Pro Ala Thr Cys Lys Ala Ala Ala Val Leu Gly
            2745            2750            2755 atg gac aag gcc gtg gcg gag cct gtc agc cgc ctg ctg gag agc    8458
Met Asp Lys Ala Val Ala Glu Pro Val Ser Arg Leu Leu Glu Ser
            2760            2765            2770 acg ctc agg agc agc cac ctg ccc agc agg gtt gga gcc ctg cac    8503
Thr Leu Arg Ser Ser His Leu Pro Ser Arg Val Gly Ala Leu His
            2775            2780            2785 ggc gtc ctc tat gtg ctg gag tgc gac ctg ctg gac gac act gcc    8548
Gly Val Leu Tyr Val Leu Glu Cys Asp Leu Leu Asp Asp Thr Ala
            2790            2795            2800 aag cag ctc atc ccg gtc atc agc gac tat ctc ctc tcc aac ctg    8593
Lys Gln Leu Ile Pro Val Ile Ser Asp Tyr Leu Leu Ser Asn Leu
            2805            2810            2815 aaa ggg atc gcc cac tgc gtg aac att cac agc cag cag cac gta    8638
Lys Gly Ile Ala His Cys Val Asn Ile His Ser Gln Gln His Val
            2820            2825            2830 ctg gtc atg tgt gcc act gcg ttt tac ctc att gag aac tat cct    8683
Leu Val Met Cys Ala Thr Ala Phe Tyr Leu Ile Glu Asn Tyr Pro
            2835            2840            2845 ctg gac gta ggg ccg gaa ttt tca gca tca ata ata cag atg tgt    8728
Leu Asp Val Gly Pro Glu Phe Ser Ala Ser Ile Ile Gln Met Cys
            2850            2855            2860 ggg gtg atg ctg tct gga agt gag gag tcc acc ccc tcc atc att    8773
Gly Val Met Leu Ser Gly Ser Glu Glu Ser Thr Pro Ser Ile Ile
            2865            2870            2875 tac cac tgt gcc ctc aga ggc ctg gag cgc ctc ctg ctc tct gag    8818
Tyr His Cys Ala Leu Arg Gly Leu Glu Arg Leu Leu Leu Ser Glu
            2880            2885            2890

| | | | | | | | | | | | |
|---|---|---|---|---|---|---|---|---|---|---|---|
| cag | ctc | tcc | cgc | ctg | gat | gca | gaa | tcg | ctg | gtc | aag ctg agt gtg | 8863 |
| Gln | Leu | Ser | Arg | Leu | Asp | Ala | Glu | Ser | Leu | Val | Lys Leu Ser Val |
| | | 2895 | | | | 2900 | | | | 2905 | |

```
cag ctc tcc cgc ctg gat gca gaa tcg ctg gtc aag ctg agt gtg        8863
Gln Leu Ser Arg Leu Asp Ala Glu Ser Leu Val Lys Leu Ser Val
        2895                2900                2905 gac aga gtg aac gtg cac agc ccg cac cgg gcc atg gcg gct ctg        8908
Asp Arg Val Asn Val His Ser Pro His Arg Ala Met Ala Ala Leu
        2910                2915                2920 ggc ctg atg ctc acc tgc atg tac aca gga aag gag aaa gtc agt        8953
Gly Leu Met Leu Thr Cys Met Tyr Thr Gly Lys Glu Lys Val Ser
        2925                2930                2935 ccg ggt aga act tca gac cct aat cct gca gcc ccc gac agc gag        8998
Pro Gly Arg Thr Ser Asp Pro Asn Pro Ala Ala Pro Asp Ser Glu
        2940                2945                2950 tca gtg att gtt gct atg gag cgg gta tct gtt ctt ttt gat agg        9043
Ser Val Ile Val Ala Met Glu Arg Val Ser Val Leu Phe Asp Arg
        2955                2960                2965 atc agg aaa ggc ttt cct tgt gaa gcc aga gtg gtg gcc agg atc        9088
Ile Arg Lys Gly Phe Pro Cys Glu Ala Arg Val Val Ala Arg Ile
        2970                2975                2980 ctg ccc cag ttt cta gac gac ttc ttc cca ccc cag gac atc atg        9133
Leu Pro Gln Phe Leu Asp Asp Phe Phe Pro Pro Gln Asp Ile Met
        2985                2990                2995 aac aaa gtc atc gga gag ttt ctg tcc aac cag cag cca tac ccc        9178
Asn Lys Val Ile Gly Glu Phe Leu Ser Asn Gln Gln Pro Tyr Pro
        3000                3005                3010 cag ttc atg gcc acc gtg gtg tat aag gtg ttt cag act ctg cac        9223
Gln Phe Met Ala Thr Val Val Tyr Lys Val Phe Gln Thr Leu His
        3015                3020                3025 agc acc ggg cag tcg tcc atg gtc cgg gac tgg gtc atg ctg tcc        9268
Ser Thr Gly Gln Ser Ser Met Val Arg Asp Trp Val Met Leu Ser
        3030                3035                3040 ctc tcc aac ttc acg cag agg gcc ccg gtc gcc atg gcc acg tgg        9313
Leu Ser Asn Phe Thr Gln Arg Ala Pro Val Ala Met Ala Thr Trp
        3045                3050                3055 agc ctc tcc tgc ttc ttt gtc agc gcg tcc acc agc ccg tgg gtc        9358
Ser Leu Ser Cys Phe Phe Val Ser Ala Ser Thr Ser Pro Trp Val
        3060                3065                3070 gcg gcg atc ctc cca cat gtc atc agc agg atg ggc aag ctg gag        9403
Ala Ala Ile Leu Pro His Val Ile Ser Arg Met Gly Lys Leu Glu
        3075                3080                3085 cag gtg gac gtg aac ctt ttc tgc ctg gtc gcc aca gac ttc tac        9448
Gln Val Asp Val Asn Leu Phe Cys Leu Val Ala Thr Asp Phe Tyr
        3090                3095                3100 aga cac cag ata gag gag gag ctc gac cgc agg gcc ttc cag tct        9493
Arg His Gln Ile Glu Glu Glu Leu Asp Arg Arg Ala Phe Gln Ser
        3105                3110                3115 gtg ctt gag gtg gtt gca gcc cca gga agc cca tat cac cgg ctg        9538
Val Leu Glu Val Val Ala Ala Pro Gly Ser Pro Tyr His Arg Leu
        3120                3125                3130 ctg act tgt tta cga aat gtc cac aag gtc acc acc tgc tga            9580
Leu Thr Cys Leu Arg Asn Val His Lys Val Thr Thr Cys
        3135                3140 gcgccatggt gggagagact gtgaggcggc agctggggcc ggagcctttg gaagtctgcg  9640
cccttgtgcc ctgcctccac cgagccagct tggtccctat gggcttccgc acatgccgcg  9700
ggcggccagg caacgtgcgt gtctctgcca tgtggcagaa tgctctttg tggcagtggc   9760 caggcaggga gtgtctgcag tcctggtggg gctgagcctg aggccttcca gaaagcagga  9820
gcagctgtgc tgcaccccat gtgggtgacc aggtcctttc tcctgatagt cacctgctgg  9880
```

```
ttgttgccag gttgcagctg ctcttgcatc tgggccagaa gtcctccctc ctgcaggctg    9940
gctgttggcc cctctgctgt cctgcagtag aaggtgccgt gagcaggctt tgggaacact   10000
ggcctgggtc tccctggtgg ggtgtgcatg ccacgccccg tgtctggatg cacagatgcc   10060
atggcctgtg ctgggccagt ggctggggt gctagacacc cggcaccatt ctcccttctc    10120
tcttttcttc tcaggattta aaatttaatt atatcagtaa agagattaat tttaacgtaa   10180
ctctttctat gcccgtgtaa agtatgtgaa tcgcaaggcc tgtgctgcat gcgacagcgt   10240
ccggggtggt ggacagggcc cccggccacg ctccctctcc tgtagccact ggcatagccc   10300
tcctgagcac ccgctgacat ttccgttgta catgttcctg tttatgcatt cacaaggtga   10360
ctgggatgta gagaggcgtt agtgggcagg tggccacagc aggactgagg acaggccccc   10420
attatcctag gggtgcgctc acctgcagcc cctcctcctc gggcacagac gactgtcgtt   10480
ctccacccac cagtcaggga cagcagcctc cctgtcactc agctgagaag gccagccctc   10540
cctggctgtg agcagcctcc actgtgtcca gagacatggg cctcccactc ctgttccttg   10600
ctagccctgg ggtggcgtct gcctaggagc tggctggcag gtgttgggac ctgctgctcc   10660
atggatgcat gccctaagag tgtcactgag ctgtgttttg tctgagcctc tctcggtcaa   10720
cagcaaagct tggtgtcttg gcactgttag tgacagagcc cagcatccct tctgcccccg   10780
ttccagctga catcttgcac ggtgaccct tttagtcagg agagtgcaga tctgtgctca    10840
tcggagactg ccccacggcc ctgtcagagc cgccactcct atccccaggc caggtccctg   10900
gaccagcctc ctgtttgcag gcccagagga gccaagtcat taaaatggaa gtggattctg   10960
gatggccggg ctgctgctga tgtaggagct ggatttggga gctctgcttg ccgactggct   11020
gtgagacgag gcagggctc tgcttcctca gccctagagg cgagccaggc aaggttggcg     11080
actgtcatgt ggcttggttt ggtcatgccc gtcgatgttt tgggtattga atgtggtaag   11140
tggaggaaat gttggaactc tgtgcaggtg ctgccttgag accccaagc ttccacctgt     11200
ccctctccta tgtggcagct ggggagcagc tgagatgtgg acttgtatgc tgcccacata   11260
cgtgaggggg agctgaaagg gagcccctcc tctgagcagc ctctgccagg cctgtatgag   11320
gcttttccca ccagctccca acagaggcct cccccagcca ggaccacctc gtcctcgtgg   11380
cggggcagca ggagcggtag aaaggggtcc gatgtttgag gaggccctta agggaagcta   11440
ctgaattata acacgtaaga aaatcaccat tccgtattgg ttgggggctc ctgtttctca   11500
tcctagcttt ttcctggaaa gcccgctaga aggtttggga acgaggggaa agttctcaga   11560
actgttggct gctccccacc cgcctcccgc ctccccgca ggttatgtca gcagctctga    11620
gacagcagta tcacaggcca gatgttgttc ctggctagat gtttacattt gtaagaaata   11680
acactgtgaa tgtaaaacag agccattccc ttggaatgca tatcgctggg ctcaacatag   11740
agtttgtctt cctcttgttt acgacgtgat ctaaaccagt ccttagcaag gggctcagaa   11800
caccccgctc tggcagtagg tgtccccac ccccaaagac ctgcctgtgt gctccggaga    11860
tgaatatgag ctcattagta aaaatgactt cacccacgca tatacataaa gtatccatgc   11920
atgtgcatat agacacatct ataattttac acacacacct ctcaagacgg agatgcatgg   11980
cctctaagag tgcccgtgtc ggttcttcct ggaagttgac tttccttaga cccgccaggt   12040
caagttagcc gcgtgacgga catccaggcg tgggacgtgg tcagggcagg gctcattcat   12100
tgcccactag gatcccactg gcgaagatgg tctccatatc agctctctgc agaagggagg   12160
aagactttat catgttccta aaaatctgtg gcaagcaccc atcgtattat ccaaattttg   12220
ttgcaaatgt gattaatttg gttgtcaagt tttgggggtg ggctgtgggg agattgcttt   12280
```

```
tgttttcctg ctggtaatat cgggaaagat tttaatgaaa ccagggtaga attgtttggc    12340
aatgcactga agcgtgtttc tttcccaaaa tgtgcctccc ttccgctgcg ggcccagctg    12400
agtctatgta ggtgatgttt ccagctgcca agtgctcttt gttactgtcc accctcattt    12460
ctgccagcgc atgtgtcctt tcaaggggaa aatgtgaagc tgaaccccct ccagacaccc    12520
agaatgtagc atctgagaag gccctgtgcc ctaaaggaca cccctcgccc ccatcttcat    12580 ggaggggtc atttcagagc cctcggagcc aatgaacagc tcctcctctt ggagctgaga     12640
tgagccccac gtggagctcg ggacggatag tagacagcaa taactcggtg tgtggccgcc    12700
tggcaggtgg aacttcctcc cgttgcgggg tggagtgagg ttagttctgt gtgtctggtg    12760
ggtggagtca ggcttctctt gctacctgtg agcatccttc ccagcagaca tcctcatcgg    12820
gctttgtccc tcccccgctt cctccctctg cggggaggac ccgggaccac agctgctggc    12880
cagggtagac ttggagctgt cctccagagg ggtcacgtgt aggagtgaga agaaggaaga    12940
tcttgagagc tgctgaggga ccttggagag ctcaggatgg ctcagacgag gacactcgct    13000
tgccgggcct gggcctcctg ggaaggaggg agctgctcag aatgccgcat gacaactgaa    13060
ggcaacctgg aaggttcagg ggccgctctt cccccatgtg cctgtcacgc tctggtgcag    13120
tcaaaggaac gccttcccct cagttgtttc taagagcaga gtctcccgct gcaatctggg    13180
tggtaactgc cagccttgga ggatcgtggc caacgtggac ctgcctacgg agggtgggct    13240
ctgacccaag tggggcctcc ttgtccaggt ctcactgctt tgcaccgtgg tcagagggac    13300
tgtcagctga gcttgagctc ccctggagcc agcagggctg tgatgggcga gtcccggagc    13360
cccacccaga cctgaatgct tctgagagca aagggaagga ctgacgagag atgtatattt    13420 aatttttaa ctgctgcaaa cattgtacat ccaaattaaa ggaaaaaat ggaaaccatc     13480 a                                                                    13481

<210> SEQ ID NO 575
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 575
ccttccctga aggttcctcc                                                    20

<210> SEQ ID NO 576
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 576
tctctattgc acattccaag                                                    20

<210> SEQ ID NO 577
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: bases at these positions are RNA
```

```
<400> SEQUENCE: 577
taaautgtca tcacc                                                    15

<210> SEQ ID NO 578
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: bases at these positions are RNA

<400> SEQUENCE: 578
taaatugtca tcacc                                                    15

<210> SEQ ID NO 579
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: Bases at these positions are RNA

<400> SEQUENCE: 579
taaattgtca ucacc                                                    15
```